(12) United States Patent
Lee et al.

(10) Patent No.: US 9,837,614 B2
(45) Date of Patent: Dec. 5, 2017

(54) CONDENSED-CYCLIC COMPOUND AND ORGANIC LIGHT-EMITTING DEVICE COMPRISING THE SAME

(71) Applicant: Samsung Display Co., Ltd., Yongin, Gyeonggi-Do (KR)

(72) Inventors: Eun-Young Lee, Yongin (KR); Seok-Hwan Hwang, Yongin (KR); Young-Kook Kim, Yongin (KR); Jun-Ha Park, Yongin (KR); Hye-Jin Jung, Yongin (KR); Jin-O Lim, Yongin (KR); Jong-Woo Kim, Yongin (KR); Sang-Hyun Han, Yongin (KR); Kwang-Hyun Kim, Yongin (KR); Eun-Jae Jeong, Yongin (KR); Soo-Yon Kim, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 756 days.

(21) Appl. No.: 14/267,148

(22) Filed: May 1, 2014

(65) Prior Publication Data

US 2015/0069342 A1    Mar. 12, 2015

(30) Foreign Application Priority Data

Sep. 6, 2013    (KR) ........................ 10-2013-0107511

(51) Int. Cl.
| | |
|---|---|
| H01L 51/00 | (2006.01) |
| H01L 51/50 | (2006.01) |
| C09K 11/06 | (2006.01) |
| C07D 401/14 | (2006.01) |
| C07D 333/76 | (2006.01) |
| C07D 401/04 | (2006.01) |
| C07D 401/10 | (2006.01) |
| C07D 403/10 | (2006.01) |
| C07D 405/04 | (2006.01) |
| C07D 405/10 | (2006.01) |
| C07D 409/10 | (2006.01) |
| C07D 409/14 | (2006.01) |
| C07D 209/88 | (2006.01) |
| C07D 307/91 | (2006.01) |

(Continued)

(52) U.S. Cl.
CPC ........ *H01L 51/0054* (2013.01); *C07D 209/88* (2013.01); *C07D 213/57* (2013.01); *C07D 215/12* (2013.01); *C07D 307/91* (2013.01); *C07D 333/76* (2013.01); *C07D 401/04* (2013.01); *C07D 401/10* (2013.01); *C07D 401/14* (2013.01); *C07D 403/10* (2013.01); *C07D 405/04* (2013.01); *C07D 405/10* (2013.01); *C07D 409/10* (2013.01); *C07D 409/14* (2013.01); *C09B 57/001* (2013.01); *C09K 11/06* (2013.01); *H01L 51/0052* (2013.01); *H01L 51/0067* (2013.01); *H01L 51/0072* (2013.01); *H01L 51/0074* (2013.01); *H01L 51/006* (2013.01); *H01L 51/0058* (2013.01); *H01L 51/5072* (2013.01)

(58) Field of Classification Search
CPC .. C07D 209/88; C07D 213/57; C07D 215/12; C07D 307/91; C07D 333/76; C07D 401/04; C07D 401/10; C07D 401/14; C07D 403/10; C07D 405/04; C07D 405/10; C07D 409/10; C07D 409/14; C09B 57/001; H01L 51/0052; H01L 51/0054; H01L 51/0058; H01L 51/006; H01L 51/0072; H01L 51/0074; H01L 51/5072; C09K 11/06

See application file for complete search history.

(56) References Cited

U.S. PATENT DOCUMENTS

| | | |
|---|---|---|
| 5,645,948 A | 7/1997 | Shi et al. |
| 6,465,115 B2 | 10/2002 | Shi et al. |

(Continued)

FOREIGN PATENT DOCUMENTS

| | | |
|---|---|---|
| JP | 10-17860 A | 1/1998 |
| JP | 11-87067 A | 3/1999 |

(Continued)

OTHER PUBLICATIONS

Machine translation for JP 2010-195708 A (publication date: Sep. 2010).*

(Continued)

*Primary Examiner* — Dawn Garrett
(74) *Attorney, Agent, or Firm* — H.C. Park & Associates, PLC

(57) ABSTRACT

A condensed-cyclic compound represented by Formula 1 and an organic light-emitting device including the condensed-cyclic compound.

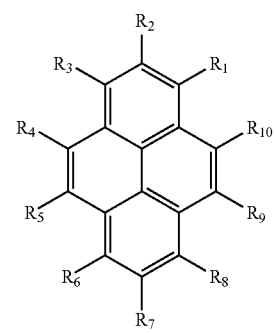

Formula 1 wherein $R_1$ to $R_{10}$ are defined as in the specification.

20 Claims, 1 Drawing Sheet

(51) Int. Cl.
*C07D 215/12* (2006.01)
*C07D 213/57* (2006.01)
*C09B 57/00* (2006.01)

(56) References Cited

U.S. PATENT DOCUMENTS

| | | |
|---|---|---|
| 6,596,415 B2 | 7/2003 | Shi et al. |
| 2003/0165715 A1 | 9/2003 | Yoon et al. |
| 2011/0121268 A1 | 5/2011 | Nagao et al. |
| 2012/0256172 A1 | 10/2012 | Ito et al. |
| 2014/0027754 A1* | 1/2014 | Ueoka .................. C07D 401/10 257/40 |

FOREIGN PATENT DOCUMENTS

| | | |
|---|---|---|
| JP | 2010-195708 A | 9/2010 |
| KR | 10-0691543 B1 | 2/2007 |
| KR | 10-2011-0040874 A | 4/2011 |
| KR | 10-2012-0051598 A | 5/2012 |
| KR | 10-2012-0057198 A | 5/2012 |
| KR | 10-2012-0104087 A | 9/2012 |
| WO | 2012173073 A1 | 12/2012 |

OTHER PUBLICATIONS

C. W. Tang and S. A. Vanslyke, Appl. Phys. Lett., 51, (1987), pp. 913-915.
Chihaya Adachi et al., Appl. Phys. Lett., 57, 531 (1990), pp. 531-533.
J. Am. Chem. Soc., 122, 1832 (2000), pp. 1832-1833.
Chem. Lett., 98 (2001), pp. 98-99.
N. Johansson et.al. Adv. Mater. 10 (1998) 1136, pp. 1136-1141.
Y.T. Tao et.al. Appl. Phys. Lett. 77 (2000) 1575, pp. 1575-1577.

* cited by examiner

10

| 190 |
| --- |
| 150 |
| 110 |

CONDENSED-CYCLIC COMPOUND AND ORGANIC LIGHT-EMITTING DEVICE COMPRISING THE SAME

CLAIM OF PRIORITY

This application makes reference to, incorporates the same herein, and claims all benefits accruing under 35 U.S.C. §119 from an application for CONDENSED-CYCLIC COMPOUND AND ORGANIC LIGHT-EMITTING DEVICE COMPRISING THE SAME, earlier filed in the Korean Intellectual Property Office on Sep. 6, 2013 and there duly assigned Serial No. 10-2013-0107511.

BACKGROUND OF THE INVENTION

Field of the Invention

The present invention relates to a condensed-cyclic compound and an organic light-emitting device including the same.

Description of the Related Art

Organic light emitting devices are self-emission devices that have wide viewing angles, a high contrast ratio, short response times, and excellent brightness, driving voltage, and response speed characteristics, and produce full-color images.

An organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are recombined in the emission layer to produce excitons. These excitons change from an excited state to a ground state, thereby generating light.

SUMMARY OF THE INVENTION

One or more embodiments of the present invention include novel condensed-cyclic compounds and organic light-emitting devices including the same.

Additional aspects will be set forth in part in the description which follows and, in part, will be apparent from the description, or may be learned by practice of the presented embodiments.

According to one or more embodiments of the present invention, provided are condensed-cyclic compounds represented by Formula 1 below.

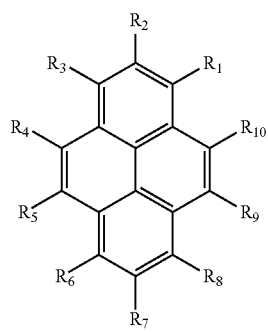

Formula 1

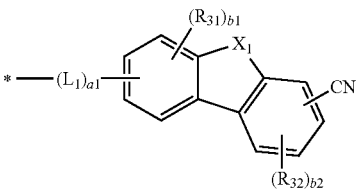

Formula 2

In Formulae 1, $R_1$ to $R_{10}$ may be each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, (wherein, the "substituted monovalent non-aromatic hetero-condensed polycyclic group" excludes a group represented by Formula 2 above), —N($Q_1$)($Q_2$), —Si($Q_3$)($Q_4$)($Q_5$) and —B($Q_6$)($Q_7$); one of $R_1$ to $R_{10}$ may be represented by Formula 2 above; in Formula 2, $X_1$ may be N($R_{21}$), O, or S; $L_1$ may be selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group; a1 may be selected from 0, 1, 2, and 3; b1 and b2 may be each independently selected from 0, 1, 2, and 3; at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic hetero-condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group (aryloxy), a $C_6$-$C_{60}$ arylthio group (arylthio), a $C_2$-$C_{60}$ heteroaryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), and —B($Q_{16}$)($Q_{17}$); a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$) and —B($Q_{36}$)($Q_{37}$); $R_{21}$, $R_{31}$, $R_{32}$, $Q_1$ to $Q_7$, $Q_{11}$ to $Q_{17}$, $Q_{21}$ to $Q_{27}$, and $Q_{31}$ to $Q_{37}$ above may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group; wherein the condensed-cyclic compounds represented by Formula 1 above may have one group represented by Formula 2 above.

Another aspect of the present invention provides an organic light-emitting device (OLED) including: a first electrode; a second electrode facing the first electrode; and an organic layer disposed between the first and second electrodes including an emission layer, wherein the organic layer may includes at least one condensed-cyclic compound described above.

BRIEF DESCRIPTION OF THE DRAWINGS

These and/or other aspects will become apparent and more readily appreciated from the following description of the embodiments, taken in conjunction with the FIGURE, which schematically illustrates a structure of an organic light-emitting device (OLED) according to an embodiment of the present invention.

DETAILED DESCRIPTION OF THE INVENTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

The condensed-cyclic compound is represented by Formula 1 below, and one of $R_1$ to $R_{10}$ of Formula 1 is a group represented by Formula 2 below:

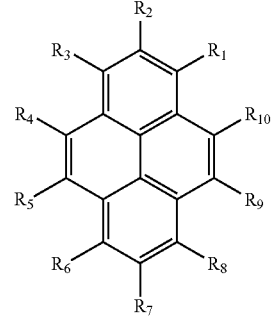

Formula 1

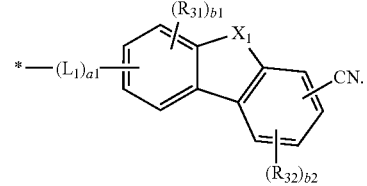

Formula 2

The condensed-cyclic compound represented by Formula 1 above has one group represented by Formula 2 above, as a substituent of the Formula 1. * of Formula 2 above is a binding site to carbon that forms a pyrene backbone of Formula 1.

In Formulae 1 above, $R_1$ to $R_{10}$ may be each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group, (wherein, the "substituted monovalent non-aromatic hetero-condensed polycyclic group" excludes a group represented by Formula 2 above), —N($Q_1$)($Q_2$), —Si($Q_3$)($Q_4$)($Q_5$) and —B($Q_6$)($Q_7$).

In Formula 1 above, $R_1$ to $R_{10}$ may be each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group and Si($Q_3$)($Q_4$)($Q_5$) (wherein, $Q_3$ to $Q_5$ may be each independently selected from a $C_1$-$C_{20}$ alkyl group, a $C_1$-$C_{20}$ alkoxy group, a phenyl group, and a naphthyl group); and one of $R_1$ to $R_{10}$ may be represented by Formula 2 above.

In the descriptions of $R_1$ to $R_{10}$ in this disclosure, the "substituted monovalent non-aromatic hetero-condensed polycyclic group" does not include a group represented by Formula 2 above. Accordingly, a condensed-cyclic compound represented by Formula 1 above has one group represented by Formula 2 above as a substituent.

In Formula 2 above, $X_1$ is N($R_{21}$), O, or S. Description of $R_{21}$ above is as described below.

According to an embodiment of the present invention, $L_1$ of Formula 2 above may be selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, and a substituted or unsubstituted divalent non-aromatic hetero-condensed polycyclic group.

According to an embodiment of the present invention, $L_1$ of Formula 2 above may be selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a napthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a napthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; but it is not limited thereto.

According to another embodiment of the present invention, $L_1$ of Formula 2 above may be represented by any one of Formulae 3-1 to 3-32 below:

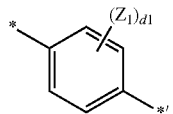

Formula 3-1

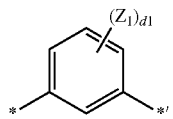

Formula 3-2

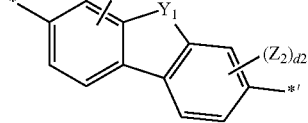

Formula 3-3

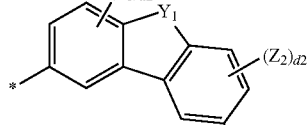

Formula 3-4

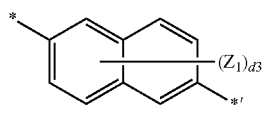

Formula 3-5

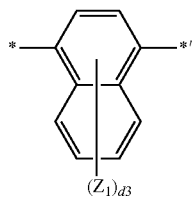

Formula 3-6

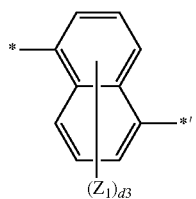

Formula 3-7

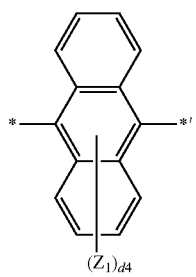

Formula 3-8

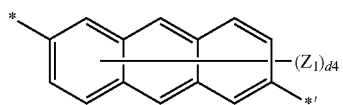

Formula 3-9

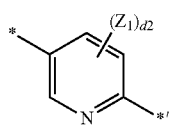

Formula 3-10

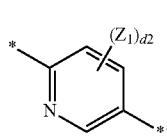

Formula 3-11

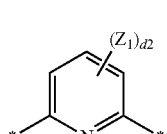

Formula 3-12

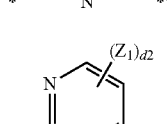

Formula 3-13

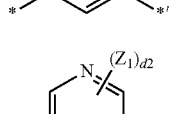

Formula 3-14

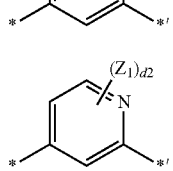

Formula 3-15

Formula 3-16
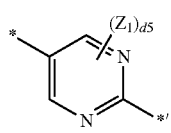

Formula 3-17
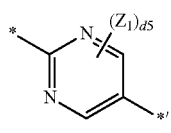

Formula 3-18
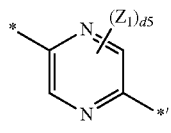

Formula 3-19
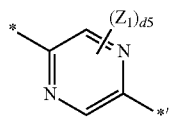

Formula 3-20
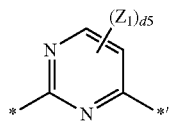

Formula 3-21
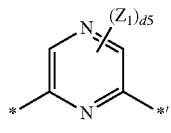

Formula 3-22
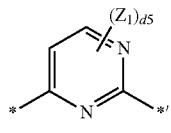

Formula 3-23
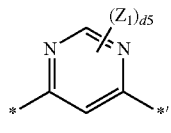

Formula 3-24
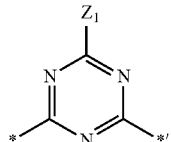

Formula 3-25
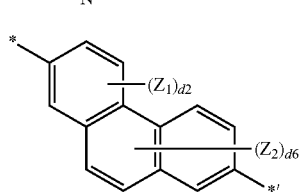

Formula 3-26
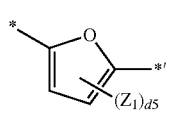

Formula 3-27
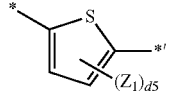

Formula 3-28
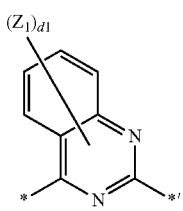

Formula 3-29
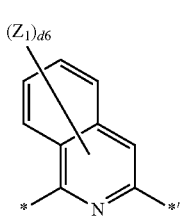

Formula 3-30
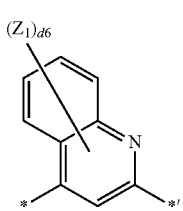

Formula 3-31
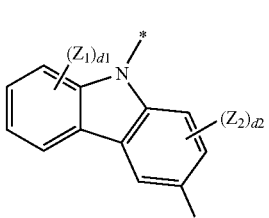

Formula 3-32
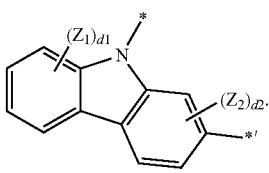

In Formulae 3-1 to 3-32 above, $Y_1$ is O, S, C($Z_3$)($Z_4$), N($Z_5$), or Si($Z_6$)($Z_7$); $Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 is selected from integers of 1 to 4; d2 is selected from integers of 1 to 3; d3 is selected from integers of 1 to 6; d4 is selected from integers of 1 to 8; d5 is 1 or 2; and d6 is selected from integers of 1 to 5.

According to another embodiment of the present invention, $L_1$ of Formula 2 above may be represented by any one of Formulae 4-1 to 4-23 below, but it is not limited thereto:

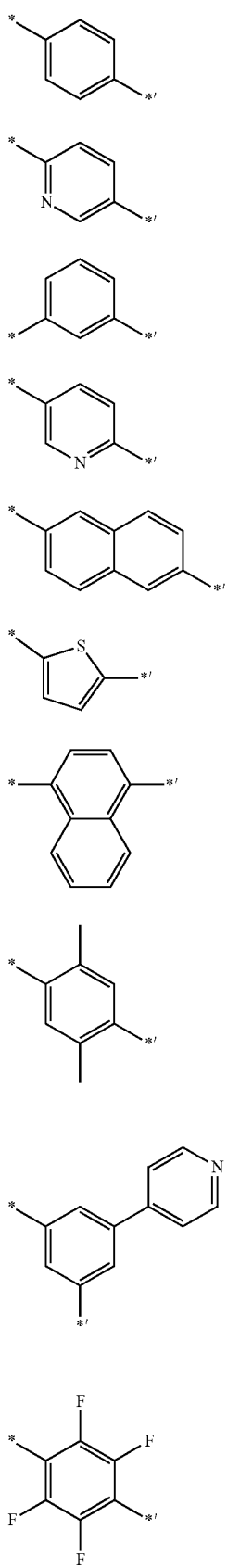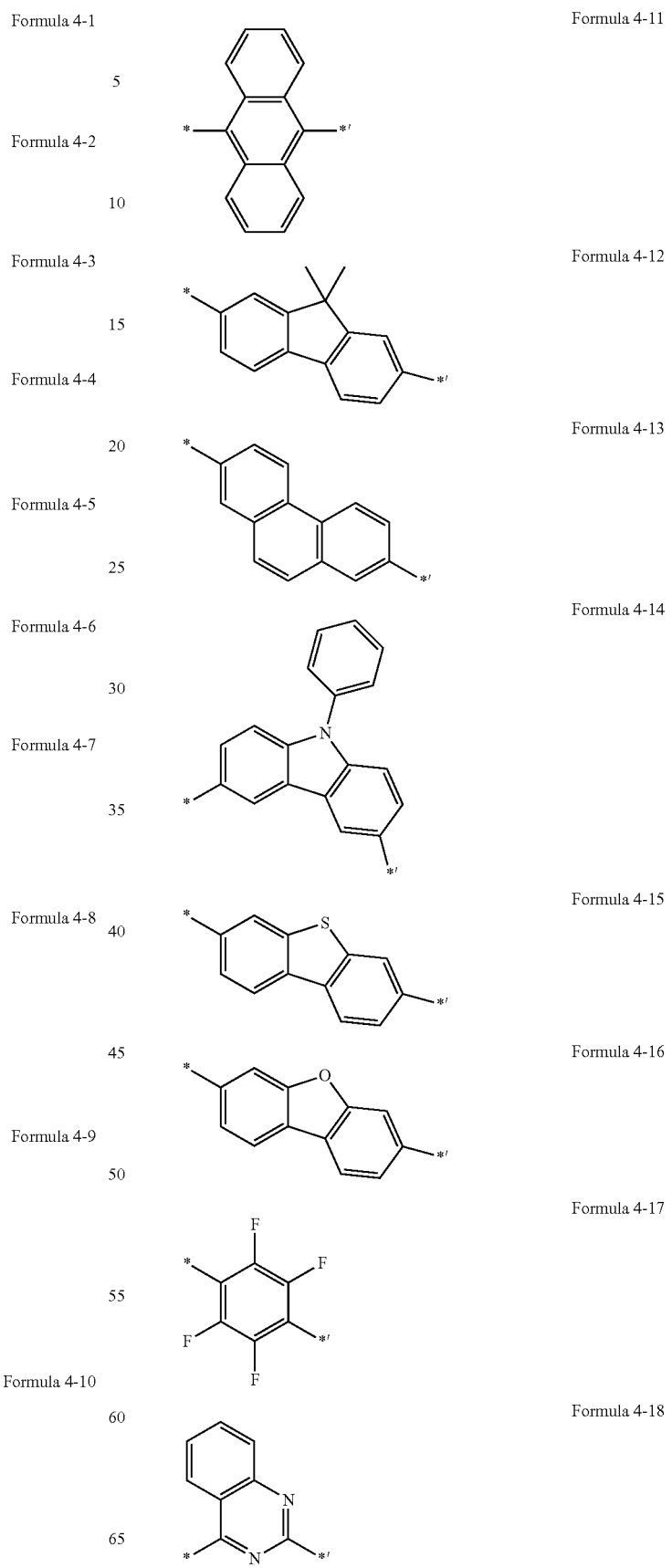

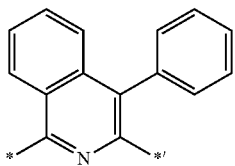
Formula 4-19

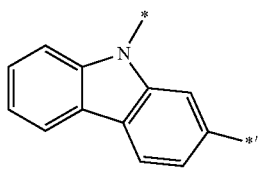
Formula 4-20

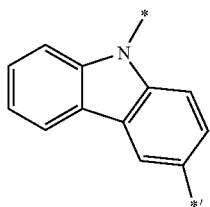
Formula 4-21

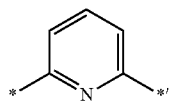
Formula 4-22

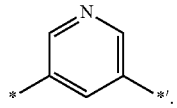
Formula 4-23 a1 in Formula 2 above may be selected from 0, 1, 2, and 3. For example, a1 in Formula 2 above may be 0 or 1. When a1 in Formula 2 above is 0, $-(L_1)_{a1}-$ is a single bond. When a1 is two or greater, a plurality of $L_1$s may be identical or different.

In Formula 2 above, $X_1$ is $N(R_{21})$; and $R_{21}$ above may be selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

According to another embodiment of the present invention, in Formula 2 above, $X_1$ is $N(R_{21})$; and $R_{21}$ above may be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but it is not limited thereto.

at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic hetero-condensed polycyclic group may be selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_2$-$C_{60}$ heteroaryl group, a monovalent non-aromatic condensed polycyclic group, a monovalent non-aromatic hetero-condensed polycyclic group, —$N(Q_{11})(Q_{12})$, —$Si(Q_{13})(Q_{14})(Q_{15})$, and —$B(Q_{16})(Q_{17})$; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —$N(Q_{21})(Q_{22})$, —$Si(Q_{23})(Q_{24})(Q_{25})$ and —$B(Q_{26})(Q_{27})$; and —$N(Q_{31})(Q_{32})$, —$Si(Q_{33})(Q_{34})(Q_{35})$ and —$B(Q_{36})(Q_{37})$.

Wherein $R_{21}$, $R_{31}$, $R_{32}$, $Q_1$ to $Q_7$, $Q_{11}$ to $Q_{17}$, $Q_{21}$ to $Q_{27}$, and $Q_{31}$ to $Q_{37}$ above may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, and a monovalent non-aromatic hetero-condensed polycyclic group.

In Formulae 1 and 2, $R_{21}$, $R_{31}$, $R_{32}$, $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but they are not limited thereto.

According to another embodiment, in Formulae 1 and 2 above, $R_{21}$ above may be selected from Formulae 5-1 to 5-35; $R_1$ to $R_{10}$ above may be each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, and Formulae 5-1 to 5-35 below, and one of $R_1$ to $R_{10}$ may be represented by Formula 2 above; and $R_{31}$ and $R_{32}$ above may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, and Formulae 5-1 to 5-35 below, but they are not limited thereto.

Formula 5-1

Formula 5-2

Formula 5-3

Formula 5-4

Formula 5-5

Formula 5-6

Formula 5-7

Formula 5-8

Formula 5-9

Formula 5-10

Formula 5-11

Formula 5-12

Formula 5-13

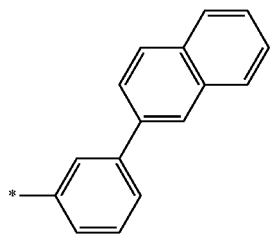
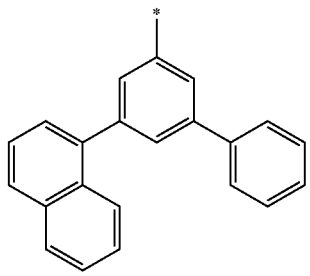
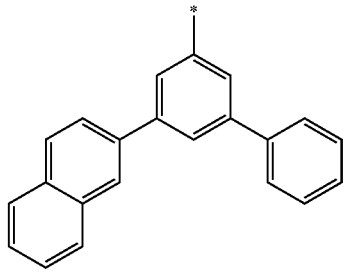
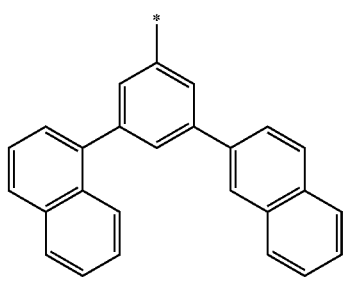
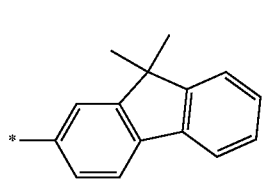
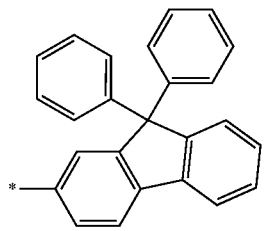

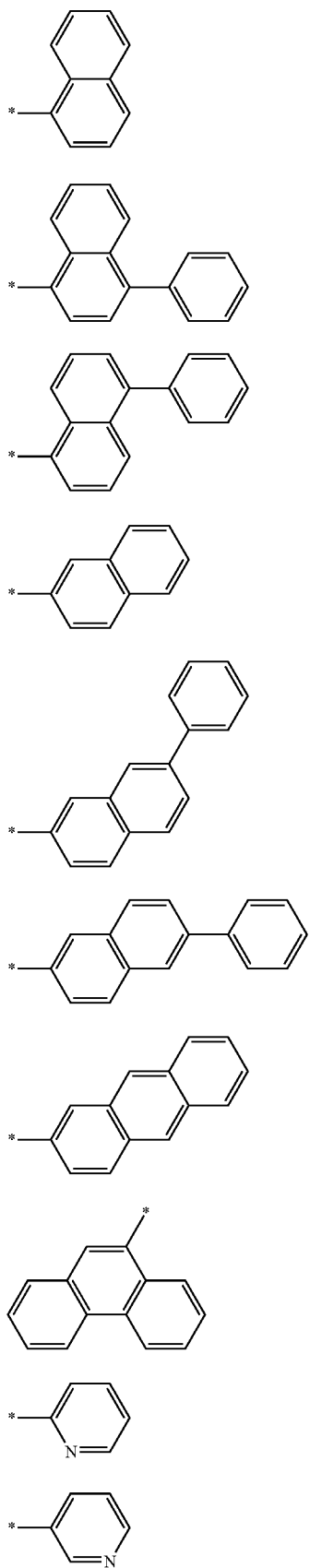
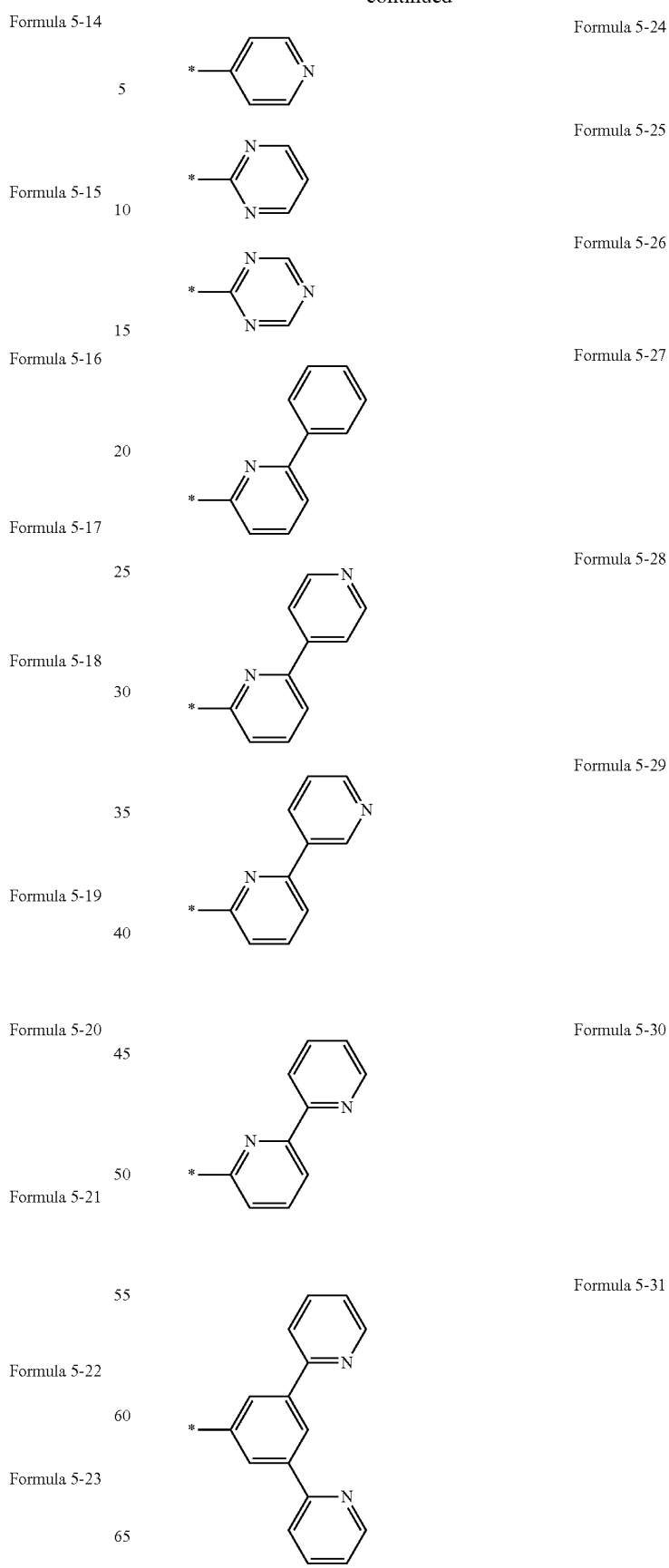

Formula 5-32

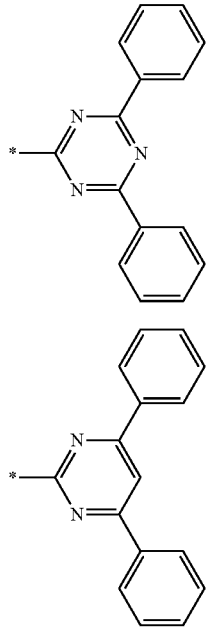

Formula 5-33

Formula 5-34

Formula 5-35

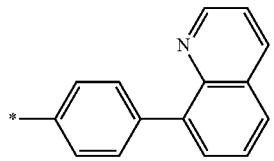

In Formulae 1 and 2 above, b1 may be selected from 0, 1, 2, and 3. For example, b1 may be 0, 1, or 2. When b1 is 2 or greater, a plurality of R31s may be identical or different. b2 may be understood by referring to the description provided in connection with b1.

For example, a condensed-cyclic compound represented by Formula 1 above may be represented by one of Formulae 1-1 to 1-12, and 1-21 to 1-32:

Formula 1-1

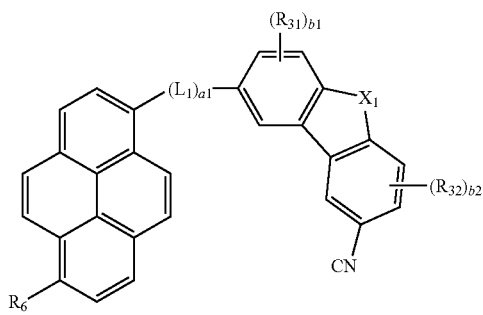

Formula 1-2

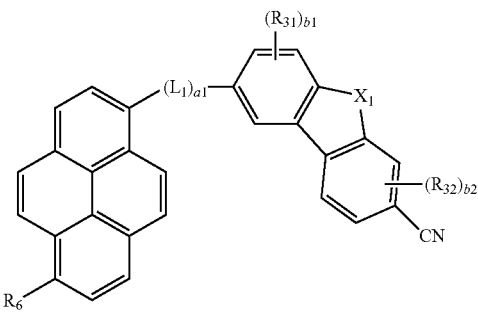

Formula 1-3

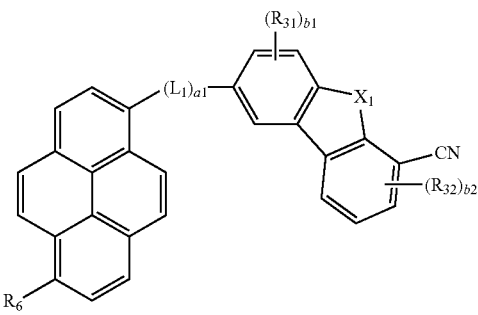

Formula 1-4

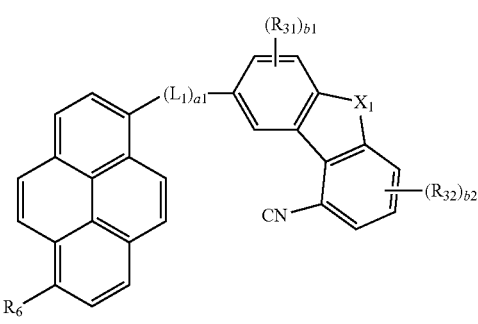

Formula 1-5

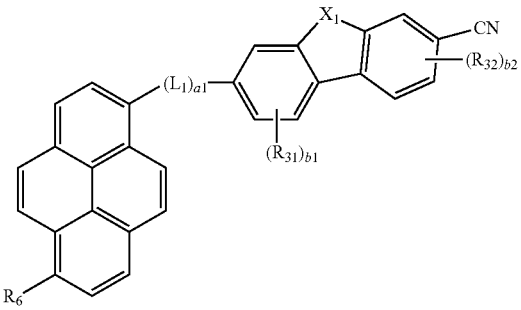

Formula 1-6
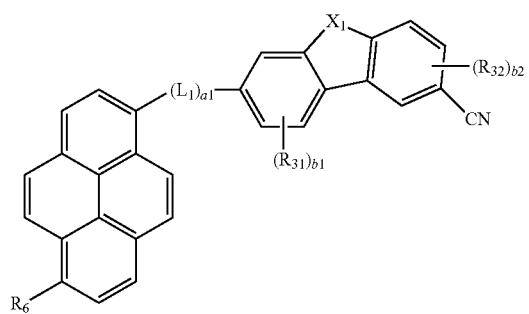
Formula 1-7
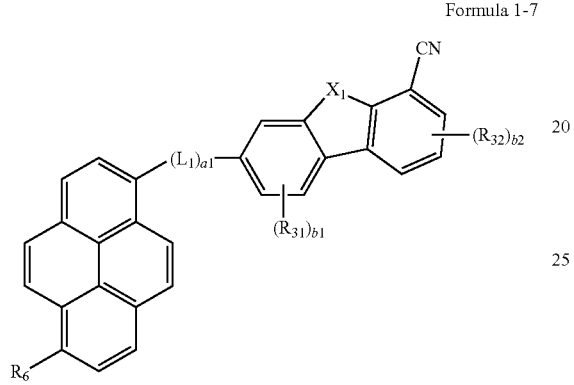
Formula 1-8
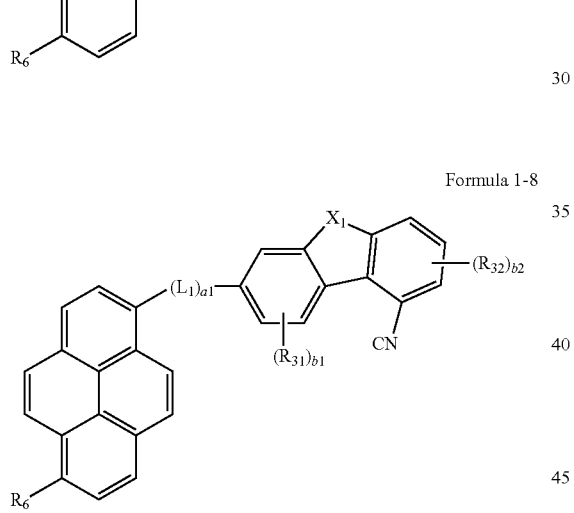
Formula 1-9
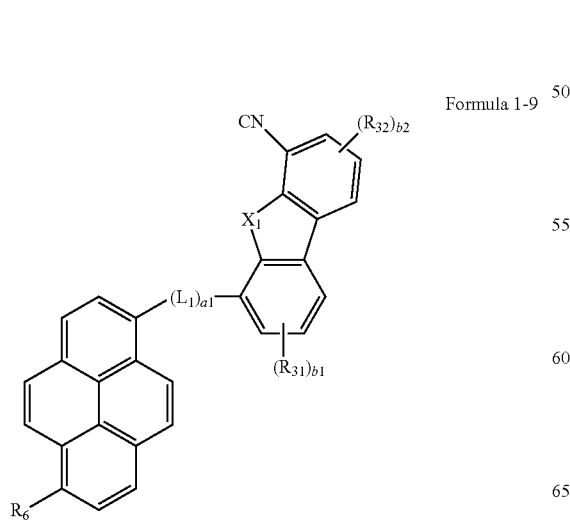
Formula 1-10
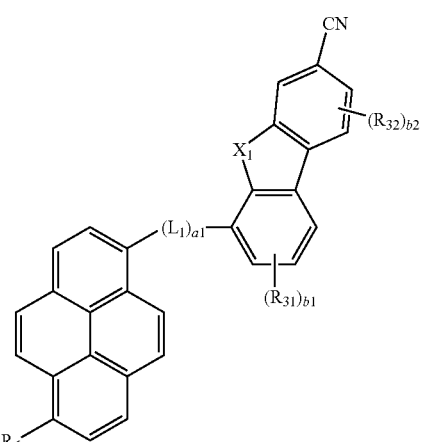
Formula 1-11
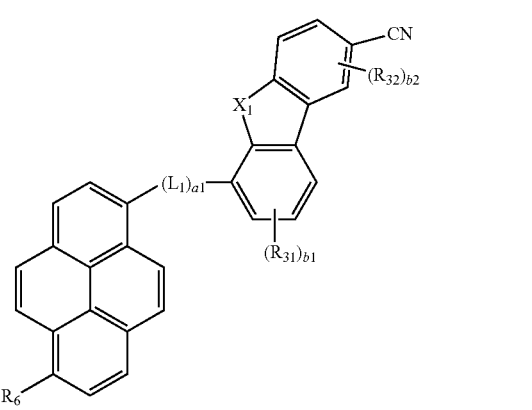
Formula 1-12
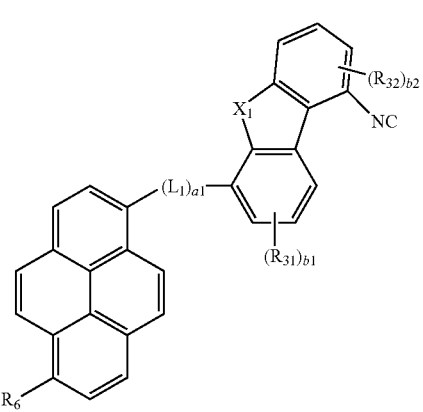

Formula 1-21
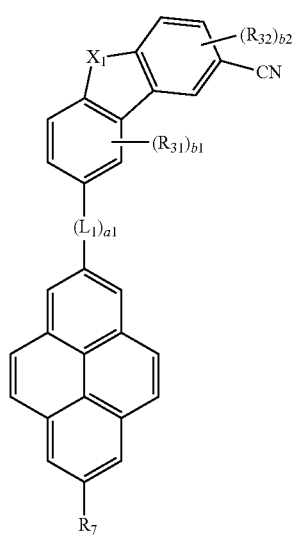
Formula 1-22
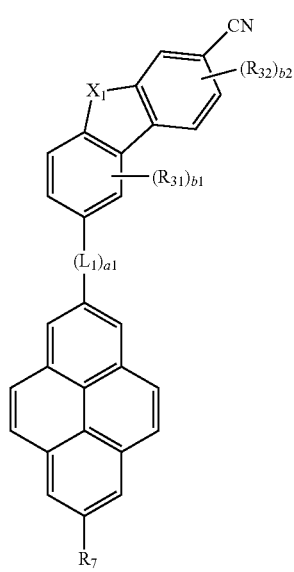
Formula 1-23
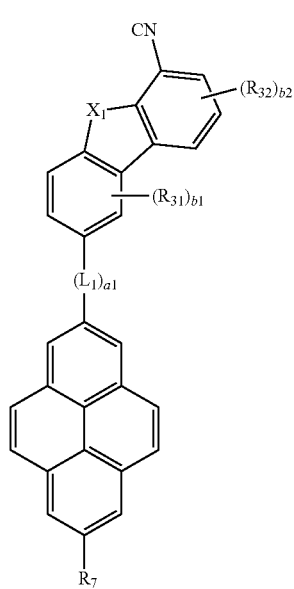
Formula 1-24
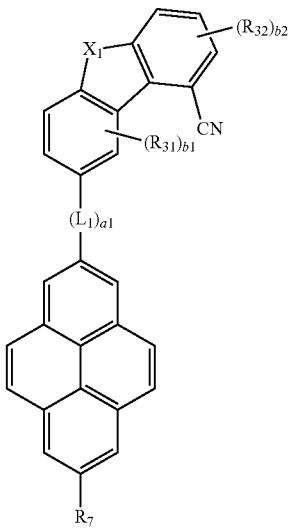
Formula 1-25
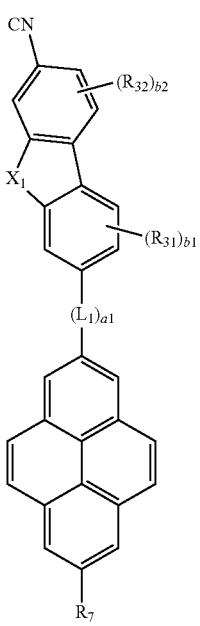

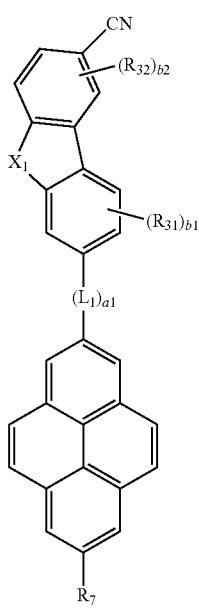
Formula 1-26
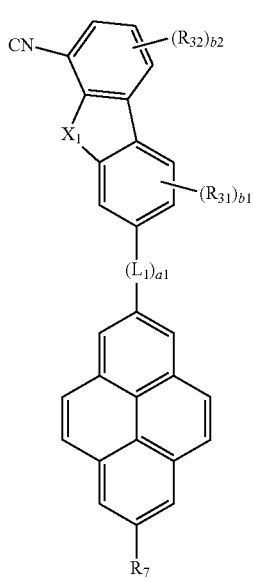
Formula 1-27
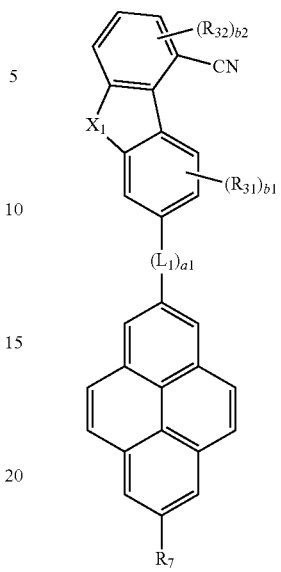
Formula 1-28
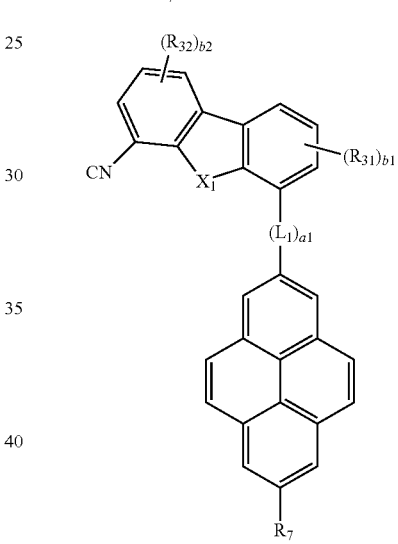
Formula 1-29
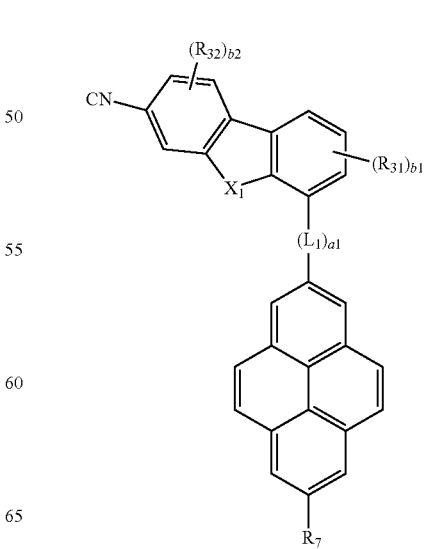
Formula 1-30

Formula 1-31

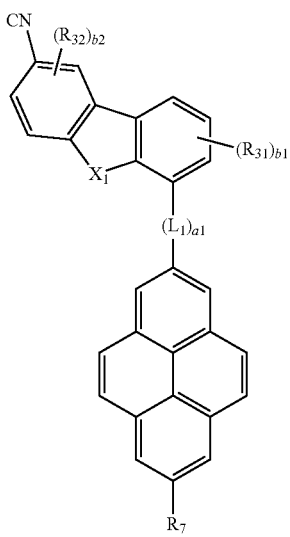

Formula 1-32

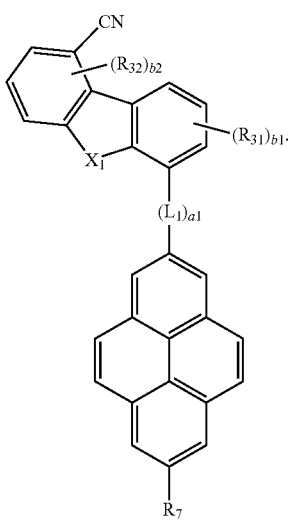

In Formulae 1-1 to 1-12, and 1-21 to 1-32 above, $X_1$, $L_1$, a1, $R_6$, $R_7$, $R_{31}$, $R_{32}$, b1 and b2 may be understood by referring to the corresponding description provided herein.

According to an embodiment of the present invention, the condensed-cyclic compound may be represented by one of Formulae 1-1 to 1-12, and 1-21 to 1-32, and $L_1$ in Formulae 1-1 to 1-12, and 1-21 to 1-32 may be represented by one of Formulae 4-1 to 4-23; a1 may be 0 or 1.

According to an embodiment of the present invention, the condensed-cyclic compound may be represented by one of Formulae 1-1 to 1-12, and 1-21 to 1-32, $X_1$ may be $N(R_{21})$, O, or S; $R_{21}$ may be selected from Formulae 5-1 to 5-35 above; $R_6$, $R_7$, $R_{31}$, and $R_{32}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, and Formulae 5-1 to 5-35 above; b1 and b2 may be each independently 0, 1, or 2, but they are not limited thereto.

According to another embodiment of the present invention, the condensed-cyclic compound represented by Formula 1 may be represented by Formulae 1-1, 1-5, 1-6, 1-9, 1-21, 1-25, 1-26, and 1-29 above.

The condensed-cyclic compound represented by Formula 1 may be Compounds 1 to 170 below, but it is not limited thereto.

1

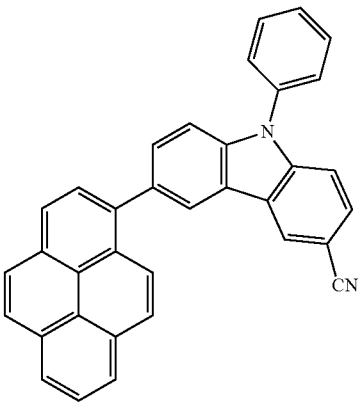

2

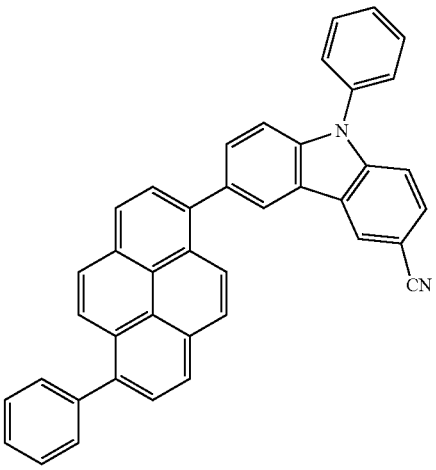

3

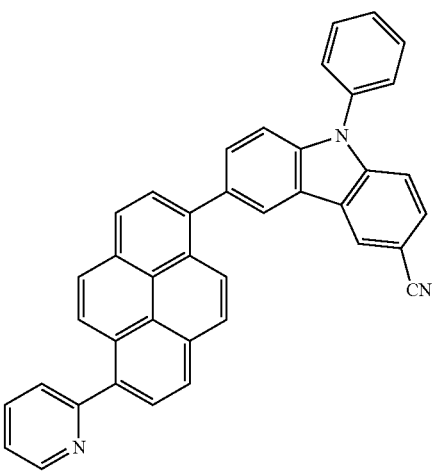

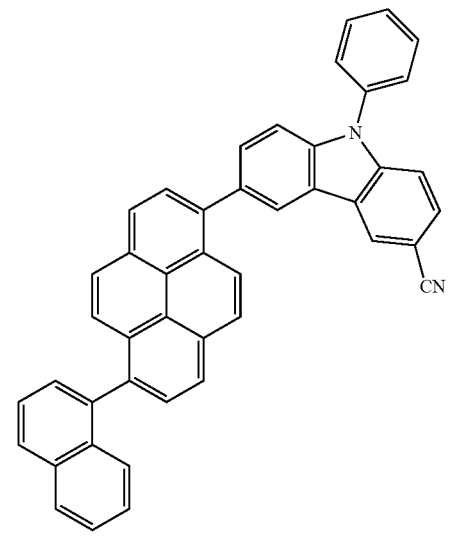
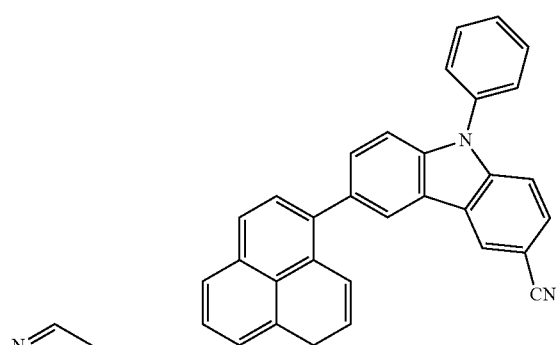
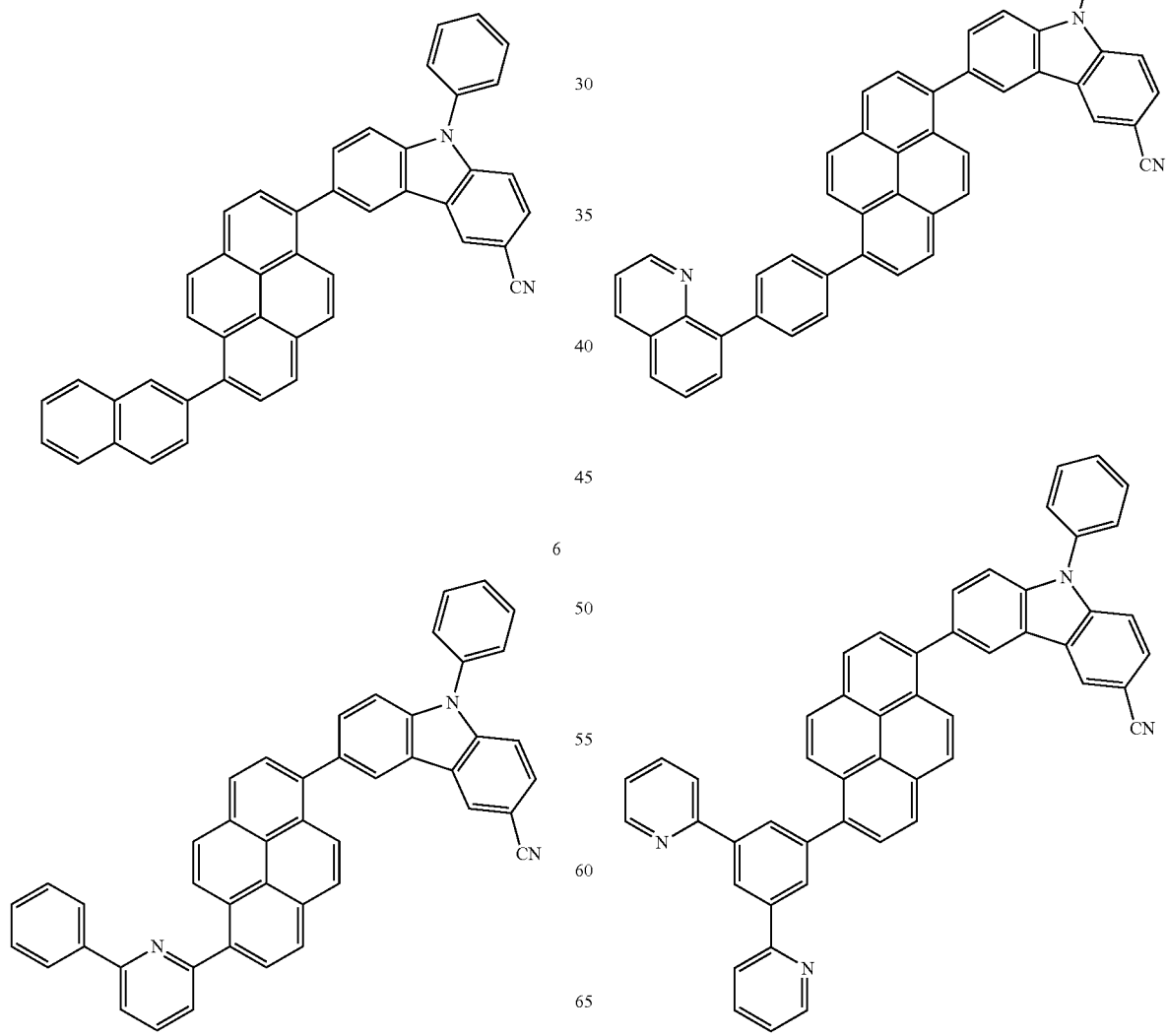

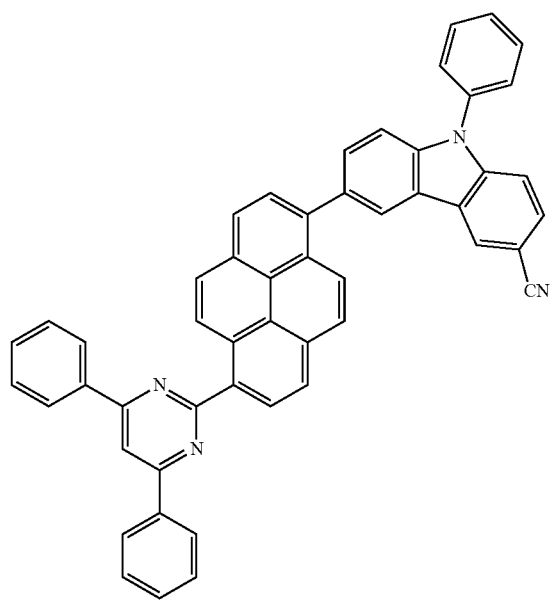
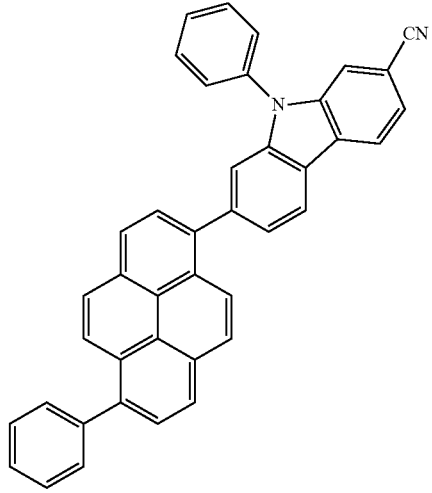

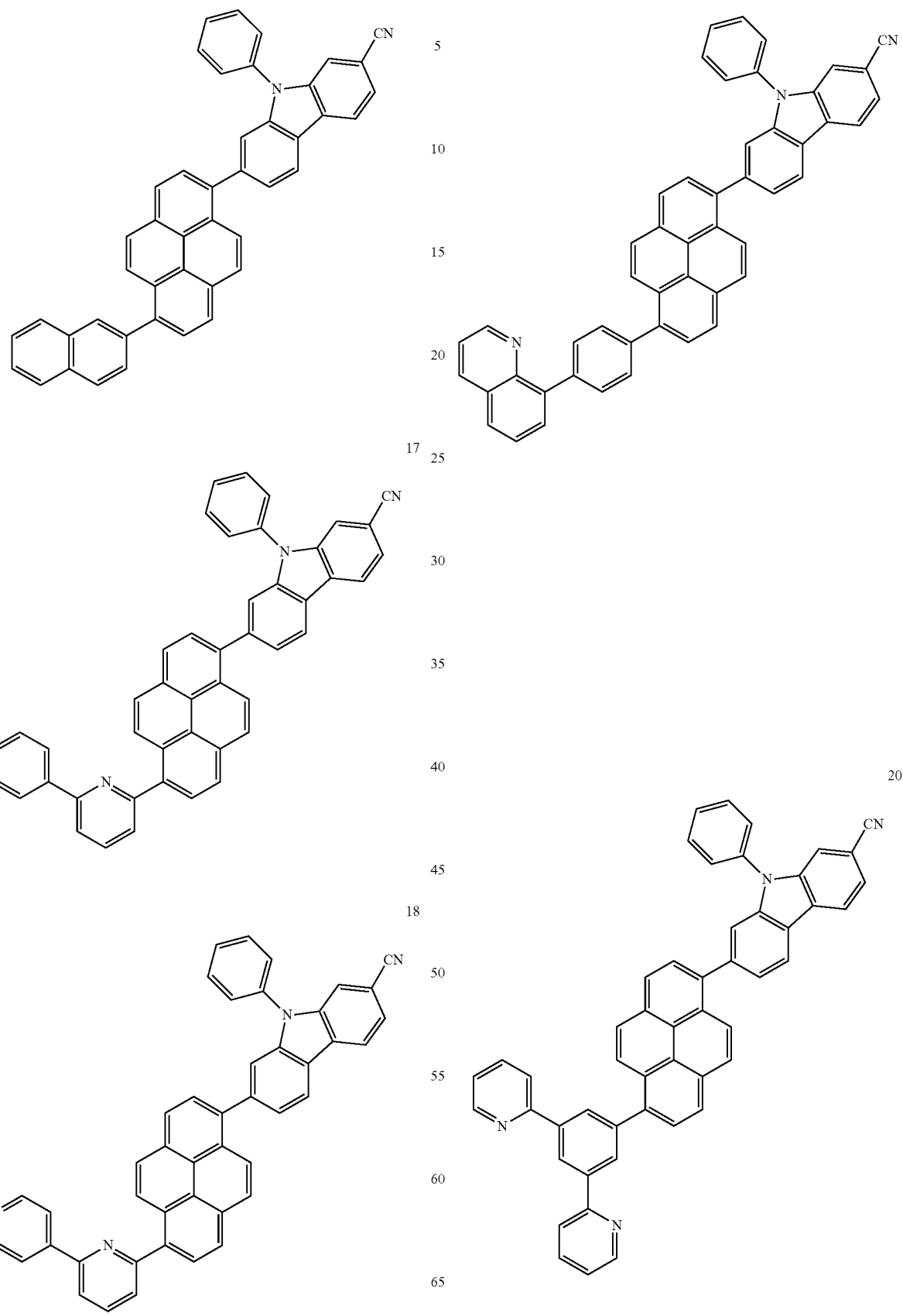

21
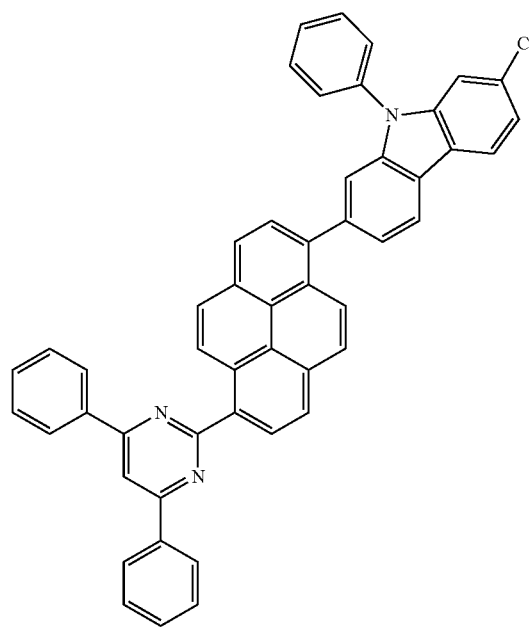
22
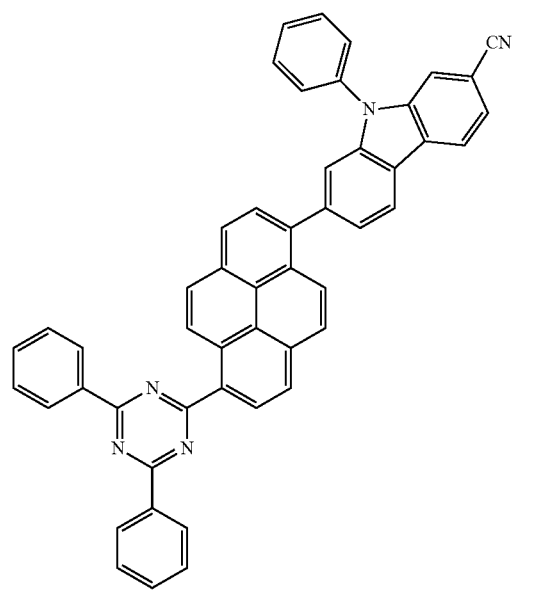
23
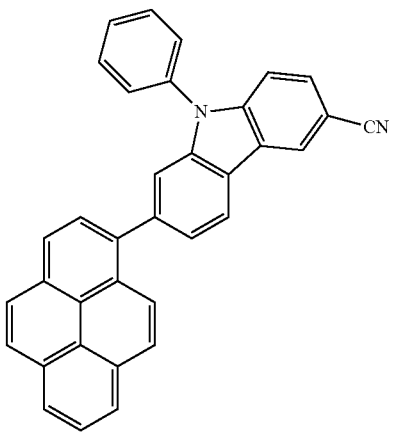
24
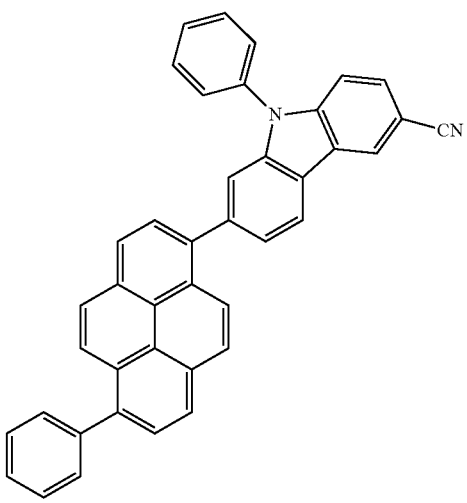
25
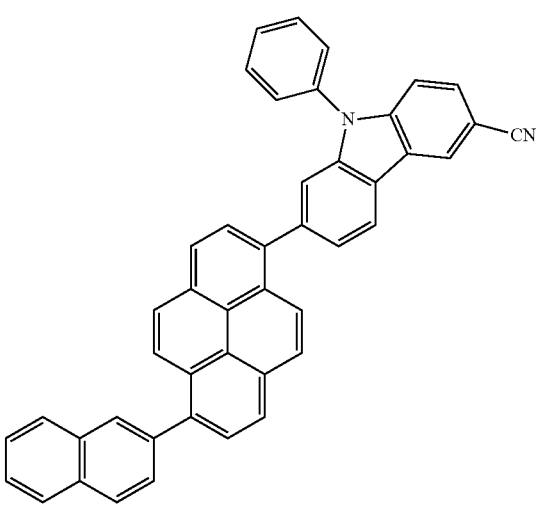

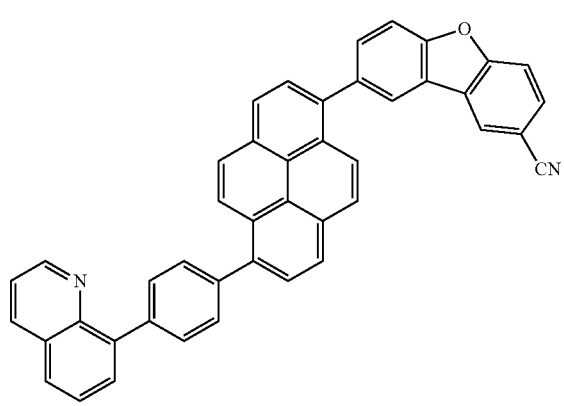
26
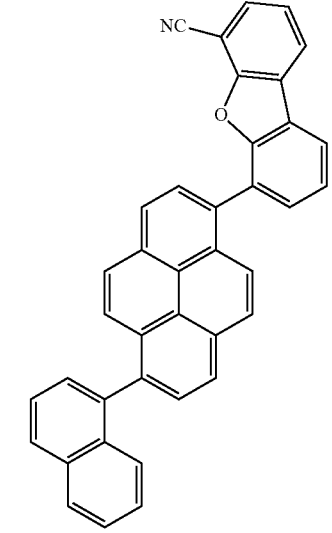
27
28
29
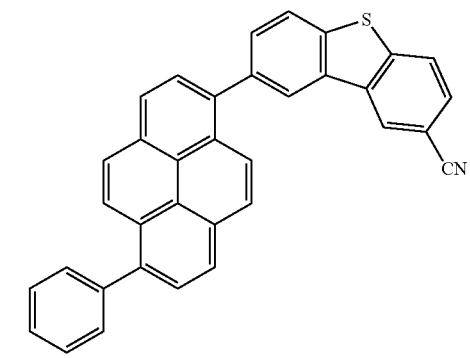
30
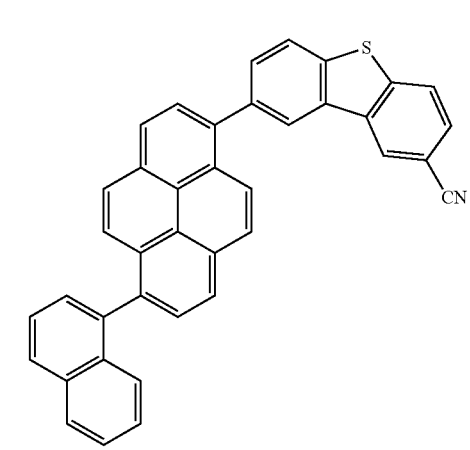
31
32

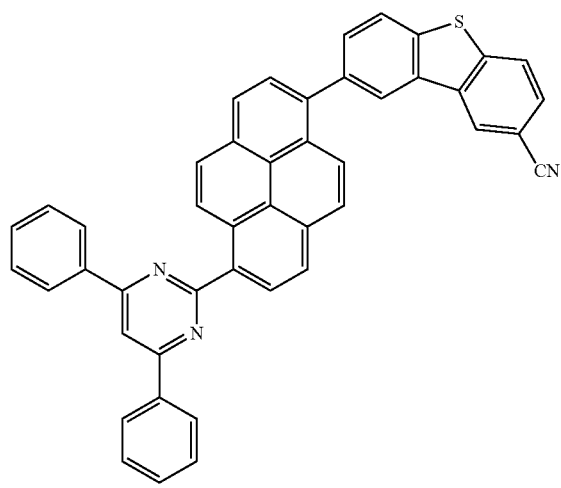
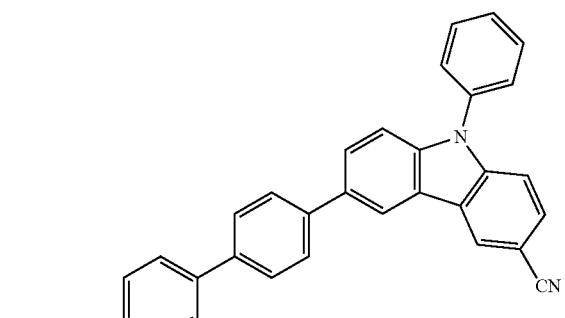

39
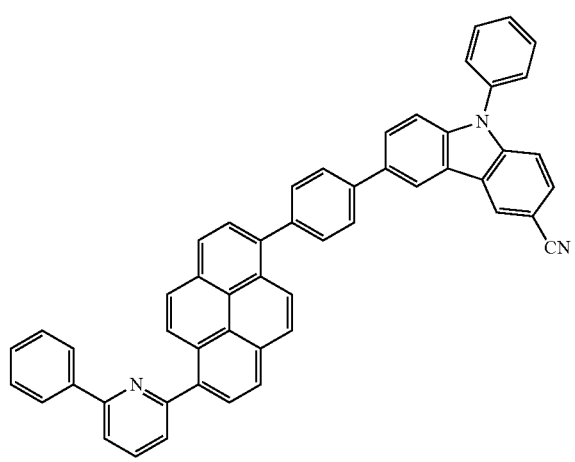
40
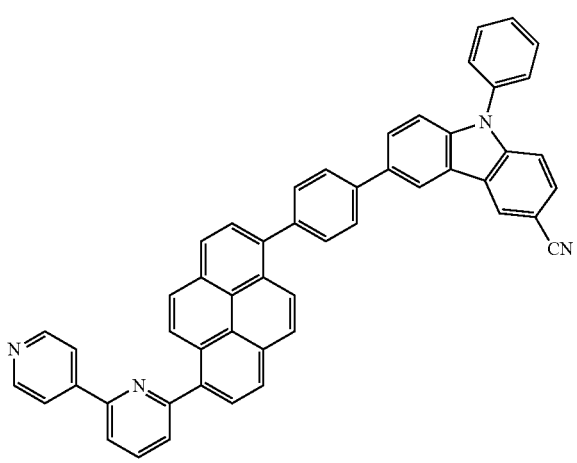
41
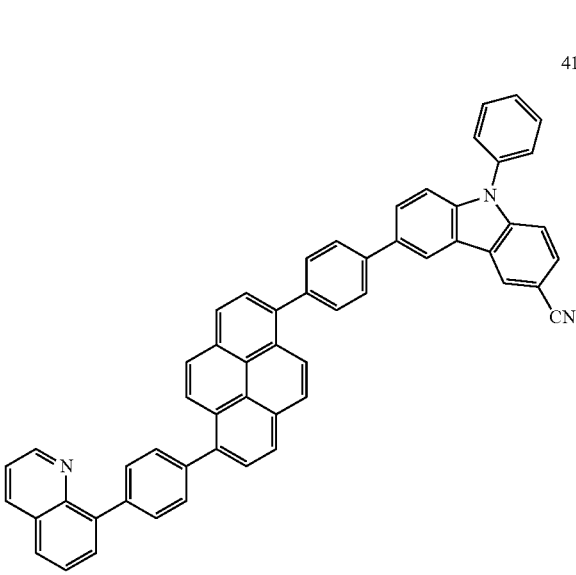
42
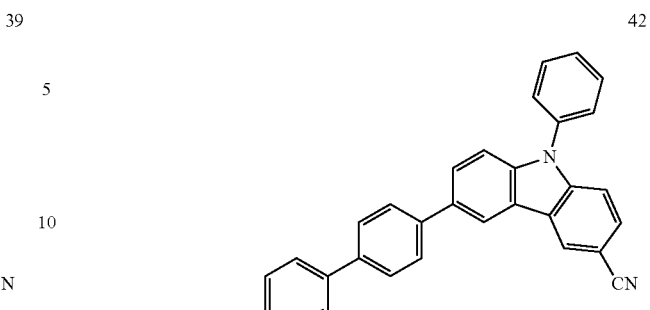
43
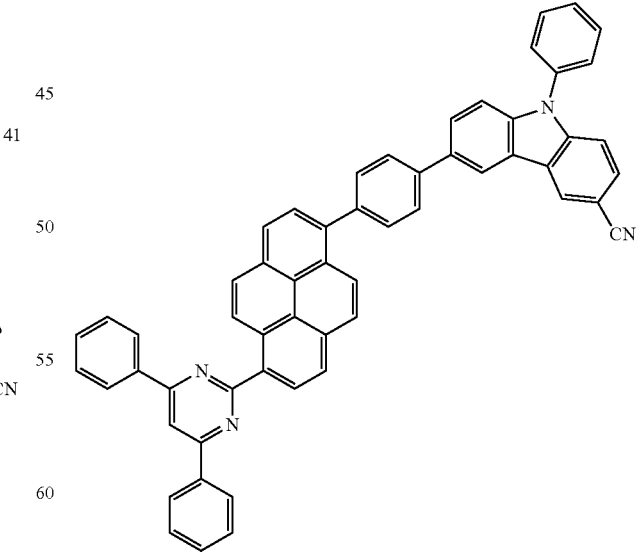

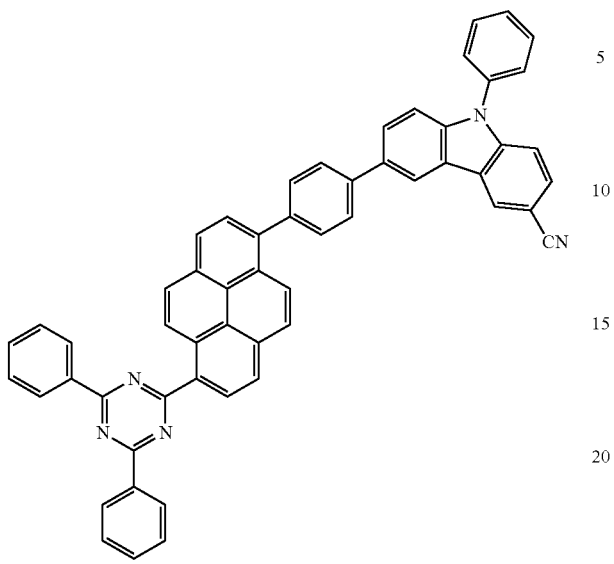
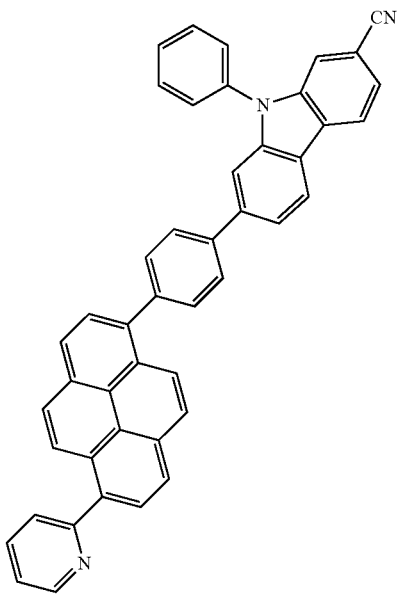
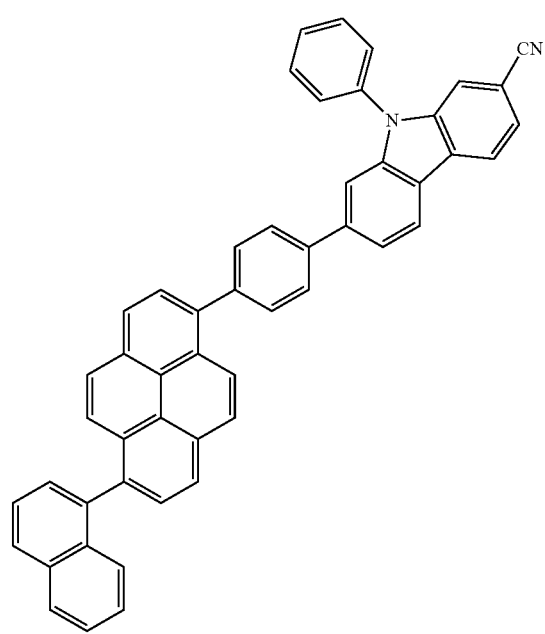

49
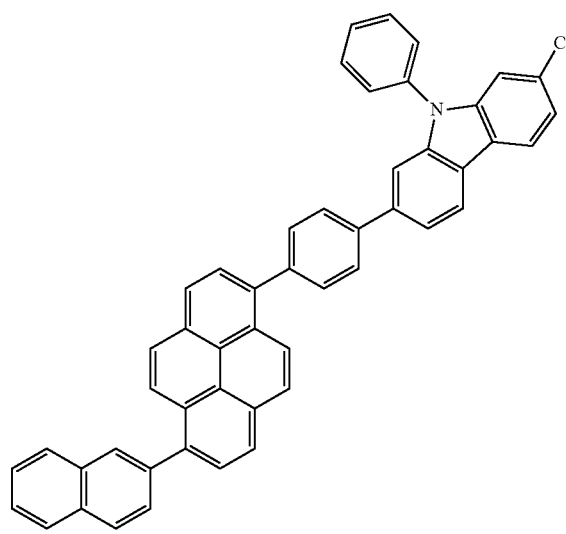
50
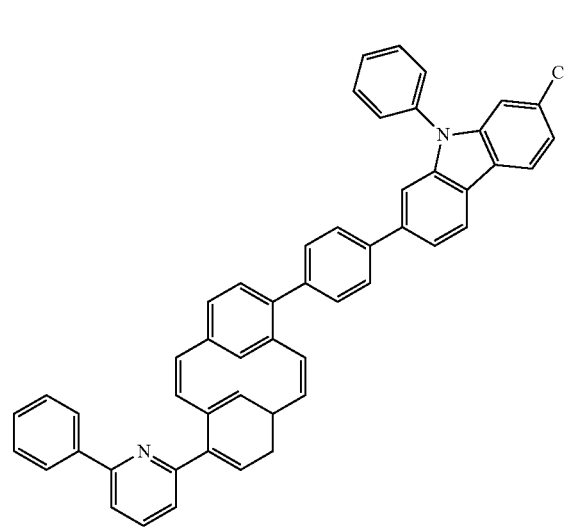
51
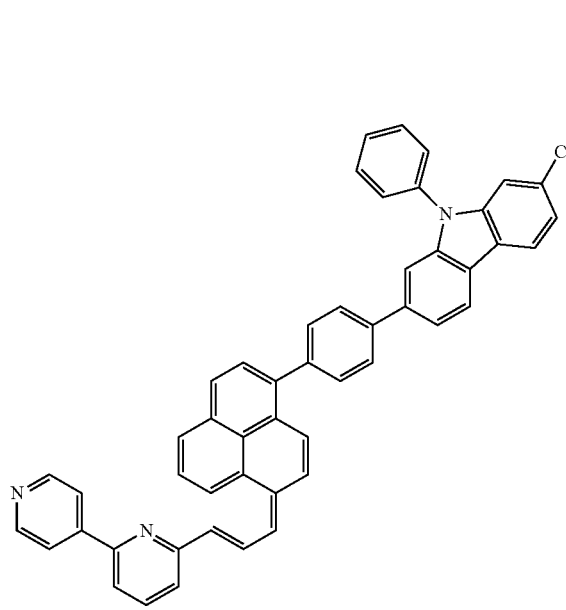
52
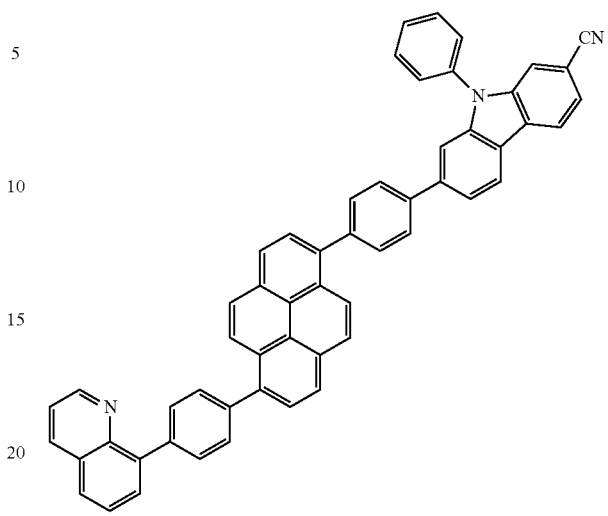
53
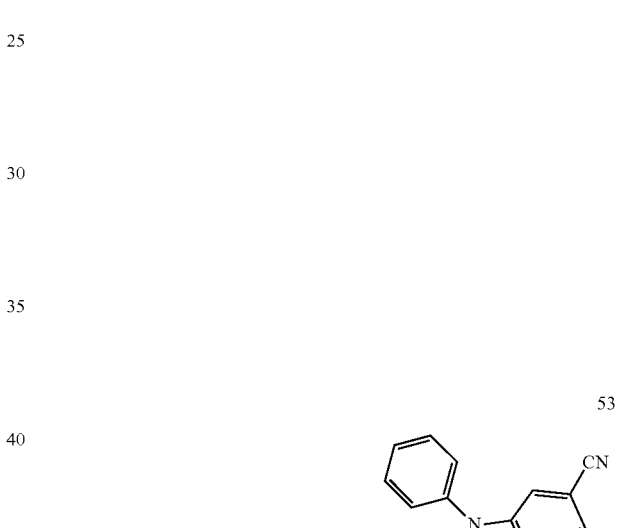

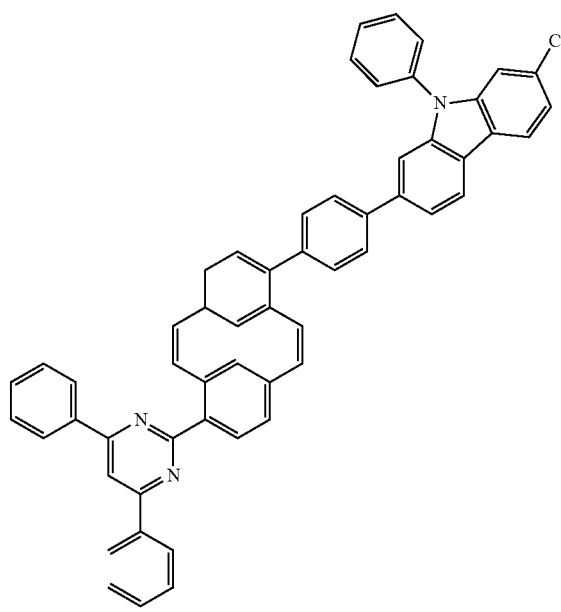
54
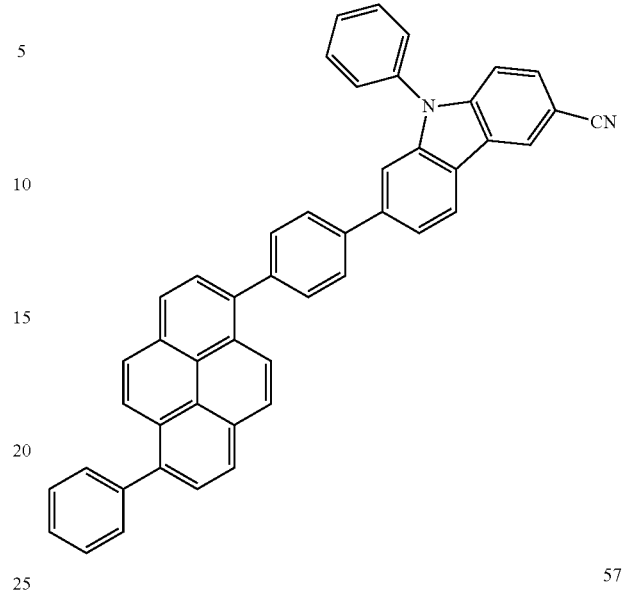
56
57
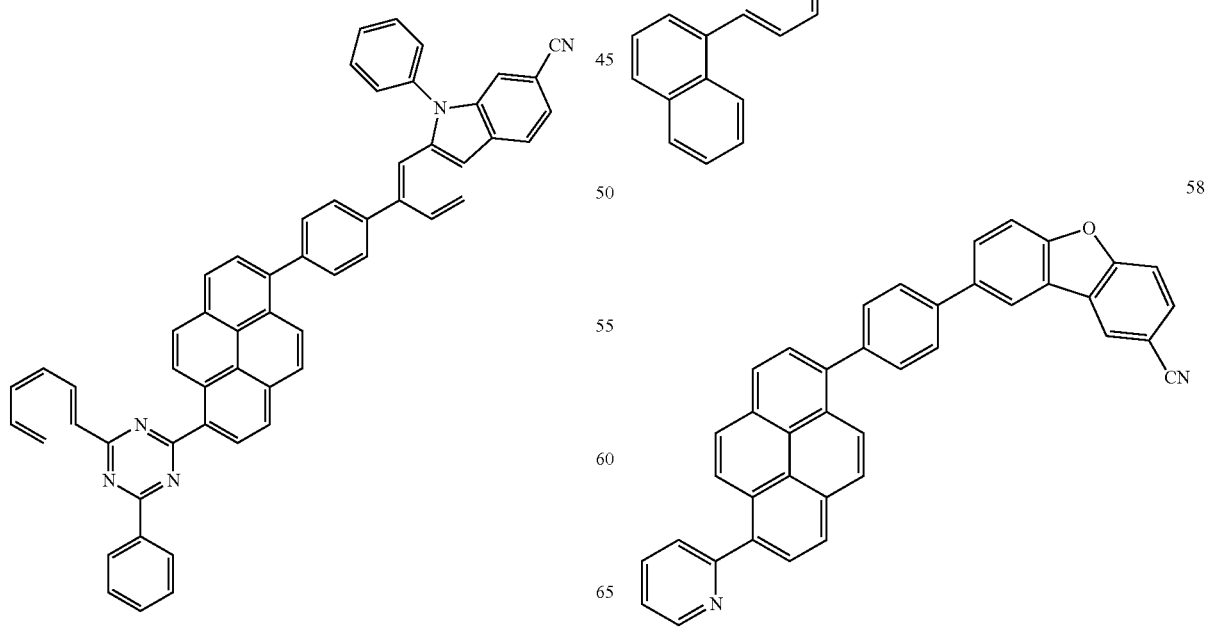
55
58

-continued
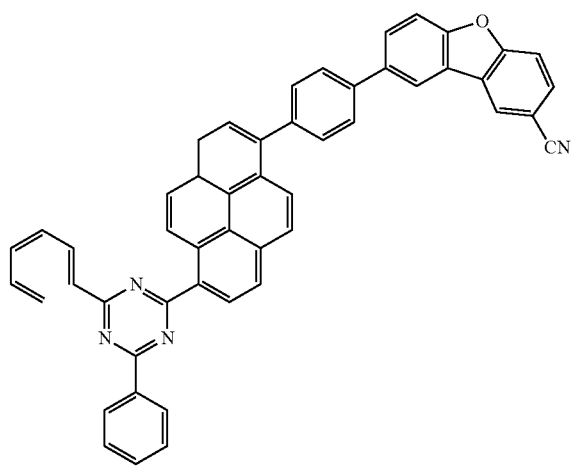
59
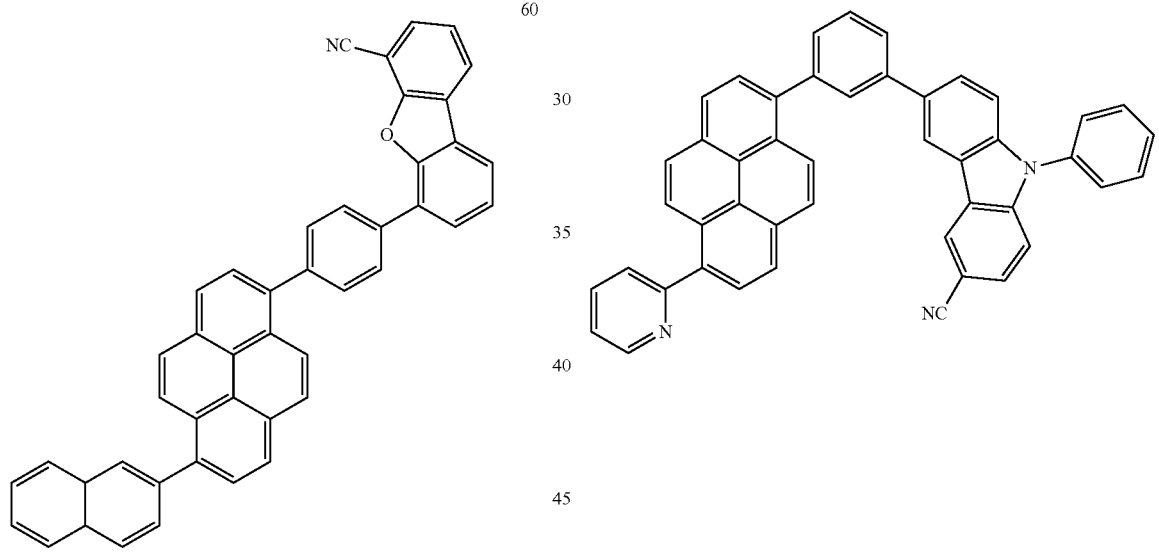
60
61
-continued
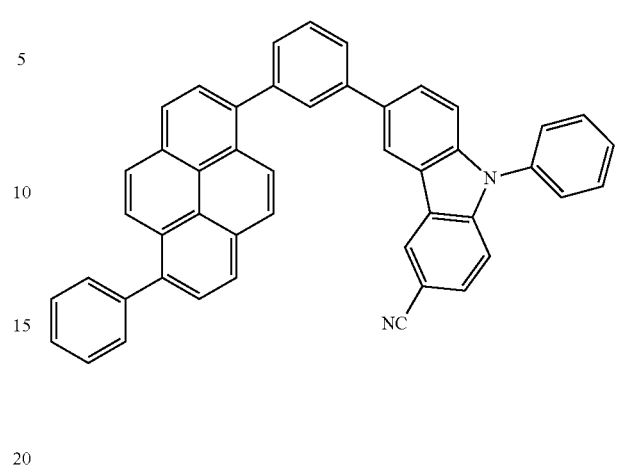
62
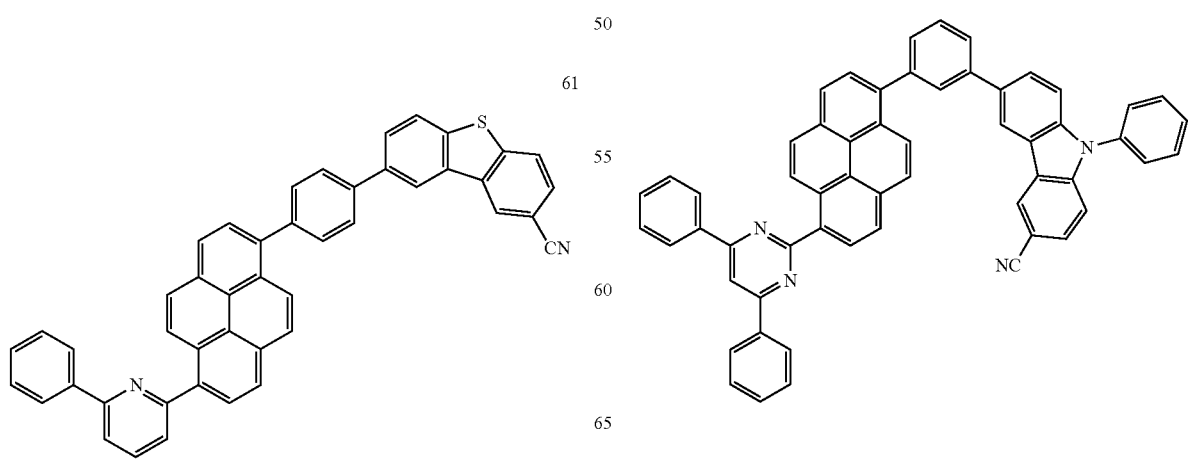
63
64

-continued
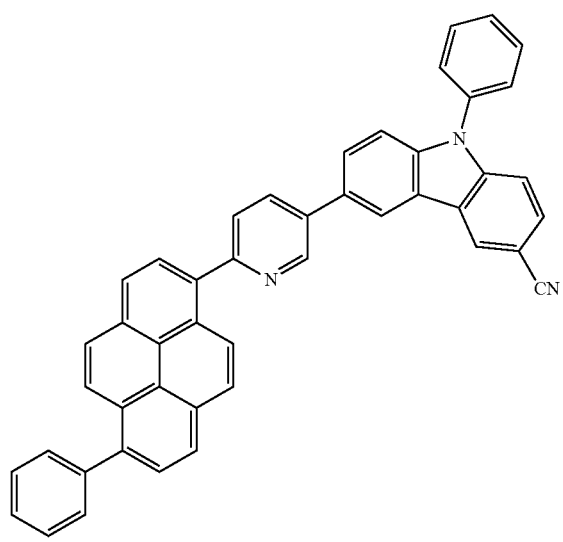
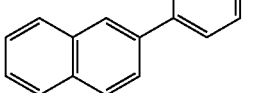
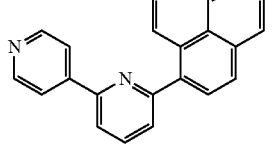
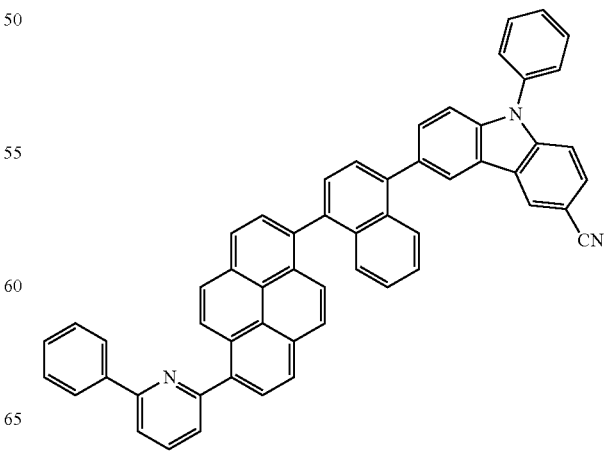

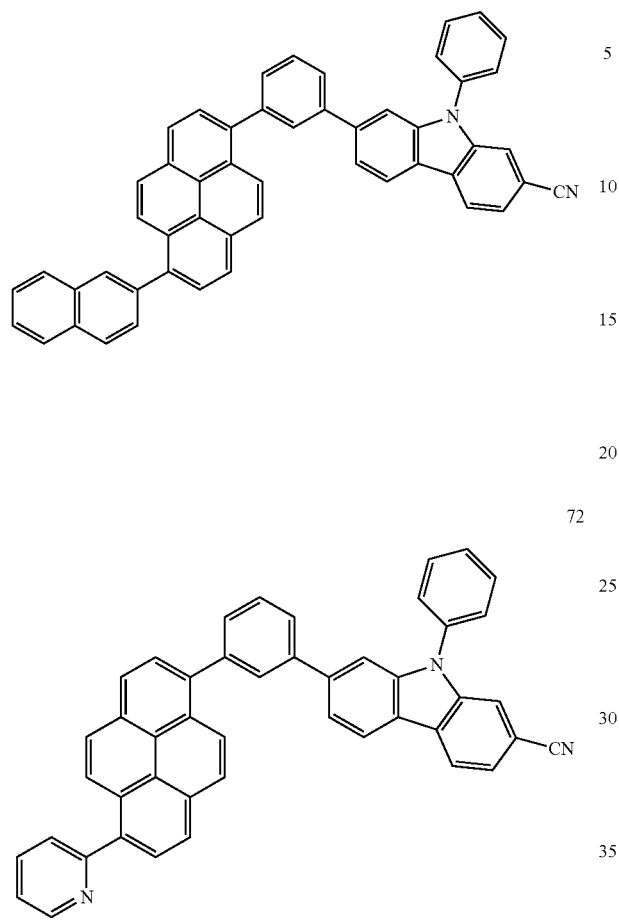
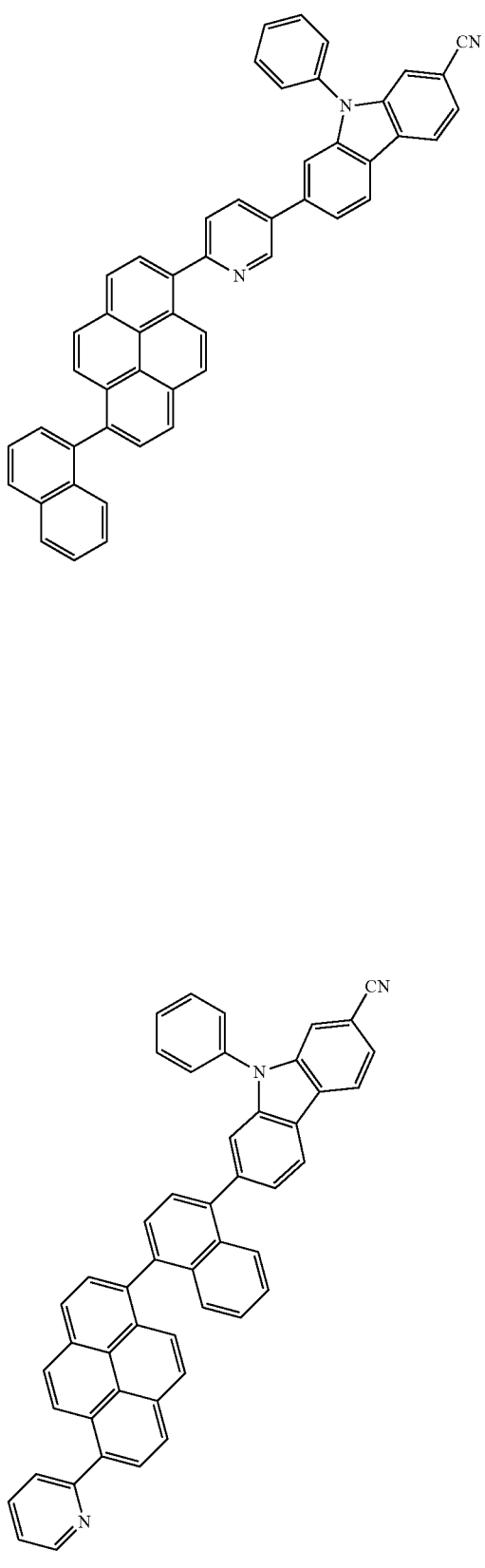

76
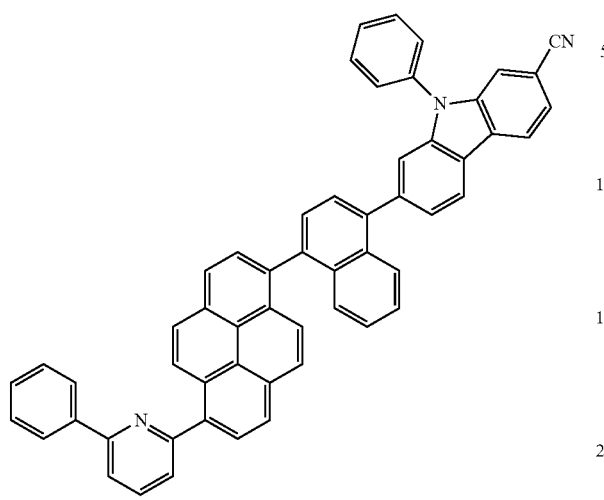
77
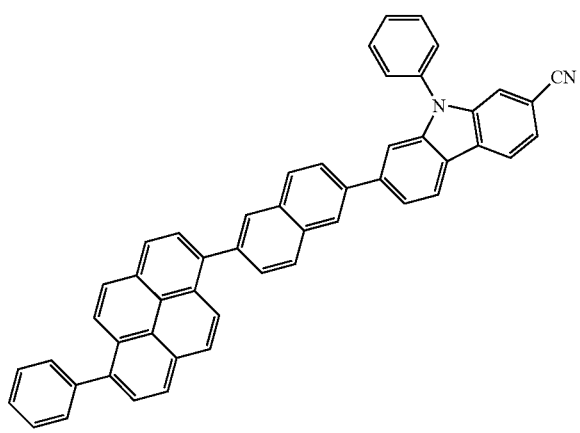
78
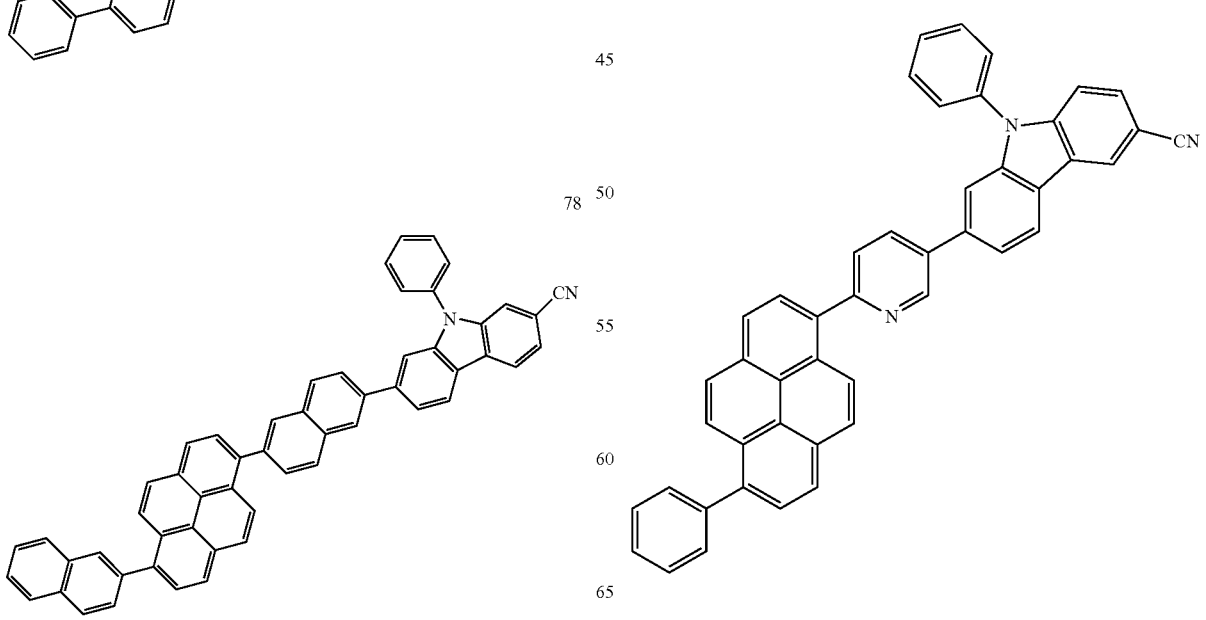
79
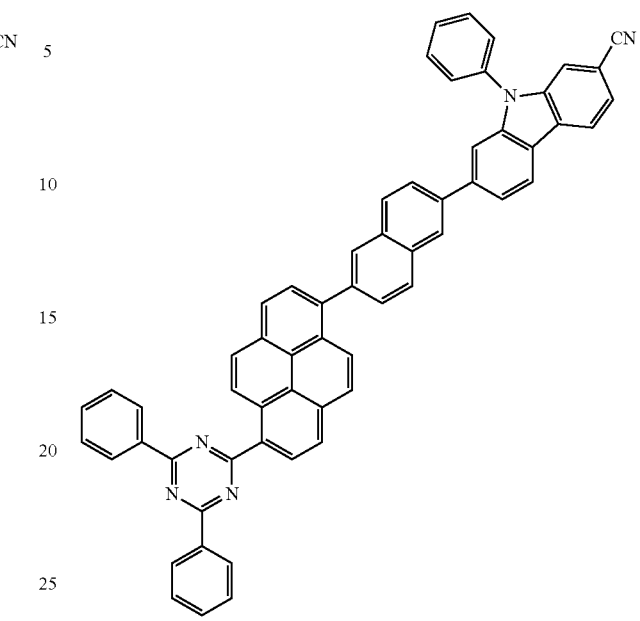
80

81
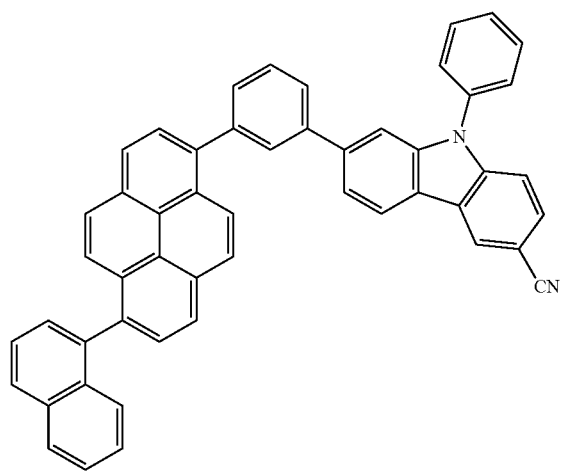
82
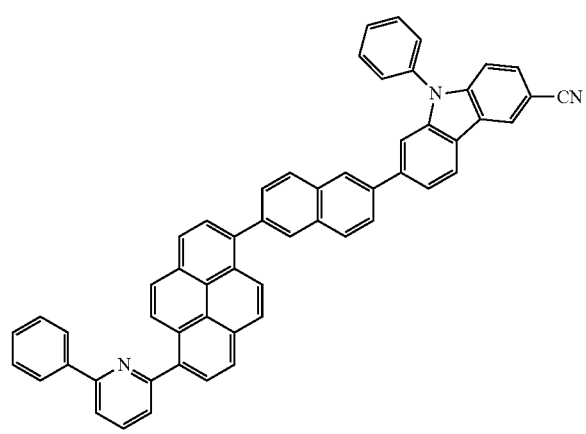
83
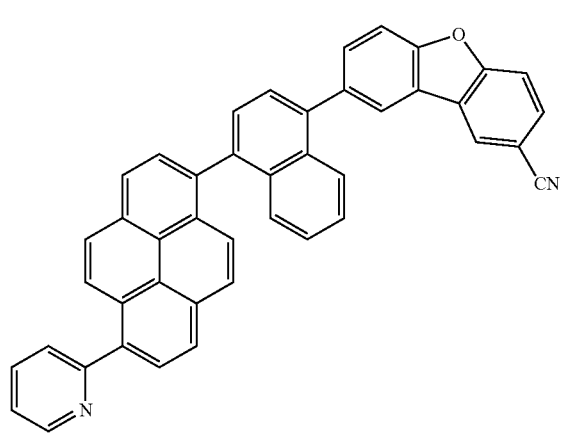
84
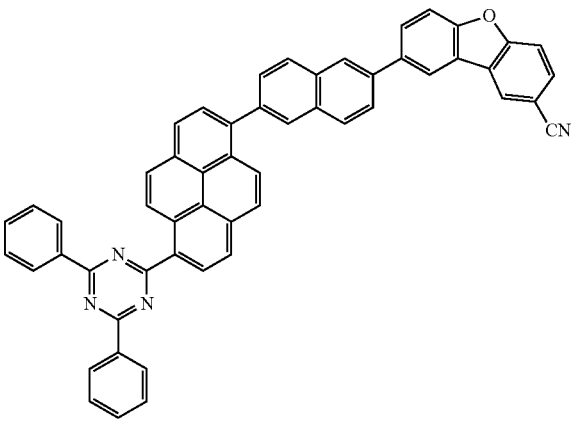
85
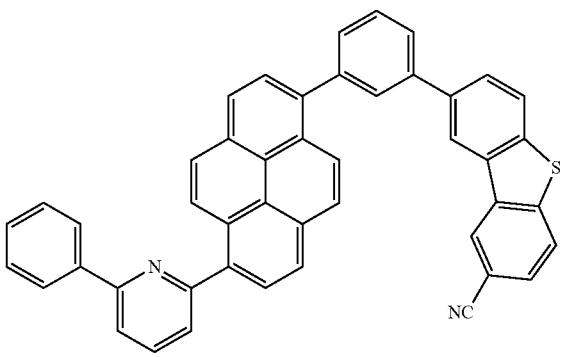
86

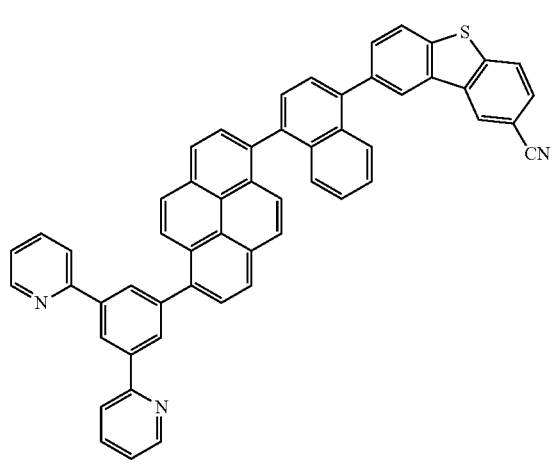
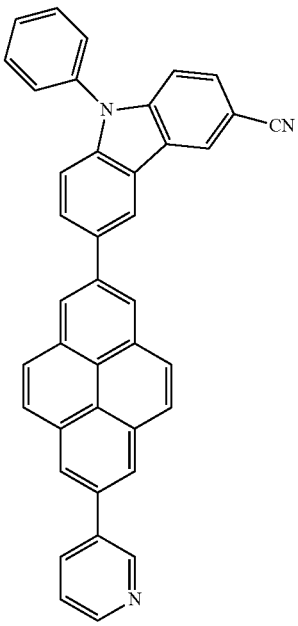

92
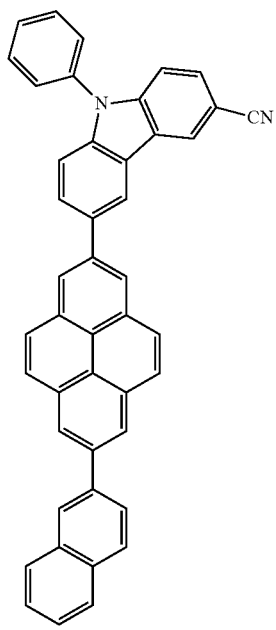
94
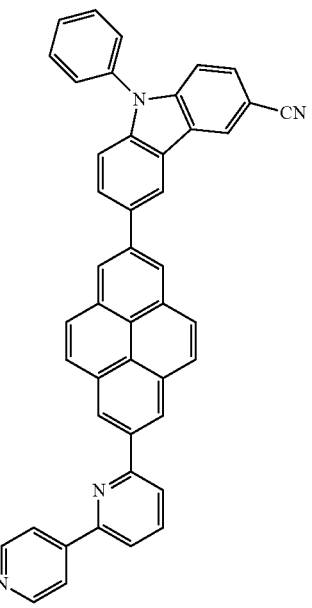
93
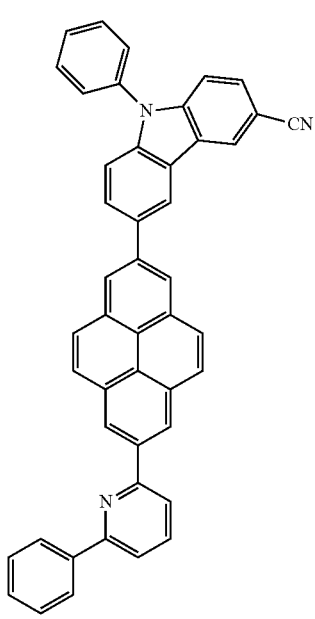
95
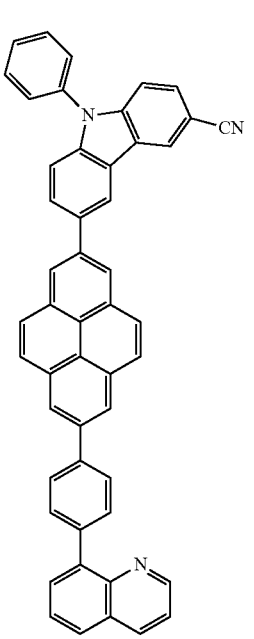

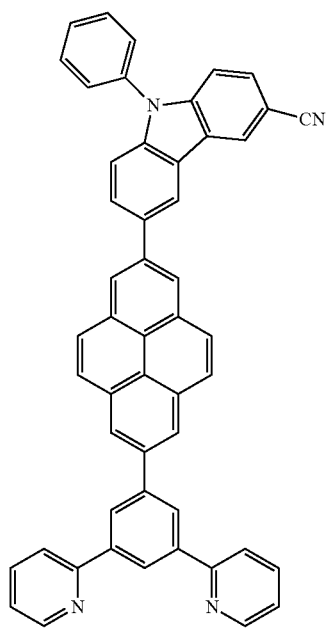
96
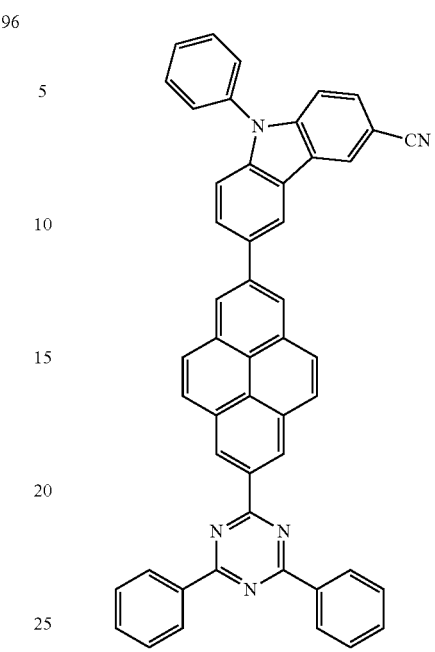
98
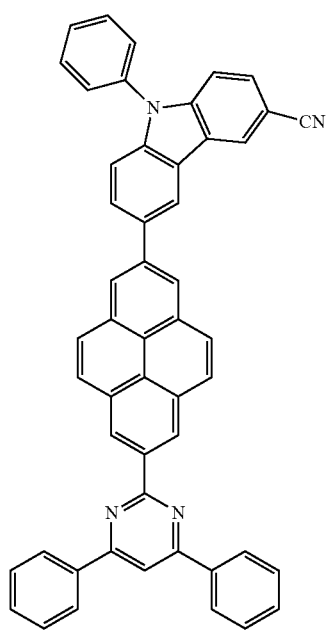
97
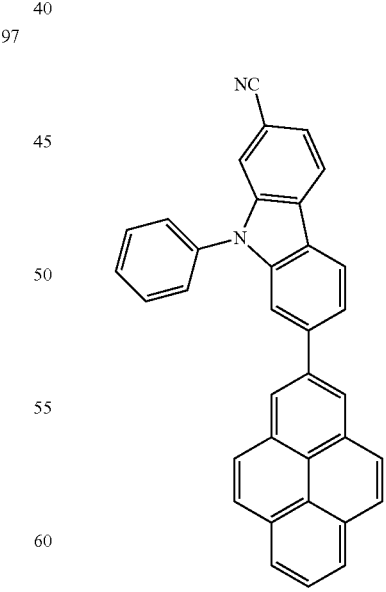
99

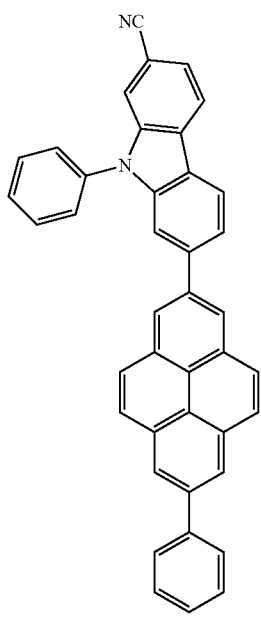
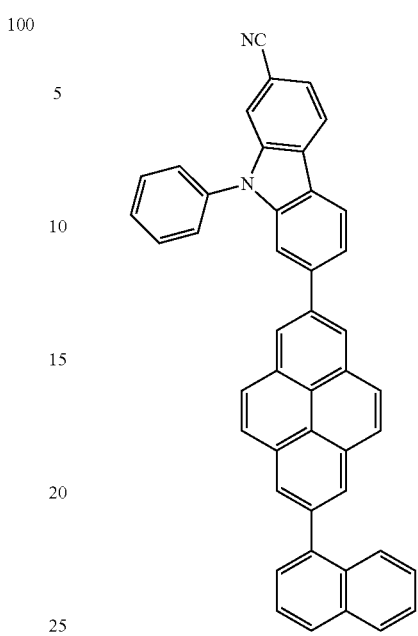

104
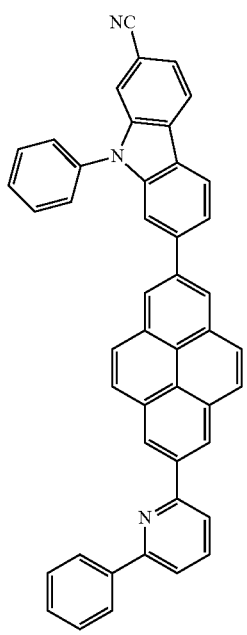
105
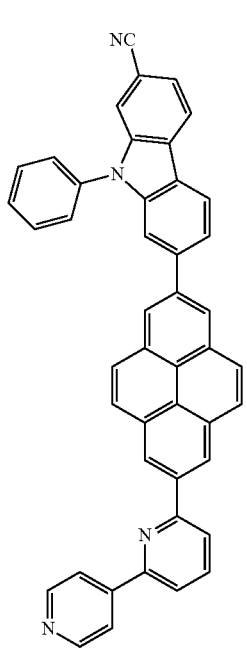
106
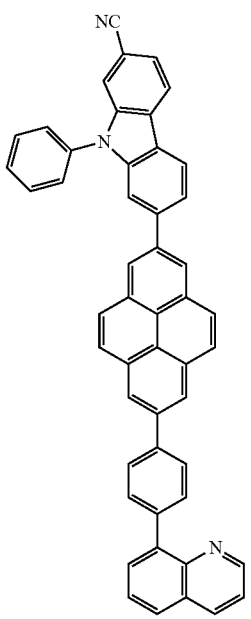
107
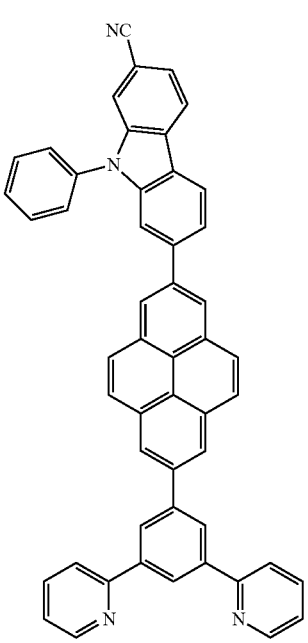

-continued
108 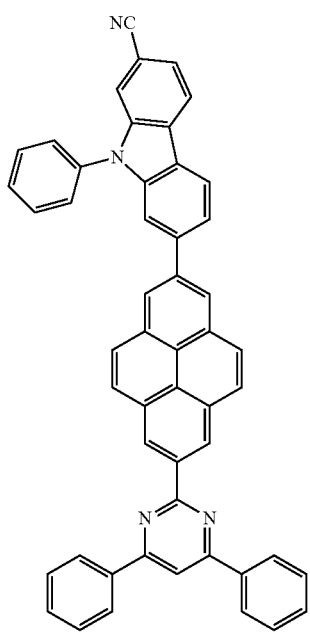
109 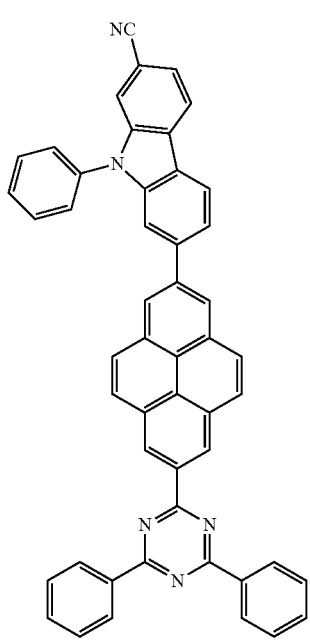
-continued
110 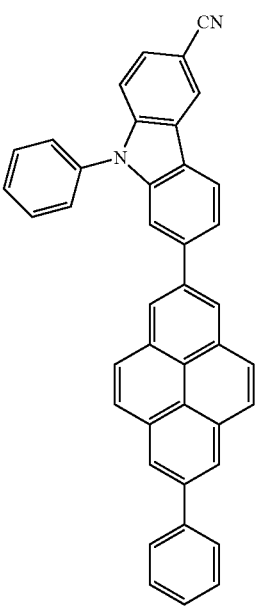
111 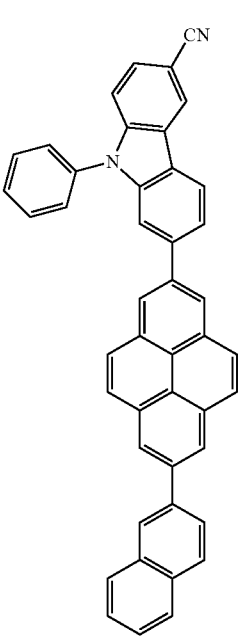

112
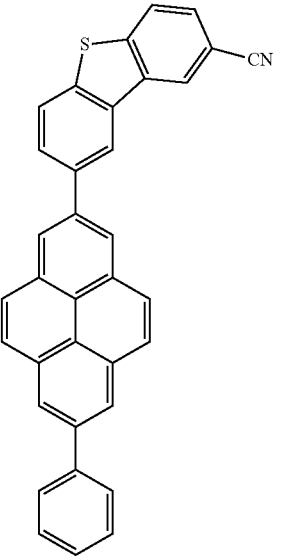
113
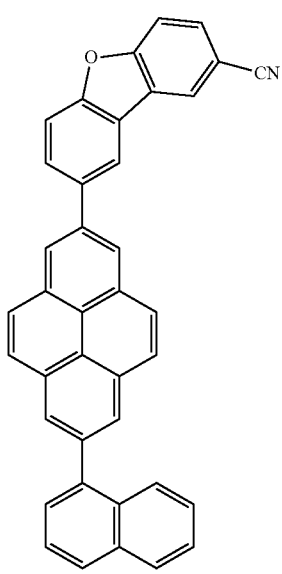
114
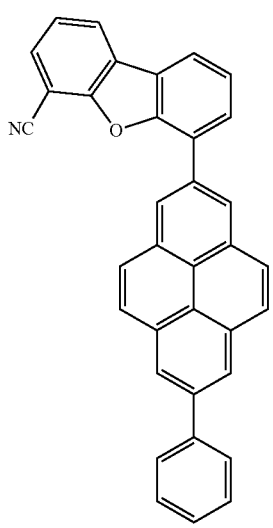
115
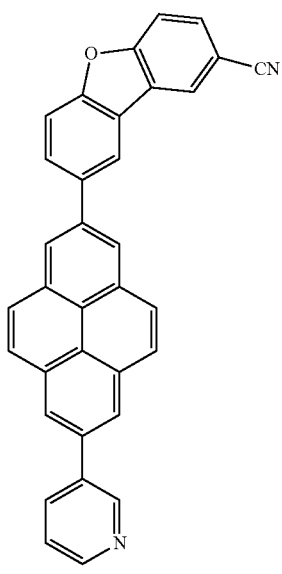
116
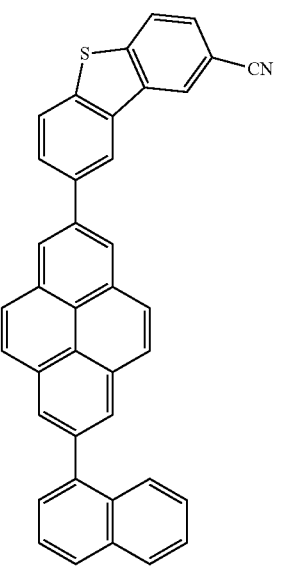

117
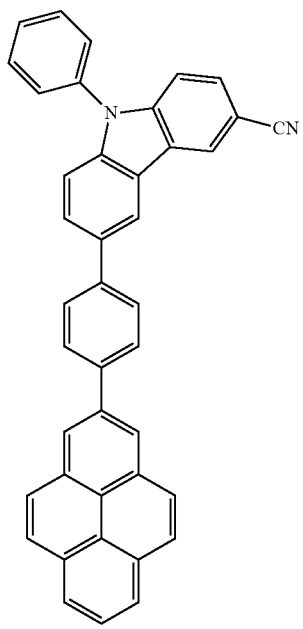
118
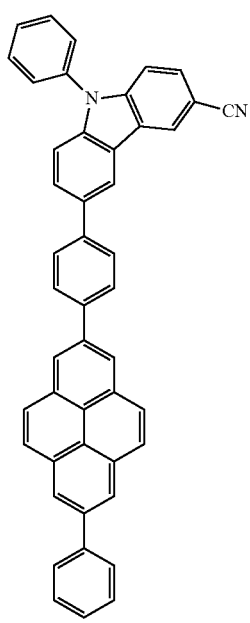
119
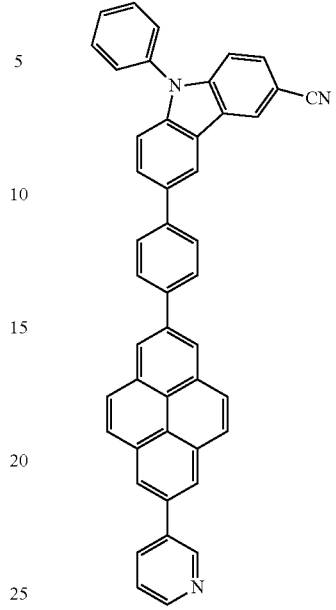
120
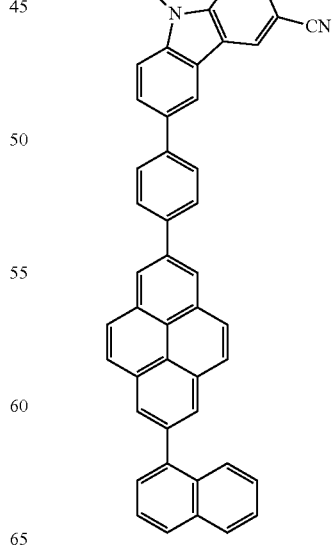

121
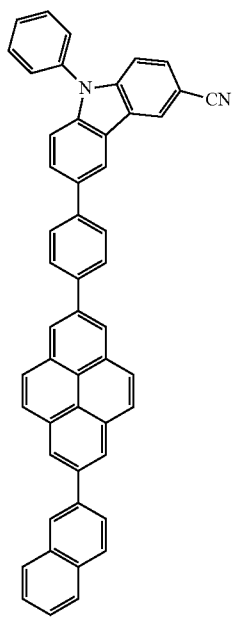
123
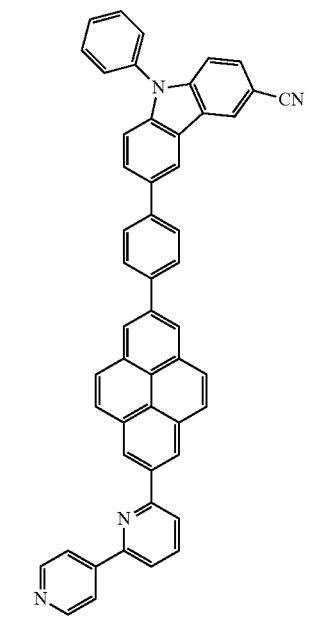
122
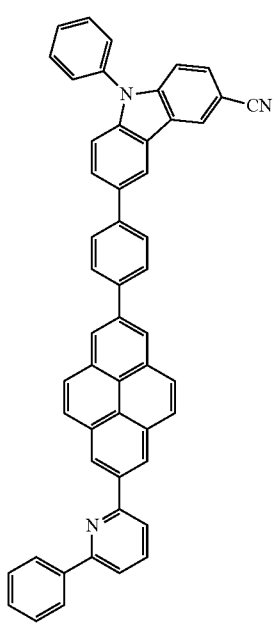
124
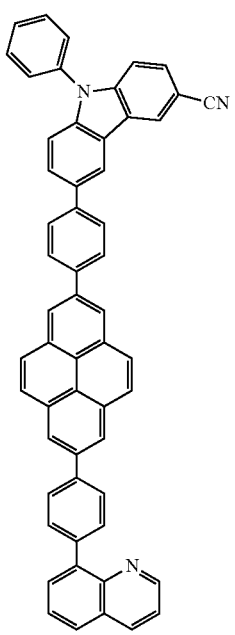

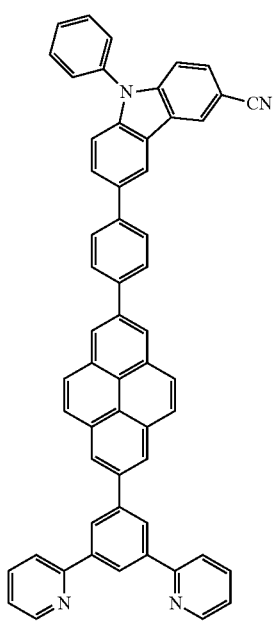
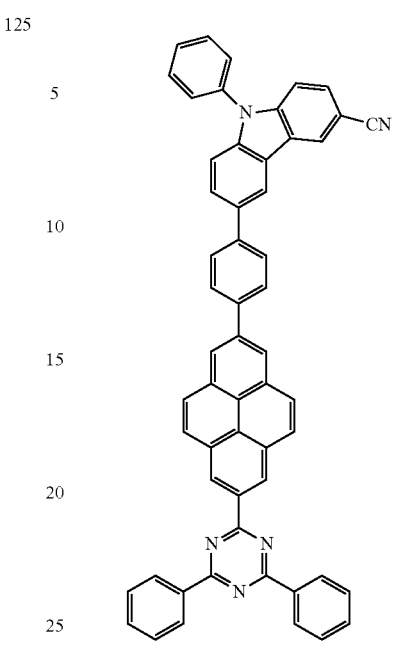

-continued
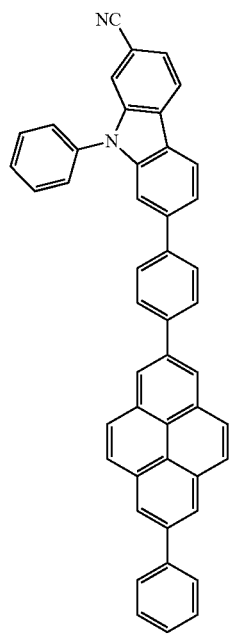
129
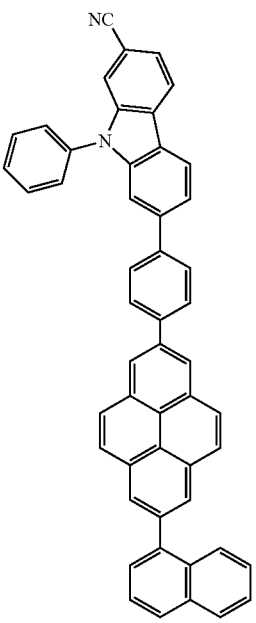
131
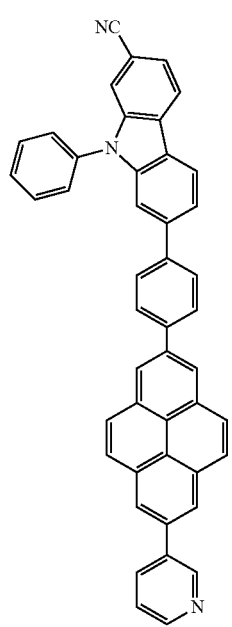
130
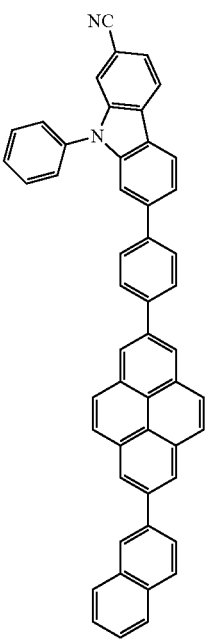
132

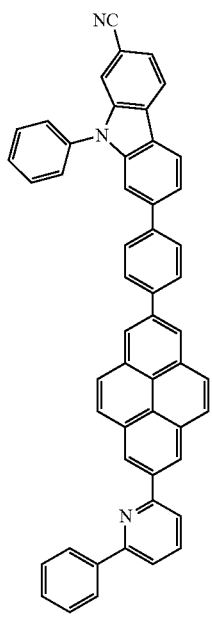
133
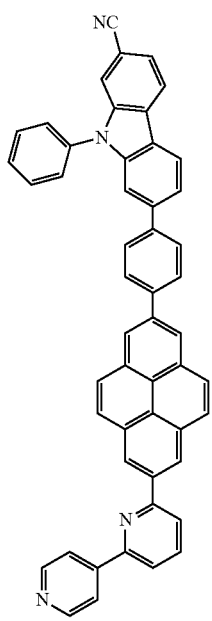
134
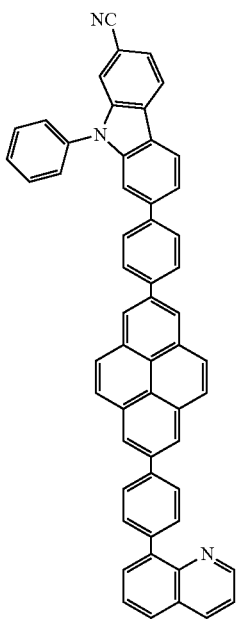
135
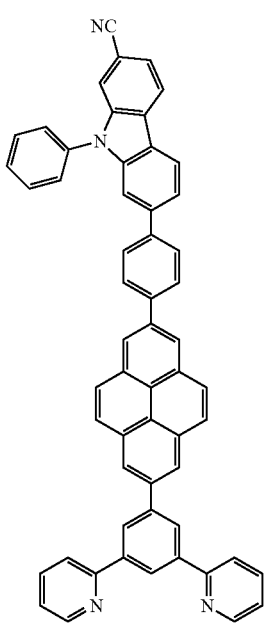
136

137
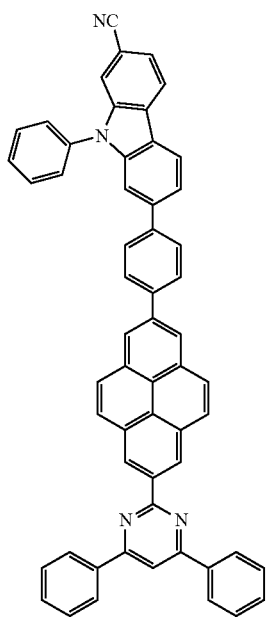
138
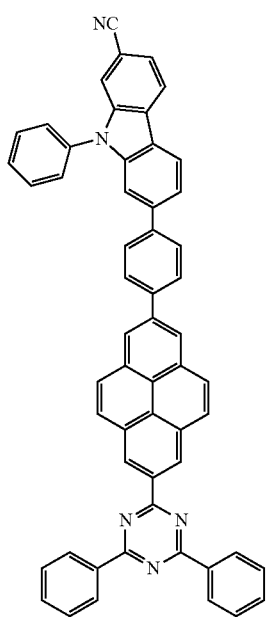
139
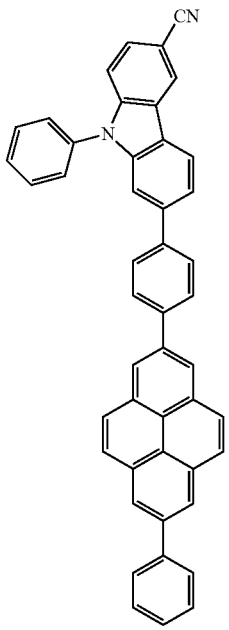
140
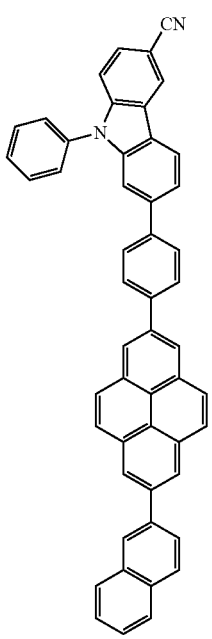

141 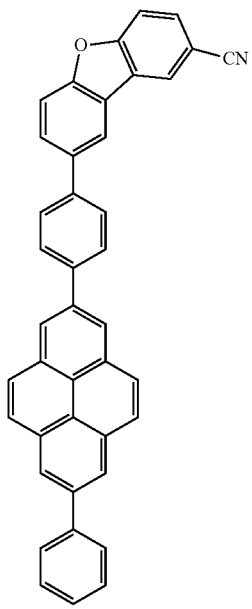
142 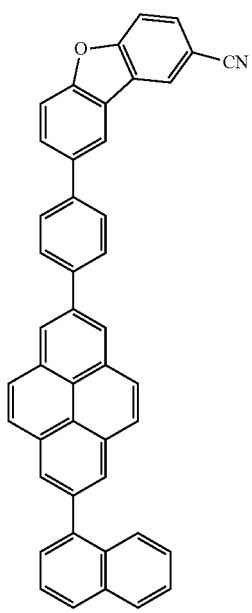
143 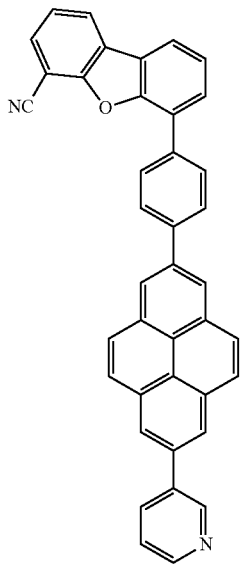
144 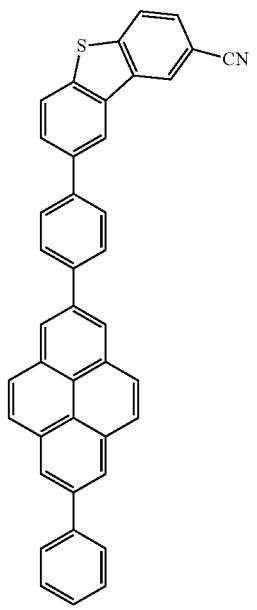

89
-continued
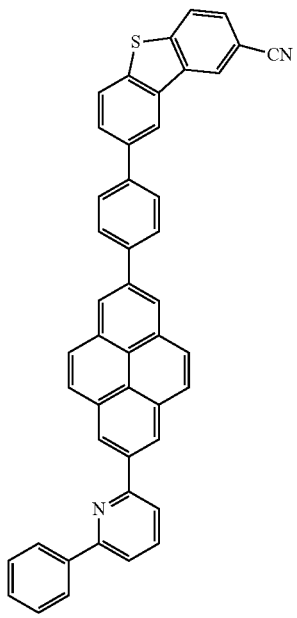
145
90
-continued
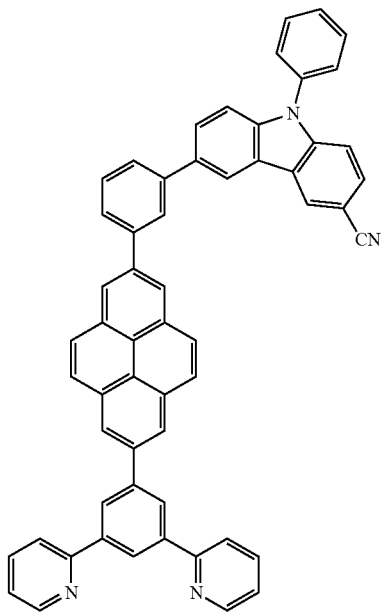
147
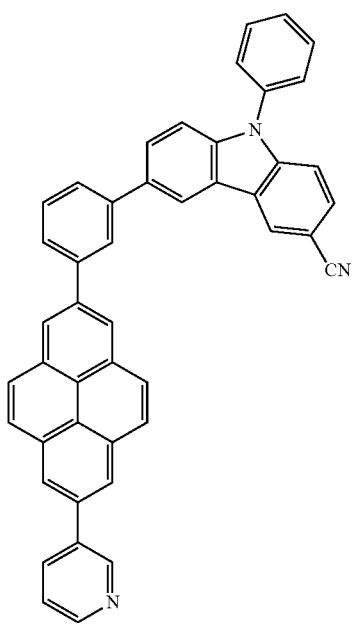
146
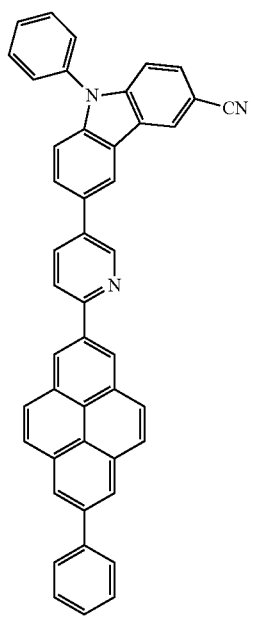
148

149
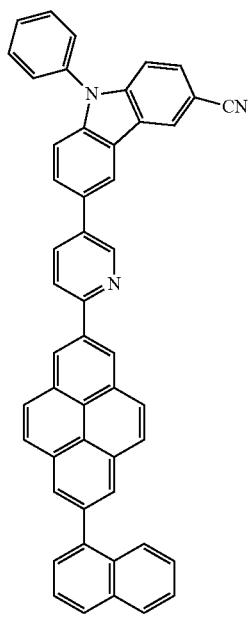
150
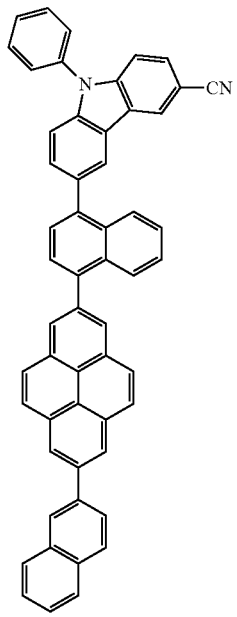
151
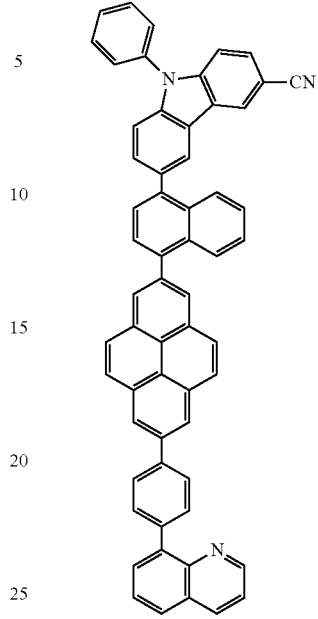
152
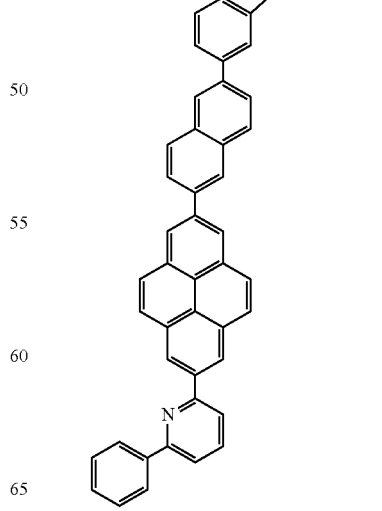

-continued
153
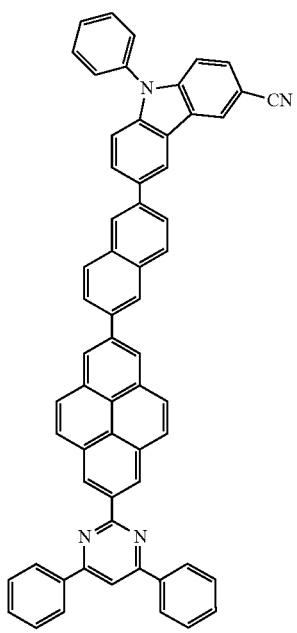
155
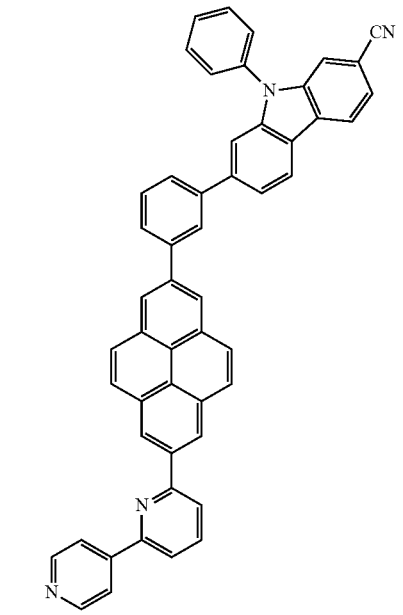
154
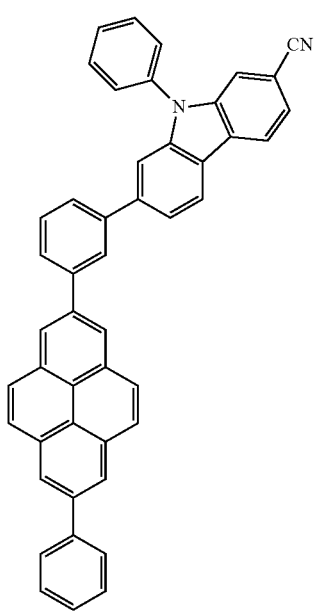
156
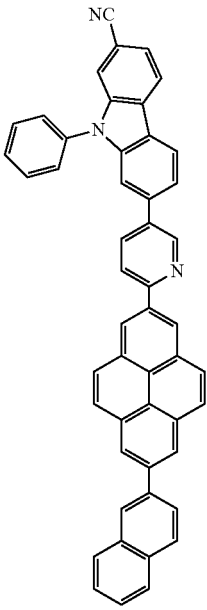

157
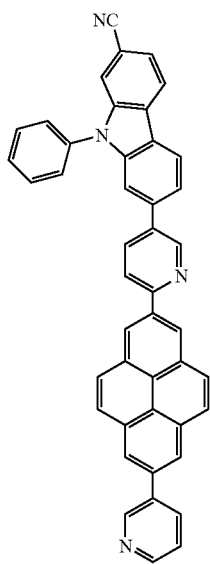
158
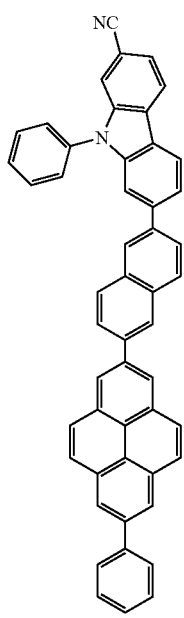
159
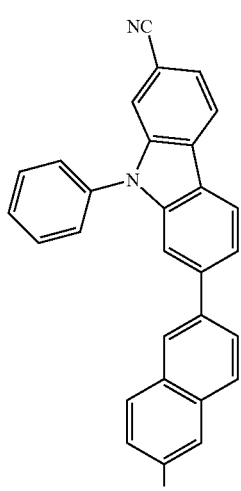
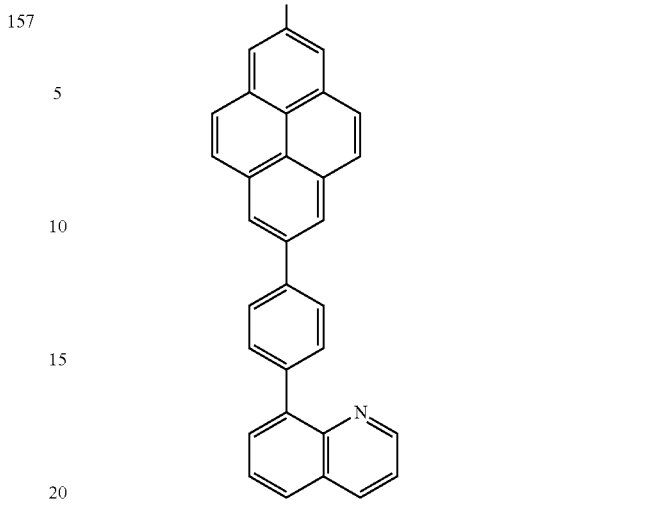
160
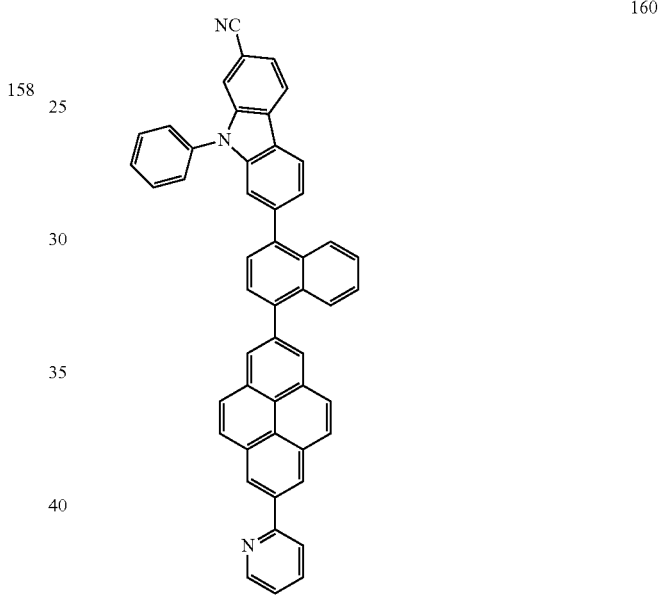
161
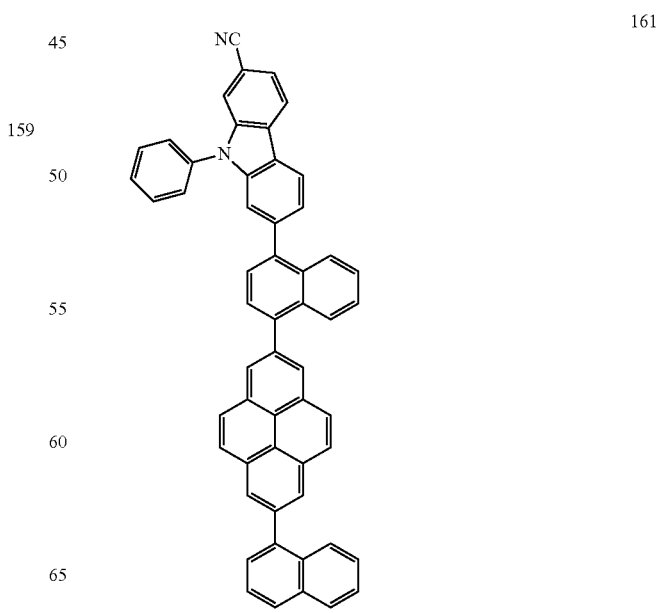

97
-continued
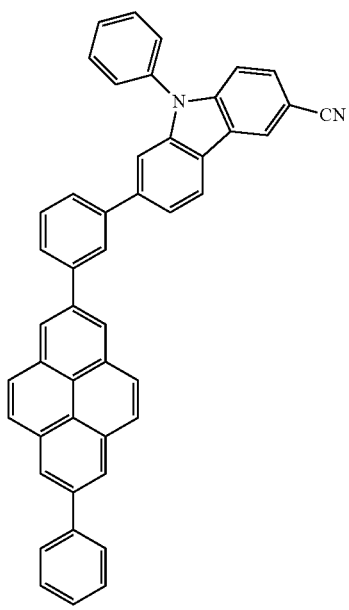
162
98
-continued
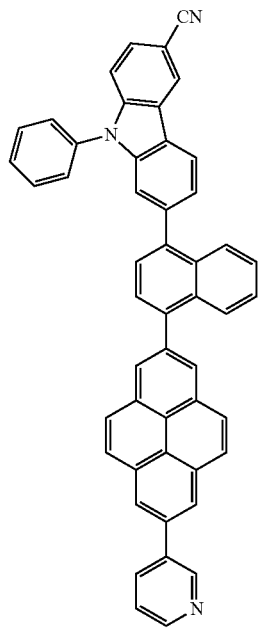
164
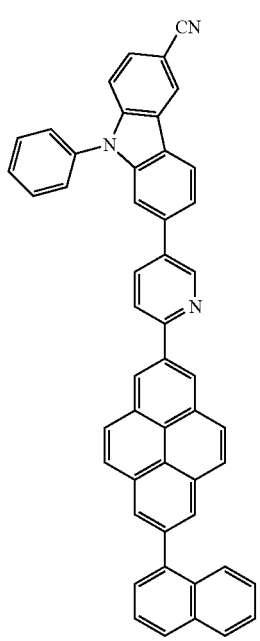
163
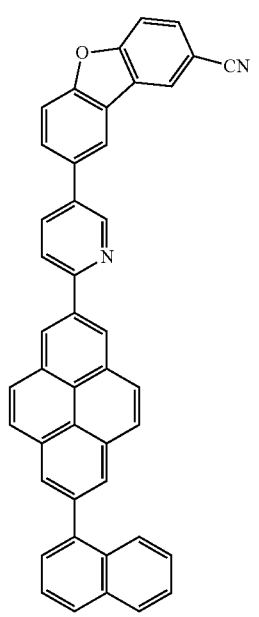
165

99
-continued
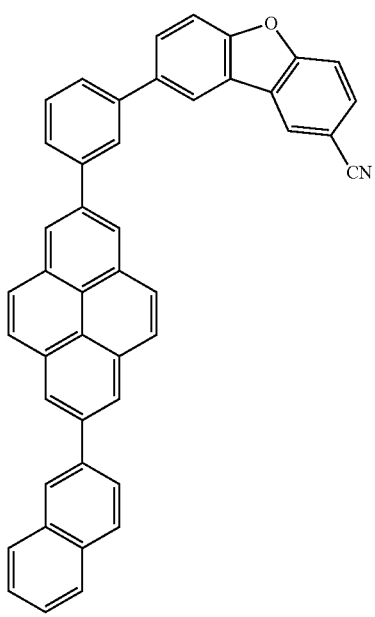
166
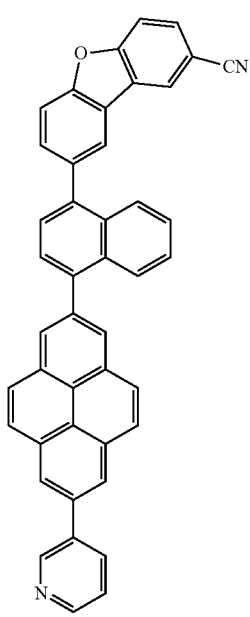
167
100
-continued
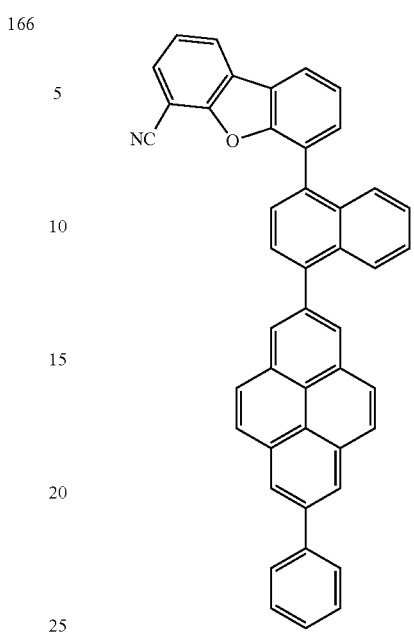
168
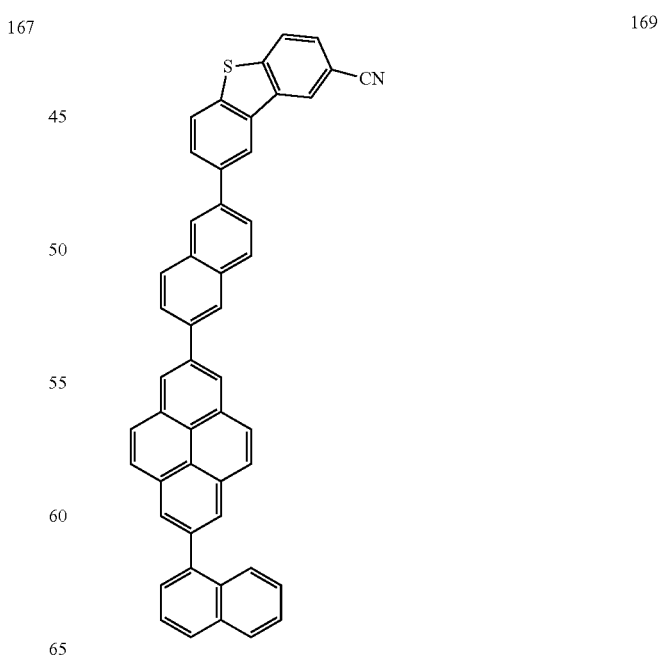
169

-continued

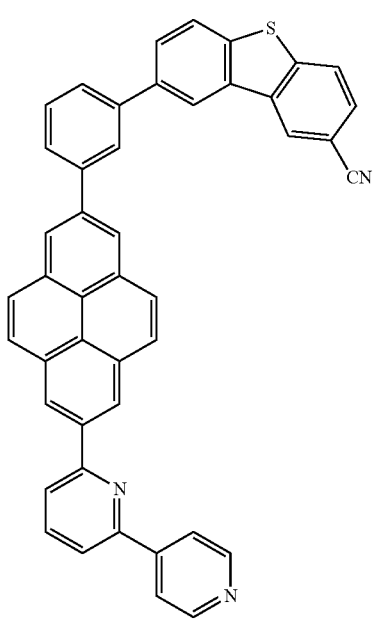

170

Formula 1 above necessarily includes one group represented by Formula 2' (see Formula 2' below) that includes a "carbazole-based ring" that is necessarily substituted with the "CN".

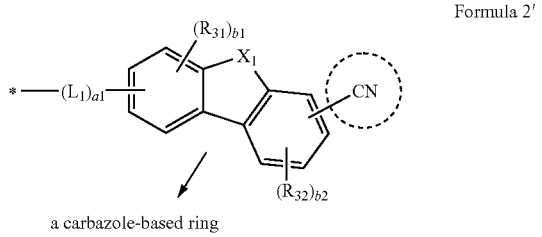

Formula 2' a carbazole-based ring

Also, because Formula 2' above includes the "carbazole-based ring" that is "necessarily" substituted with the "CN", an intermolecular bonding force may be enhanced.

Accordingly, an organic light-emitting device including the compound represented by Formula 1 above may have a long lifespan. Accordingly, an organic light-emitting device including the condensed-cyclic compound represented by Formula 1 may have low driving voltage, high efficiency, high brightness, and long lifespan.

The condensed-cyclic compound represented by Formula 1 may be synthesized by using a known organic synthesis method. A synthesis method of the condensed-cyclic compound may be obvious to one of ordinary skill in the art in view of the following embodiments.

The condensed-cyclic compound of Formula 1 may be used between a pair of electrodes of an organic light-emitting device. For example, the condensed-cyclic compound may be included in an electron transport region. For example, in an electron transport layer (ETL).

Accordingly, an organic light-emitting device according to an embodiment of the present invention may includes: a first electrode; a second electrode facing the first electrode; and an organic layer disposed between the first and second electrodes comprising an emission layer, wherein the organic layer may include at least one condensed-cyclic compound represented by Formula 1 described above.

The expression "(an organic layer) may include at least one condensed-cyclic compound" used herein includes a case in which "(an organic layer) includes one condensed-cyclic compound of Formula 1 and a case in which (an organic layer) includes two or more different condensed-cyclic compounds of Formula 1".

For example, the organic layer may include, as the condensed-cyclic compound, only Compound 1. In this regard, Compound 1 may exist in an electron transport layer of the organic light-emitting device.

In another embodiment of the present invention, the organic layer may include, as the condensed-cyclic compound, Compound 1 and Compound 2. In this regard, Compound 1 and Compound 2 may exist in the same layer (for example, Compound 1 and Compound 2 may both exist in an electron transport layer), or different layers (for example, Compound 1 may exist in an emission layer and Compound 2 may exist in an electron transport layer).

The organic layer may include i) a hole transport region disposed between the first electrode and the emission layer comprising at least one of a hole injection layer, a hole transport layer, a buffer layer, and an electron blocking layer, and ii) an electron transport region disposed between the emission layer and the second electrode comprising at least one of a hole blocking layer, an electron transport layer, and an electron injection layer.

The electron transport region may include the condensed-cyclic compound represented by Formula 1. For example, the electron transport region may include an electron transport layer including the condensed-cyclic compound represented by Formula 1.

The expression "organic layer" used herein refers to a single layer and/or a plurality of layers disposed between the first and second electrodes of an organic light-emitting device. A material of the "organic layer" is not limited to an organic material.

The FIGURE is a schematic view of an organic light-emitting device 10 according to an embodiment of the present invention. The organic light-emitting device 10 includes a first electrode 110, an organic layer 150, and a second electrode 190.

Hereinafter, the structure of an organic light-emitting device according to an embodiment of the present invention and a method of manufacturing an organic light-emitting device according to an embodiment of the present invention, will be described in connection with the FIGURE.

In the FIGURE, a substrate may be additionally disposed under the first electrode 110 or above the second electrode 190. The substrate may be a glass substrate or a transparent plastic substrate, each with excellent mechanical strength, thermal stability, transparency, surface smoothness, ease of handling, and water repellency.

The first electrode 110 may be formed by depositing or sputtering a material for forming the first electrode 110 on the substrate. When the first electrode 110 is an anode, the material for the first electrode 110 may be selected from materials with a high work function for an easy hole injection. The first electrode 110 may be a reflective electrode or a transmissive electrode. The material for the first electrode 110 may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, a material for forming the first electrode 110 may include at least one of magnesium (Mg), aluminum (Al), aluminum-lithium (Al—Li), calcium (Ca), magnesium-indium (Mg—In), and magnesium-silver (Mg—Ag).

The first electrode 110 may have a single-layer structure, or a multi-layer structure including two or more layers. For example, the first electrode 110 may have a three-layered structure of ITO/Ag/ITO, but the structure of the first electrode 120 is not limited thereto.

The organic layer 150 may be disposed on the first electrode 110. The organic layer 150 may include an emission layer.

The organic layer 150 may further include a hole transport region disposed between the first electrode 110 and the emission layer, and an electron transport region disposed between the emission layer and the second electrode 190.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but the hole transport region and the electron transport region are not limited thereto.

The hole transport region may have a single-layered structure formed of a single material, a single-layered structure formed of different materials, or a multi-layered structure having a plurality of layers formed of different materials.

For example, the hole transport region may have a single-layered structure formed of different materials, or a structure of HIL/HTL, a structure of HIL/HTL/buffer layer, a structure of HIL/buffer layer, a structure of HTL/buffer layer, or a structure of HIL/HTL/EBL, wherein layers of each structure are sequentially stacked from the first electrode 110 in this stated order, but are not limited thereto.

When the hole transport region includes a HIL, the HIL may be formed on the first electrode 110 by using various methods, such as vacuum deposition, spin coating, casting, a Langmuir-Blodgett (LB) method, ink-jet printing, laser-printing, or laser-induced thermal imaging.

When a HIL is formed by vacuum deposition, for example, the vacuum deposition may be performed at a deposition temperature of about 100° C. to about 500° C., at a vacuum degree of about $10^{-8}$ to about $10^{-3}$ torr, and at a deposition rate of about 0.01 to about 100 Å/sec in consideration of a compound for a HIL to be deposited, and the structure of a HIL to be formed.

When a HIL is formed by spin coating, the spin coating may be performed at a coating rate of about 2000 rpm to about 5000 rpm, and at a temperature of about 80° C. to 200° C. in consideration of a compound for a hole injection layer to be deposited, and the structure of a HIL to be formed.

When the hole transport region includes a HTL, the HTL may be formed on the first electrode 110 or the HIL by using various methods, such as vacuum deposition, spin coating, casting, an LB method, ink-jet printing, laser-printing, or laser-induced thermal imaging.

When the HTL is formed by vacuum deposition or spin coating, deposition and coating conditions for the HTL may be determined by referring to the deposition and coating conditions for the HIL.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

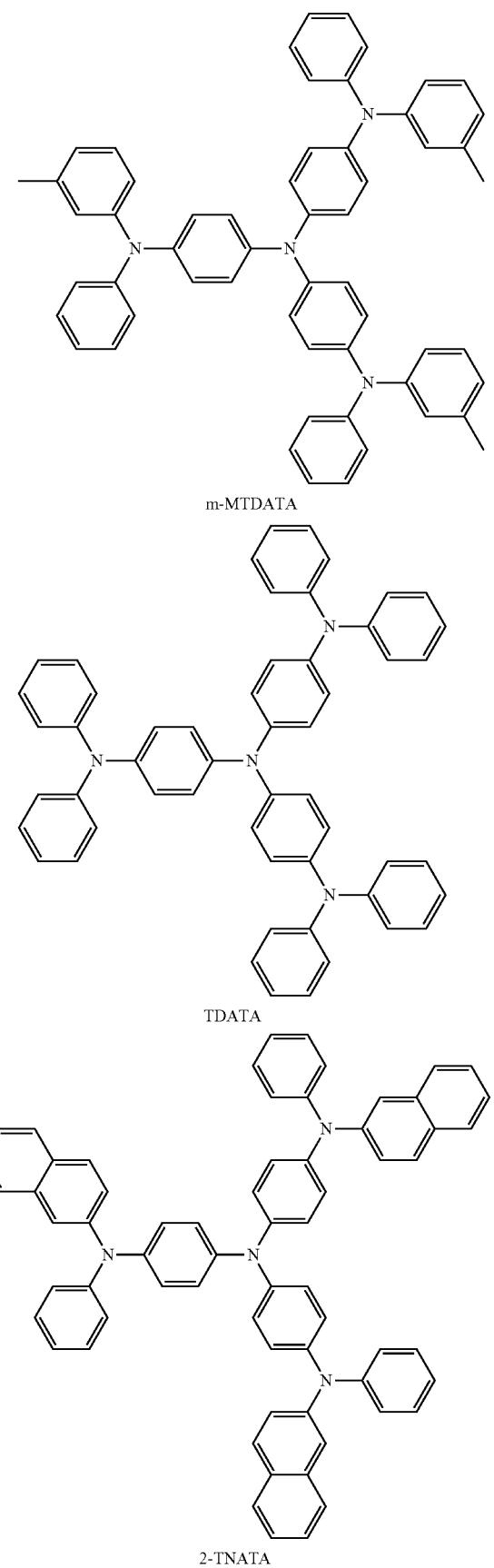

m-MTDATA

TDATA

2-TNATA

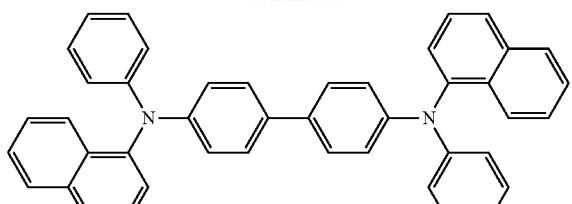

NPB

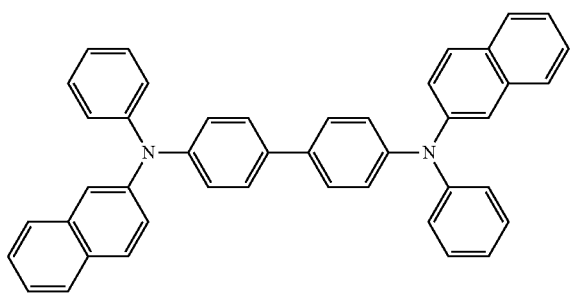

β-NPB

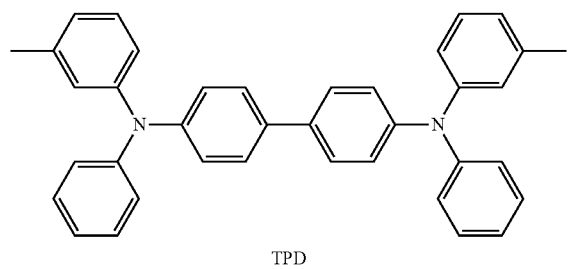

TPD

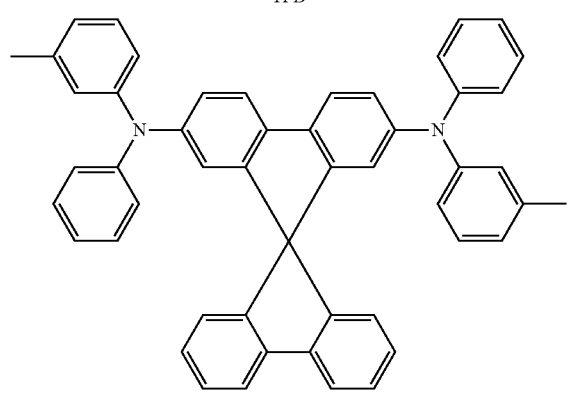

Spiro-TPD

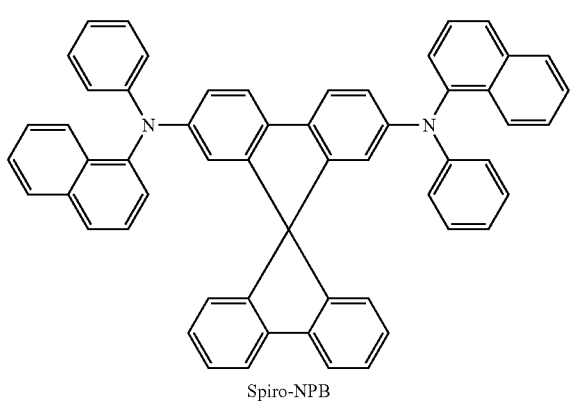

Spiro-NPB

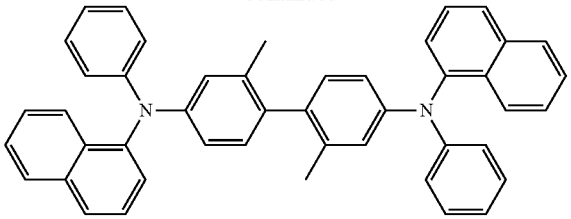

α-NPB

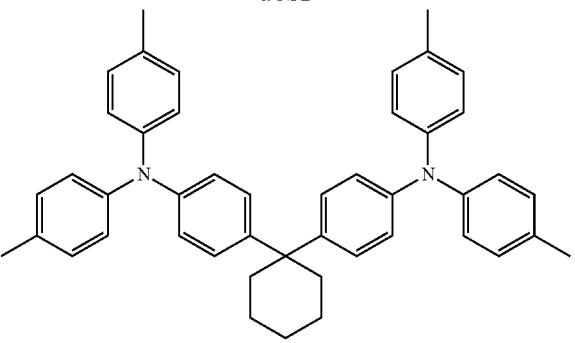

TAPC

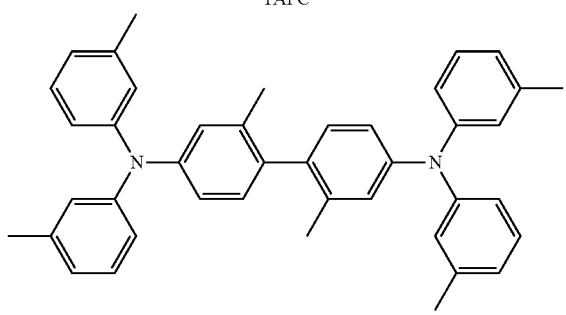

HMTPD

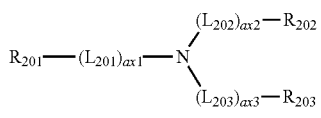

Formula 201

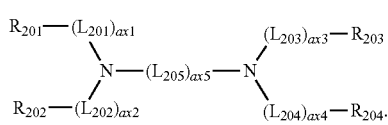

Formula 202

Wherein in Formulae 201 and 202, $L_{201}$ to $L_{205}$ may be understood by referring to the description provided herein in connection with $L_1$; xa1 to xa4 may be each independently selected from 0, 1, 2, and 3; xa5 may be selected from 1, 2, 3, 4, and 5; and $R_{201}$ to $R_{204}$ may be understood by referring to the description provided herein in connection with $R_{21}$.

In Formulae 201 and 202, $L_{201}$ to $L_{205}$ may be each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group; xa1 to xa4 may be each independently 0, 1, or 2; xa5 may be 1, 2, or 3; and $R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but they are not limited thereto.

The compound represented by Formula 201 may be represented by Formula 201A:

Formula 201A

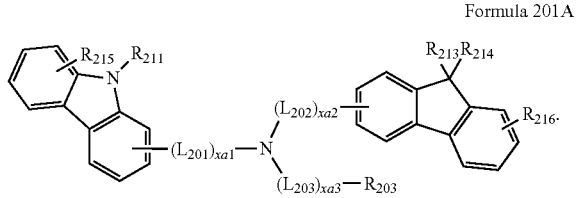

For example, the compound represented by Formula 201 may be represented by Formula 201A-1 below, but is not limited thereto:

Formula 201A-1

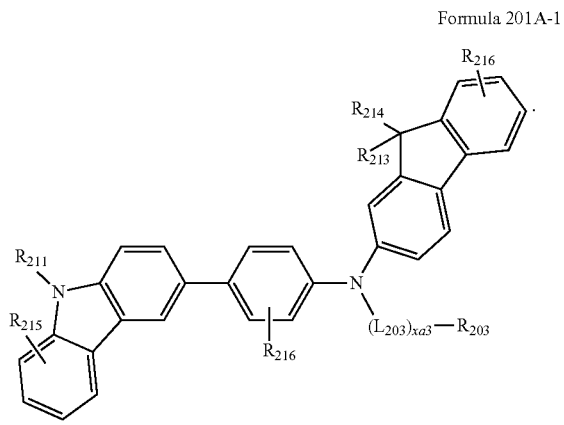

For example, the compound represented by Formula 202 may be represented by Formula 202A below, but is not limited thereto:

Formula 202A

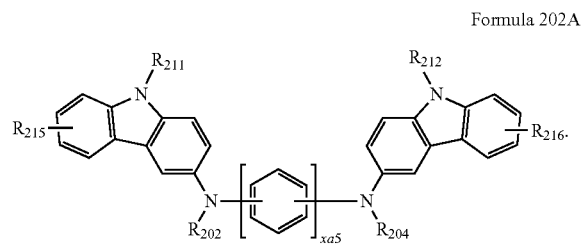

$L_{201}$ to $L_{203}$, xa1 to xa3, xa5, and $R_{202}$ to $R_{204}$ in Formulae 201A, 201A-1, and 202A are already described above, $R_{211}$ and $R_{212}$ may be understood by referring to the description provided in connection with $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, arylthio group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group.

For example, $L_{201}$ to $L_{203}$ in Formulae 201A, 201A-1, and 202A may be each independently selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenalenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; xa1 to xa3 may be each independently selected from 0 or 1; $R_{202}$ to $R_{204}$, $R_{211}$, and $R_{212}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; $R_{213}$ and $R_{214}$ may be each independently selected from a $C_1$-$C_{20}$ alkyl group and a $C_1$-$C_{20}$ alkoxy group; a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; xa5 may be 1 or 2.

$R_{213}$ and $R_{214}$ in Formulae 201A and 201A-1 may bind to each other to form a saturated or unsaturated ring.

The compound represented by Formula 201 and the compound represented by Formula 202 may include compounds HT1 to HT20 illustrated below, but are not limited thereto.

HT1

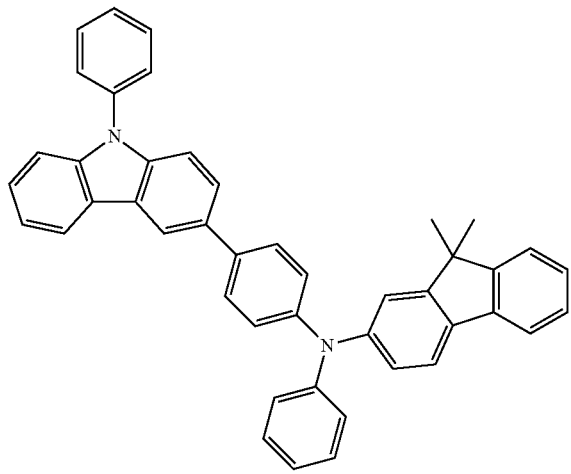

HT2

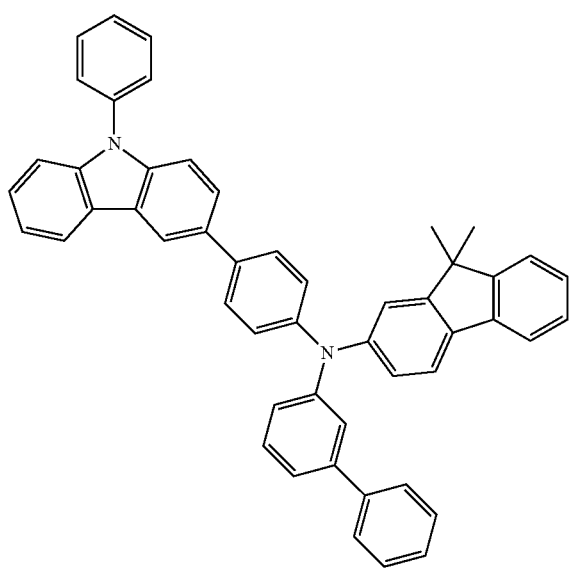

HT3

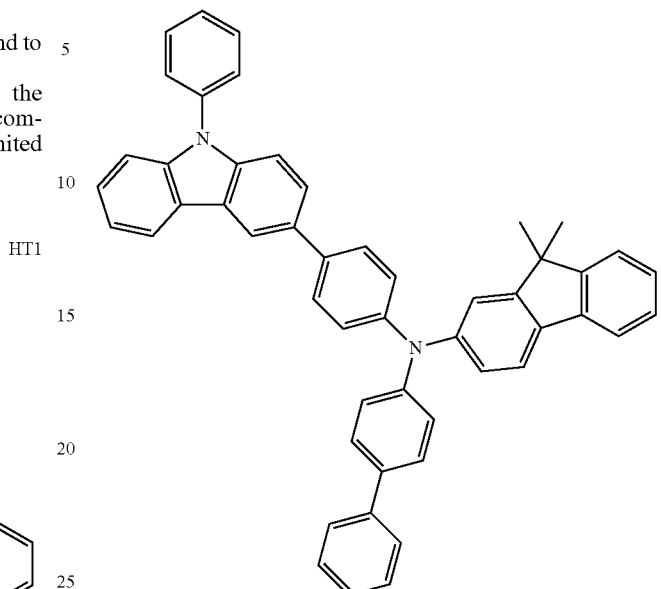

HT4

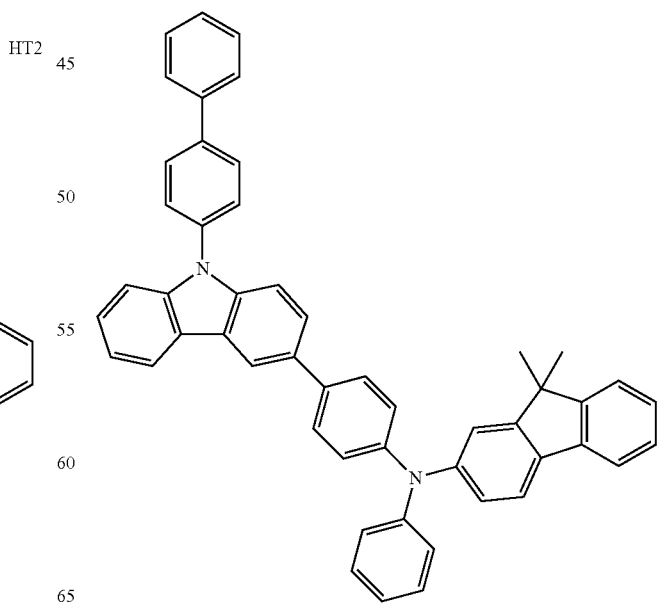

HT5
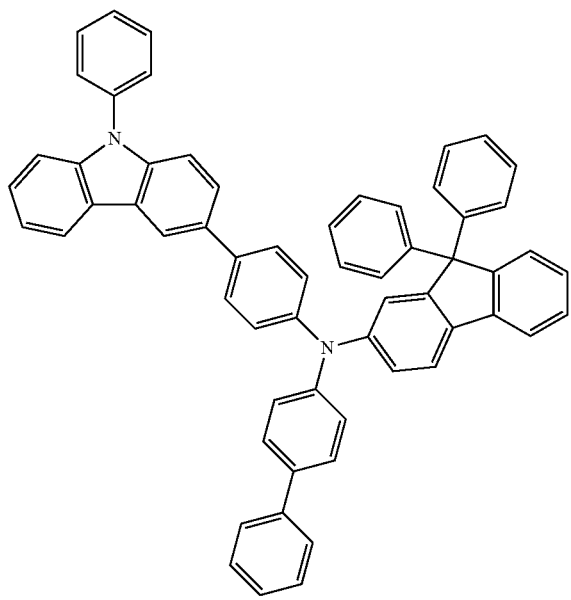
HT6
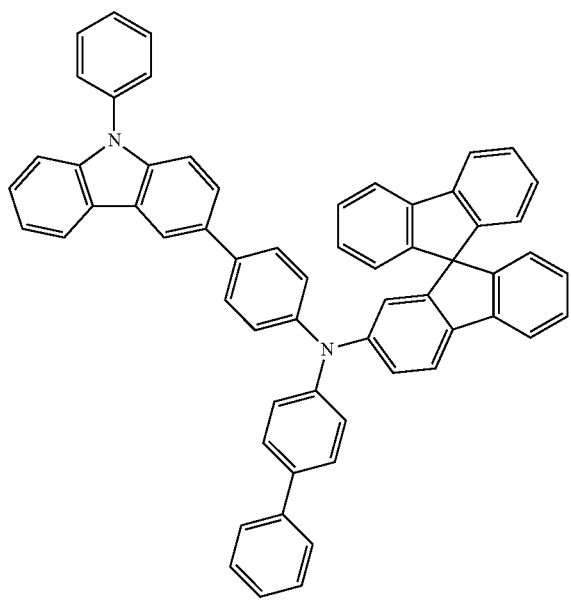
HT7
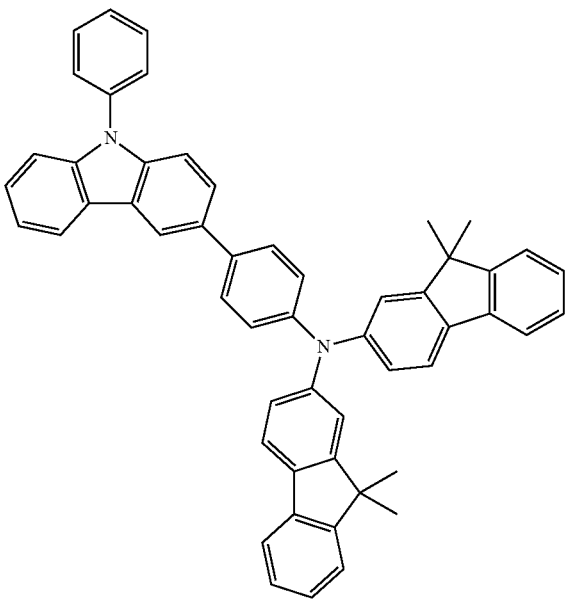
HT8
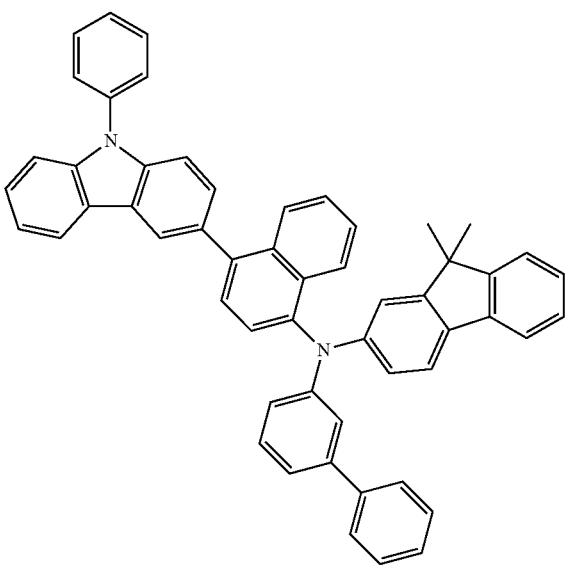

HT9
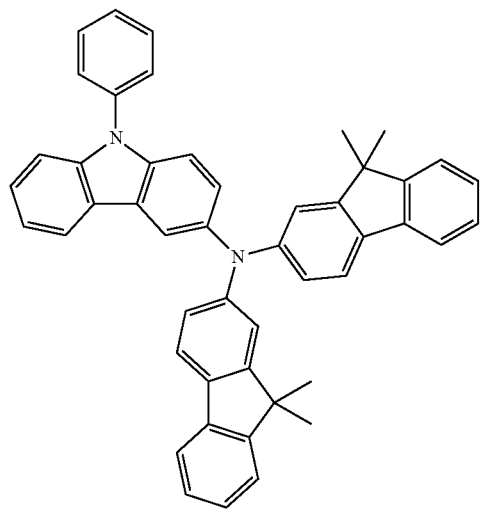
HT10
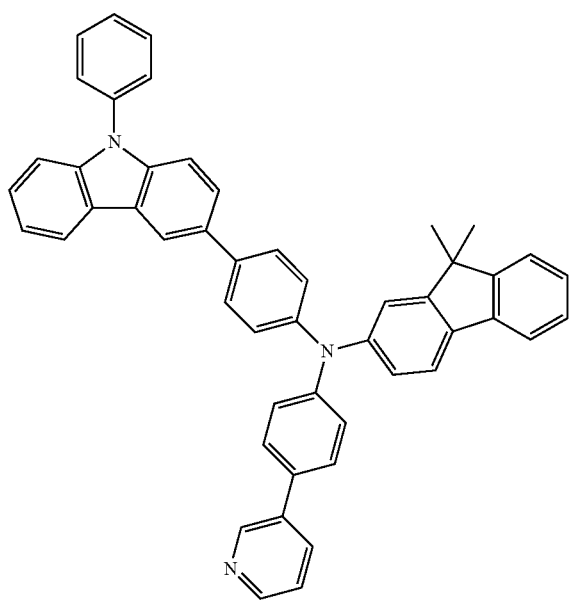
HT11
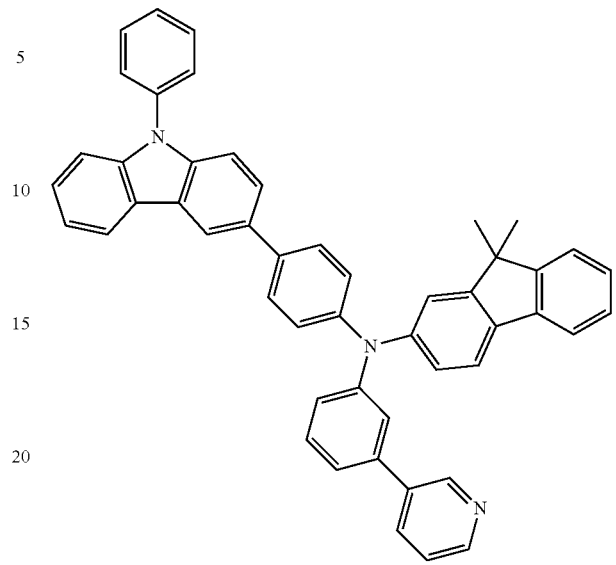
HT12
HT13
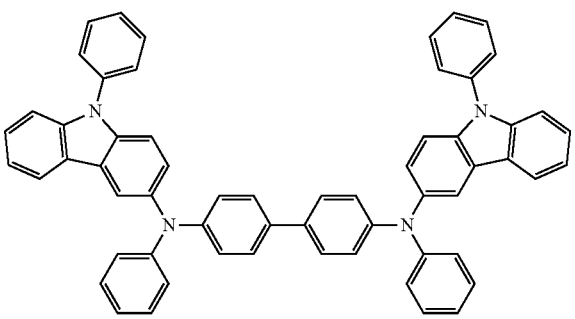

HT14
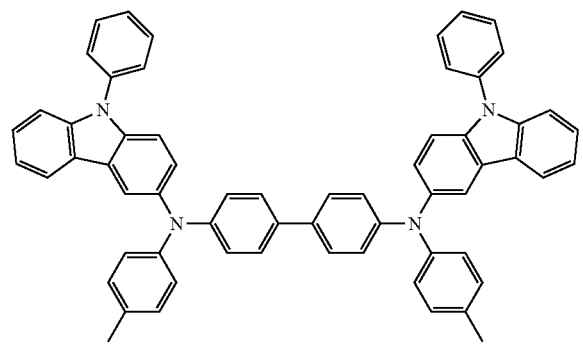

HT18
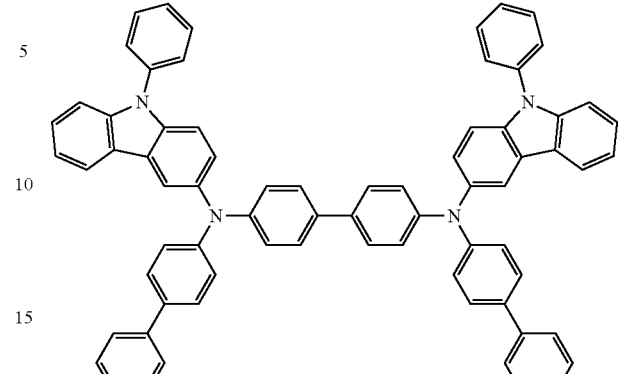

HT15
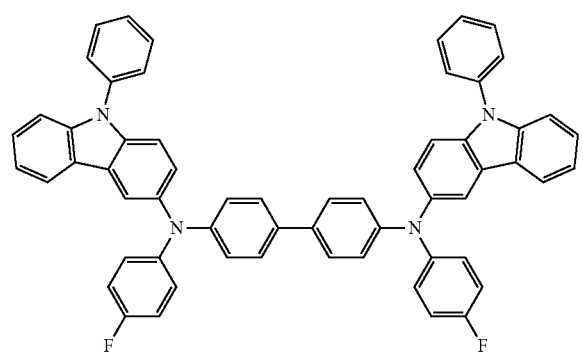

HT19
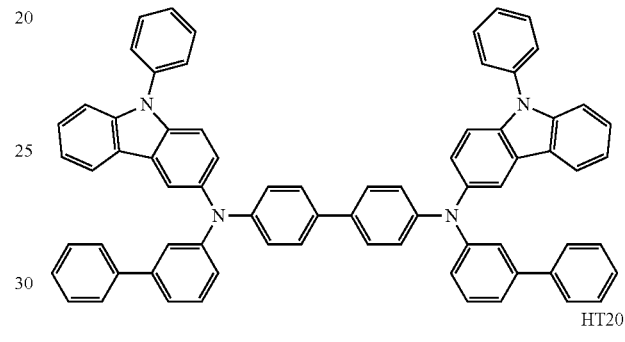

HT16
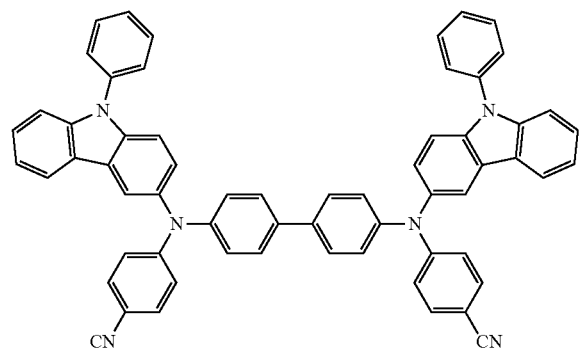

HT20
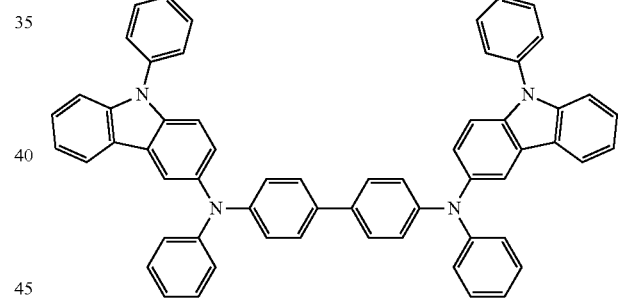

HT17
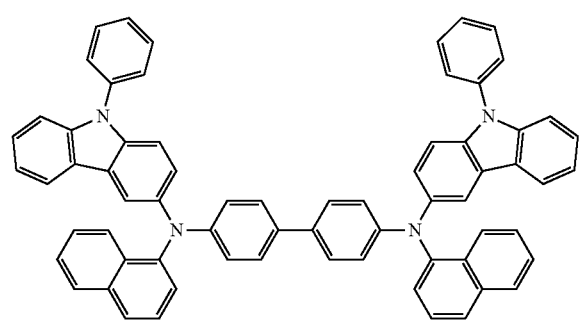

A thickness of the hole transport region may be in a range of about 100 Å to about 10000 Å, for example, about 100 Å to about 1000 Å. When the hole transport region includes a HIL and a HTL, a thickness of the HIL may be in a range of about 100 Å to about 10000 Å, for example, about 100 Å to about 1000 Å, and a thickness of the HTL may be in a range of about 50 Å to about 2000 Å, for example, about 100 Å to about 1500 Å. When the thicknesses of the hole transport region: the HIL and the HTL are within these ranges, satisfactory hole transporting characteristics may be obtained without a substantial increase in driving voltage.

The hole transport region may further include, in addition to these materials, a charge-generating material for the improvement of conductive properties. The charge-generating material may be homogeneously or non-homogeneously dispersed in the hole transport region.

The charge-generating material may be, for example, a p-dopant. The p-dopant may be one of a quinone derivative, a metal oxide, and a cyano group-containing compound, but is not limited thereto. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and Compound HT-D1 illustrated below, but are not limited thereto.

Compound HT-D1

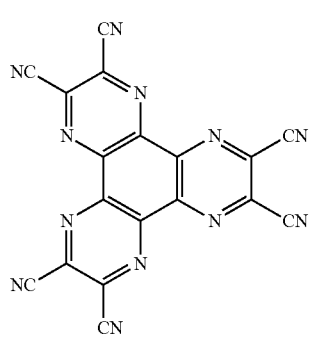

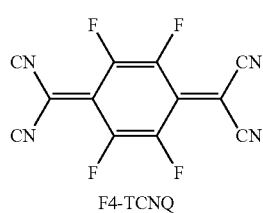

F4-TCNQ

The hole transport region may further include, in addition to the HIL and the HTL, at least one of a buffer layer and an EBL. The buffer layer may compensate for an optical resonance distance according to a wavelength of light emitted from the EML, and thus, a light-emission efficiency of an organic light-emitting device may be improved. For a material of the buffer layer, materials of the hole transport region may be used. The EBL prevents injection of electrons from the electron transport region.

An EML may be formed on the first electrode 110 or the hole transport region by using various methods, such as vacuum deposition, spin coating, casting, an LB method, ink-jet printing, laser-printing, or laser-induced thermal imaging. When the EML is formed by vacuum deposition or spin coating, deposition and coating conditions for the EML may be determined by referring to the deposition and coating conditions for the HIL.

When the organic light-emitting device 10 is a full color organic light-emitting device, the EML may be patterned into a red EML, a green EML, and a blue EML, according to a sub-pixel. In some embodiments, the EML may have a stacked structure of a red EML, a green EML, and a blue EML, or may include a red-light emission material, a green-light emission material, and a blue-light emission material, which are mixed with each other in a single layer, to emit white light.

The EML may include a host and a dopant.

The host may include at least one selected from TPBi, TBADN, AND (also referred to as "ADN"), CBP, CDBP, and TCP:

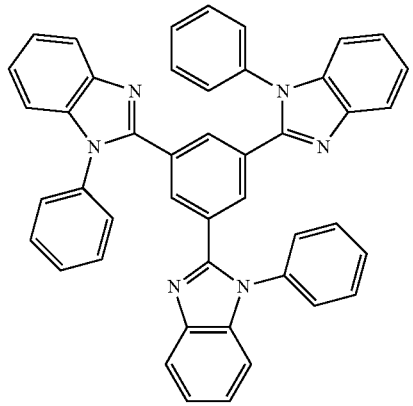

TPBi

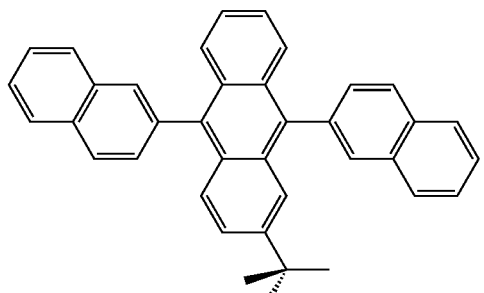

TBADN

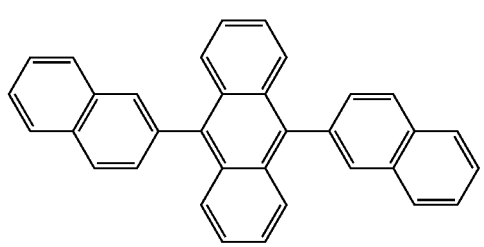

ADN

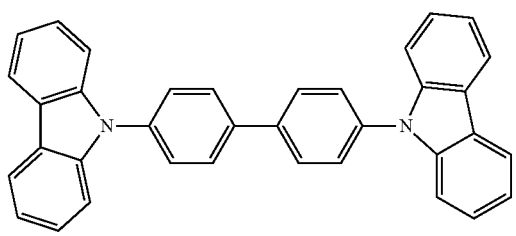

CBP

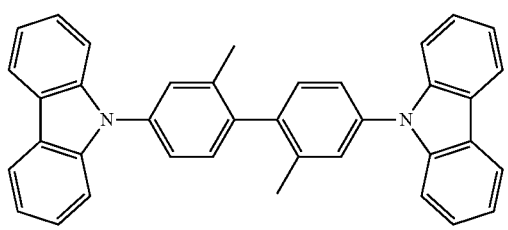

CDBP

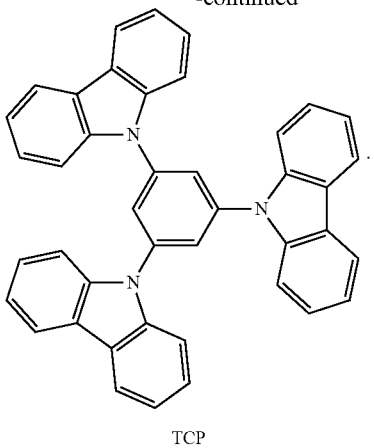

TCP

According to another embodiment of the present invention, the host may include a compound represented by Formula 301 below.

Ar$_{301}$-[(L$_{301}$)$_{xb1}$-R$_{301}$]$_{xb2}$    Formula 301

Wherein in Formula 301, Ar$_{301}$ may be selected from a naphthalene, a heptalene, a fluorenene, a spiro-fluorenene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; a naphthalene, a heptalene, a fluorenene, a spiro-fluorenene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_2$-C$_{10}$ heterocycloalkyl group, a C$_3$-C$_{10}$ cycloalkenyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, a monovalent non-aromatic hetero-condensed polycyclic group, and —Si(Q$_{301}$)(Q$_{302}$)(Q$_{303}$) (wherein Q$_{301}$ to Q$_{303}$ may be each independently selected from a hydrogen, a C$_1$-C$_{60}$ alkyl group, a C$_2$-C$_{60}$ alkenyl group, C$_6$-C$_{60}$ aryl group, and a C$_2$-C$_{60}$ heteroaryl group); L$_{301}$ may be understood by referring to the description provided in connection with L$_{201}$; R$_{301}$ may be selected from a C$_1$-C$_{20}$ alkyl group and a C$_1$-C$_{20}$ alkoxy group; a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; xb1 may be selected from 0, 1, 2, and 3; and xb2 may be selected from 1, 2, 3, and 4.

For example, in Formula 301, L$_{301}$ may be selected from a phenylene group, a naphthylene group, a fluorenylene group, a spiro-fluorenylene group, a benzofluorenylene group, a dibenzofluorenylene group, a phenalenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenalenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; R$_{301}$ may be selected from a C$_1$-C$_{20}$ alkyl group and a C$_1$-C$_{20}$ alkoxy group; a C$_1$-C$_{20}$ alkyl group and a C$_1$-C$_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but it is not limited thereto.

For example, the host may include a compound represented by Formula 301A below:

Formula 301A

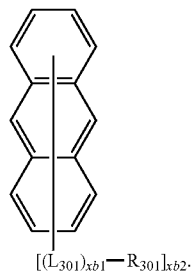

$[(L_{301})_{xb1}\!-\!R_{301}]_{xb2}.$

Substituents of Formula 301A are already described above.

The compound represented by Formula 301 may include at least one of Compounds H1 to H42, but is not limited thereto:

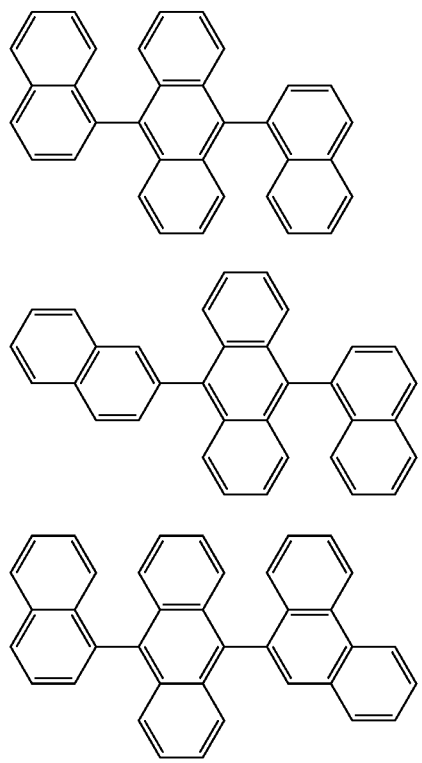

H1

H2

H3

-continued

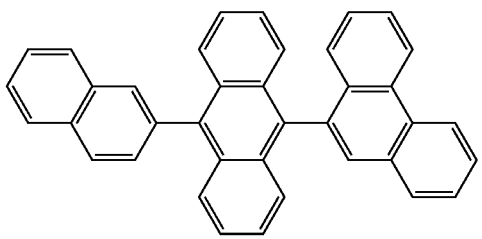

H4

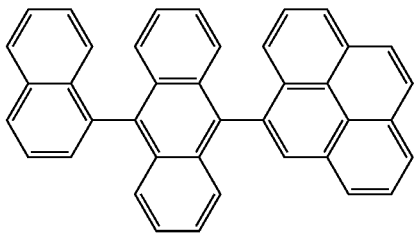

H5

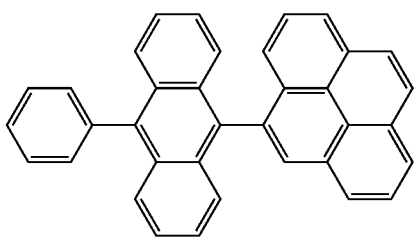

H6

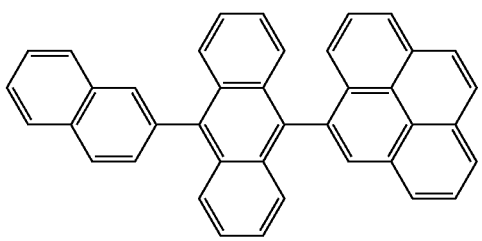

H7

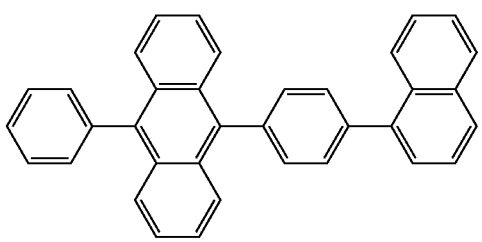

H8

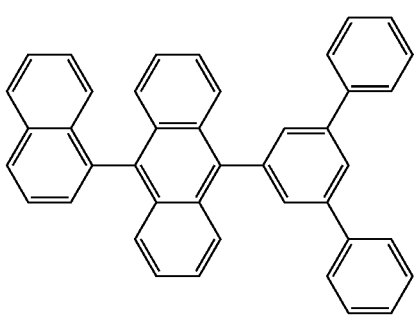

H9

H10
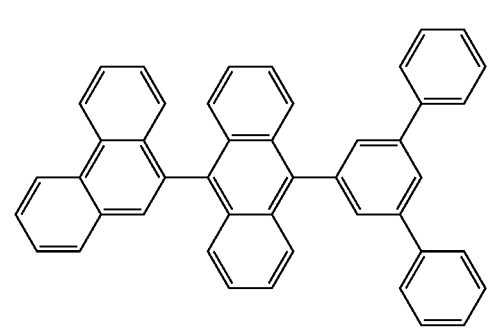
H11
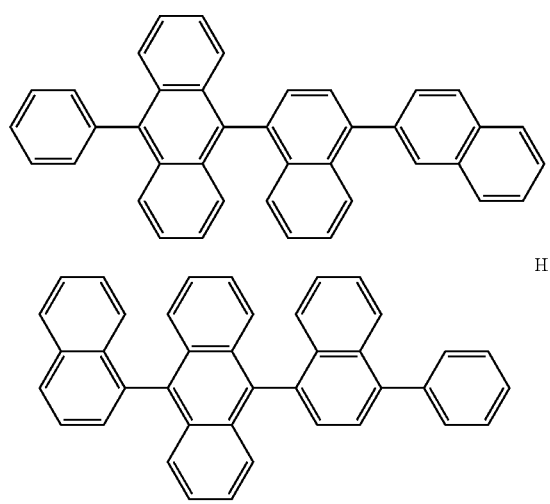
H12
H13
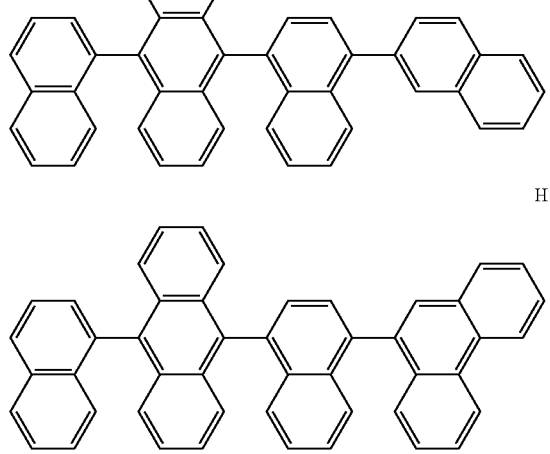
H14
H15
H16
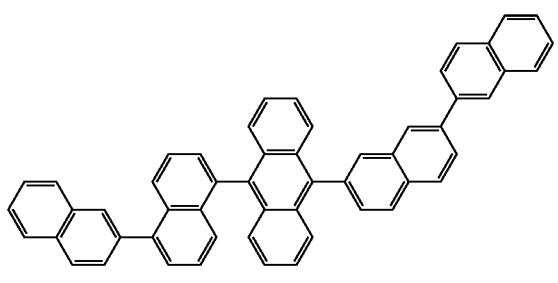
H17
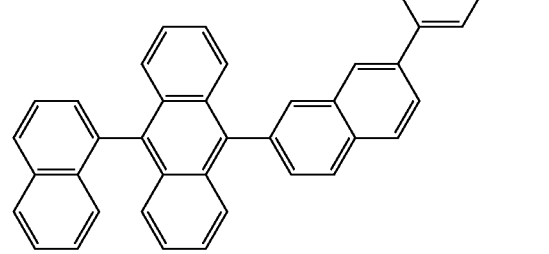
H18
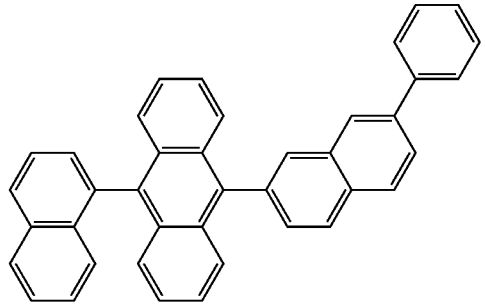
H19
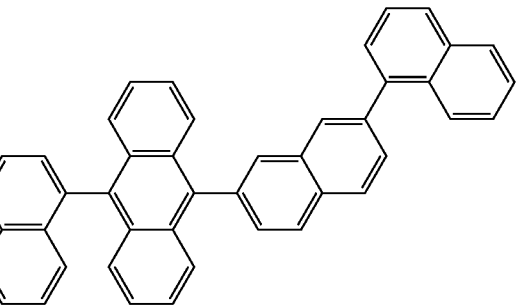

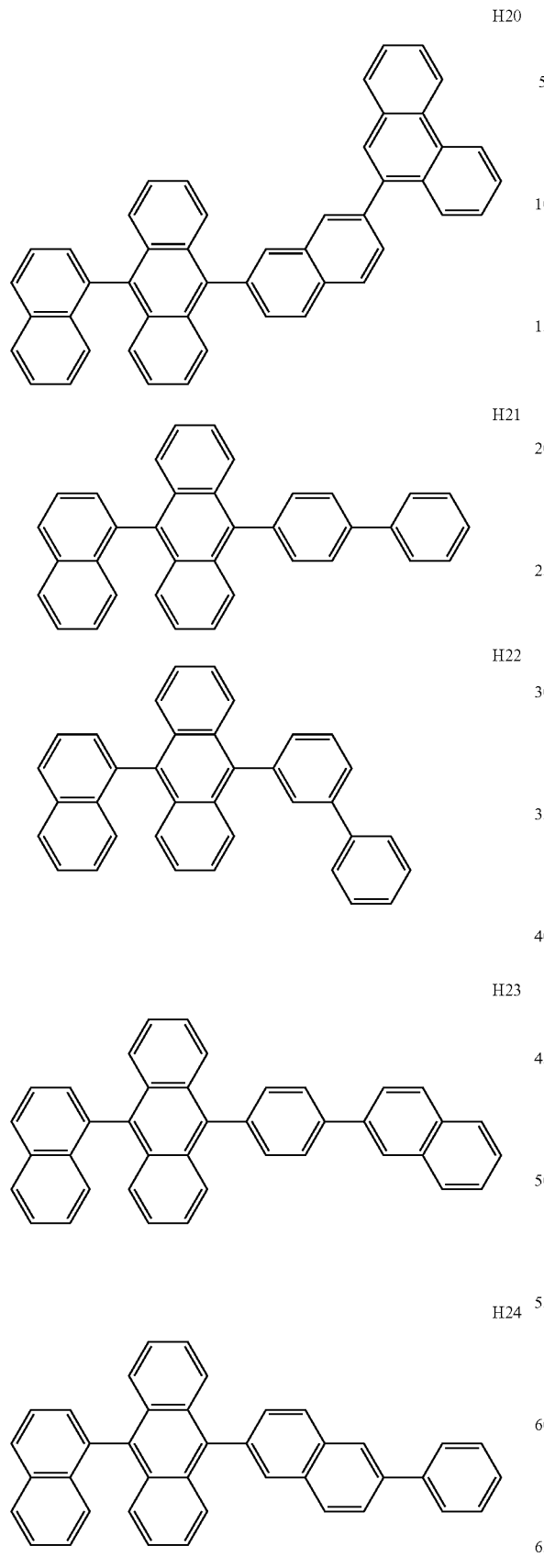
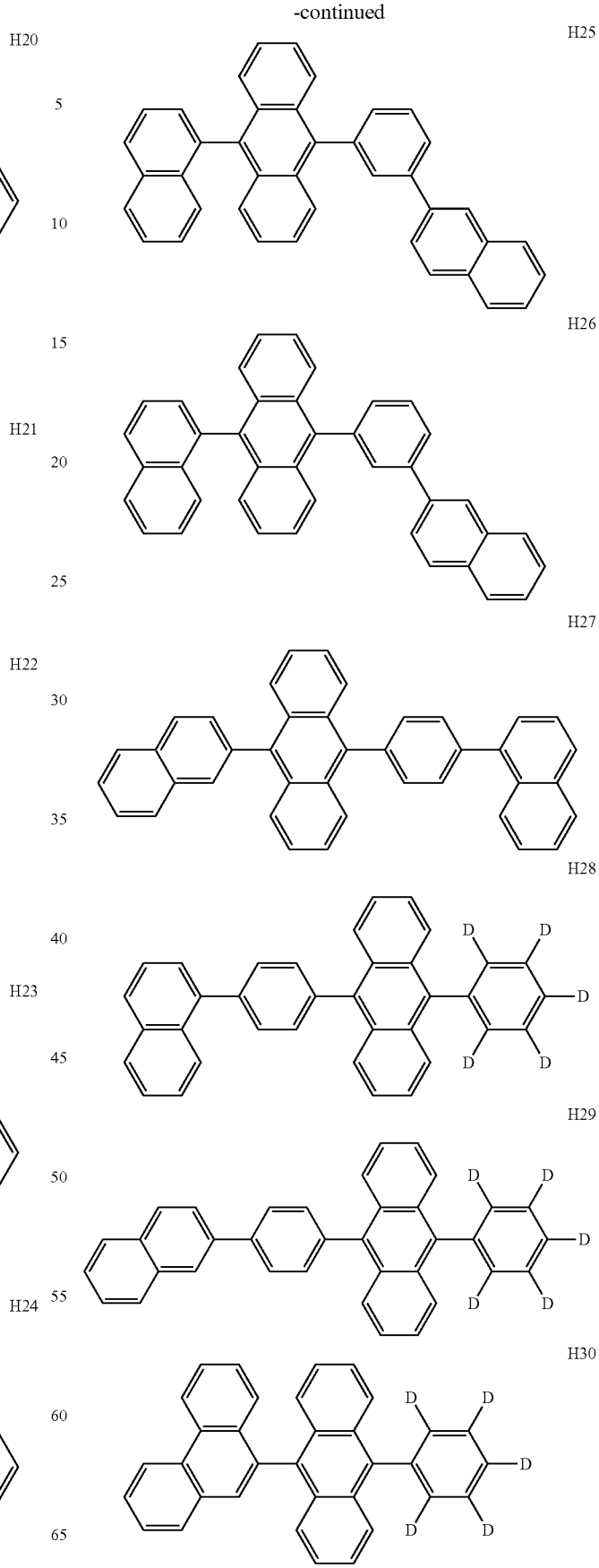

H31
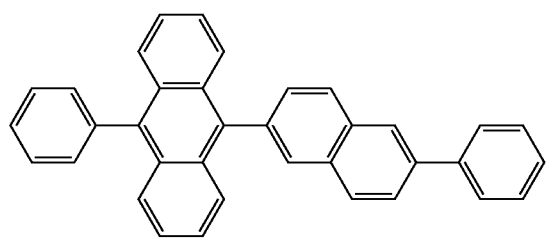
H32
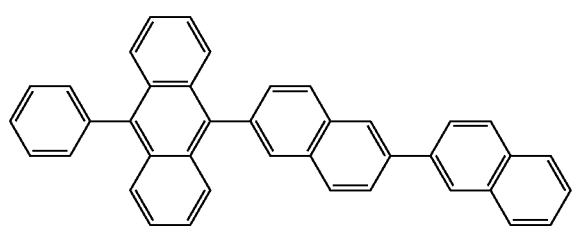
H33
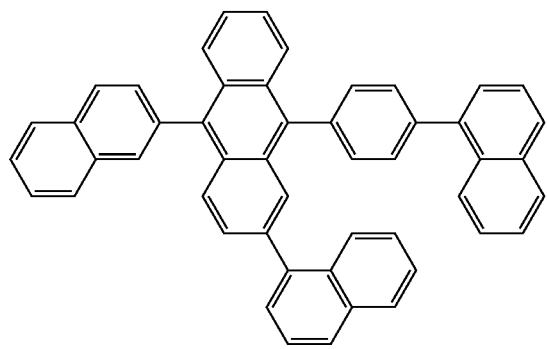
H34
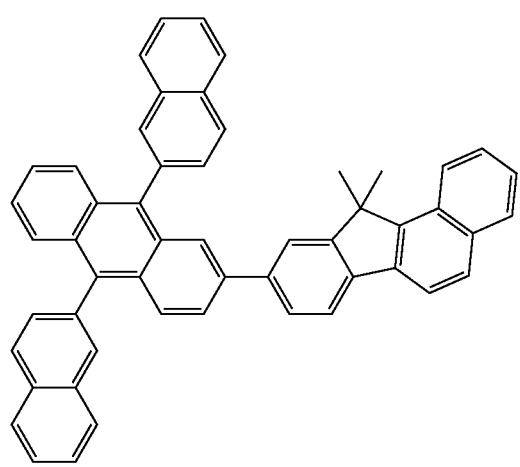
H35
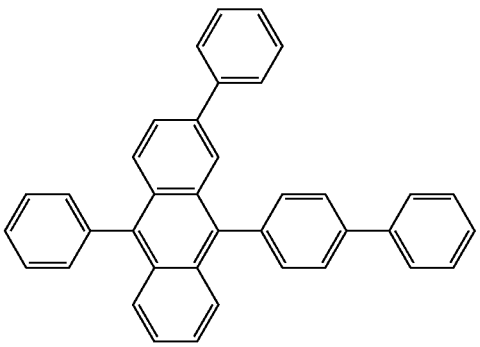
H36
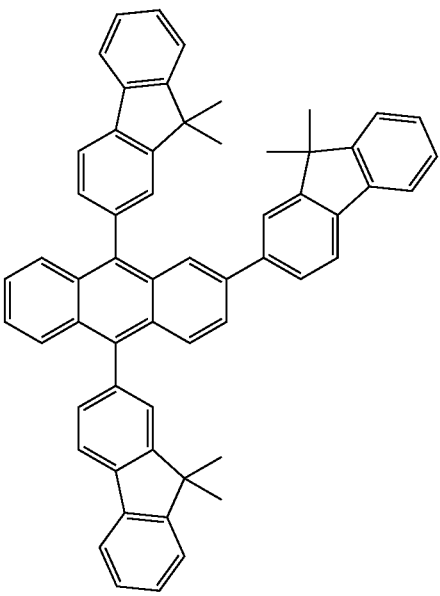
H37
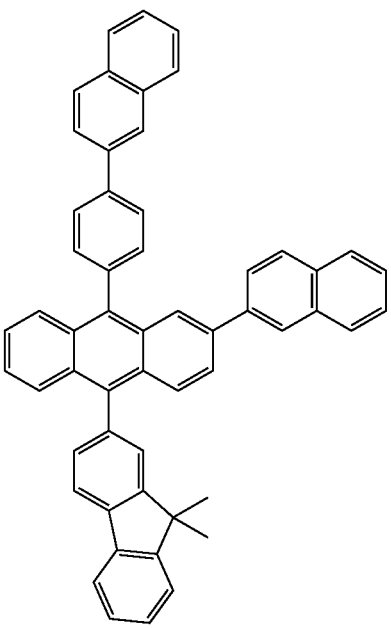

H38
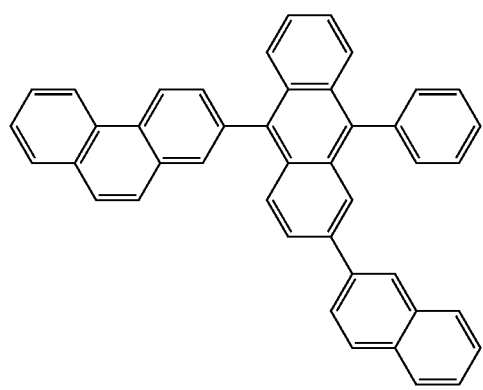
H41
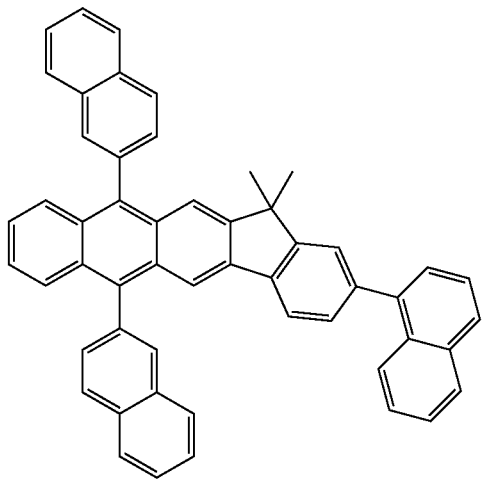
H39
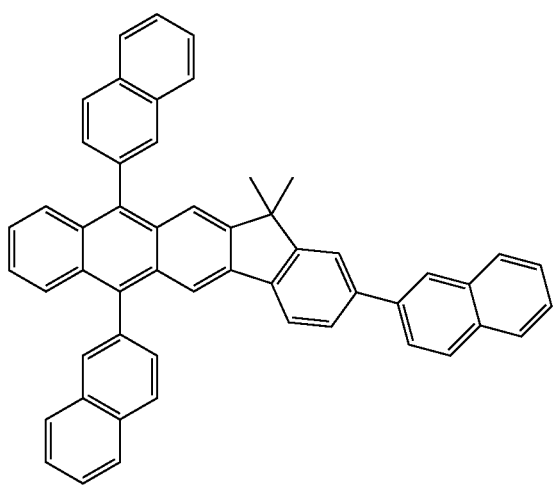
H42
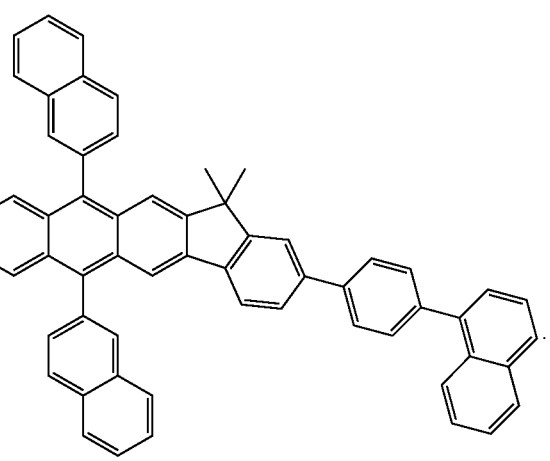
According to another embodiment of the present invention, the compound represented by Formula 301 may include at least one of Compounds H43 to H49 below, but are not limited thereto:
H40
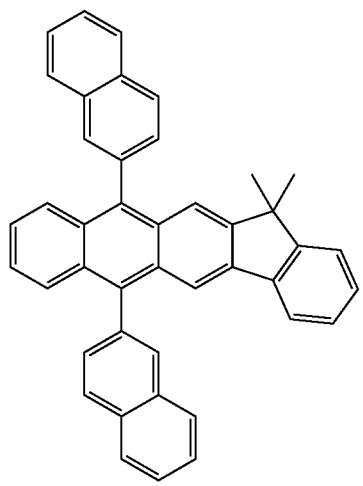
H43
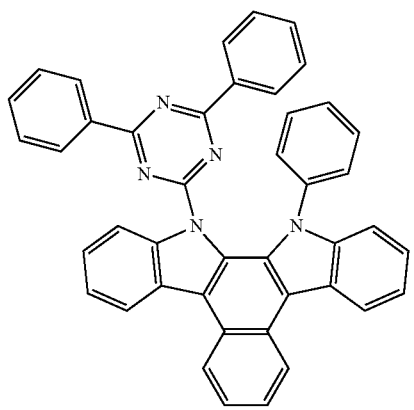

133
-continued
H44
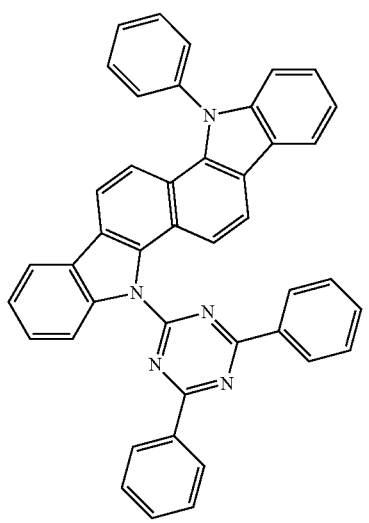
H45
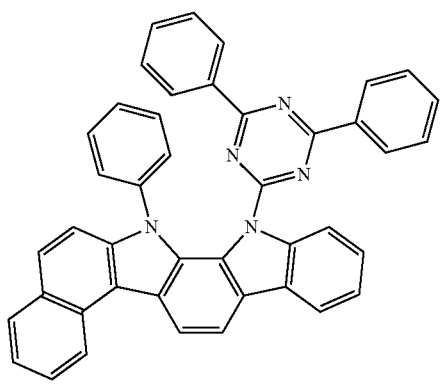
H46
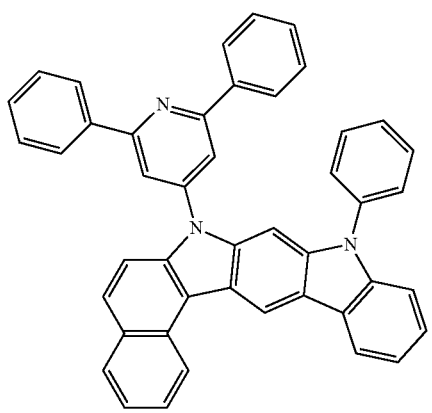
134
-continued
H47
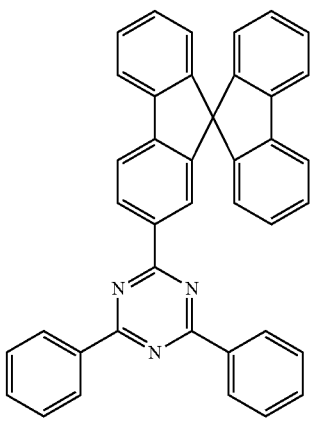
H48
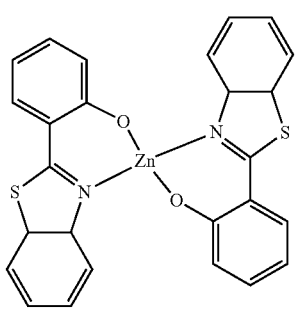
H49
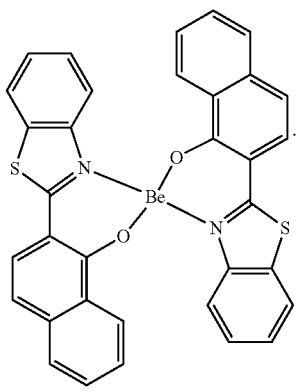
The dopant may be at least one selected from a fluorescent dopant and a phosphorescent dopant.
The phosphorescent dopant may include an organometallic complex represented by Formula 401 below:
Formula 401
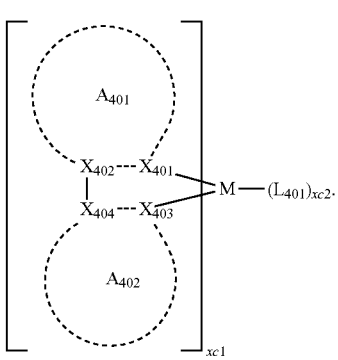

Wherein in Formula 401, M may be selected from iridium (Ir), platinum (Pt), osmium (Os), titanium (Ti), zirconium (Zr), hafnium (Hf), europium (Eu), terbium (Tb), and thulium (Tm); $X_{401}$ to $X_{404}$ may be each independently nitrogen or carbon; $A_{401}$ and $A_{402}$ rings may be each independently selected from a substituted or unsubstituted benzene, a substituted or unsubstituted a naphthalene, a substituted or unsubstituted fluorenene, a substituted or unsubstituted a spiro-fluorenene, a substituted or unsubstituted indene, a substituted or unsubstituted pyrrol, a substituted or unsubstituted thiopene, a substituted or unsubstituted furan, a substituted or unsubstituted imidazole, a substituted or unsubstituted pyrrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline a substituted or unsubstituted a carbazolyl, a substituted or unsubstituted benzoimidazole, a substituted or unsubstituted benzofuran, a substituted or unsubstituted benzothiopene, a substituted or unsubstituted isobenzothiopene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiopene; at least one substituent of the substituted benzene, substituted a naphthalene, substituted a fluorenene, substituted a spiro-fluorenene, substituted indene, substituted pyrrol, substituted thiopene, substituted furan, substituted imidazole, substituted pyrrazole, substituted thiazole, substituted isothiazole, substituted oxazole, substituted isooxazole, substituted pyridine, substituted pyrazine, substituted pyrimidine, substituted pyridazine, substituted quinoline, substituted isoquinoline, substituted benzoquinoline, substituted quinoxaline, substituted quinazoline, substituted a carbazolyl, substituted benzoimidazole, substituted benzofuran, substituted benzothiopene, substituted isobenzothiopene, substituted benzooxazole, substituted isobenzooxazole, substituted triazole, substituted oxadiazole, substituted triazine, substituted dibenzofuran, and substituted dibenzothiopene may be selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, —N($Q_{401}$)($Q_{402}$), —Si($Q_{403}$)($Q_{404}$)($Q_{405}$), and —B($Q_{406}$)($Q_{407}$); a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group; a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$) and —B($Q_{426}$)($Q_{427}$); $L_{401}$ is an organic ligand; xc1 is 1, 2, or 3; and xc2 is 0, 1, 2, or 3. Descriptions for $Q_{401}$ to $Q_{407}$, $Q_{411}$ to $Q_{417}$ and $Q_{421}$ to $Q_{427}$ are same as the descriptions for $Q_1$.

$L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propandionate, 2,2,6,6-tetramethyl-3,5-heptandionate, or hexafluoroacetonate), a carboxylic acid ligand (for example, picolinate, dimethyl-3-pyrazolecarboxylate, or benzoate), a carbon mono-oxide ligand, an isonitrile ligand, a cyano ligand, and a phosphorous ligand (for example, phosphine and phosphite), but is not limited thereto.

When $A_{401}$ in Formula 401 has two or more substituents, the substituents of $A_{401}$ may bind to each other to form a saturated or unsaturated ring.

When $A_{401}$ in Formula 402 has two or more substituents, the substituents of $A_{402}$ may bind to each other to form a saturated or unsaturated ring.

When xc1 in Formula 401 is two or more, a plurality of ligands

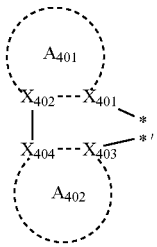

in Formula 401 may be identical or different. When xc1 in Formula 401 is two or more, $A_{401}$ and $A_{402}$ may be respectively directly connected to $A_{401}$ and $A_{402}$ of other neighboring ligands with or without a linker (for example, a $C_1$-$C_5$ alkylene group, or —N(R')— (wherein R' may be a $C_1$-$C_{10}$ alkyl group or a $C_6$-$C_{20}$ aryl group) or —C(=O)—) therebetween.
The phosphorescent dopant may include at least one of Compounds PD1 to PD74 below, but is not limited thereto:
PD1
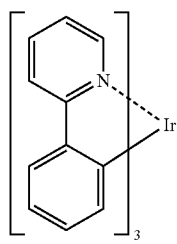
PD2
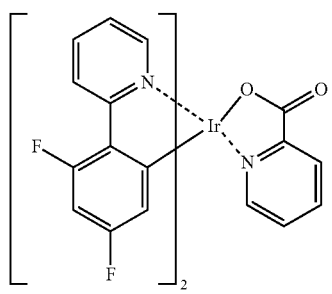
PD3
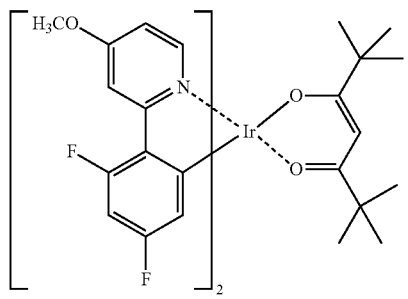
PD4
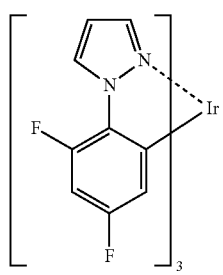
PD5
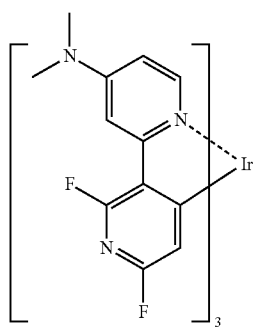
PD6
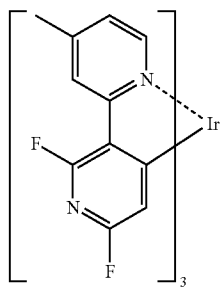
PD7
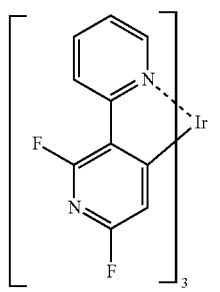
PD8
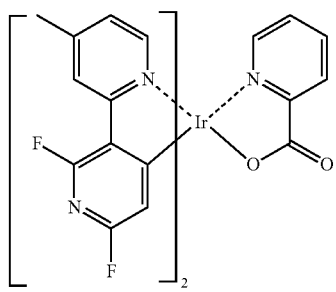
PD9
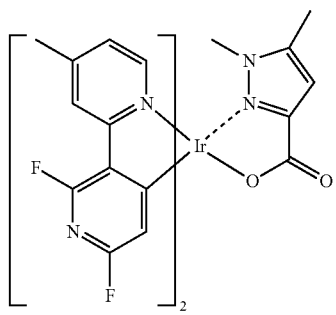
PD10
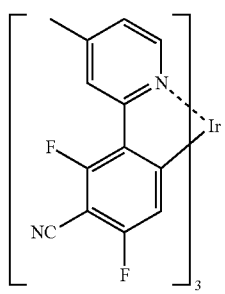

PD11 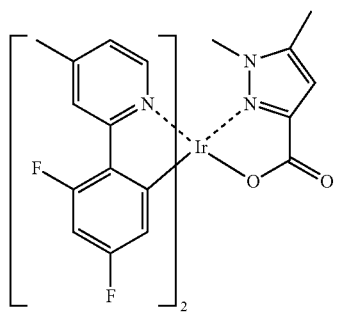
PD12 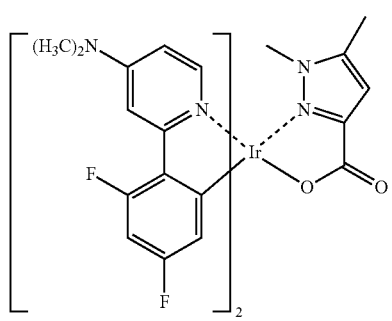
PD13 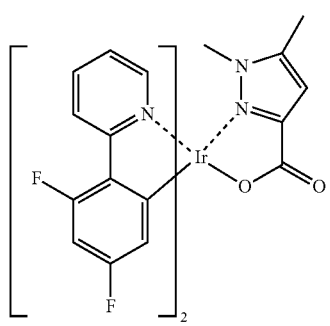
PD14 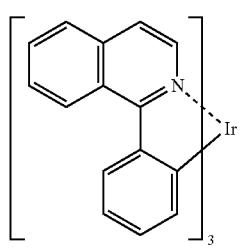
PD15 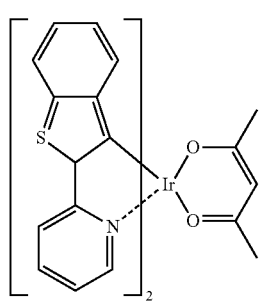
PD16 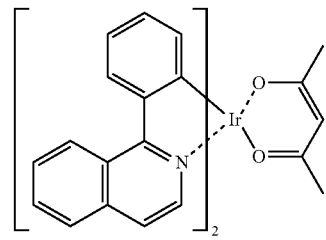
PD17 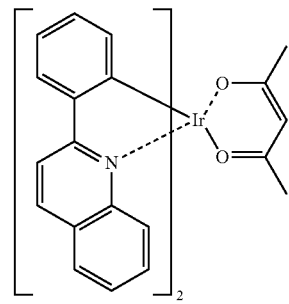
PD18 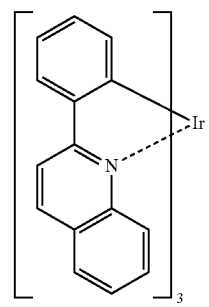
PD19 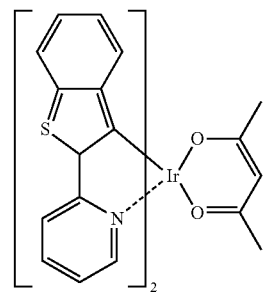
PD20 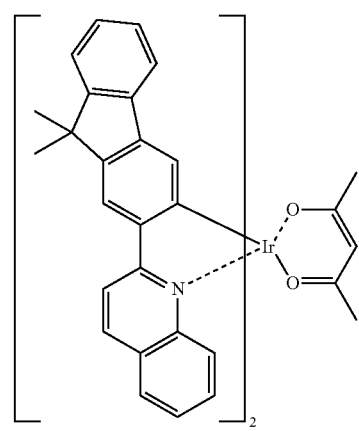

PD21 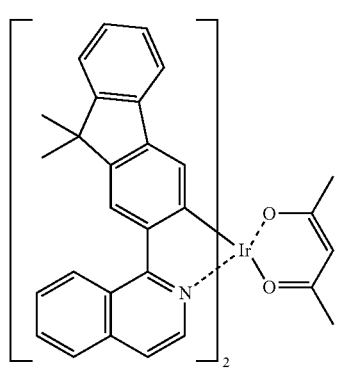
PD22 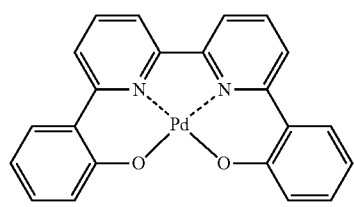
PD23 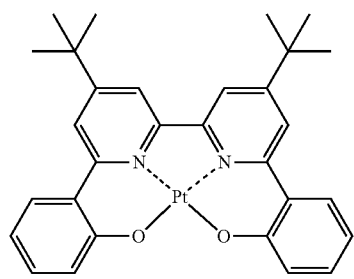
PD24 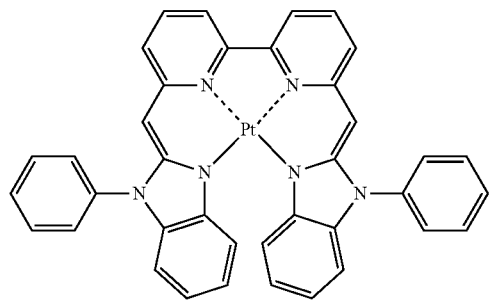
PD25 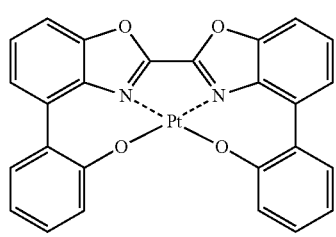
PD26 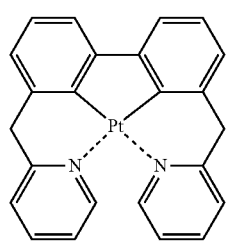
PD27 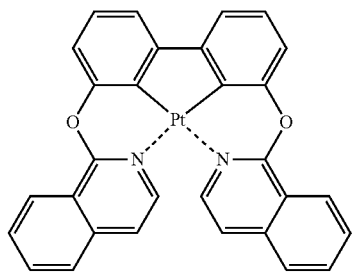
PD28 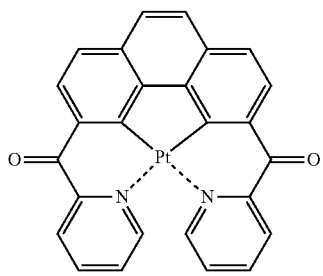
PD29 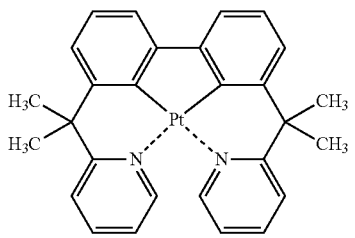
PD30 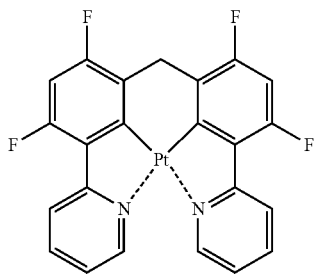
PD31 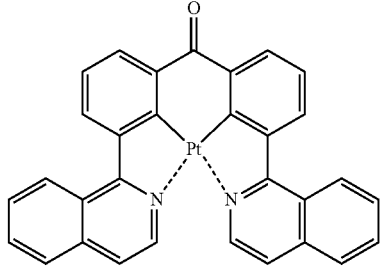
PD32 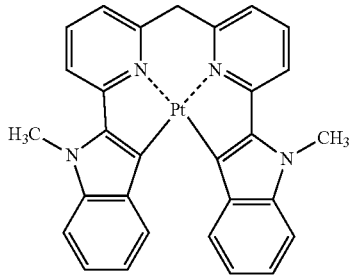

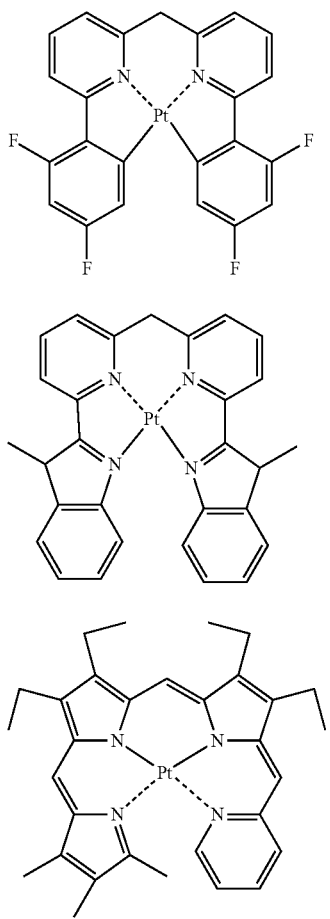
PD33
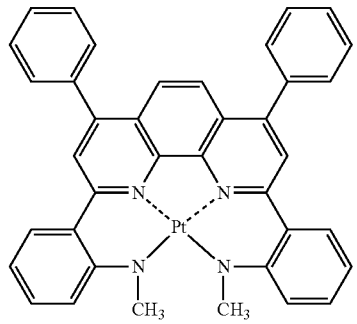
PD38
PD34
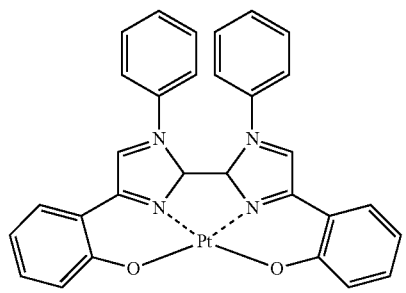
PD39
PD35
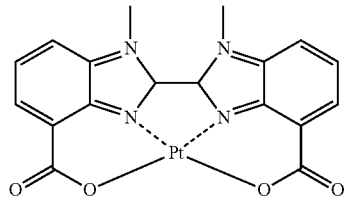
PD40
PD36
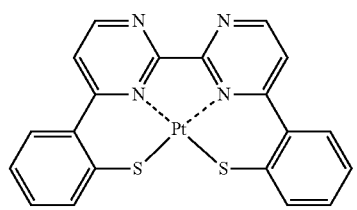
PD41
PD37
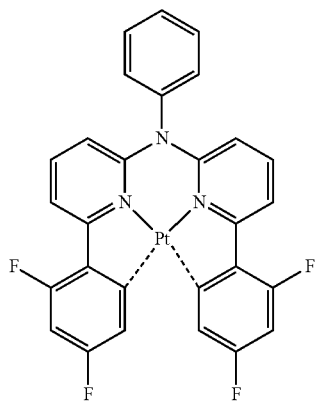
PD42

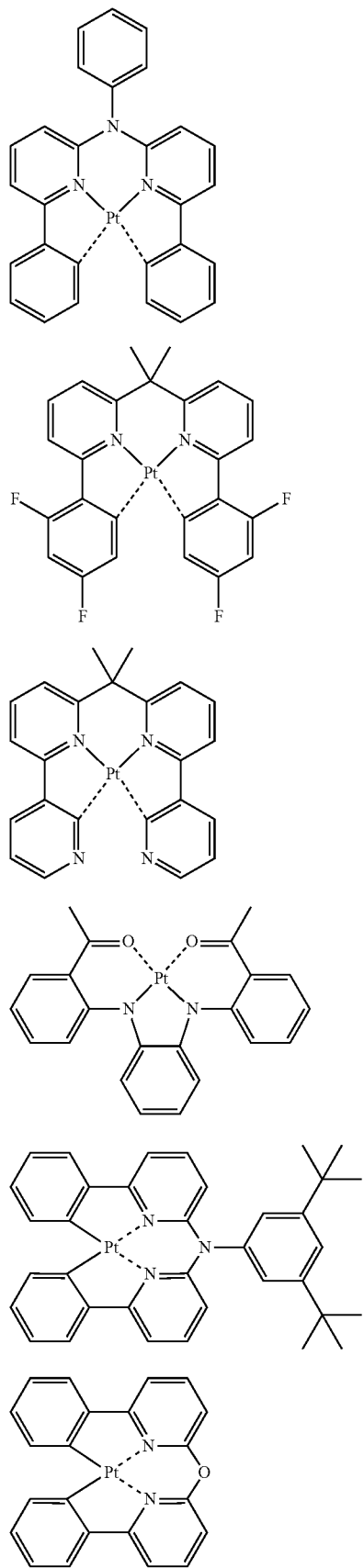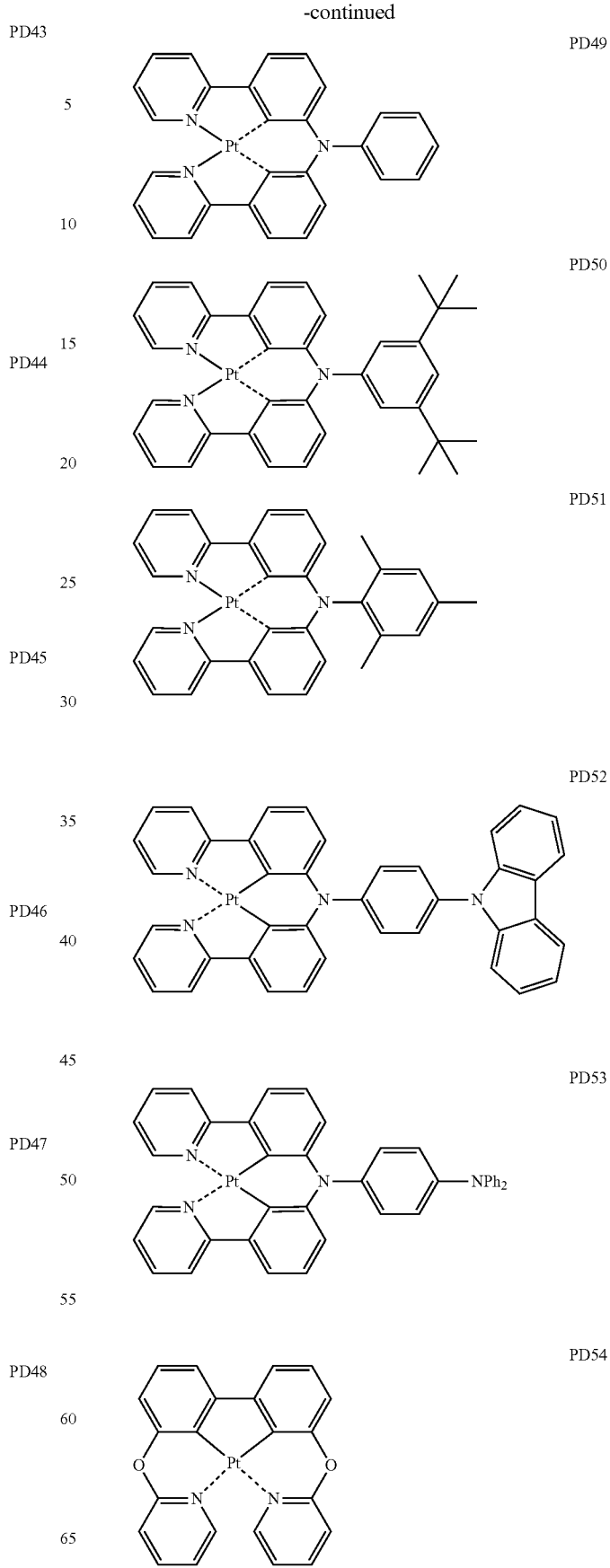

-continued
PD55 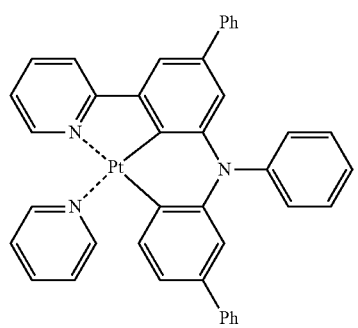
PD56 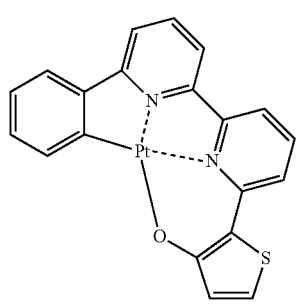
PD57 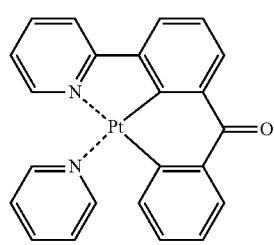
PD58 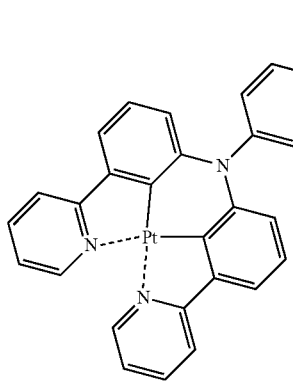
PD59 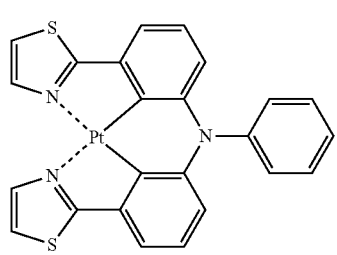
-continued
PD60 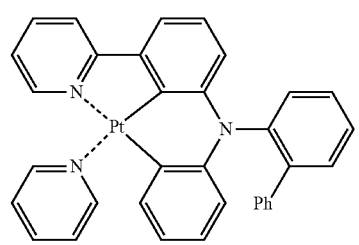
PD61 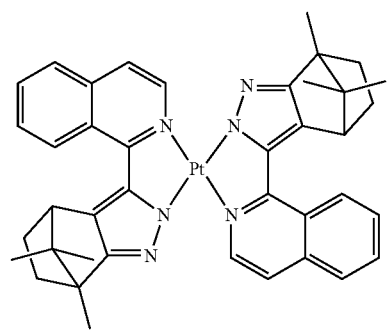
PD62 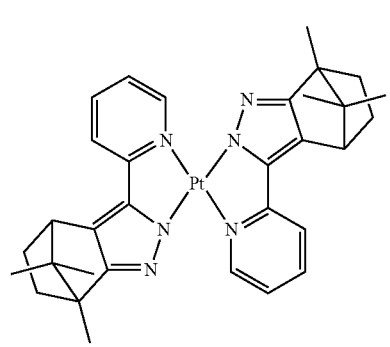
PD63 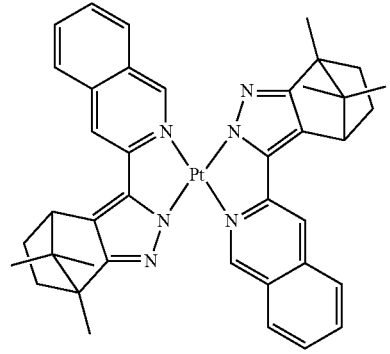
PD64 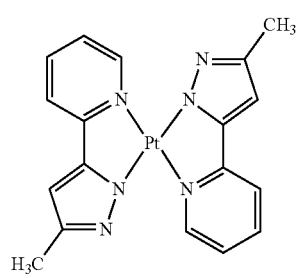

PD65 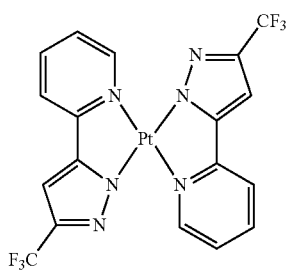
PD66 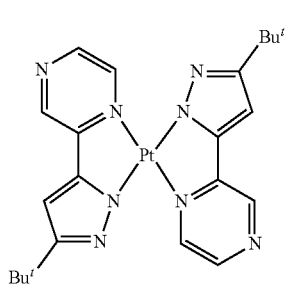
PD67 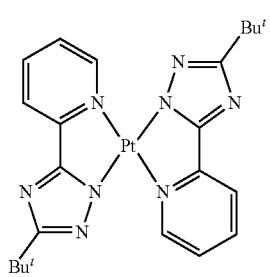
PD68 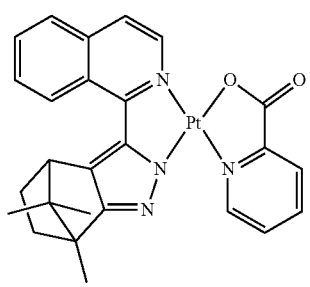
PD69 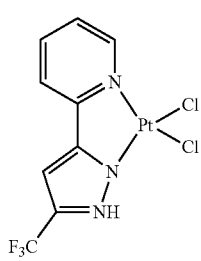
PD70 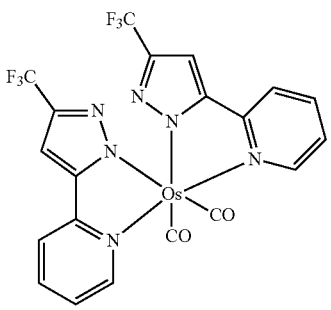
PD71 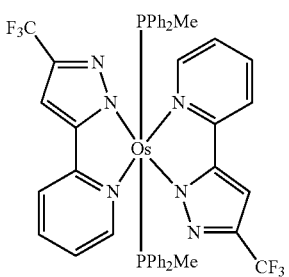
PD72 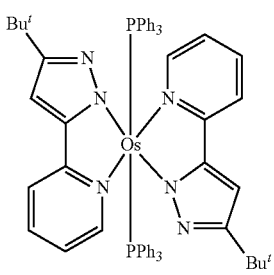
PD73 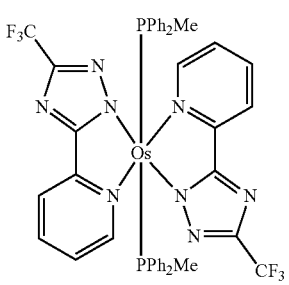
PD74 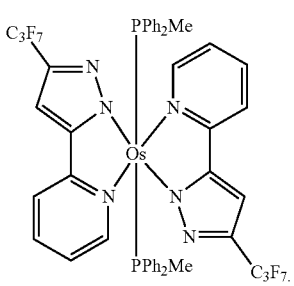
According to another embodiment of the present invention, the phosphorescent dopant may include PtOEP:

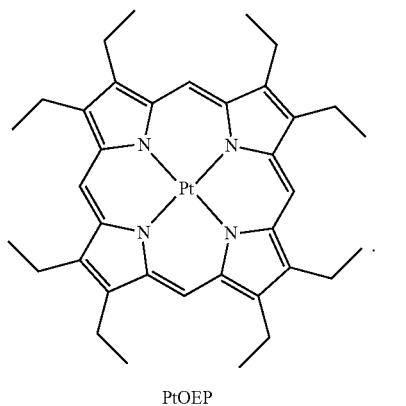
PtOEP
The fluorescent dopant may include at least one selected from DPAVBi, BDAVBi, TBPe, DCM, DCJTB, Coumarin 6, and C545T.
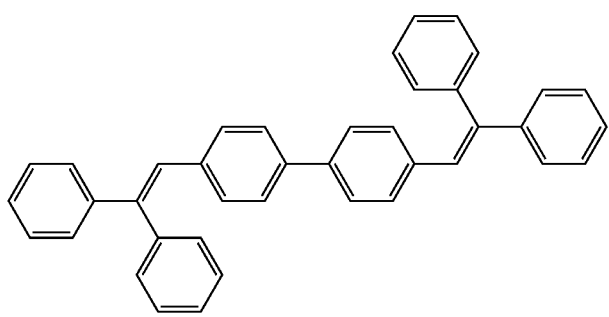
DPVBi
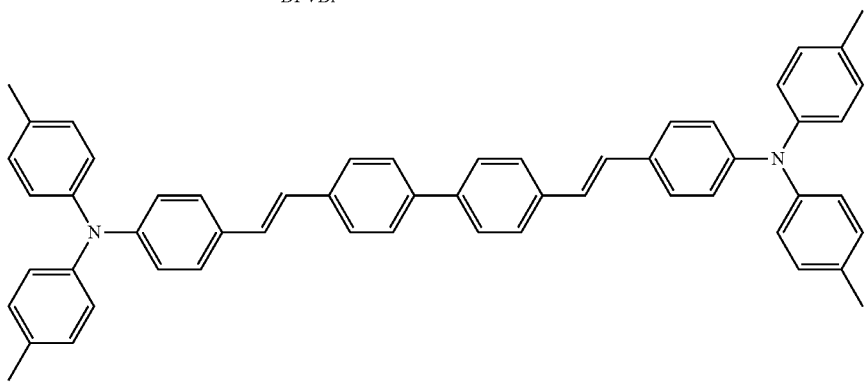
DPAVBi
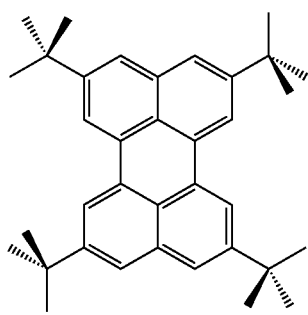
TBPe
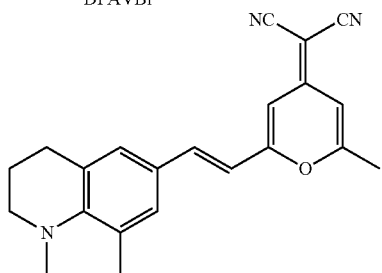
DCM -continued

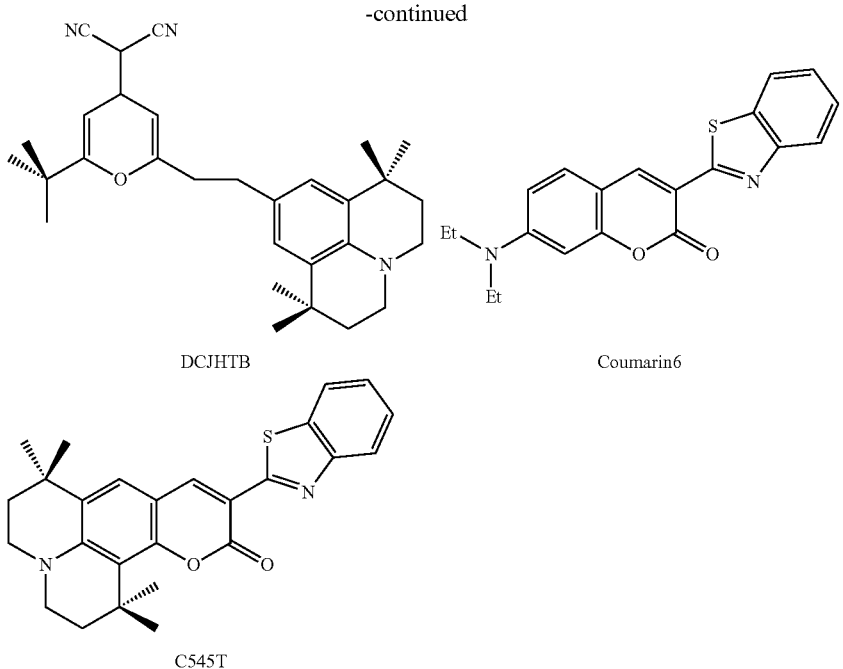

DCJHTB

Coumarin6

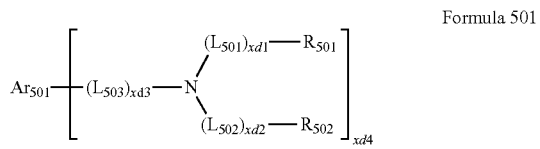

C545T

According to another embodiment of the present invention, the fluorescent dopant may include a compound represented by Formula 501 below.

Formula 501
$$Ar_{501}\left[-(L_{503})_{xd3}-N\begin{matrix}(L_{501})_{xd1}-R_{501}\\ \\(L_{502})_{xd2}-R_{502}\end{matrix}\right]_{xd4}$$

Wherein in Formula 501, $Ar_{501}$ may be selected from a naphthalene, a heptalene, a fluorenene, a spiro-fluorenene, a benzofluorenylene, a dibenzofluorenylene, a phenalene, a phenanthrene, an anthracene, a fluoranthene, a triphenylene, a pyrene, a chrysene, a naphthacene, a picene, a perylene, a pentaphene, and an indenoanthracene; a naphthalene, a heptalene, a fluorenene, a spiro-fluorenene, a benzofluorenylene, a dibenzofluorenylene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ arylthio group, a $C_6$-$C_{60}$ aryloxy group, a $C_2$-$C_{60}$ heteroaryl group, a monovalent non-aromatic condensed polycyclic group, a monovalent non-aromatic hetero-condensed polycyclic group, and —Si($Q_{501}$)($Q_{502}$)($Q_{503}$) (wherein, $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group);

$L_{501}$ to $L_{503}$ may be understood by referring to the description provided herein in connection with $L_{201}$; $R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group; xd1 to xd3 may be each independently selected from 0, 1, 2, and 3; and xb4 may be selected from 1, 2, 3, and 4.

The fluorescent host may include at least one of Compounds FD1 to FD8 below:

FD1
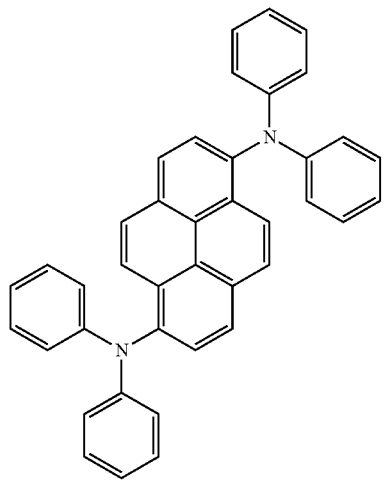
FD2
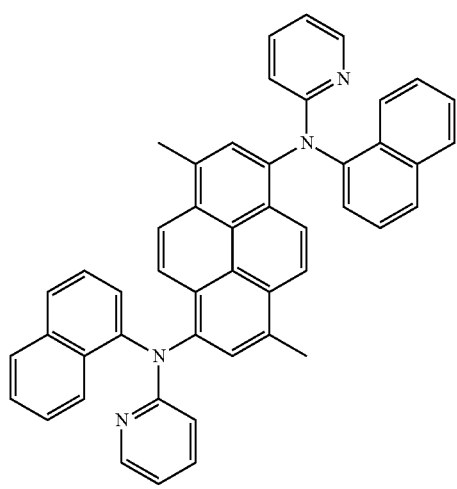
FD3
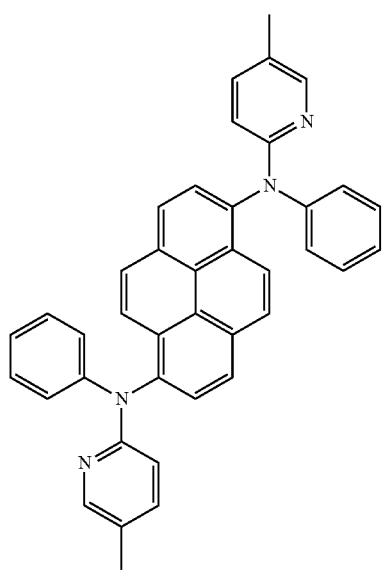
FD4
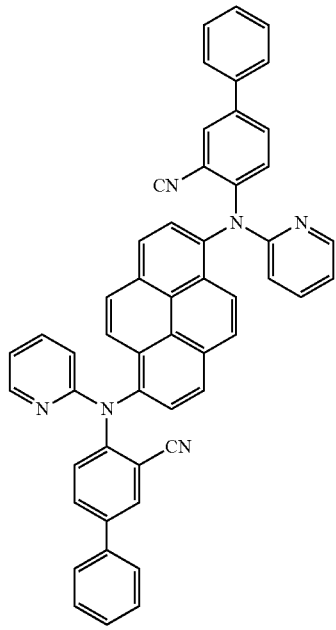
FD5
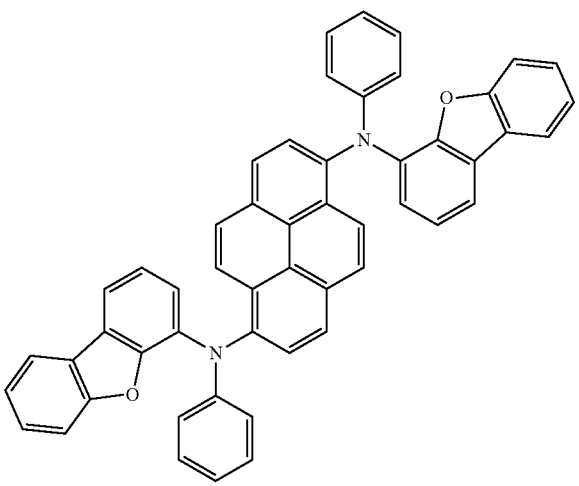
FD6
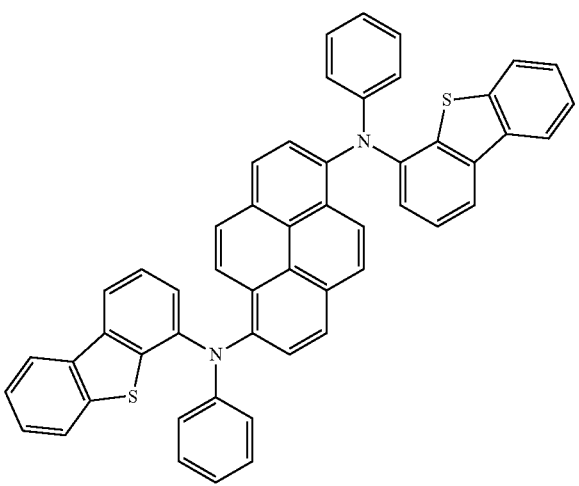

-continued

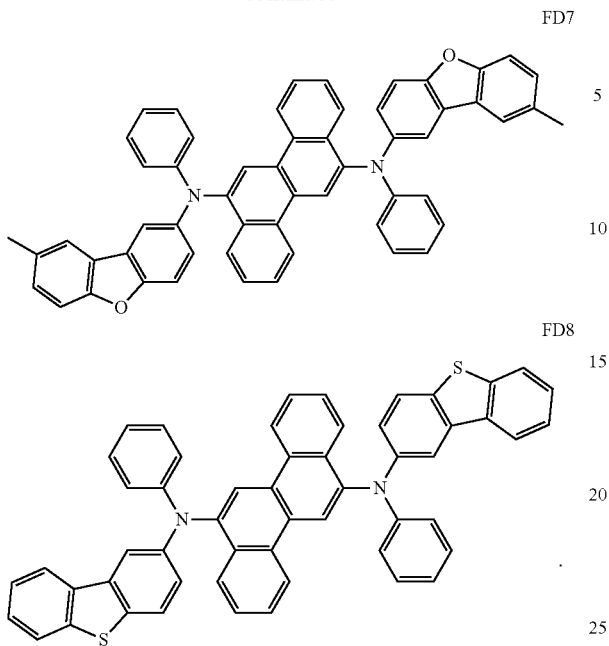

FD7

FD8

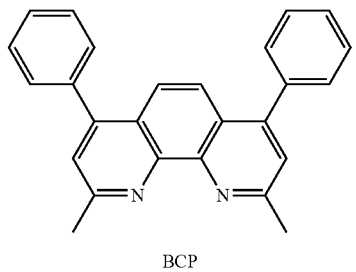

BCP

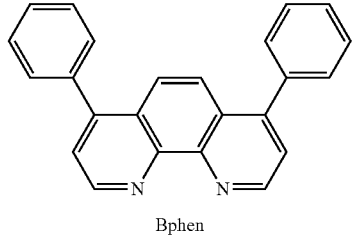

Bphen

An amount of the dopant in the EML may be, in general, in a range of about 0.01 to about 15 parts by weight based on 100 parts by weight of the host, but is not limited thereto.

A thickness of the EML may be in a range of about 100 Å to about 1000 Å, for example, about 200 Å to about 600 Å. When the thickness of the EML is within this range, excellent light-emission characteristics may be obtained without a substantial increase in driving voltage.

Then, an electron transport region may be disposed on the EML.

The electron transport region may include at least one selected from a HBL, an ETL, and an EIL, but is not limited thereto.

For example, the electron transport region may have a structure of ETL/EIL or a structure of HBL/ETL/EIL, wherein layers of each structure are sequentially stacked from the EML in the stated order, but is not limited thereto.

According to an embodiment of the present invention, the organic layer 150 of the organic light-emitting device may include an electron transport region disposed between the EML and the second electrode 190, wherein the electron transport region includes the condensed-cyclic compound represented by Formula 1.

The electron transport region may include a HBL. When the EML includes a phosphorescent dopant, the HBL may be formed to prevent diffusion of excitons or holes into an ETL.

When the electron transport region includes a HBL, the HBL may be formed on the EML by using various methods, such as vacuum deposition, spin coating casting, an LB method, ink-jet printing, laser-printing, or laser-induced thermal imaging. When the HBL is formed by vacuum deposition or spin coating, deposition and coating conditions for the HBL may be determined by referring to the deposition and coating conditions for the HIL.

The HBL may include, for example, at least one of BCP and Bphen, but is not limited thereto.

A thickness of the HBL may be in a range of about 20 Å to about 1000 Å, for example, about 30 Å to about 300 Å. When the thickness of the HBL is within these ranges, the HBL may have excellent hole blocking characteristics without a substantial increase in driving voltage.

The electron transport region may include an ETL. The ETL may be formed on the EML or the HBL by using various methods, such as vacuum deposition, spin coating casting, an LB method, ink-jet printing, laser-printing, or laser-induced thermal imaging. When an ETL is formed by vacuum deposition or spin coating, deposition and coating conditions for the ETL may be determined by referring to the deposition and coating conditions for the HIL.

According to an embodiment of the present invention, the organic layer 150 of the organic light-emitting device may include an electron transport region disposed between the EML and the second electrode 190, wherein the electron transport region includes an ETL, and the ETL includes the condensed-cyclic compound represented by Formula 1.

The ETL may further include, in addition to the condensed-cyclic compound represented by Formula 1, at least one selected from BCP, Bphen, and Alq₃, Balq, TAZ, and NTAZ, which are illustrated below.

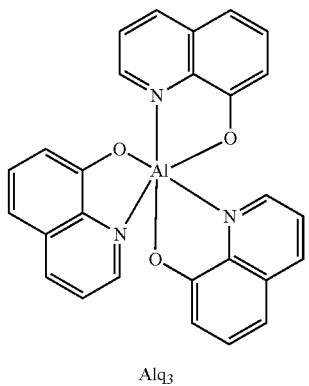

Alq₃

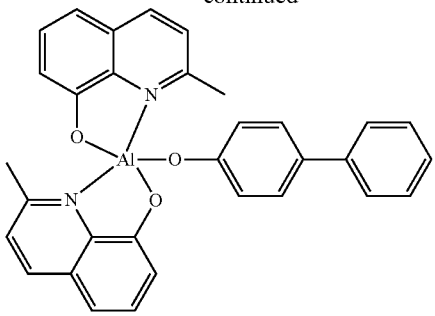

BAlq

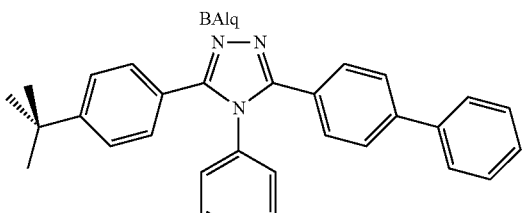

TAZ

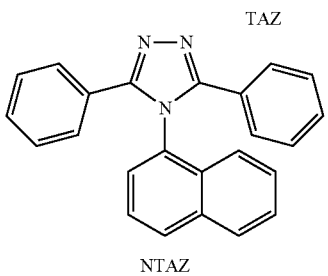

NTAZ

A thickness of the ETL may be in a range of about 100 Å to about 1000 Å, for example, about 150 Å to about 500 Å. When the thickness of the ETL is within the range described above, the ETL may have satisfactory electron transportation characteristics without a substantial increase in driving voltage.

Also, the ETL may further include, in addition to the materials described above, a metal-containing material.

The metal-containing material may include a Li complex. The Li complex may include, for example, Compound ET-D1 (lithium quinolate, LiQ) or ET-D2.

ET-D1

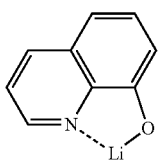

ET-D2

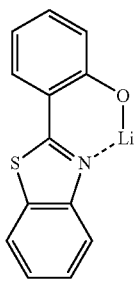

The electron transport region may include an EIL that allows electrons to be easily provided from the second electrode 190.

The EIL may be formed on the ETL by using various methods, such as vacuum deposition, spin coating casting, an LB method, ink-jet printing, laser-printing, or laser-induced thermal imaging. When an EIL is formed by vacuum deposition or spin coating, deposition and coating conditions for the EIL may be determined by referring to the deposition and coating conditions for the HIL.

The EIL may include at least one selected from LiF, NaCl, CsF, $Li_2O$, BaO, and LiQ.

A thickness of the EIL may be in a range of about 1 Å to about 100 Å, for example, about 3 Å to about 90 Å. When the thickness of the EIL is within the range described above, the EIL may have satisfactory electron transportation characteristics without a substantial increase in driving voltage.

The second electrode 190 is disposed on the organic layer 150 having the structure described above. The second electrode 190 may be a cathode that is an electron injection electrode, and in this regard, a material for forming the second electrode 190 may be a material having a low work function, and such a material may be a metal, an alloy, an electrically conductive compound, or a mixture thereof. Detailed examples of the second electrode 190 may be lithium (Li), magnesium (Mg), aluminum (Al), aluminum-lithium (Al—Li), calcium (Ca), magnesium-indium (Mg—In), or magnesium-silver (Mg—Ag). According to another embodiment of the present invention, the material for forming the second electrode 190 may be ITO or IZO. The second electrode 190 may be a reflective electrode, a semi-transmissive electrode, or a transmissive electrode.

Hereinbefore, the organic light-emitting device has been described with reference to the FIGURE, but is not limited thereto.

A $C_1$-$C_{60}$ alkyl group used herein refers to a linear or branched aliphatic hydrocarbon monovalent group having 1 to 60 carbon atoms, and detailed examples thereof may be a methyl group, an ethyl group, a propyl group, an isobutyl group, a sec-butyl group, a tert-butyl group, a pentyl group, an iso-amyl group, and a hexyl group. A $C_1$-$C_{60}$ alkylene used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof may be a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group, and detailed examples thereof may be an ethenyl group, a prophenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or terminal of the $C_2$-$C_{60}$ alkyl group, and detailed examples thereof may be an ethynyl group and a propynyl group. A $C_2$-$C_{60}$ alkynylene group herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms, and detailed examples thereof may be a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_2$-$C_{10}$ heterocycloalkyl group used herein refers to a monovalent monocyclic group having at least one heteroatom selected from N, O, P, and S as a ring-forming atom and 3 to 10 carbon atoms, and detailed examples thereof may be tetrahydrofuranyl and tetrahydrothiophenyl. A $C_2$-$C_{10}$ heterocycloalkylene group used herein refers to a divalent group having the same structure as the $C_2$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity, and detailed examples thereof may be a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_3$-$C_{10}$ heterocycloalkenyl group used herein refers to a monovalent monocyclic group that has at least one heteroatom selected from N, O, P, and S as a ring-forming atom, 3 to 10 carbon atoms, and at least one double bond in its ring. Detailed examples of the $C_3$-$C_{10}$ heterocycloalkenyl group may be a 2,3-hydrofuranyl group and a 2,3-hydrothiophenyl group. A $C_2$-$C_{10}$ heterocycloalkenylene group used herein refers to a divalent group having the same structure as the $C_3$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group may be a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one heteroatom selected from N, O, P, and S as a ring-forming atom, and 2 to 60 carbon atoms. A $C_2$-$C_{60}$ heteroarylene group used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl group may be a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group (for example, having 6 to 80 carbon atoms) used herein refers to a monovalent group that has two or more rings condensed to each other, only carbon atoms as a ring-forming atom, and non-aromaticity in the entire molecular structure. A detailed example of the monovalent non-aromatic condensed polycyclic group may be a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group (for example, having 2 to 80 carbon atoms) used herein refers to a monovalent group that has two or more rings condensed to each other, has a heteroatom selected from N, O P, and S, other than carbon atoms, as a ring forming atom, and has non-aromacity in the entire molecular structure. Detailed examples of the monovalent non-aromatic condensed heteropolycyclic group may be a carbazolyl group. A divalent non-aromatic condensed heteropolycyclic group used herein refers to a divalent group having the same structure as the monovalent non-aromatic condensed heteropolycyclic group.

The term "Ph" used herein refers to a phenyl group, the term "Me" used herein refers to a methyl group, the term "Et" used herein refers to an ethyl group, and the term "tert-Bu" or "But" used herein refers to a tert-butyl group.

Hereinafter, an organic light-emitting device according to an embodiment of the present invention will be described in detail with reference to Synthesis Examples and Examples. The wording "B was used instead of A" used in describing Synthesis Examples means that a molar equivalent of A was identical to a molar equivalent of B.

EXAMPLES

Synthesis Example 1: Synthesis of Compound 2

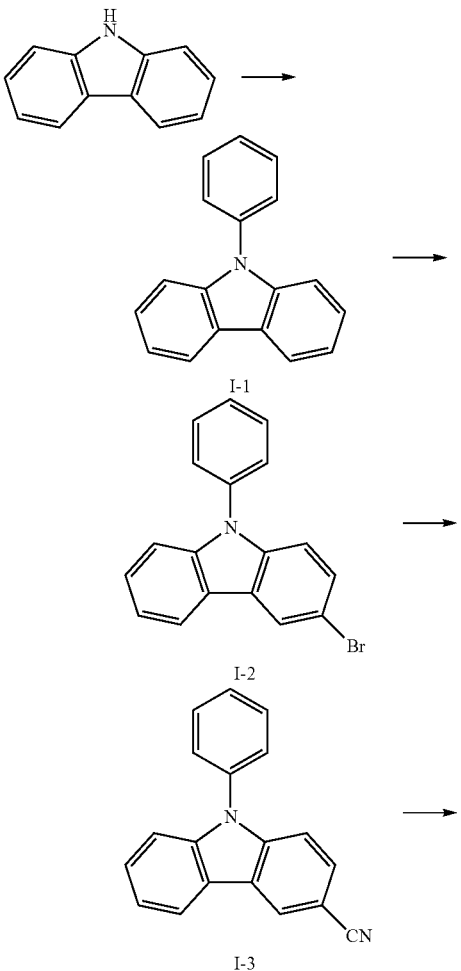

-continued

I-4

I-5

I-1

I-2

I-3

-continued

I-4

I-5

I-6

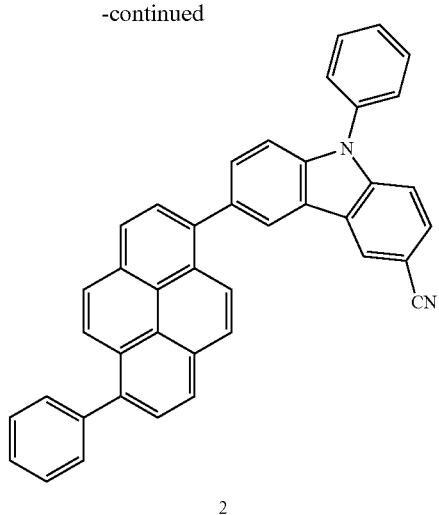

2

1) Synthesis of Intermediate I-1

5.02 g (30 mmol) of 9H-carbazole, 4.71 g (30 mmol) of bromobenzene, 1.14 g (18 mmol) of copper powder, and 6.22 g (45 mmol) of $K_2CO_3$ were dissolved in 80 mL of o-dichlorobenzene to prepare a reaction solution, and then the reaction solution was stirred at a temperature of 180° C. for 24 hours. The reaction solution was cooled to room temperature, 60 mL of water was added thereto, and a resultant reaction solution was extracted three times by using 50 mL of ethyl acetate to obtain an organic layer. The organic layer was dried by using magnesium sulfate and then a solvent was evaporated therefrom to obtain residues. The residues were separated and purified by using silica gel column chromatography to obtain 5.47 g (yield 75%) of Intermediate I-1. The obtained compound was identified by LC-MS. $C_{18}H_{13}N$: $M^+$ 243.10.

2) Synthesis of Intermediate I-2

5.47 g (22.5 mmol) of Intermediate I-1 was completely dissolved in 80 mL of $CH_2Cl_2$ to prepare a solution, and then 4.00 g (22.5 mmol) of N-bromosuccinimide was added to the solution to prepare a reaction solution, and the reaction solution was stirred at room temperature for 12 hours. 60 mL of water was added to the reaction solution, and then the reaction solution was extracted three times by using 50 mL of $CH_2Cl_2$ to obtain an organic layer. The organic layer was dried by using magnesium sulfate, a solvent was evaporated therefrom, and then, the reaction solution was re-crystallized by using methanol to obtain 6.16 g (yield 85%) of Intermediate I-2. The obtained compound was identified by LC-MS. $C_{18}H_{12}BrN$: $M^+$ 321.01.

3) Synthesis of Intermediate I-3

6.16 g (19.1 mmol) of Intermediate I-2 and 2.57 g (28.7 mmol) of CuCN were dissolved in 70 mL of DMF to prepare a mixture, and then, the mixture was stirred at a temperature of 150° C. for 24 hours to prepare a reaction solution. The reaction solution was cooled to room temperature, and then, 60 mL of ammonia water and 60 mL of water were added thereto and then the reaction solution extracted three times by using 50 mL of $CH_2Cl_2$ to obtain an organic layer. The organic layer obtained therefrom was dried by using magnesium sulfate and then a solvent was evaporated therefrom to obtain residues. The residues were separated and purified by using silica gel column chromatography to obtain 4.71 g (yield: 92%) of Intermediate I-3. The obtained compound was identified by LC-MS. $C_{19}H_{12}N_2$: $M^+$ 268.1.

4) Synthesis of Intermediate I-4

4.71 g (17.6 mmol) of Intermediate I-3 was completely dissolved in 80 mL of $CH_2Cl_2$, 3.13 g (17.6 mmol) of N-bromosuccinimide was added thereto to prepare a reaction solution, and the reaction solution was stirred at room temperature for 8 hours. 60 mL of water was added to the reaction solution, and then the reaction solution was extracted three times by using 50 mL of $CH_2Cl_2$ to obtain an organic layer. The organic layer was dried by using magnesium sulfate, and then, a solvent was evaporated therefrom, and then, the reaction solution was re-crystallized by using methanol to obtain 5.81 g (yield 95%) of Intermediate I-4. The obtained compound was identified by LC-MS. $C_{19}H_{11}BrN_2$: $M^+$ 346.0.

5) Synthesis of Intermediate I-5

5.0 g (14.4 mmol) of Intermediate I-4, 4.02 g (15.8 mmol) of bis-(pinacolato)diboron, 4.24 g (43.2 mmol) of KOAc, 0.35 g (0.43 mmol) of palladium (diphenyl phosphino ferrocene)chloride were dissolved in 80 mL of DMSO in a 250 mL flask to prepare a reaction solution and then the reaction solution was refluxed at a temperature of 80° C. for 12 hours. After cooling the reaction solution to room temperature, 50 mL of distilled water was added to the reaction solution, and the reaction solution was extracted three times by using 50 mL of $CH_2Cl_2$ to obtain an organic layer. The organic layer was dried by using magnesium sulfate and then a solvent was evaporated from the organic layer to obtain residues. The obtained residues were washed with ethanol and then dried to obtain 4.88 g (yield 86%) of Intermediate I-5. The obtained compound was identified by LC-MS. $C_{19}H_1BrN_2$: $M^+$ 346.0. $C_{25}H_{23}BN_2O_2$: $M^+$ 394.2.

6) Synthesis of Intermediate I-6

5.40 g (15 mmol) of 1,6-dibromopyrene, 1.21 g (10 mmol) of phenyl boronic acid, 0.29 g (0.25 mmol) of tetrakis(triphenylphosphine)palladium $(Pd(PPh_3)_4)$, and 0.62 g (4.48 mmol) of $K_2CO_3$ were dissolved in 60 mL of a mixture solution of $THF/H_2O$ (a volume ratio of 2/1) to prepare a reaction solution, and then the reaction solution was stirred at a temperature of 70° C. for 5 hours. The reaction solution was cooled to room temperature, 50 mL of water was added thereto, and the reaction solution was extracted three times with 50 mL of ethylether to obtain an organic layer. The obtained organic layer was dried with magnesium sulfate and a solvent was evaporated from the organic layer to obtain residues. The obtained residues were separated and purified by using magnesium sulfate by using silica gel column chromatography to obtain 2.32 g (yield 65%) of Intermediate I-6. The obtained compound was identified by using LC-MS. $C_{22}H_{13}Br$: $M^+$ 356.0.

Synthesis of Compound 2

2.32 g (6.5 mmol) of Intermediate I-6, 2.56 g (6.5 mmol) of Intermediate I-5, 0.37 g (0.32 mmol) of $Pd(PPh_3)_4$, and 2.57 g (18.6 mmol) of $K_2CO_3$ were dissolved in 60 mL of a mixture solution of $THF/H_2O$ (volume ratio of 2/1) to prepare a reaction solution and then the reaction solution was stirred at a temperature of 80° C. for 12 hours. After cooling the reaction solution to room temperature, the reaction solution was extracted three times by using 40 mL of water and 40 mL of ethyl acetate to obtain an organic layer. The obtained organic layer was dried by using magnesium sulfate and a solvent was evaporated therefrom to obtain residues. The obtained residues were separated and purified by using silica gel column chromatography to obtain 2.69 g (yield 76%) of Compound 2. The obtained compound was identified by using MS/FAB and $^1H$ NMR. $C_{41}H_{24}N_2$ cal. 544.19, found 544.22.

Synthesis Example 2: Synthesis of Compound 6

2.91 g (yield 72%) of Compound 6 was obtained in the same manner as in Synthesis Example 1, except that 6-phenyl-pyridine-2-boronic acid was used instead of phenyl boronic acid used in the synthesis of Intermediate I-6. The obtained compound was identified by using MS/FAB and $^1$H NMR. $C_{46}H_{27}N_3$ cal. 621.22, found 621.18.

Synthesis Example 3: Synthesis of Compound 16

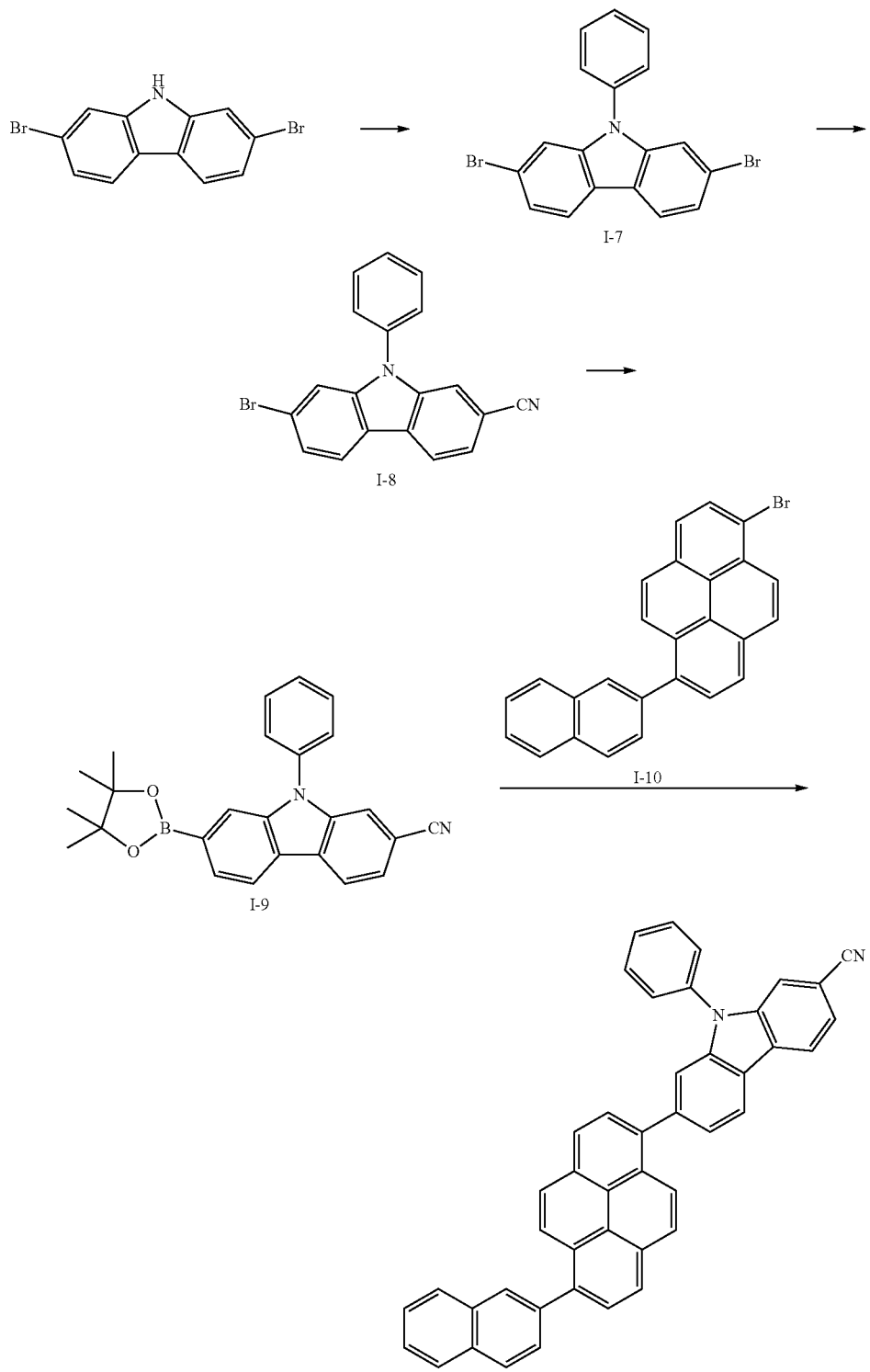

1) Synthesis of Intermediate I-7

8.78 g (yield 73%) of Intermediate I-7 was obtained in the same manner as in the synthesis of Intermediate I-1 in Synthesis Example 1, except that 2,7-dibromo-9H-carbazole was used instead of 9H-carbazole. The obtained compound was identified by using LC-MS. $C_{18}H_{11}Br_2N$: $M^+$ 398.9.

2) Synthesis of Intermediate I-8

3.57 g (yield 47%) of Intermediate I-8 was obtained in the same manner as in the synthesis of Intermediate I-3 in Synthesis Example 1, except that Intermediate I-7 was used instead of Intermediate I-2. The obtained compound was identified by using LC-MS. $C_{19}H_{11}BrN_2$: $M^+$ 346.0.

3) Synthesis of Intermediate I-9

3.57 g (10.3 mmol) of Intermediate I-8, 2.87 g (11.3 mmol) of bis-(pinacolato)diboron, 3.03 g (30.9 mmol) of KOAc, 0.25 g (0.31 mmol) of palladium(diphenyl phosphino ferrocene)chloride were dissolved in 70 mL of DMSO in a 250 mL flask to prepare a reaction solution, and the reaction solution was refluxed at a temperature of 80° C. for 12 hours. After cooling the reaction solution to room temperature, 40 mL of distilled water was added to the reaction solution, and the reaction solution was extracted three times with 40 mL of methylene chloride to obtain an organic layer. The obtained organic layer was dried by using magnesium sulfate and a solvent was evaporated therefrom to obtain residues. The obtained residues were washed with ethanol and then dried to obtain 3.14 g (yield 82%) of Intermediate I-9. The obtained compound was identified by using LC-MS. $C_{25}H_{23}BN_2O_2$: $M^+$ 394.2.

4) Synthesis of Intermediate I-10

Intermediate I-10 was synthesized in the same manner as in the synthesis of Intermediate I-6 in Synthesis Example 1, except that 2-naphthyl boronic acid was used instead of phenyl boronic acid.

5) Synthesis of Compound 16

2.74 g (yield 71%) of Compound 16 was obtained in the same manner as in the synthesis of Compound 2 in Synthesis Example 1, except that Intermediate I-9 and Intermediate I-10 were used instead of Intermediate I-5 and Intermediate I-6, respectively. The obtained compound was identified by using MS/FAB and $^1$H NMR. $C_{45}H_{26}N_2$ cal. 594.21, found 594.25.

Synthesis Example 4: Synthesis of Compound 27

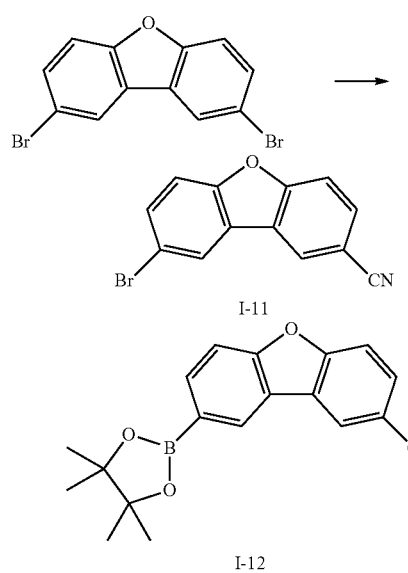

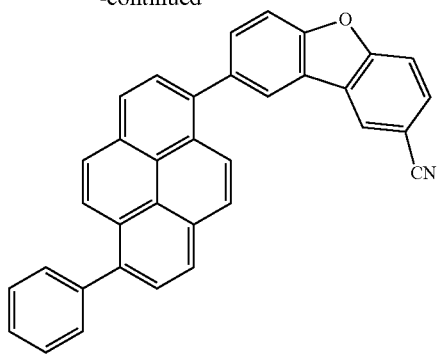

27

1) Synthesis of Intermediate I-11

2.23 g (yield 43%) of Intermediate I-11 was obtained in the same manner as in the synthesis of Intermediate I-3 in Synthesis Example 1, except that 2,8-dibromo-dibenzofuran was used instead of Intermediate I-2. The obtained compound was identified by using LC-MS. $C_{13}H_6BrNO$: $M^+$ 270.9.

2) Synthesis of Intermediate I-12

2.07 g (yield 79%) of Intermediate I-12 was obtained in the same manner as in the synthesis of Intermediate I-9 in Synthesis Example 3, except that Intermediate I-11 was used instead of Intermediate I-8. The obtained compound was identified by using LC-MS. $C_{19}H_{18}BNO_3$: $M^+$ 319.1.

3) Synthesis of Compound 27

2.31 g (yield 76%) of Compound 27 was obtained in the same manner as in the synthesis of Compound 2 in Synthesis Example 1, except that Intermediate I-12 was used instead of Intermediate I-5. The obtained compound was identified by using MS/FAB and $^1$H NMR. $C_{35}H_{19}NO$ cal. 469.15, found 469.11.

Synthesis Example 5: Synthesis of Compound 32

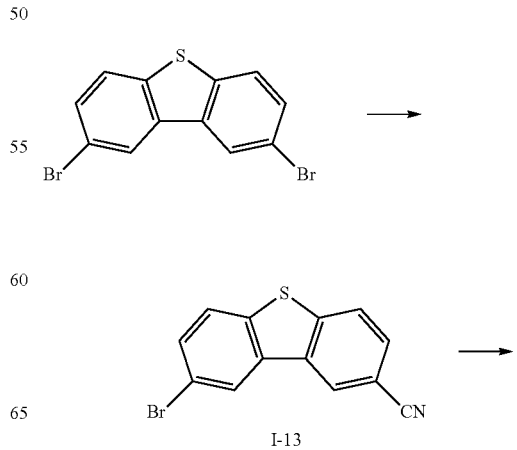

-continued

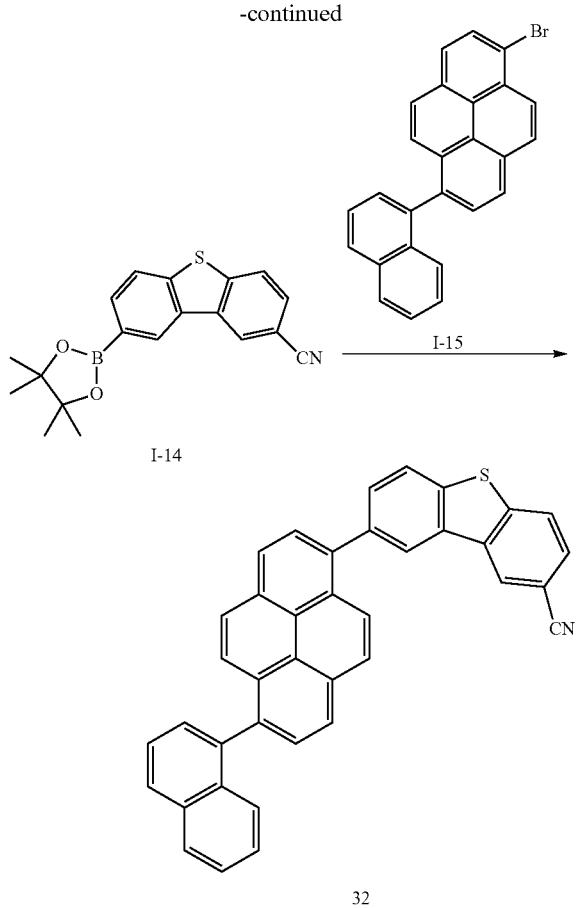

1) Synthesis of Intermediate I-13

2.47 g (yield 45%) of Intermediate I-13 was obtained in the same manner as in the synthesis of Intermediate I-3 in Synthesis Example 1, except that 2,8-dibromo-dibenzothiopene was used instead of Intermediate I-2. The obtained compound was identified by using LC-MS. $C_{13}H_6BrNS$: $M^+$ 286.9.

2) Synthesis of Intermediate I-14

2.21 g (yield 77%) of Intermediate I-14 was obtained in the same manner as in the synthesis of Intermediate I-9 in Synthesis Example 3, except that Intermediate I-13 was used instead of Intermediate I-8. The obtained compound was identified by using LC-MS. $C_{19}H_{18}BNO_2S$: $M^+$ 335.1.

3) Synthesis of Intermediate I-15

Intermediate I-15 was synthesized in the same manner as in the synthesis of Intermediate I-6 in Synthesis Example 1, except that 1-naphthyl boronic acid was used instead of phenyl boronic acid.

4) Synthesis of Compound 32

2.57 g (yield 73%) of Compound 32 was obtained in the same manner as in the synthesis of Compound 2 in Synthesis Example 1, except that Intermediate I-14 and Intermediate I-15 were used instead of Intermediate I-5 and Intermediate I-6, respectively. The obtained compound was identified by using MS/FAB and $^1$H NMR. $C_{39}H_{21}NS$ cal. 535.14, found 535.17.

Synthesis Example 6: Synthesis of Compound 69

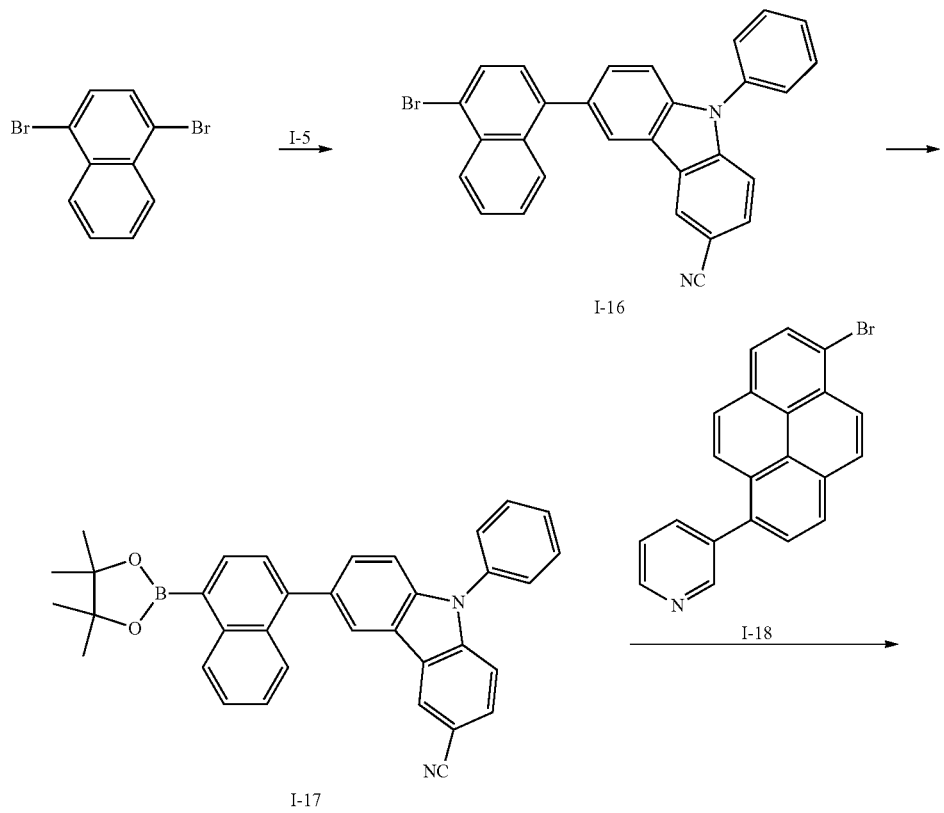

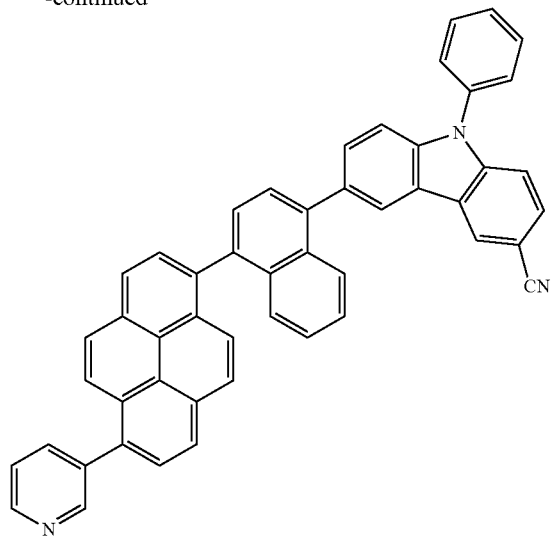

69

1) Synthesis of Intermediate I-16

3.27 g (yield 69%) of Intermediate I-16 was obtained in the same manner as in the synthesis of Compound 2 in Synthesis Example 1, except that 1,4-dibromonaphthalene was used instead of Intermediate I-6. The obtained compound was identified by using LC-MS. $C_{29}H_{17}BrN_2$: $M^+$ 472.1.

2) Synthesis of Intermediate I-17

2.87 g (yield 80%) of Intermediate I-17 was obtained in the same manner as in the synthesis of Intermediate I-9 in Synthesis Example 3, except that Intermediate I-16 was used instead of Intermediate I-8. The obtained compound was identified by using LC-MS. $C_{35}H_{29}BN_2O_2$: $M^+$ 520.2.

3) Synthesis of Intermediate I-18

Intermediate I-18 was synthesized in the same manner as in the synthesis of Intermediate I-6 in Synthesis Example 1, except that 3-pyridine boronic acid was used instead of phenyl boronic acid.

4) Synthesis of Compound 69

2.67 g (yield 72%) of Compound 69 was obtained in the same manner as in the synthesis of Compound 2 in Synthesis Example 1, except that Intermediate I-17 and Intermediate I-18 were used instead of Intermediate I-5 and Intermediate I-6, respectively. The obtained compound was identified by using LC-MS. $C_{50}H_{29}N_3$ cal. 671.24, found 671.27.

Synthesis Example 7: Synthesis of Compound 89

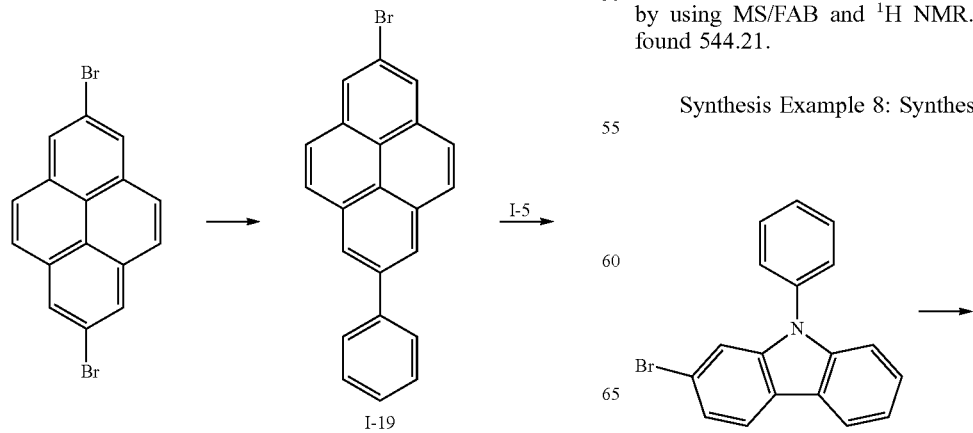

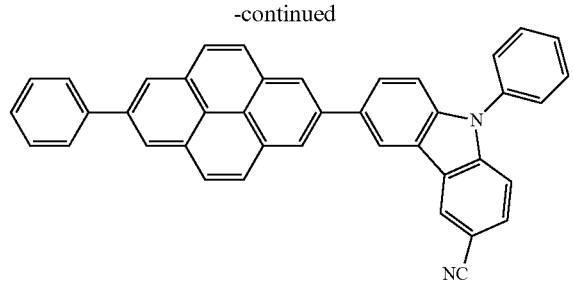

89

1) Synthesis of Intermediate I-19

3.69 g (yield 69%) of Intermediate I-19 was obtained in the same manner as in the synthesis of Intermediate I-6 in Synthesis Example 1, except that 2,7-dibromopyrene was used instead of 1,6-dibromopyrene. The obtained compound was identified by using LC-MS. $C_{22}H_{13}Br$: $M^+$ 356.0.

2) Synthesis of Compound 89

3.93 g (yield 70%) of Compound 89 was obtained in the same manner as in the synthesis of Compound 2 in Synthesis Example 1, except that Intermediate I-19 was used instead of Intermediate I-6. The obtained compound was identified by using MS/FAB and $^1H$ NMR. $C_{41}H_{24}N_2$ cal. 544.19, found 544.21.

Synthesis Example 8: Synthesis of Compound 23

-continued

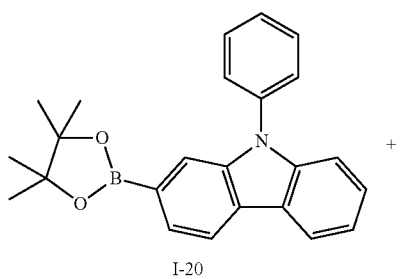

I-20

+

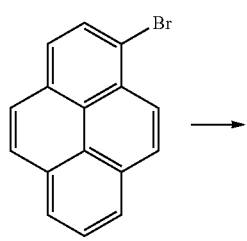

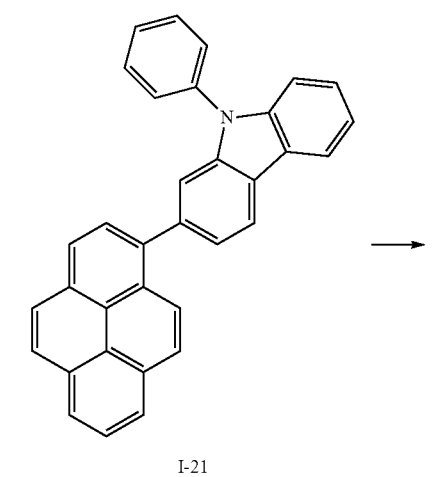

I-21

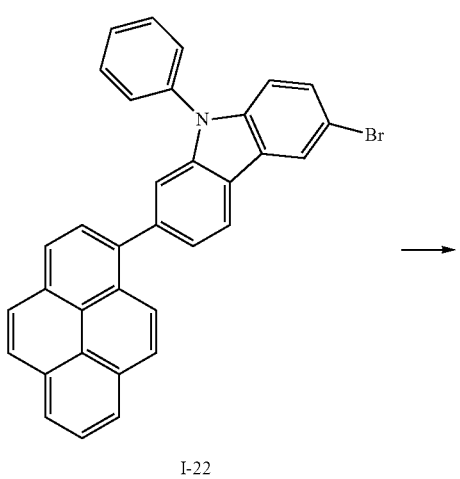

I-22

-continued

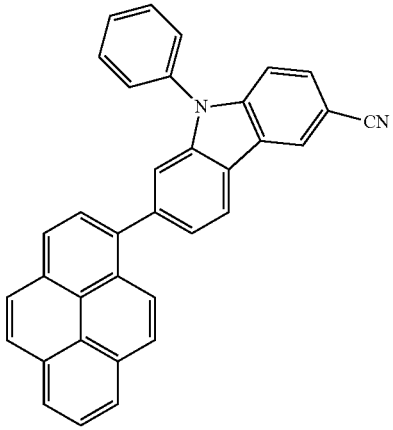

23

1) Synthesis of Intermediate I-20

Intermediate I-20 was synthesized in the same manner as in the synthesis of Intermediate I-5 in Synthesis Example 1, except that 2-bromo-9-phenyl-9H-carbazole was used instead of Intermediate I-4.

2) Synthesis of Intermediate I-21

Intermediate I-21 was synthesized in the same manner as in the synthesis of Intermediate I-6 in Synthesis Example 1, except that 1-bromopyrene and Intermediate I-20 were used instead of 1,6-dibromopyrene and phenyl boronic acid, respectively.

3) Synthesis of Intermediate I-22

Intermediate I-22 was synthesized in the same manner as in the synthesis of Intermediate I-2 in Synthesis Example 1, except that Intermediate I-21 was used instead of Intermediate I-1.

4) Synthesis of Compound 23

2.28 g (yield 75%) of Compound 23 was obtained in the same manner as in the synthesis of Intermediate I-3 in Synthesis Example 1, except that Intermediate I-22 was used instead of Intermediate I-2. The obtained compound was identified by using MS/FAB and $^1$H NMR. $C_{35}H_{20}N_2$ cal. 468.16, found 468.15.

Synthesis Example 9: Synthesis of Compound 36

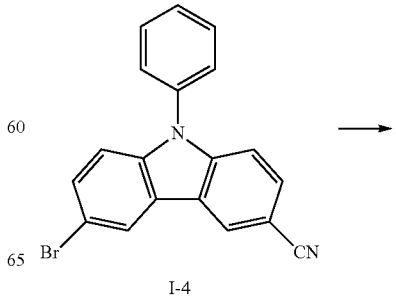

I-4

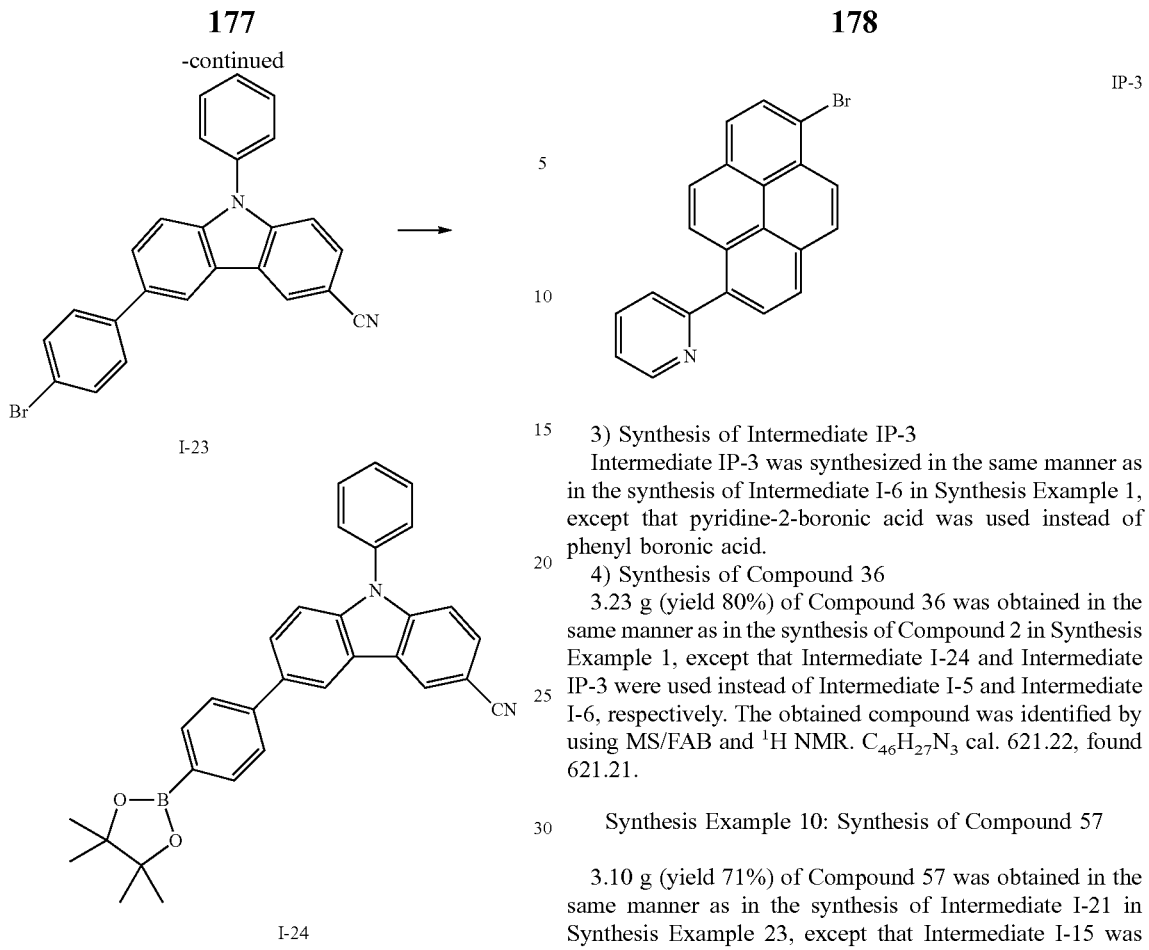

1) Synthesis of Intermediate I-23

5.81 g (16.7 mmol) of Intermediate I-4, 3.53 g (17.6 mmol) of 4-bromophenyl boronic acid, 0.68 g (0.59 mmol) of Pd(PPh$_3$)$_4$, and 4.85 g (35.1 mmol) of K$_2$CO$_3$ were dissolved in 60 mL of THF and 30 mL of H$_2$O to prepare a reaction solution, and the reaction solution was stirred at a temperature of 80° C. for 12 hours. After cooling the reaction solution to room temperature, the reaction solution was extracted three times with 30 mL of water and 30 mL of ethyl acetate to obtain an organic layer. The obtained organic layer was dried with magnesium sulfate and a solvent was evaporated therefrom to obtain residues. The obtained residues were separated and purified by using silica gel column chromatography to obtain 5.30 g (yield 75%) of Intermediate I-23. The obtained compound was identified by using LC-MS. C$_{25}$H$_{15}$BrN$_2$: M$^+$ 422.0.

2) Synthesis of Intermediate I-24

5.81 g (12.6 mmol) of Intermediate I-23, 0.46 g (0.63 mmol) of Pd(dppf)$_2$Cl$_2$, and 3.71 g (37.8 mmol) of KOAc were dissolved in 80 mL of DMSO to prepare a reaction solution, and the reaction solution was stirred at a temperature of 150° C. for 24 hours. After cooling the reaction solution to room temperature, 100 mL of water was added to the reaction solution and then the reaction solution was extracted three times with 50 mL of CH$_2$Cl$_2$ to obtain an organic layer. The obtained organic layer was dried with magnesium sulfate and a solvent was evaporated therefrom to obtain residues. The obtained residues were separated and purified by using silica gel column chromatography to obtain 4.15 g (yield 70%) of Intermediate I-24. The obtained compound was identified by using LC-MS. C$_{31}$H$_{27}$BN$_2$O$_2$: M$^+$ 470.2.

3) Synthesis of Intermediate IP-3

Intermediate IP-3 was synthesized in the same manner as in the synthesis of Intermediate I-6 in Synthesis Example 1, except that pyridine-2-boronic acid was used instead of phenyl boronic acid.

4) Synthesis of Compound 36

3.23 g (yield 80%) of Compound 36 was obtained in the same manner as in the synthesis of Compound 2 in Synthesis Example 1, except that Intermediate I-24 and Intermediate IP-3 were used instead of Intermediate I-5 and Intermediate I-6, respectively. The obtained compound was identified by using MS/FAB and $^1$H NMR. C$_{46}$H$_{27}$N$_3$ cal. 621.22, found 621.21.

Synthesis Example 10: Synthesis of Compound 57

3.10 g (yield 71%) of Compound 57 was obtained in the same manner as in the synthesis of Intermediate I-21 in Synthesis Example 23, except that Intermediate I-15 was used instead of 1-bromopyrene. The obtained compound was identified by using MS/FAB and $^1$H NMR. C$_{51}$H$_{30}$N$_2$ cal. 670.24, found 670.23.

Synthesis Example 11: Synthesis of Compound 10

3.09 g (yield 68%) of Compound 10 was obtained in the same manner as in the synthesis of Compound 2 in Synthesis Example 1, except that Intermediate IP-1 was used instead of Intermediate I-6. The obtained compound was identified by using MS/FAB and $^1$H NMR. C$_{51}$H$_{30}$N$_4$ cal. 698.25, found 698.24.

Synthesis Example 12: Synthesis of Compound 19

3.14 g (yield 72%) of Compound 19 was obtained in the same manner as in the synthesis of Compound 2 in Synthesis Example 1, except that Intermediate I-9 and Intermediate IP-2 were used instead of Intermediate I-5 and Intermediate I-6, respectively. The obtained compound was identified by using MS/FAB and $^1$H NMR. C$_{50}$H$_{29}$N$_3$ cal. 671.24, found 671.22.

Synthesis Example 13: Synthesis of Compound 42

3.47 g (yield 69%) of Compound 42 was obtained in the same manner as in the synthesis of Compound 2 in Synthesis Example 1, except that Intermediate I-24 and Intermediate IP-4 were used instead of Intermediate I-5 and Intermediate I-6, respectively. The obtained compound was identified by using MS/FAB and $^1$H NMR. C$_{57}$H$_{34}$N$_4$ cal. 774.28, found 774.30.

Synthesis Example 14: Synthesis of Compound 50

3.22 g (yield 71%) of Compound 50 was obtained in the same manner as in the synthesis of Compound 2 in Synthesis Example 1, except that Intermediate I-25 and Intermediate IP-5 were used instead of Intermediate I-5 and Intermediate I-6, respectively. The obtained compound was identified by using MS/FAB and $^1$H NMR. $C_{52}H_{31}N_3$ cal. 697.25, found 697.26.

Synthesis Example 15: Synthesis of Compound 58

2.66 g (yield 75%) of Compound 58 was obtained in the same manner as in the synthesis of Compound 2 in Synthesis Example 1, except that Intermediate I-26 and Intermediate IP-3 were used instead of Intermediate I-5 and Intermediate I-6, respectively. The obtained compound was identified by using MS/FAB and $^1$H NMR. $C_{40}H_{22}N_2O$ cal. 546.17, found 546.15.

Synthesis Example 16: Synthesis of Compound 64

3.17 g (yield 63%) of Compound 64 was obtained in the same manner as in the synthesis of Compound 2 in Synthesis Example 1, except that Intermediate I-27 and Intermediate IP-1 were used instead of Intermediate I-5 and Intermediate I-6, respectively. The obtained compound was identified by using MS/FAB and $^1$H NMR. $C_{57}H_{34}N_4$ cal. 774.28, found 774.29.

Synthesis Example 17: Synthesis of Compound 73

2.67 g (yield 66%) of Compound 73 was obtained in the same manner as in the synthesis of Compound 2 in Synthesis Example 1, except that Intermediate I-28 and Intermediate I-6 were used instead of Intermediate I-5 and Intermediate I-6, respectively. The obtained compound was identified by using MS/FAB and $^1$H NMR. $C_{46}H_{27}N_3$ cal. 621.22, found 621.24.

Synthesis Example 18: Synthesis of Compound 77

3.31 g (yield 76%) of Compound 77 was obtained in the same manner as in the synthesis of Compound 2 in Synthesis Example 1, except that Intermediate I-29 and Intermediate I-6 were used instead of Intermediate I-5 and Intermediate I-6, respectively. The obtained compound was identified by using MS/FAB and $^1$H NMR. $C_{51}H_{30}N_2$ cal. 670.24, found 670.22.

Synthesis Example 19: Synthesis of Compound 83

2.64 g (yield 68%) of Compound 83 was obtained in the same manner as in the synthesis of Compound 2 in Synthesis Example 1, except that Intermediate I-30 and Intermediate IP-3 were used instead of Intermediate I-5 and Intermediate I-6, respectively. The obtained compound was identified by using MS/FAB and $^1$H NMR. $C_{44}H_{24}N_2O$ cal. 596.19, found 596.21.

Synthesis Example 20: Synthesis of Compound 85

2.44 g (yield 63%) of Compound 85 was obtained in the same manner as in the synthesis of Compound 2 in Synthesis Example 1, except that Intermediate I-31 and Intermediate I-10 were used instead of Intermediate I-5 and Intermediate I-6, respectively. The obtained compound was identified by using MS/FAB and $^1$H NMR. $C_{45}H_{25}NO$ cal. 595.19, found 595.20.

Synthesis Example 21: Synthesis of Compound 96

3.32 g (yield 73%) of Compound 96 was obtained in the same manner as in the synthesis of Compound 2 in Synthesis Example 1, except that Intermediate IP-6 were used instead of Intermediate I-6, respectively. The obtained compound was identified by using MS/FAB and $^1$H NMR. $C_{51}H_{30}N_4$ cal. 698.25, found 698.24.

Synthesis Example 22: Synthesis of Compound 103

3.13 g (yield 81%) of Compound 103 was obtained in the same manner as in the synthesis of Compound 2 in Synthesis Example 1, except that Intermediate I-9 and Intermediate IP-7 were used instead of Intermediate I-5 and Intermediate I-6, respectively. The obtained compound was identified by using MS/FAB and $^1$H NMR. $C_{45}H_{26}N_2$ cal. 594.21, found 594.20.

Synthesis Example 23: Synthesis of Compound 109

3.41 g (yield 75%) of Compound 109 was obtained in the same manner as in the synthesis of Compound 2 in Synthesis Example 1, except that Intermediate I-9 and Intermediate IP-8 were used instead of Intermediate I-5 and Intermediate I-6, respectively. The obtained compound was identified by using MS/FAB and $^1$H NMR. $C_{50}H_{29}N_5$ cal. 699.24, found 699.25.

Synthesis Example 24: Synthesis of Compound 116

2.71 g (yield 78%) of Compound 116 was obtained in the same manner as in the synthesis of Compound 2 in Synthesis Example 1, except that Intermediate I-14 and Intermediate IP-9 were used instead of Intermediate I-5 and Intermediate I-6, respectively. The obtained compound was identified by using MS/FAB and $^1$H NMR. $C_{39}H_{21}NS$ cal. 535.14, found 535.15.

Synthesis Example 25: Synthesis of Compound 117

2.90 g (yield 82%) of Compound 117 was obtained in the same manner as in the synthesis of Compound 2 in Synthesis Example 1, except that Intermediate I-24 and Intermediate IP-10 were used instead of Intermediate I-5 and Intermediate I-6, respectively. The obtained compound was identified by using MS/FAB and $^1$H NMR. $C_{41}H_{24}N_2$ cal. 544.19, found 544.21.

Synthesis Example 26: Synthesis of Compound 127

3.88 g (yield 77%) of Compound 127 was obtained in the same manner as in the synthesis of Compound 2 in Synthesis Example 1, except that Intermediate I-24 and Intermediate IP-8 were used instead of Intermediate I-5 and Intermediate I-6, respectively. The obtained compound was identified by using MS/FAB and $^1$H NMR. $C_{56}H_{33}N_5$ cal. 775.27, found 775.28.

Synthesis Example 27: Synthesis of Compound 134

3.36 g (yield 74%) of Compound 134 was obtained in the same manner as in the synthesis of Compound 2 in Synthesis Example 1, except that Intermediate I-25 and Intermediate IP-11 were used instead of Intermediate I-5 and Intermediate I-6, respectively. The obtained compound was identified by using MS/FAB and $^1$H NMR. $C_{51}H_{30}N_4$ cal. 698.25, found 698.26.

Synthesis Example 28: Synthesis of Compound 143

2.56 g (yield 72%) of Compound 143 was obtained in the same manner as in the synthesis of Compound 2 in Synthesis Example 1, except that Intermediate I-32 and Intermediate IP-12 were used instead of Intermediate I-5 and Intermediate I-6, respectively. The obtained compound was identified by using MS/FAB and $^1$H NMR. $C_{40}H_{22}N_2O$ cal. 546.17, found 546.18.

Synthesis Example 29: Synthesis of Compound 147

3.48 g (yield 69%) of Compound 147 was obtained in the same manner as in the synthesis of Compound 2 in Synthesis Example 1, except that Intermediate I-27 and Intermediate IP-13 were used instead of Intermediate I-5 and Intermediate I-6, respectively. The obtained compound was identified by using MS/FAB and $^1$H NMR. $C_{57}H_{34}N_4$ cal. 774.28, found 774.30.

Synthesis Example 30: Synthesis of Compound 151

3.79 g (yield 73%) of Compound 151 was obtained in the same manner as in the synthesis of Compound 2 in Synthesis Example 1, except that Intermediate I-17 and Intermediate IP-14 were used instead of Intermediate I-5 and Intermediate I-6, respectively. The obtained compound was identified by using MS/FAB and $^1$H NMR. $C_{60}H_{35}N_3$ cal. 797.28, found 797.30.

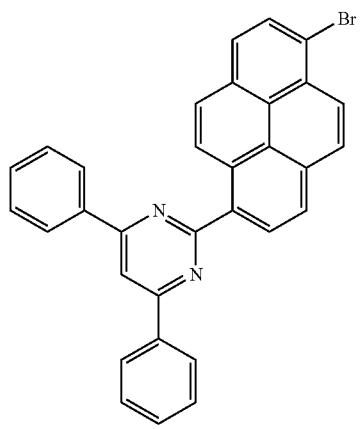

IP-1

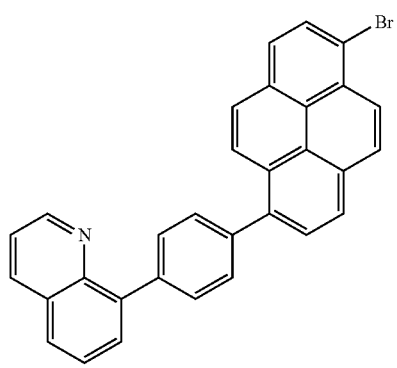

IP-2

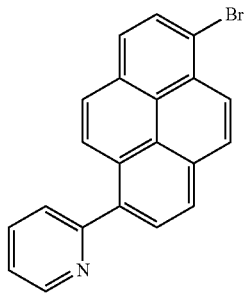

IP-3

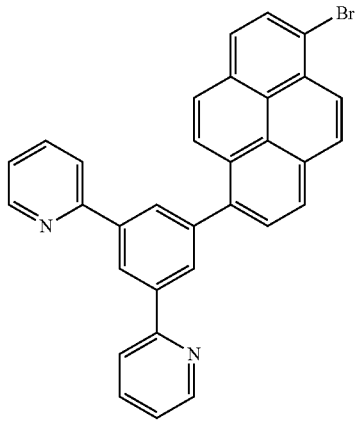

IP-4

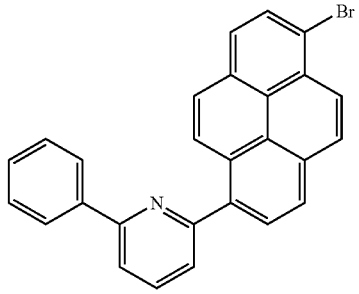

IP-5

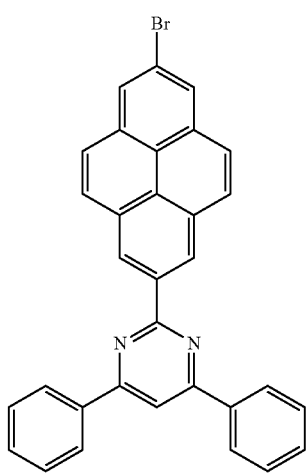

IP-6

IP-7
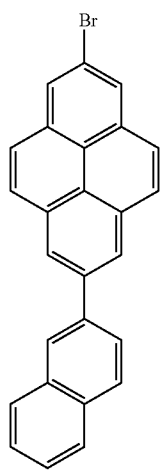
IP-8
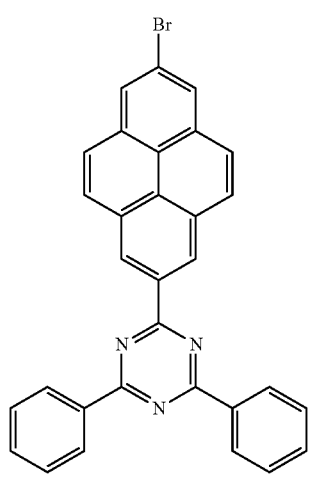
IP-9
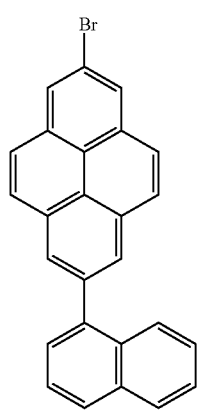
IP-10
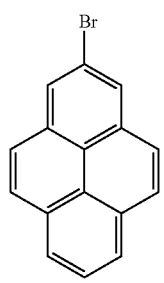
IP-11
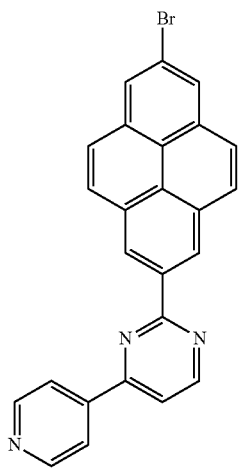
IP-12
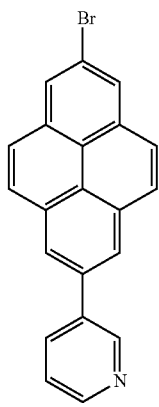
IP-13
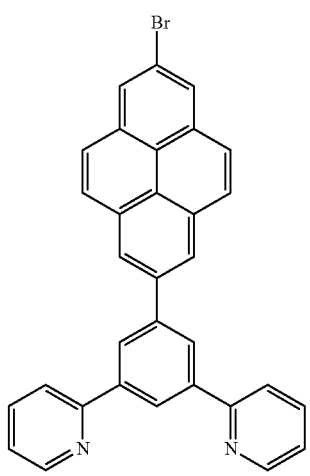

-continued
IP-14
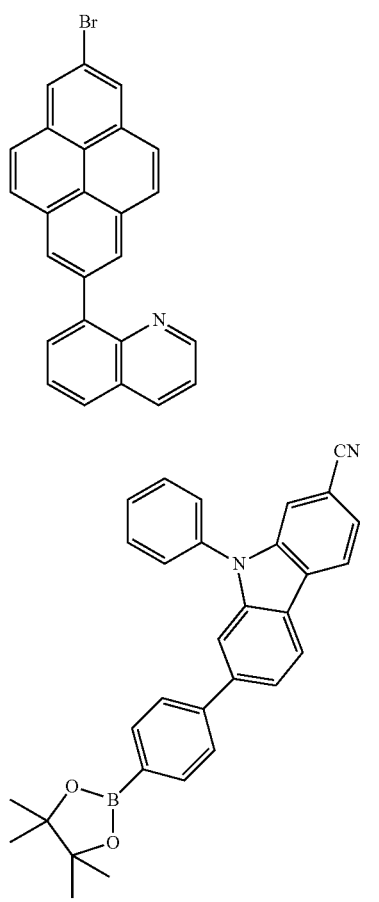
I-25
I-26
I-27
I-28
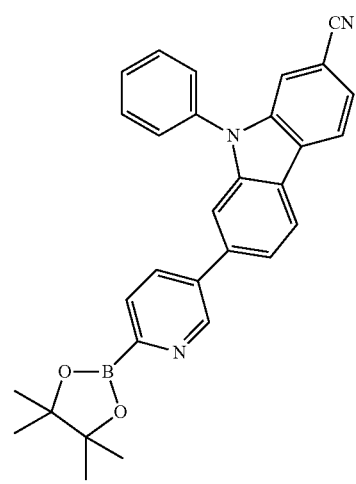
I-29
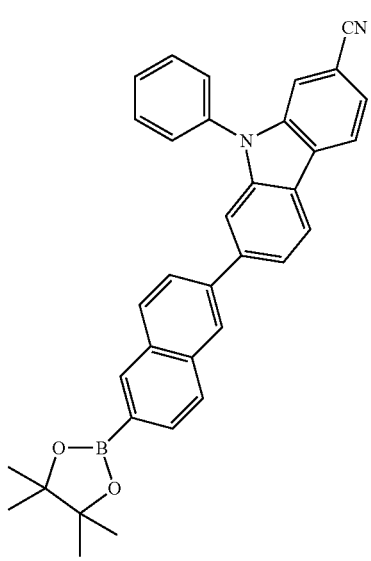
I-30
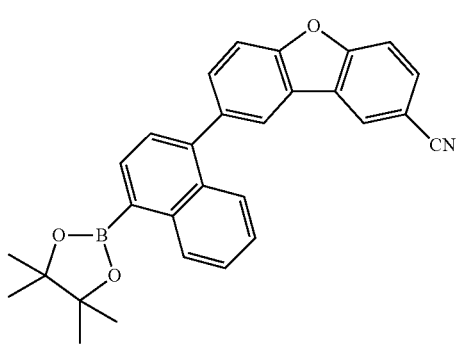

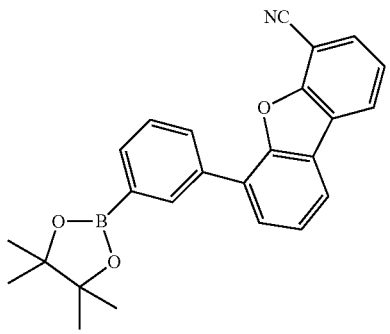

I-31

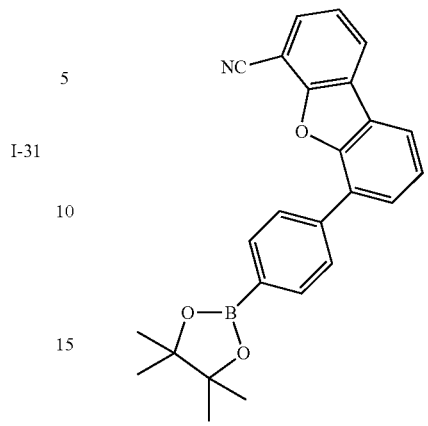

I-32

Table 1 below shows results of ¹H NMR and MS/FAB of compounds synthesized above.

Synthesis methods of compounds other than the compounds shown in Table 1 below may be obvious to one of ordinary skill in the art by referring to Synthesis Examples 1 to 30.

TABLE 1

| Compound | ¹H NMR (CDCl₃, 400 MHz) | MS/FAB found | MS/FAB calc. |
|---|---|---|---|
| 2 | δ = 8.16-8.14 (m, 2H), 8.12-8.11 (m, 1H), 8.03-8.00 (m, 2H), 7.98-7.96 (m, 3H), 7.89-7.87 (dd, 1H), 7.84-7.81 (m, 2H), 7.67 (d, 1H), 7.65-7.64 (m, 2H), 7.62 (d, 1H), 7.53-7.46 (m, 6H), 7.41-7.38 (m, 1H) 7.31-7.29 (m, 1H), 7.27-7.25 (dd, 1H) | 544.22 | 544.19 |
| 6 | δ = 8.42 (d, 1H), 8.29-8.28 (m, 2H), 8.26-8.25 (m, 1H), 8.18 (d, 1H), 8.16-8.15 (m, 1H), 8.08-8.07 (m, 1H), 8.02 (d, 1H), 7.98-7.89 (m, 2H), 7.84-7.79 (m, 3H), 7.72-7.70 (m, 2H), 7.67-7.62 (m, 3H), 7.52-7.47 (m, 6H), 7.42-7.38 (m, 1H), 7.34-7.28 (m, 2H) | 621.18 | 621.22 |
| 10 | δ = 8.41 (d, 1H), 8.32-8.29 (m, 7H), 8.28-8.27 (m, 1H), 8.22 (d, 1H), 8.11 (d, 1H), 8.00 (d, 1H), 7.97 (s, 2H), 7.89-7.87 (m, 1H), 7.67-7.62 (m, 3H), 7.53-7.47 (m, 8H), 7.34-7.26 (m, 4H) | 698.21 | 698.25 |
| 16 | δ = 8.24-8.22 (m, 1H), 8.14-8.13 (m, 1H), 8.07-8.05 (m, 1H), 8.03-8.01 (m, 2H), 8.00-7.99 (m, 2H), 7.99-7.98 (m, 1H), 7.94-7.90 (m, 2H), 7.89-7.88 (m, 2H), 7.86-7.84 (m, 1H), 7.81-7.76 (m, 4H), 7.62-7.57 (m, 2H), 7.55-7.52 (m, 5H), 7.34-7.29 (m, 2H) | 594.25 | 594.21 |
| 19 | δ = 8.45-8.44 (dd, 1H), 8.34-8.32 (dd, 1H), 8.24-8.18 (m, 2H), 8.12-8.10 (m, 2H), 8.08-8.05 (m, 2H), 8.03-7.99 (m, 3H), 7.97-7.93 (m, 2H), 7.85-7.77 (m, 3H), 7.71 (s, 4H), 7.61-7.57 (m, 3H), 7.53-7.51 (m, 3H), 7.47-7.45 (m, 1H), 7.34-7.28 (m, 2H) | 671.22 | 671.24 |
| 23 | δ = 8.28-8.26 (m, 1H), 8.19-8.18 (m, 1H), 8.15-8.14 (m, 1H), 8.12-8.11 (m, 1H), 8.09-8.08 (m, 2H), 8.04-7.98 (m, 3H), 7.88-7.84 (m, 2H), 7.80-7.78 (m, 1H), 7.64-7.62 (dd, 1H), 7.55-7.48 (m, 4H), 7.34-7.33 (m, 1H), 7.31-7.27 (m, 2H) | 468.20 | 468.16 |
| 27 | δ = 8.36-8.35 (m, 1H), 8.29-8.28 (m, 1H), 8.12-8.10 (m, 1H), 8.05-8.02 (m, 3H), 8.00-7.98 (m, 2H), 7.89-7.83 (m, 3H), 7.81-7.78 (m, 1H), 7.69-7.67 (m, 1H), 7.65-7.64 (m, 1H), 7.63-7.62 (m, 1H), 7.52-7.47 (m, 2H), 7.41-7.37 (m, 1H) | 469.11 | 469.15 |
| 32 | δ = 8.37-8.36 (m, 1H), 8.27-8.26 (m, 1H), 8.16 (d, 1H), 8.14 (d, 1H), 8.03-7.99 (m, 3H), 7.95-7.89 (m, 2H), 7.87-7.85 (dd, 1H), 7.82-7.75 (m, 2H), 7.69-7.67 (m, 3H), 7.64-7.58 (m, 3H), 7.47-7.45 (dd, 1H), 7.31-7.27 (tt, 1H), 7.05-7.01 (tt, 1H) | 535.17 | 535.14 |
| 36 | δ = 8.41-8.38 (m, 2H), 8.26-8.25 (m, 1H), 8.19-8.18 (m, 1H), 8.11-8.10 (m, 1H), 8.06-8.04 (m, 1H), 8.00-7.95 (m, 4H), 7.92-7.89 (m, 1H), 7.87-7.82 (m, 2H), 7.76-7.73 (m, 2H), 7.70-7.60 (m, 5H), 7.52-7.46 (m, 4H), 7.34-7.23 (m, 3H) | 621.19 | 621.22 |
| 42 | δ = 8.38-8.36 (m, 2H), 8.31 (d, 2H), 8.27 (t, 1H), 8.21-8.19 (m, 2H), 8.16-8.15 (m, 1H), 8.10-8.09 (m, 1H), 8.01-7.94 (m, 4H), 7.92-7.90 (m, 2H), 7.85-7.81 (m, 2H), 7.75-7.70 (m, 6H), 7.65-7.60 (m, 3H), 7.53-7.46 (m, 4H), 7.34-7.26 (m, 4H) | 774.25 | 774.28 |

TABLE 1-continued

| Compound | ¹H NMR (CDCl₃, 400 MHz) | MS/FAB found | MS/FAB calc. |
|---|---|---|---|
| 50 | δ = 8.40 (d, 1H), 8.18-8.16 (m, 2H), 8.12-8.08 (m, 2H), 8.03-7.99 (m, 3H), 7.93-7.91 (m, 2H), 7.89-7.86 (m, 3H), 7.83-7.79 (m, 3H), 7.76-7.71 (m, 3H), 7.66-7.64 (dd, 1H), 7.61-7.58 (m, 2H), 7.55-7.53 (m, 4H), 7.50-7.47 (m, 2H), 7.42-7.39 (m, 1H), 7.33-7.28 (m, 2H) | 697.21 | 697.25 |
| 57 | δ = 8.22-8.21 (m, 1H), 8.11-8.10 (m, 1H), 8.02-8.00 (m, 3H), 7.95-7.92 (m, 2H), 7.89-7.86 (m, 3H), 7.83-7.81 (m, 2H), 7.80-7.78 (m, 2H), 7.77-7.74 (m, 1H), 7.65-7.63 (m, 1H), 7.62-7.58 (m, 4H), 7.54-7.48 (m, 5H), 7.33-7.25 (m, 4H), 7.04-7.00 (m, 1H) | 670.25 | 670.24 |
| 58 | δ = 8.34-8.32 (dd, 1H), 8.31-8.30 (m, 1H), 8.23-8.21 (m, 1H), 8.18-8.17 (m, 1H), 8.12-8.10 (m, 1H), 8.05 (d, 1H), 8.00-7.99 (m, 1H), 7.94-7.84 (m, 4H), 7.82-7.78 (m, 2H), 7.76-7.73 (m, 4H), 7.70-7.59 (m, 4H), 7.25-7.22 (m, 1H) | 546.21 | 546.17 |
| 64 | δ = 8.45 (d, 1H), 8.25-8.21 (m, 7H), 8.15 (d, 1H), 8.11-8.07 (m, 2H), 8.03-7.96 (m, 4H), 7.83-7.81 (m, 1H), 7.76-7.74 (m, 1H), 7.67-7.62 (m, 3H), 7.59-7.56 (m, 1H), 7.53-7.46 (m, 8H), 7.42-7.39 (m, 1H), 7.32-7.26 (m, 4H) | 774.31 | 774.28 |
| 69 | δ = 8.44-8.43 (m, 1H), 8.28-8.26 (m, 1H), 8.22-8.21 (m, 1H), 8.19 (d, 1H), 8.11-8.09 (m, 1H), 8.06-8.02 (m, 3H), 7.98-7.81 (m, 8H), 7.69-7.62 (m, 4H), 7.52-7.47 (m, 4H), 7.42-7.38 (m, 1H), 7.34-7.27 (m, 2H), 7.06-7.01 (m, 2H) | 671.27 | 671.24 |
| 73 | δ = 8.57-8.56 (dd, 1H), 8.40-8.39 (d, 1H), 8.09-8.03 (m, 6H), 7.99-7.89 (m, 6H), 7.75-7.73 (dd, 1H), 7.67-7.63 (m, 2H), 760-7.58 (dd, 1H), 7.54-7.48 (m, 6H), 7.45-7.44 (m, 1H), 7.41-7.37 (m, 1H), 7.32-7.27 (m, 1H) | 621.19 | 621.22 |
| 77 | δ = 8.22-8.21 (m, 1H), 8.10-8.09 (m, 1H), 8.06-8.03 (m, 6H), 8.01-7.98 (m, 5H), 7.86-7.85 (dd, 1H), 7.83-7.80 (m, 2H), 7.76-7.72 (m, 3H), 7.64-7.62 (m, 1H), 7.60-7.58 (dd, 1H), 7.55-7.53 (m, 4H), 7.51-7.47 (m, 2H), 7.42-7.36 (m, 2H), 7.33-7.28 (m, 1H) | 670.26 | 670.24 |
| 83 | δ = 8.38-8.37 (dd, 1H), 8.35 (d, 1H), 8.25-8.24 (m, 1H), 8.21-8.20 (m, 1H), 8.08-8.02 (m, 3H), 7.99-7.92 (m, 2H), 7.88-7.82 (m, 5H), 7.78-7.76 (m, 1H), 7.71-7.62 (m, 6H), 7.28-7.25 (m, 1H), 7.08-7.03 (m, 2H) | 596.22 | 596.19 |
| 85 | δ = 8.21-8.19 (m, 1H), 8.13-8.12 (m, 1H), 8.10-8.08 (dd, 1H), 8.06-8.03 (m, 3H), 8.01-7.98 (m, 2H), 7.93-7.90 (m, 4H), 7.88-7.87 (m, 1H), 7.86-7.85 (m, 2H), 7.84-7.82 (m, 2H), 7.78-7.74 (m, 2H), 7.62-7.53 (m, 5H), 7.48-7.44 (m, 1H) | 595.15 | 595.19 |
| 89 | δ = 8.18-8.17 (m, 3H), 8.16-8.15 (m, 1H), 8.13-8.12 (m, 2H), 7.97-7.96 (m, 2H), 7.94-7.92 (m, 2H), 7.79-7.78 (dd, 2H), 7.76-7.74 (m, 2H), 7.65-7.63 (dd, 1H), 7.53-7.43 (m, 7H), 7.34-7.26 (m, 2H) | 544.21 | 544.19 |
| 96 | δ = 8.36-8.34 (m, 2H), 8.23-8.21 (m, 3H), 8.19-8.18 (m, 2H), 8.14-8.13 (m, 3H), 8.12-8.11 (m, 1H), 8.01-7.96 (m, 4H), 7.79 (d, 2H), 7.74-7.71 (m, 4H), 7.65-7.63 (dd, 1H), 7.51-7.46 (m, 4H), 7.34-7.26 (m, 4H) | 689.28 | 698.25 |
| 103 | δ = 8.28-8.26 (m, 2H), 8.19-8.18 (m, 2H), 8.13-8.12 (m, 1H), 8.03-7.98 (m, 4H), 7.97-7.93 (m, 6H), 7.88-7.85 (m, 2H), 7.76-7.74 (dd, 1H), 7.62-7.57 (m, 2H), 7.54 (s, 2H), 7.53-7.51 (m, 3H), 7.33-7.27 (m, 1H) | 594.19 | 594.21 |
| 109 | δ = 8.45-8.44 (m, 2H), 8.40-8.39 (m, 2H), 8.38-8.37 (m, 2H), 8.24-8.23 (m, 2H), 8.20-8.19 (m, 2H), 8.14-8.13 (m, 2H), 8.03-7.98 (m, 3H), 7.88-7.87 (m, 1H), 7.76-7.74 (dd, 1H), 7.63-7.58 (m, 5H), 7.55-7.51 (m, 4H), 7.42-7.38 (tt, 2H), 7.32-7.27 (m, 1H) | 699.28 | 699.24 |
| 116 | δ = 8.41-8.40 (m, 1H), 8.35-8.34 (m, 1H), 8.22 (d, 2H), 8.19 (d, 2H), 8.09-8.07 (m, 1H), 8.03-8.01 (m, 1H), 7.99-7.96 (m, 5H), 7.92-7.90 (m, 1H), 7.77-7.76 (m, 1H), 7.75-7.74 (m, 1H), 7.69-7.67 (dd, 1H), 7.51-7.42 (m, 2H), 7.25-7.21 (m, 1H), 7.18-7.15 (m, 1H) | 535.11 | 535.14 |
| 117 | δ = 8.31-8.30 (m, 1H), 8.29-8.28 (m, 2H), 8.23-8.22 (m, 1H), 8.20-8.19 (m, 2H), 8.10-8.09 (m, 1H), 8.06-8.05 (m, 1H), 8.03-8.00 (m, 2H), 7.98-7.97 (m, 1H), 7.87-7.86 (m, 1H), 7.85-7.81 (m, 4H), 7.65-7.61 (m, 2H), 7.53-7.46 (m, 4H), 7.34-7.26 (m, 2H) | 544.23 | 544.19 |
| 127 | δ = 8.31-8.30 (m, 1H), 8.29-8.28 (m, 2H), 8.23-8.22 (m, 1H), 8.20-8.19 (m, 2H), 8.10-8.09 (m, 1H), 8.06-8.05 (m, 1H), 8.03-8.00 (m, 2H), 7.98-7.97 (m, 1H), 7.87-7.86 (m, 1H), 7.85-7.81 (m, 4H), 7.65-7.61 (m, 2H), 7.53-7.46 (m, 4H), 7.34-7.26 (m, 2H) | 775.30 | 775.27 |
| 134 | δ = 8.33-8.31 (m, 2H), 8.27-8.26 (m, 2H), 8.19-8.18 (m, 2H), 8.15-8.14 (m, 1H), 8.12-8.11 (m, 1H), 8.03-8.01 (m, 5H), 7.99-7.98 (m, 1H), 7.93-7.88 (m, 5H), 7.84-7.81 (m, 1H), 7.76-7.71 (m, 3H), 7.60-7.58 (dd, 1H), 7.54-7.51 (m, 4H), 7.33-7.27 (m, 2H) | 698.27 | 698.25 |

TABLE 1-continued

| Compound | $^1$H NMR (CDCl$_3$, 400 MHz) | MS/FAB found | calc. |
|---|---|---|---|
| 143 | δ = 8.55-8.54 (m, 1H), 8.38-8.36 (m, 1H), 8.28-8.26 (dd, 1H), 8.23-8.22 (m, 2H), 8.19-8.18 (m, 2H), 8.11-8.08 (dd, 1H), 8.05-8.01 (m, 2H), 7.99-7.98 (m, 1H), 7.94-7.91 (m, 3H), 7.87-7.82 (m, 3H), 7.77-7.74 (m, 2H), 7.57-7.53 (m, 1H), 7.48-7.44 (m, 2H) | 546.20 | 546.17 |
| 147 | δ = 8.36-8.34 (m, 2H), 8.26-8.24 (m, 3H), 8.21-8.20 (m, 2H), 8.17-8.16 (m, 2H), 8.13-8.11 (m, 2H), 8.02-8.00 (m, 2H), 7.99-7.98 (m, 1H), 7.97-7.96 (m, 2H), 7.83-7.81 (m, 1H), 7.73-7.67 (m, 5H), 7.65-7.60 (m, 2H), 7.55-7.46 (m, 5H), 7.32-7.23 (m, 5H) | 774.31 | 774.28 |
| 151 | δ = 8.47-8.45 (dd, 1H), 8.30-8.28 (dd, 1H), 8.24-8.22 (m, 5H), 8.20-8.19 (m, 1H), 8.17-8.16 (m, 1H), 8.12-8.10 (m, 1H), 8.00-7.97 (m, 5H), 7.94-7.90 (m, 1H), 7.86-7.81 (m, 3H), 7.74-7.70 (m, 3H), 7.66-7.62 (m, 3H), 7.58-7.56 (m, 1H), 7.52-7.47 (m, 5H), 7.34-7.26 (m, 2H), 7.07-7.03 (m, 2H) | 797.32 | 797.28 |
| 162 | δ = 8.35-8.34 (m, 2H), 8.28-8.27 (m, 1H), 8.25-8.24 (m, 2H), 8.02-8.00 (m, 1H), 7.98-7.96 (m, 2H), 7.95-7.92 (m, 3H), 7.81-7.79 (dd, 1H), 7.76-7.73 (m, 2H), 7.70-7.67 (m, 1H), 7.66-7.62 (m, 2H), 7.54-7.50 (m, 4H), 7.45-7.42 (m, 3H), 7.36-7.34 (m, 1H), 7.32-7.25 (m, 3H) | 620.19 | 620.23 |

Example 1

An ITO glass substrate (a product of Corning Co., Ltd) including an ITO layer having a thickness of 15 Ω/cm$^2$ (1200 Å) was cut to a size of 50 mm×50 mm×0.7 mm, sonicated by using isopropyl alcohol and pure water each for 5 minutes, and cleaned by irradiating ultraviolet rays and exposing to ozone for 30 minutes. Then, the ITO glass substrate was mounted on a vacuum deposition apparatus.

2-TNATA was deposited on the ITO layer acting as an anode to form a hole injection layer having a thickness of 600 Å, NPB was deposited on the hole injection layer to form a hole transport layer having a thickness of 300 Å, and then, DNA (host) and DPAVBi (dopant) were co-deposited at a weight ratio of 98:2 on the emission layer to form an emission layer having a thickness of 300 Å.

Thereafter, Compound 2 was deposited on the emission layer to form an electron transport layer having a thickness of 300 Å, LiF was deposited on the electron transport layer to form an electron injection layer having a thickness of 10 Å, and Al was deposited on the electron injection layer to form a cathode having a thickness of 3000 Å, thereby completing the manufacture of an organic light-emitting device.

Example 2

An organic light-emitting device was manufactured in the same manner as in Example 1, except that in forming an electron transport layer, Compound 10 was used instead of Compound 2.

Example 3

An organic light-emitting device was manufactured in the same manner as in Example 1, except that in forming an electron transport layer, Compound 16 was used instead of Compound 2.

Example 4

An organic light-emitting device was manufactured in the same manner as in Example 1, except that in forming an electron transport layer, Compound 32 was used instead of Compound 2.

Example 5

An organic light-emitting device was manufactured in the same manner as in Example 1, except that in forming an electron transport layer, Compound 36 was used instead of Compound 2.

Example 6

An organic light-emitting device was manufactured in the same manner as in Example 1, except that in forming an electron transport layer, Compound 50 was used instead of Compound 2.

Example 7

An organic light-emitting device was manufactured in the same manner as in Example 1, except that in forming an electron transport layer, Compound 57 was used instead of Compound 2.

Example 8

An organic light-emitting device was manufactured in the same manner as in Example 1, except that in forming an electron transport layer, Compound 58 was used instead of Compound 2.

Example 9

An organic light-emitting device was manufactured in the same manner as in Example 1, except that in forming an electron transport layer, Compound 77 was used instead of Compound 2.

Example 10

An organic light-emitting device was manufactured in the same manner as in Example 1, except that in forming an electron transport layer, Compound 89 was used instead of Compound 2.

Example 11

An organic light-emitting device was manufactured in the same manner as in Example 1, except that in forming an electron transport layer, Compound 103 was used instead of Compound 2.

Example 12

An organic light-emitting device was manufactured in the same manner as in Example 1, except that in forming an electron transport layer, Compound 117 was used instead of Compound 2.

Example 13

An organic light-emitting device was manufactured in the same manner as in Example 1, except that in forming an electron transport layer, Compound 127 was used instead of Compound 2.

Example 14

An organic light-emitting device was manufactured in the same manner as in Example 1, except that in forming an electron transport layer, Compound 134 was used instead of Compound 2.

Example 15

An organic light-emitting device was manufactured in the same manner as in Example 1, except that in forming an electron transport layer, Compound 143 was used instead of Compound 2.

Example 16

An organic light-emitting device was manufactured in the same manner as in Example 1, except that in forming an electron transport layer, Compound 147 was used instead of Compound 2.

Comparative Example 1

An organic light-emitting device was manufactured in the same manner as in Example 1, except that in forming an electron transport layer, Alq$_3$ was used instead of Compound 2.

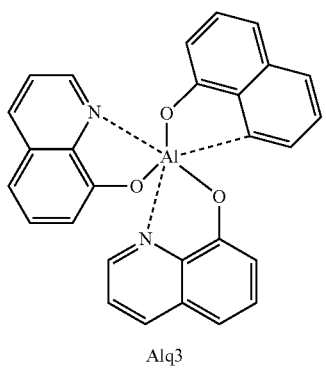

Alq3

Comparative Example 2

An organic light-emitting device was manufactured in the same manner as in Example 1, except that in forming an electron transport layer, Compound A was used instead of Compound 2.

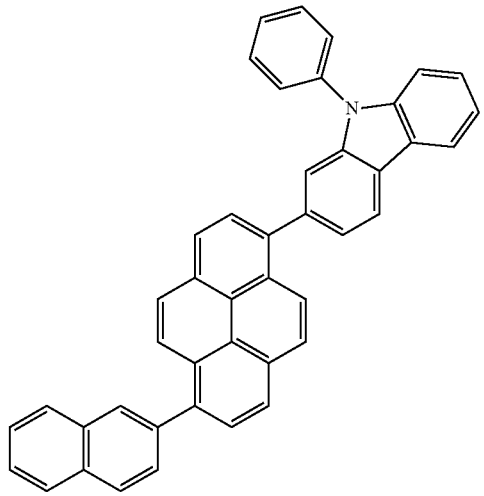

Compound A

Comparative Example 3

An organic light-emitting device was manufactured in the same manner as in Example 1, except that in forming an electron transport layer, Compound B was used instead of Compound 2.

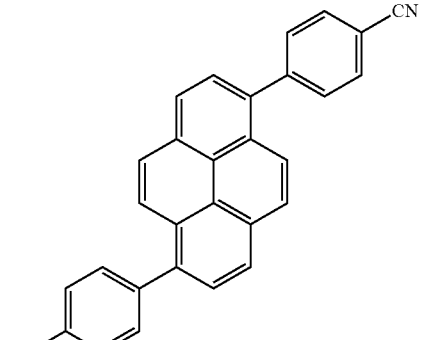

Compound B

Evaluation Example 1

The driving voltage, current density, brightness, efficiency, and half-life of the organic light-emitting devices manufactured according to Examples 1 to 16, and Comparative Examples 1 and 3 were measured by using a Kethley SMU 236 and a brightness photometer PR650, and results thereof are shown in Table 2. The half-life is a period of time that is taken until the brightness of the organic light-emitting device reduces down to 50% from the initial brightness after operating the organic light-emitting device.

TABLE 2

| | Electron Transport Layer | Driving voltage (V) | Current density (mA/cm$^2$) | Brightness (cd/m$^2$) | Efficiency (cd/A) | Emission color | Half-life (hr @ 100 mA/cm$^2$) |
|---|---|---|---|---|---|---|---|
| Example 1 | Compound 2 | 5.42 | 50 | 3220 | 6.44 | Blue | 505 |
| Example 2 | Compound 10 | 4.97 | 50 | 3415 | 6.83 | Blue | 448 |
| Example 3 | Compound 16 | 5.51 | 50 | 3335 | 6.67 | Blue | 513 |
| Example 4 | Compound 32 | 5.59 | 50 | 3190 | 6.38 | Blue | 379 |
| Example 5 | Compound 36 | 5.04 | 50 | 3460 | 6.92 | Blue | 457 |
| Example 6 | Compound 50 | 5.12 | 50 | 3380 | 6.76 | Blue | 439 |
| Example 7 | Compound 57 | 5.62 | 50 | 3235 | 6.47 | Blue | 487 |
| Example 8 | Compound 58 | 4.83 | 50 | 3340 | 6.68 | Blue | 368 |
| Example 9 | Compound 77 | 5.48 | 50 | 3275 | 6.55 | Blue | 508 |
| Example 10 | Compound 89 | 5.53 | 50 | 3235 | 6.47 | Blue | 501 |
| Example 11 | Compound 103 | 5.70 | 50 | 3255 | 6.51 | Blue | 491 |
| Example 12 | Compound 117 | 5.44 | 50 | 3200 | 6.40 | Blue | 485 |
| Example 13 | Compound 127 | 4.89 | 50 | 3510 | 7.02 | Blue | 434 |
| Example 14 | Compound 134 | 4.99 | 50 | 3460 | 6.92 | Blue | 440 |
| Example 15 | Compound 143 | 5.01 | 50 | 3305 | 6.61 | Blue | 325 |
| Example 16 | Compound 147 | 4.96 | 50 | 3390 | 6.78 | Blue | 438 |
| Comparative Example 1 | Alq$_3$ | 7.35 | 50 | 2065 | 4.13 | Blue | 145 |
| Comparative Example 2 | Compound A | 7.15 | 50 | 2265 | 4.53 | Blue | 243 |
| Comparative Example 3 | Compound B | 6.15 | 50 | 2525 | 5.05 | Blue | 252 |

From Table 2, it may be concluded that the driving voltage, current density, brightness, efficiency, and half-life of the organic light-emitting devices manufactured according to Examples 1 to 16 are higher than the driving voltage, current density, brightness, efficiency, and half-life of the organic light-emitting devices manufactured according to Comparative Examples 1 and 3.

As described above, according to the one or more of the above embodiments of the present invention, an organic light-emitting device including a condensed-cyclic compound represented by Formula 1 may have a low driving voltage, high efficiency, high brightness, and a long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A condensed-cyclic compound represented by Formula 1:

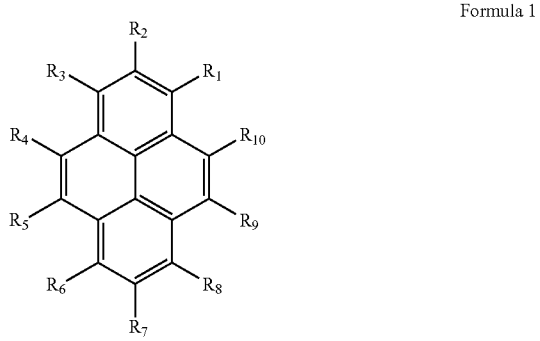

Formula 1

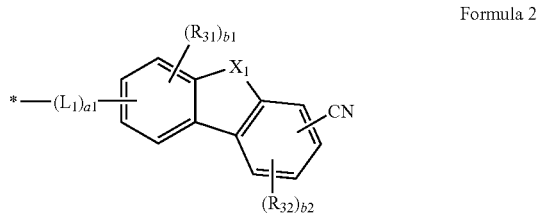

Formula 2 wherein in Formulae 1, $R_1$ to $R_{10}$ are each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic hetero-condensed polycyclic group (wherein, the "substituted monovalent non-aromatic hetero-condensed polycyclic group" does not include a group represented by Formula 2 above), —N($Q_1$)($Q_2$), —Si($Q_3$)($Q_4$)($Q_5$), or —B($Q_6$)($Q_7$);

one of $R_1$ to $R_{10}$ is represented by Formula 2 above;

in Formulae 2, $X_1$ is N($R_{21}$), O, or S;

$L_1$ is selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic hetero-condensed polycyclic group;

a1 is selected from 0, 1, 2, or 3;

b1 and b2 are each independently selected from 0, 1, 2, or 3;

at least one substituent of the substituted $C_3$-$C_{10}$ cycloalkylene group, substituted $C_2$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_2$-$C_{60}$ heteroarylene group, substituted divalent non-aromatic condensed polycyclic group, substituted divalent non-aromatic hetero-condensed polycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_2$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_2$-$C_{60}$ heteroaryl group, substituted monovalent non-aromatic condensed polycyclic group, and substituted monovalent non-aromatic hetero-condensed polycyclic group is selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{11}$)($Q_{12}$), —Si($Q_{13}$)($Q_{14}$)($Q_{15}$), or —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic hetero-condensed polycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic hetero-condensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic hetero-condensed polycyclic group, —N($Q_{21}$)($Q_{22}$), —Si($Q_{23}$)($Q_{24}$)($Q_{25}$) or —B($Q_{26}$)($Q_{27}$); or —N($Q_{31}$)($Q_{32}$), —Si($Q_{33}$)($Q_{34}$)($Q_{35}$) and —B($Q_{36}$)($Q_{37}$);

$R_{21}$, $R_{31}$, $R_{32}$, $Q_1$ to $Q_7$, $Q_{11}$ to $Q_{17}$, $Q_{21}$ to $Q_{27}$, and $Q_{31}$ to $Q_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, or a monovalent non-aromatic hetero-condensed polycyclic group; wherein the condensed-cyclic compound represented by Formula 1 above has one group represented by Formula 2 above.

2. The condensed-cyclic compound of claim 1, wherein $L_1$ of Formula 2 above is selected from a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a napthacenylene group, a picenylene group, a perylenylene group, a pentaphenylene group, a hexacenylene group, a pentacenylene group, a rubicenylene group, a coronenylene group, an ovalenylene group, a pyrrolylene group, thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group or an imidazopyrimidinylene group; or a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a napthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, or an imidazopyrimidinyl group.

3. The condensed-cyclic compound of claim 1, wherein $L_1$ of Formula 2 above is represented by one of Formulae 3-1 to 3-32:

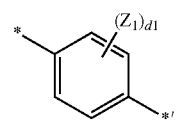

Formula 3-1

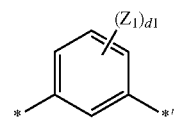

Formula 3-2

-continued
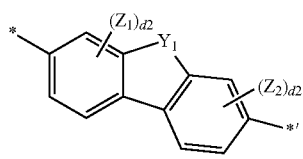
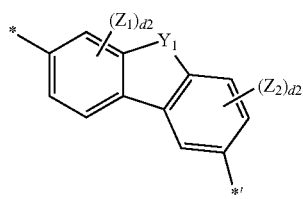
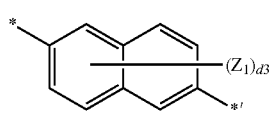
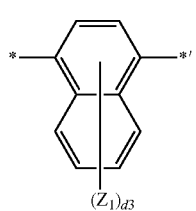
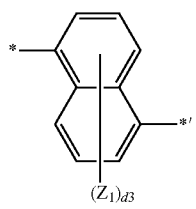
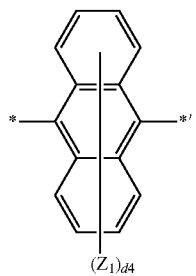
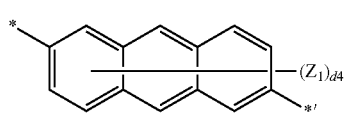
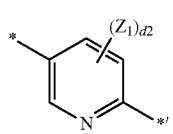
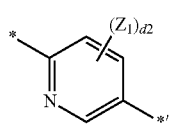
-continued
Formula 3-3
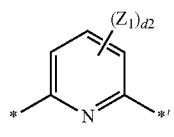
Formula 3-4
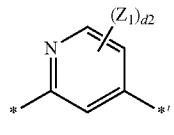
Formula 3-5
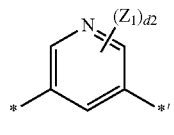
Formula 3-6
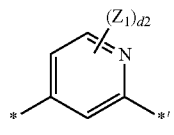
Formula 3-7
Formula 3-8
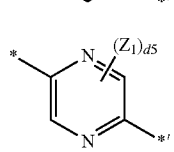
Formula 3-9
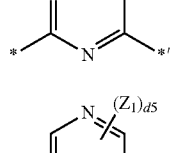
Formula 3-10
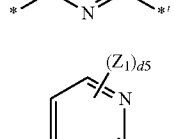
Formula 3-11
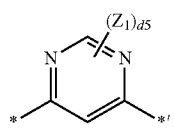
Formula 3-12
Formula 3-13
Formula 3-14
Formula 3-15
Formula 3-16
Formula 3-17
Formula 3-18
Formula 3-19
Formula 3-20
Formula 3-21
Formula 3-22
Formula 3-23

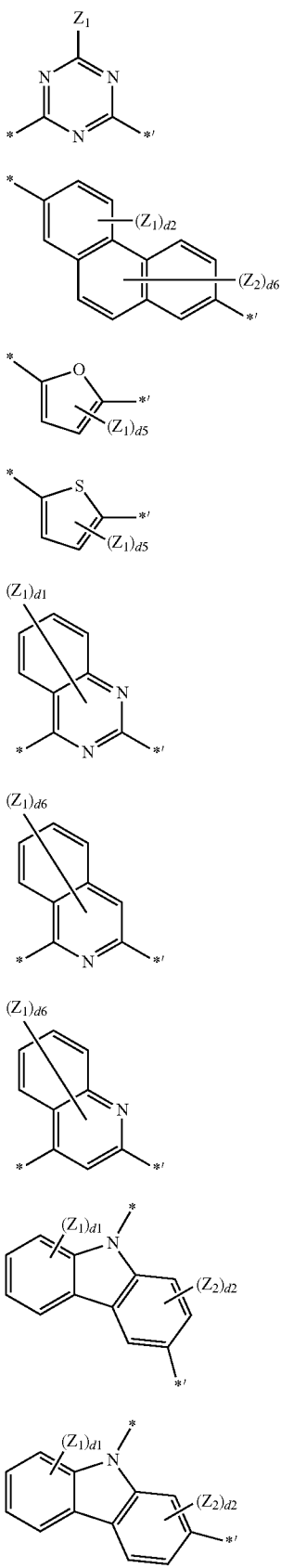

Formula 3-24

Formula 3-25

Formula 3-26

Formula 3-27

Formula 3-28

Formula 3-29

Formula 3-30

Formula 3-31

Formula 3-32 in Formulae 3-1 to 3-32, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group, d1 is selected from integers of 1 to 4;
d2 is selected from integers of 1 to 3;
d3 is selected from integers of 1 to 6;
d4 is selected from integers of 1 to 8;
d5 is 1 or 2; and
d6 is selected from integers of 1 to 5.

4. The condensed-cyclic compound of claim 1, wherein $L_1$ of Formula 2 above is represented by one of Formulae 4-1 to 4-23:

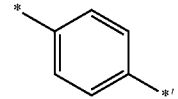

Formula 4-1

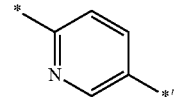

Formula 4-2

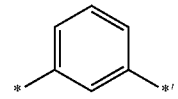

Formula 4-3

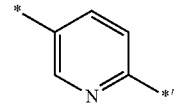

Formula 4-4

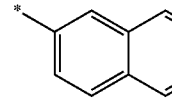

Formula 4-5

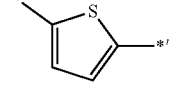

Formula 4-6

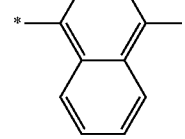

Formula 4-7

-continued

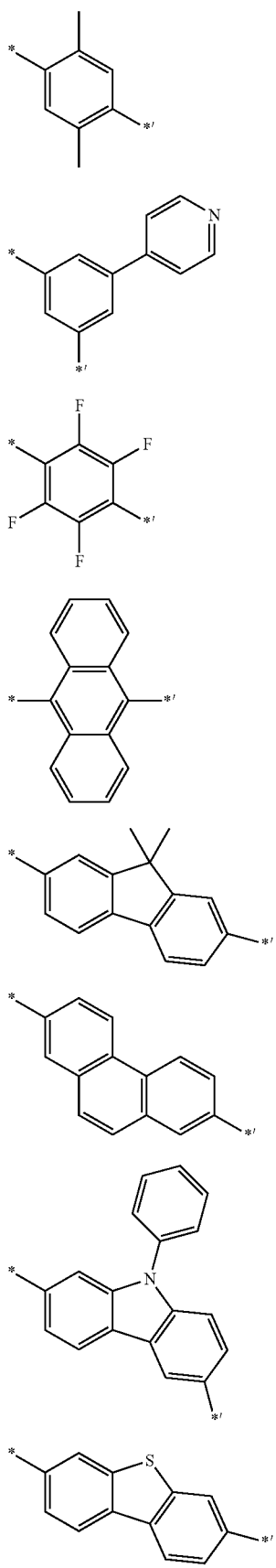

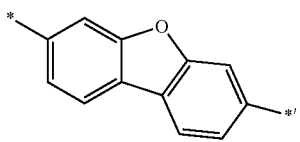
Formula 4-16

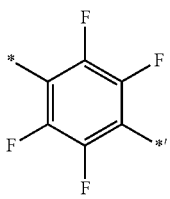
Formula 4-17

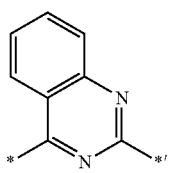
Formula 4-18

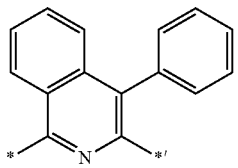
Formula 4-19

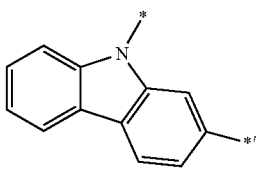
Formula 4-20

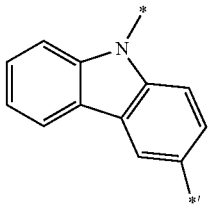
Formula 4-21

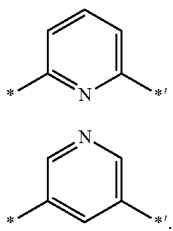
Formula 4-22

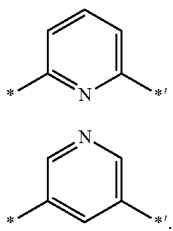
Formula 4-23

5. The condensed-cyclic compound of claim 1, wherein a1 of Formula 2 above is 0 or 1.

6. The condensed-cyclic compound of claim 1, wherein $X_1$ of Formula 2 above is $N(R_{21})$; and $R_{21}$ is selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, or an imidazopyrimidinyl group; or a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a pthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, a thiadiazolyl group, an imidazopyridinyl group, or an imidazopyrimidinyl group.

7. The condensed-cyclic compound of claim 1, wherein $X_1$ is $N(R_{21})$; and $R_{21}$ is selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group.

8. The condensed-cyclic compound of claim 1, wherein $R_1$ to $R_{10}$ are each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, or $Si(Q_3)(Q_4)(Q_5)$ (wherein, $Q_3$ to $Q_5$ are each independently selected from a $C_1$-$C_{20}$ alkyl group, a $C_1$-$C_{20}$ alkoxy group, a phenyl group, and a naphthyl group); wherein, one of $R_1$ to $R_{10}$ above is represented by Formula 2 above.

9. The condensed-cyclic compound of claim 1, wherein in Formula 1 above, $R_1$ or $R_2$ is a group represented by Formula 2 above.

10. The condensed-cyclic compound of claim 1, wherein $R_{21}$ above is selected from Formulae 5-1 to 5-35 below;

$R_1$ to $R_{10}$ above are each independently selected from a group represented by Formula 2 above, a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, or Formulae 5-1 to 5-35 below, wherein one of $R_1$ to $R_{10}$ above is represented by Formula 2 above;

$R_{31}$ and $R_{32}$ above are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, or Formulae 5-1 to 5-35 below:

Formula 5-1

Formula 5-2

Formula 5-3

Formula 5-4

Formula 5-5

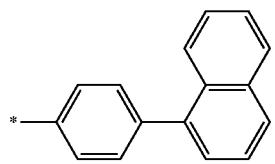

Formula 5-6

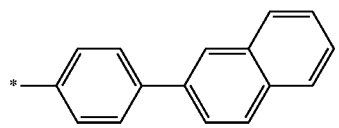

Formula 5-7

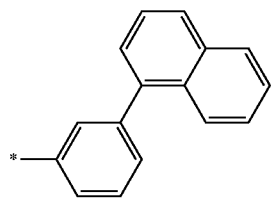

Formula 5-8

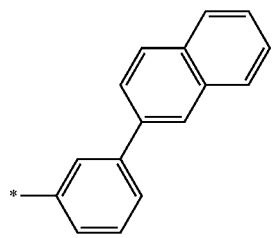

Formula 5-9

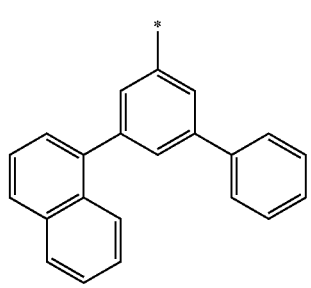

Formula 5-10

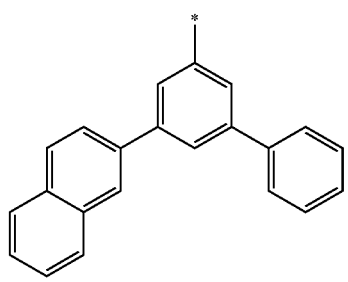

Formula 5-11

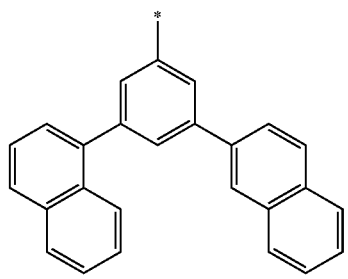

-continued
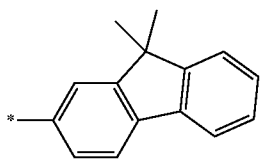
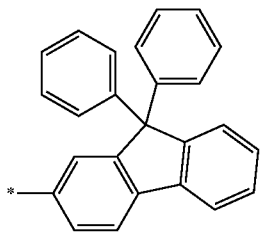
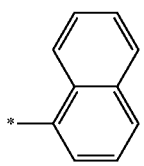
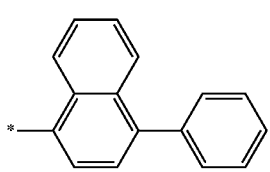
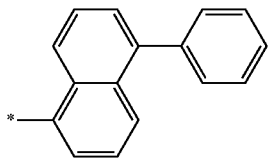
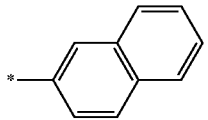
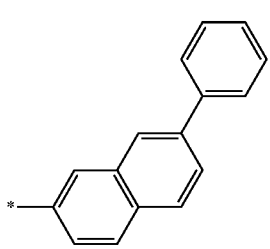
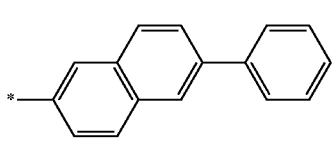
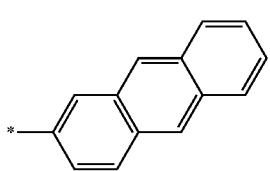
-continued
Formula 5-12
Formula 5-13
Formula 5-14
Formula 5-15
Formula 5-16
Formula 5-17
Formula 5-18
Formula 5-19
Formula 5-20
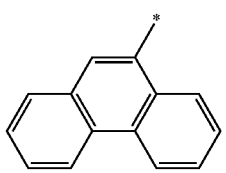
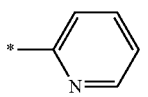
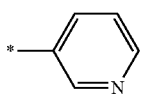
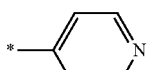
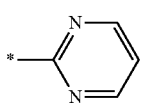
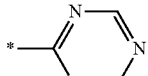
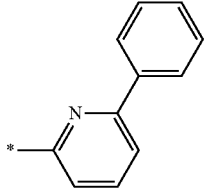
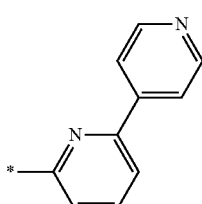
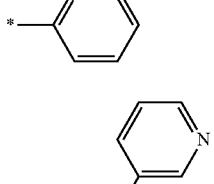
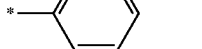
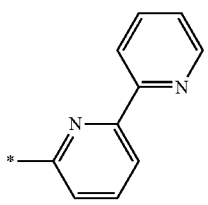
Formula 5-21
Formula 5-22
Formula 5-23
Formula 5-24
Formula 5-25
Formula 5-26
Formula 5-27
Formula 5-28
Formula 5-29
Formula 5-30

Formula 5-31
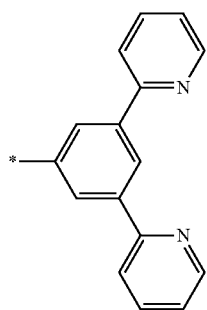
Formula 5-32
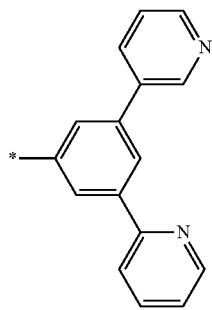
Formula 5-33
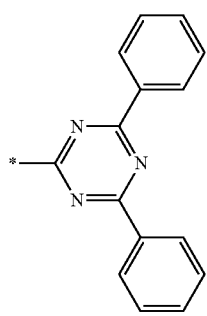
Formula 5-34
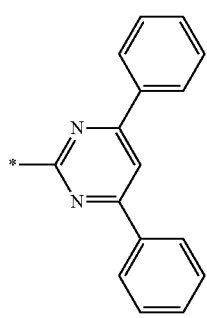
Formula 5-35
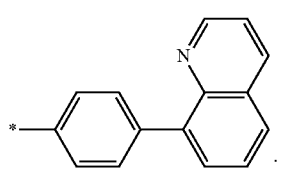
Formula 1-1
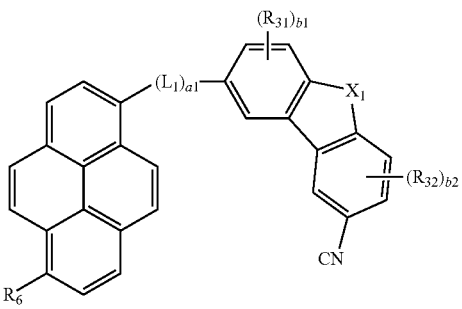
Formula 1-2
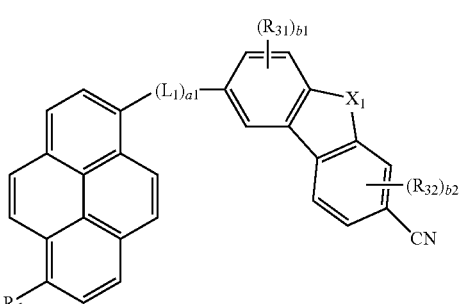
Formula 1-3
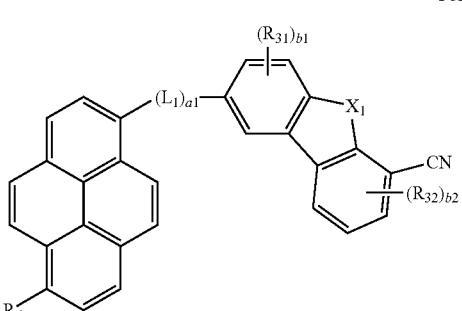
Formula 1-4
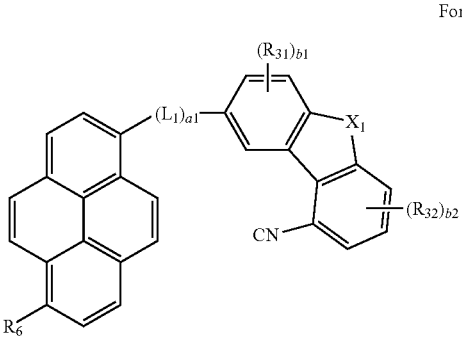
Formula 1-5
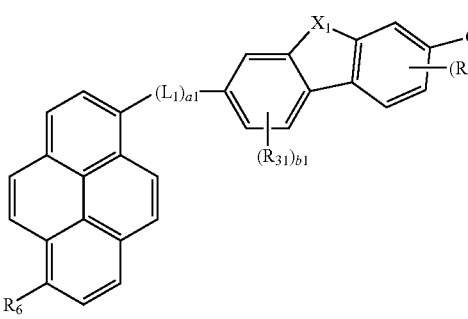
11. The condensed-cyclic compound of claim 1, wherein the condensed-cyclic compound is represented by one of Formulae 1-1 to 1-12 and 1-21 to 1-32 below:

-continued
Formula 1-6
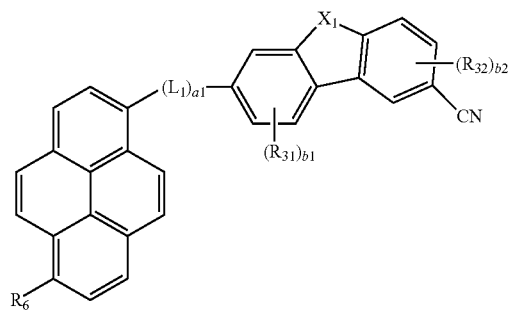
Formula 1-7
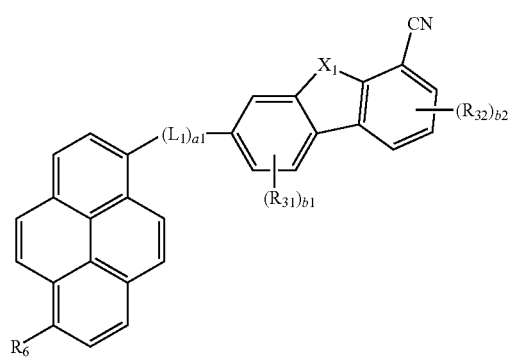
Formula 1-8
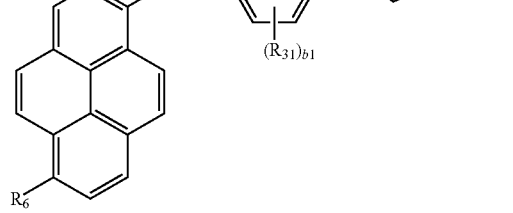
Formula 1-9
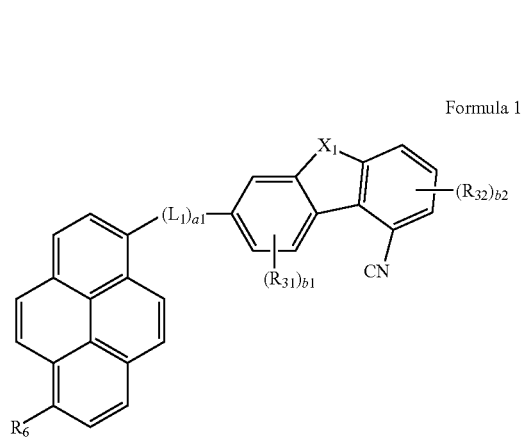
-continued
Formula 1-10
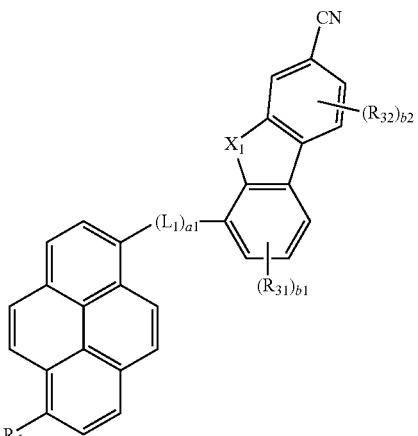
Formula 1-11
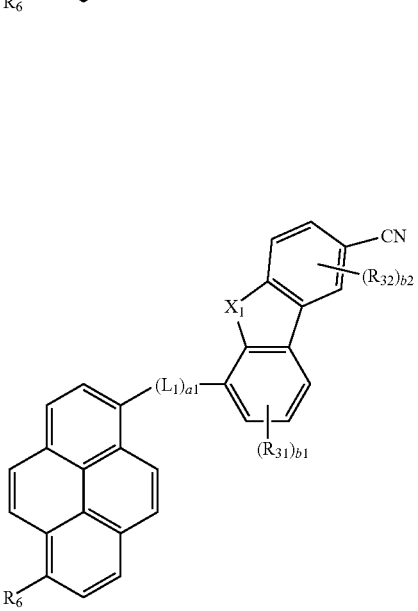
Formula 1-12
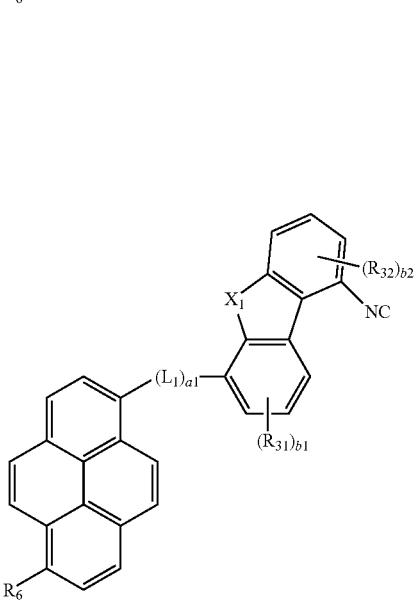

-continued
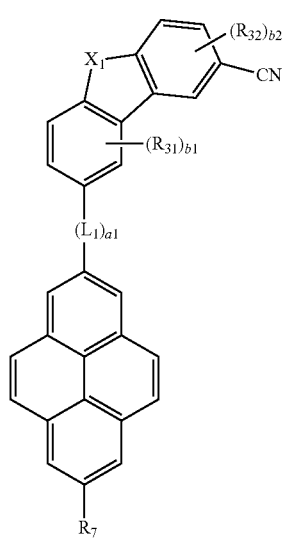
Formula 1-21
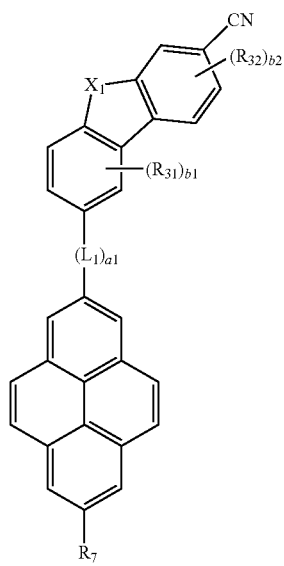
Formula 1-22
Formula 1-23
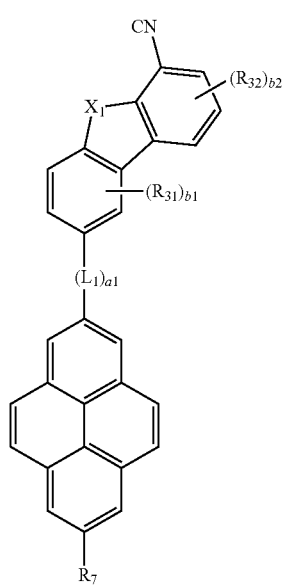
-continued
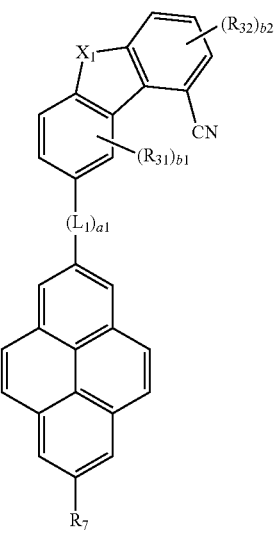
Formula 1-24
Formula 1-25
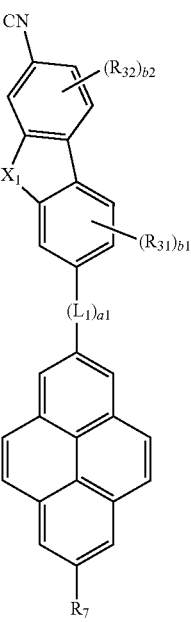

Formula 1-26
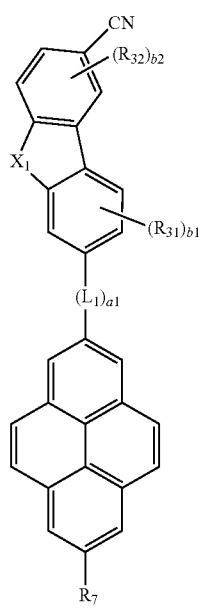
Formula 1-27
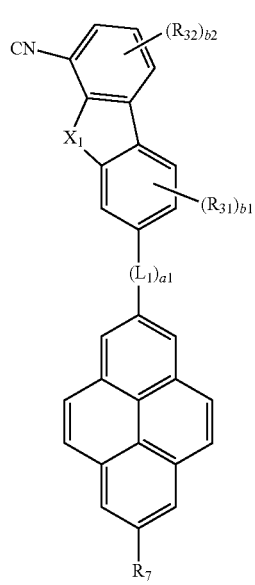
Formula 1-28
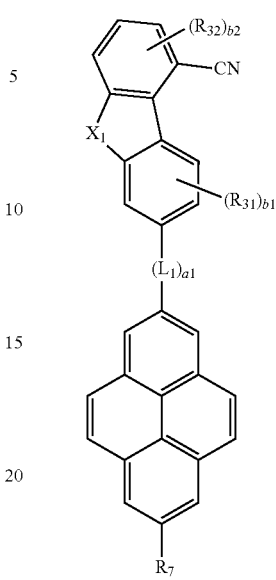
Formula 1-29
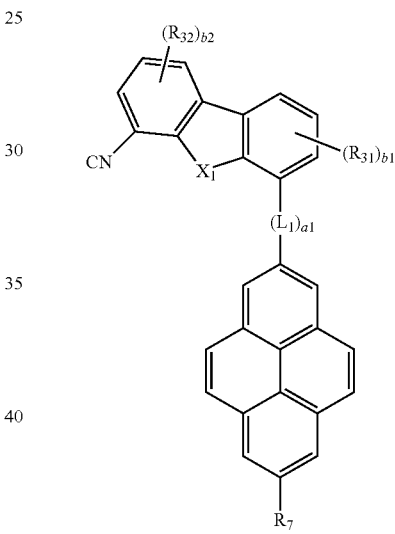
Formula 1-30
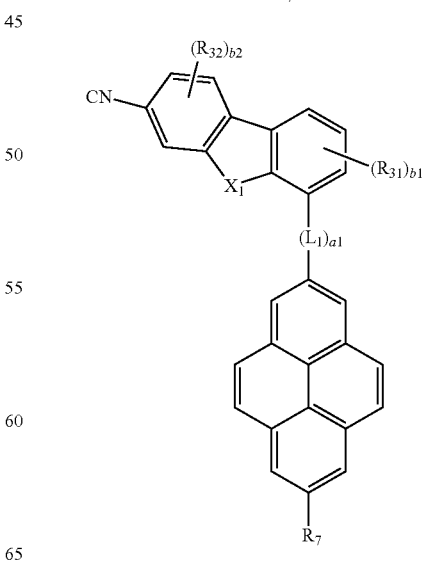

221
-continued
Formula 1-31
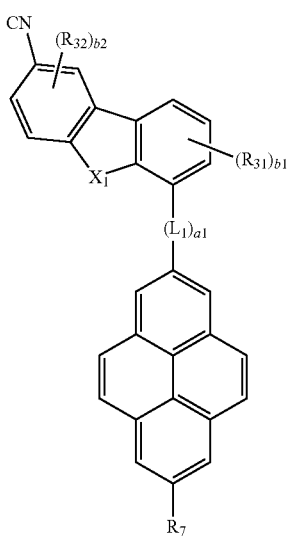
Formula 1-32
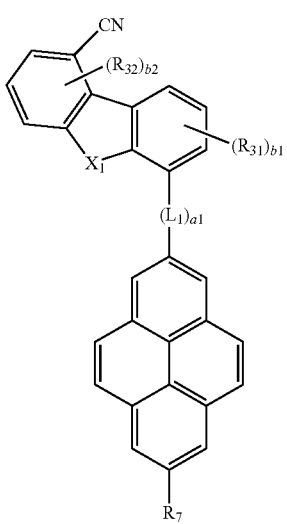
in Formulae 1-1 to 1-12 and 1-21 to 1-32 above, descriptions of $X_1$, $L_1$, a1, $R_6$, $R_7$, $R_{31}$, $R_{32}$, b1, and b2 are as described in claim 1.
12. The condensed-cyclic compound of claim 11, wherein in Formulae 1-1 to 1-12 and 1-21 to 1-32, $L_1$ is one of Formulae 4-1 to 4-23 below and a1 is 0 or 1:
Formula 4-1
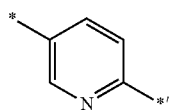
Formula 4-2
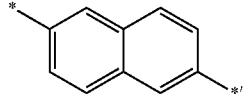
Formula 4-3
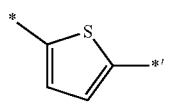
222
-continued
Formula 4-4
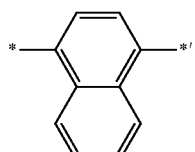
Formula 4-5
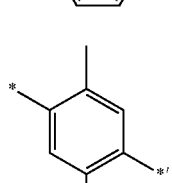
Formula 4-6
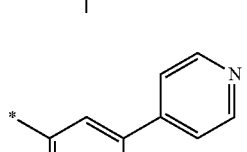
Formula 4-7
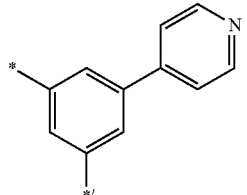
Formula 4-8
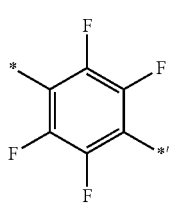
Formula 4-9
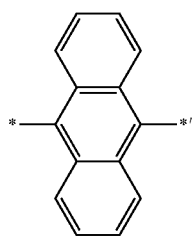
Formula 4-10
Formula 4-11
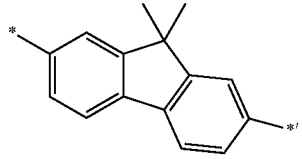
Formula 4-12

-continued

Formula 4-13
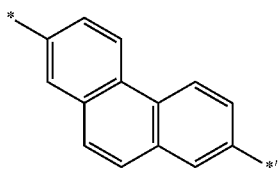

Formula 4-14
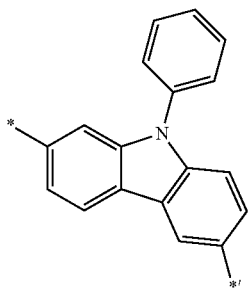

Formula 4-15
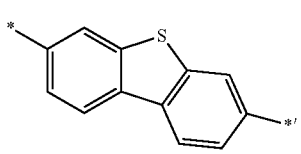

Formula 4-16
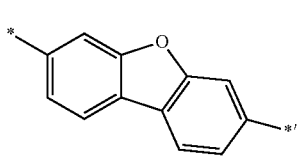

Formula 4-17
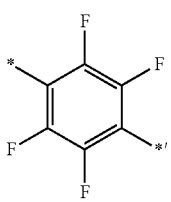

Formula 4-18
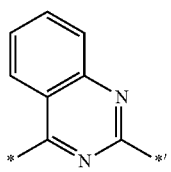

Formula 4-19
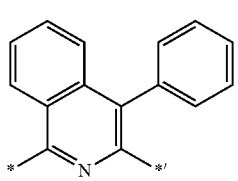

Formula 4-20
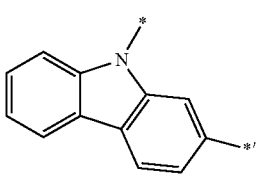

-continued

Formula 4-21
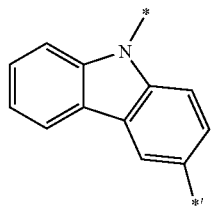

Formula 4-22
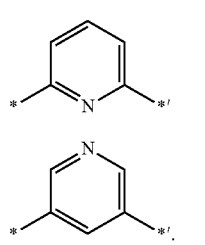

Formula 4-23
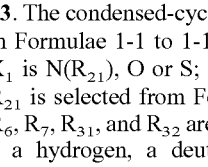

13. The condensed-cyclic compound of claim 11, wherein in Formulae 1-1 to 1-12 and 1-21 to 1-32, $X_1$ is $N(R_{21})$, O or S;

$R_{21}$ is selected from Formulae 5-1 to 5-35;

$R_6$, $R_7$, $R_{31}$, and $R_{32}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, or Formulae 5-1 to 5-35 below:

Formula 5-1
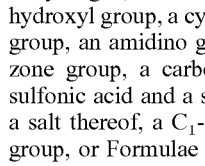

Formula 5-2
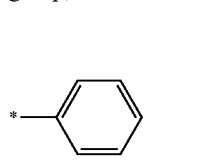

Formula 5-3
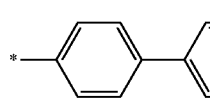

Formula 5-4
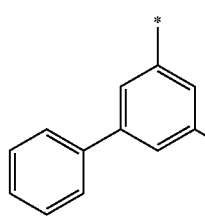

Formula 5-5
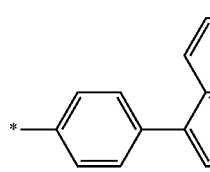

225
-continued
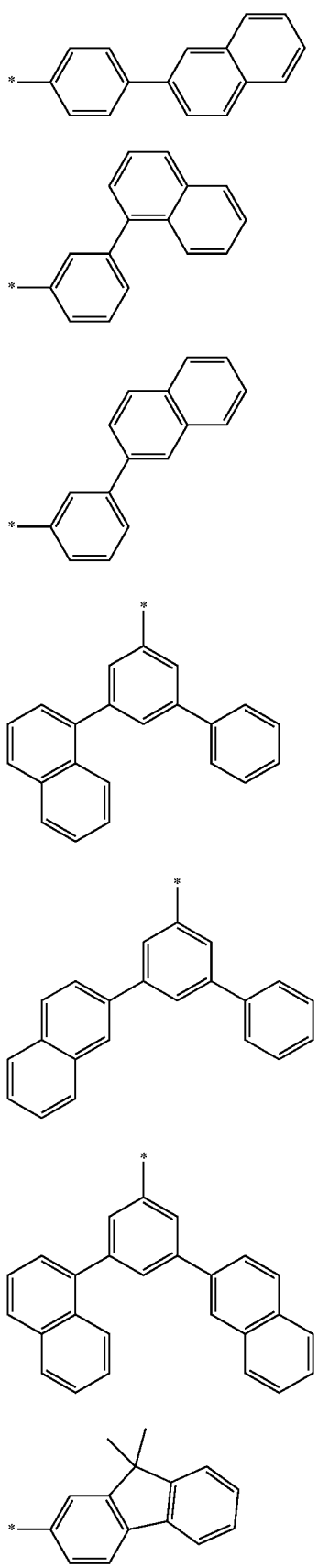
226
-continued
Formula 5-6
Formula 5-7
Formula 5-8
Formula 5-9
Formula 5-10
Formula 5-11
Formula 5-12
Formula 5-13
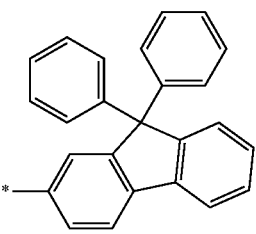
Formula 5-14
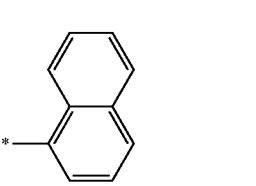
Formula 5-15
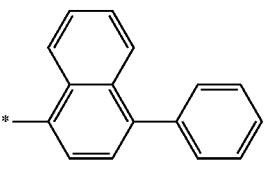
Formula 5-16
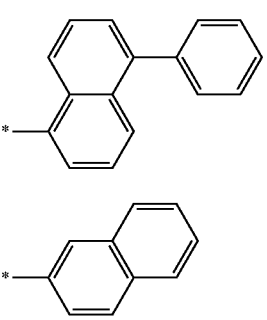
Formula 5-17
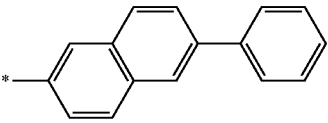
Formula 5-18
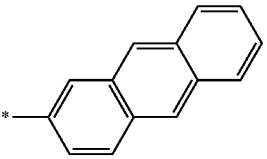
Formula 5-19
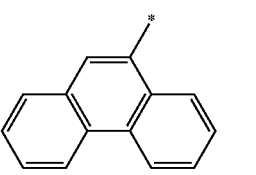
Formula 5-20
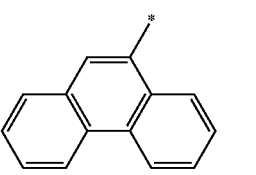
Formula 5-21
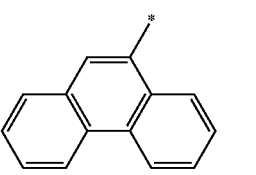

-continued
Formula 5-22
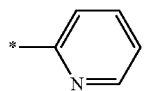
Formula 5-23
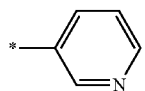
Formula 5-24
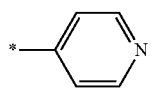
Formula 5-25
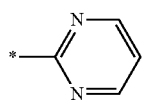
Formula 5-26
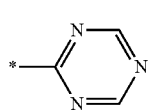
Formula 5-27
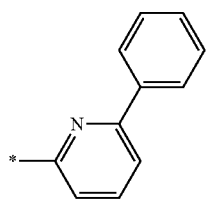
Formula 5-28
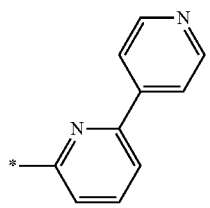
Formula 5-29
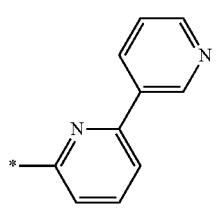
Formula 5-30
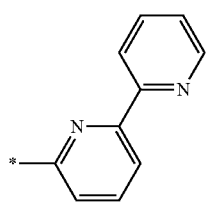
-continued
Formula 5-31
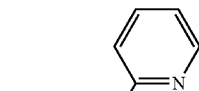
Formula 5-32
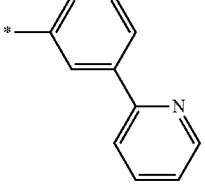
Formula 5-33
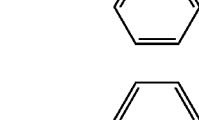
Formula 5-34
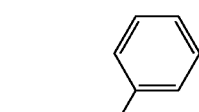
Formula 5-35
14. The condensed-cyclic compound of claim 11, wherein the condensed-cyclic compound is represented by one of Formulae 1-1, 1-5, 1-6, 1-9, 1-21, 1-25, 1-26, and 1-29.
15. The condensed-cyclic compound of claim 1, wherein the condensed-cyclic compound is one of Compounds 1 to 170:

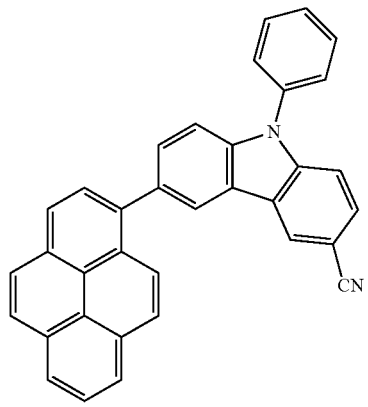
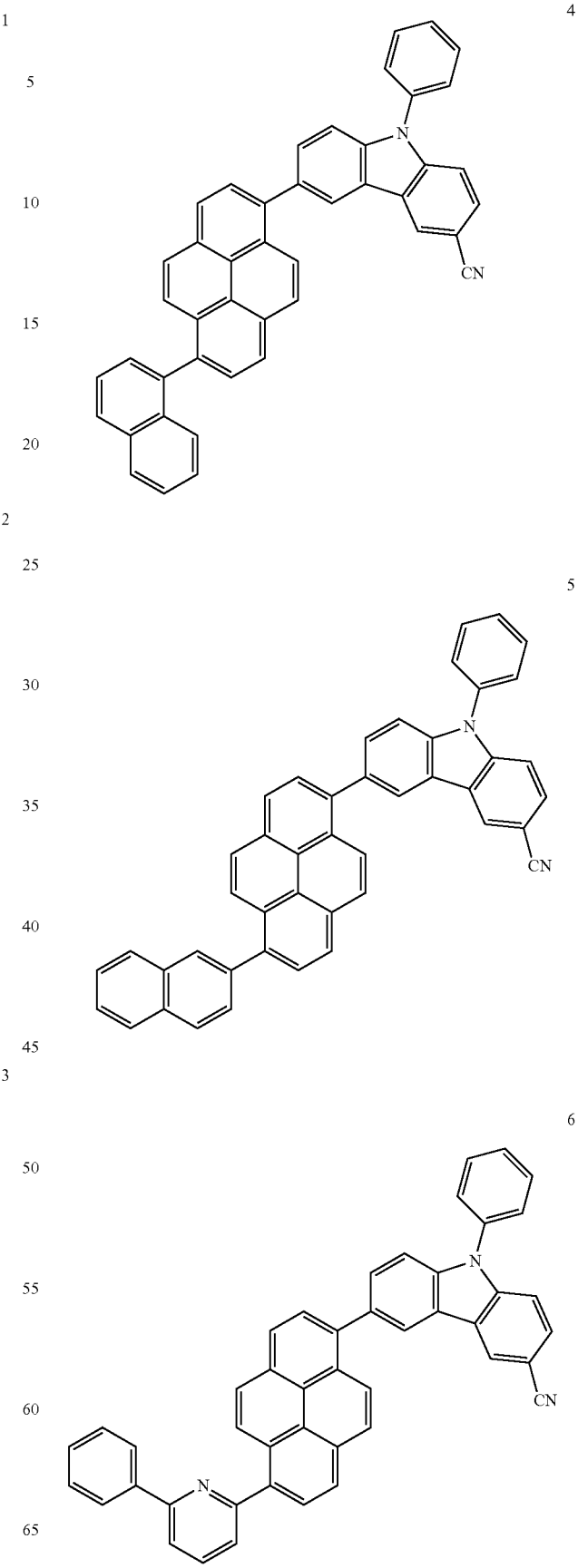

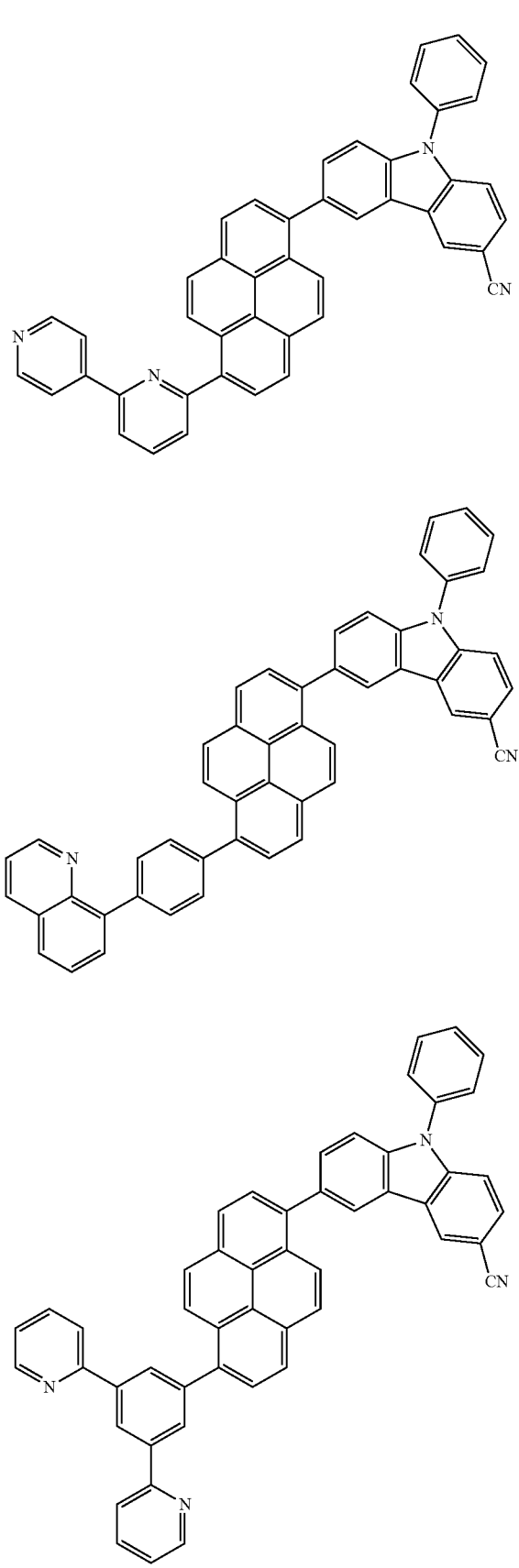
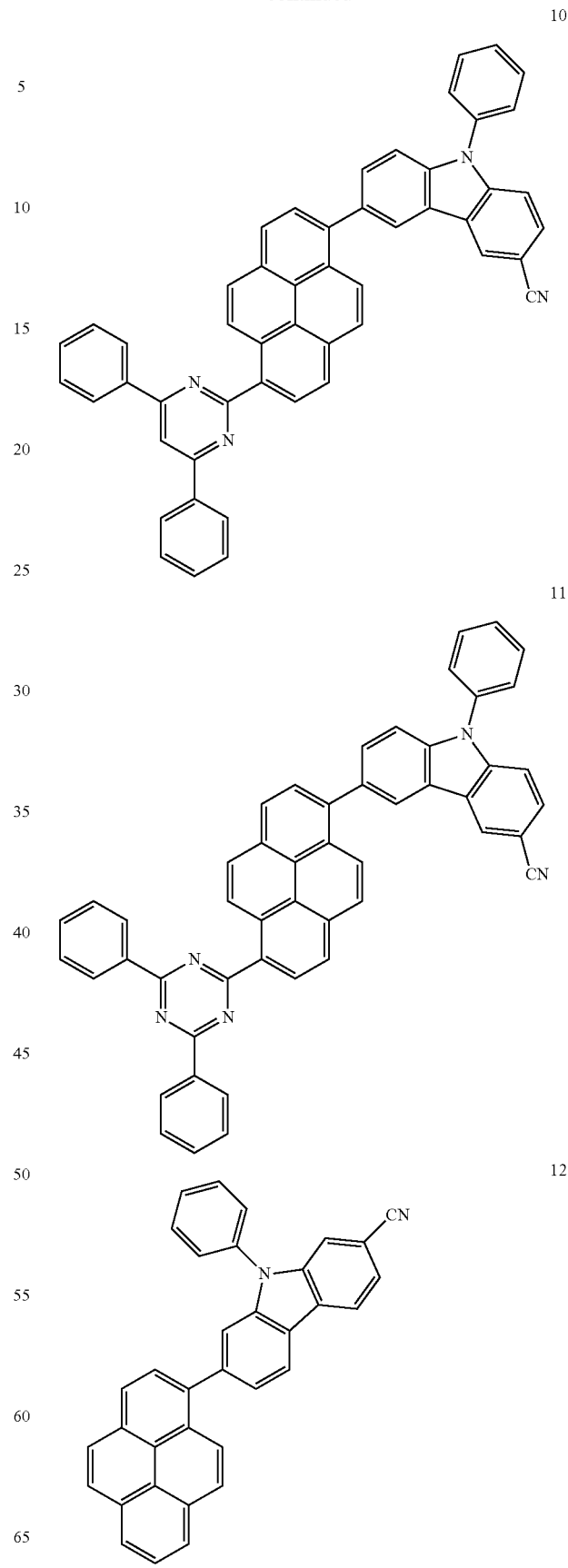

13
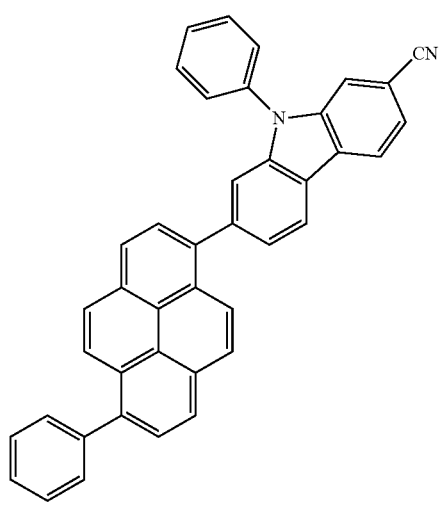
14
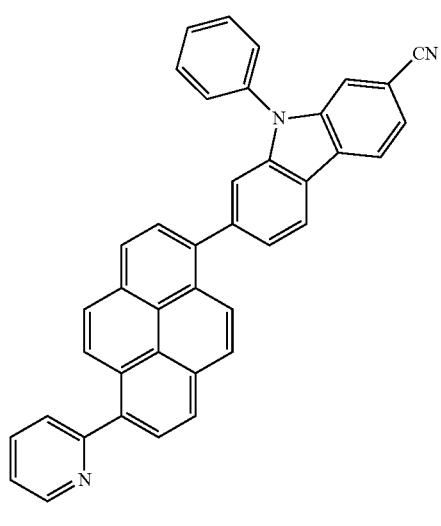
15
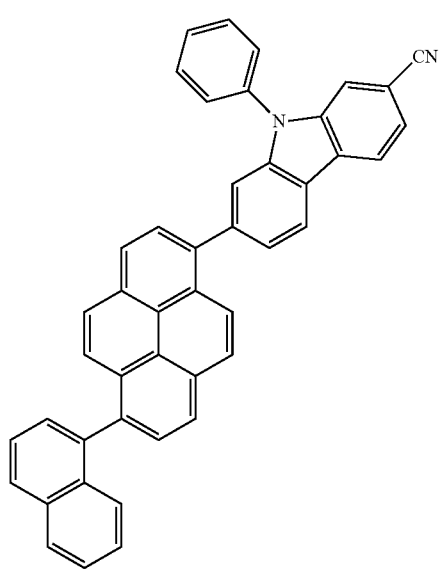
16
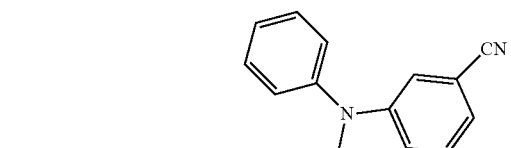
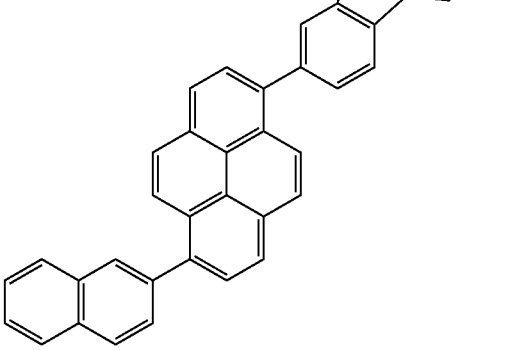
17
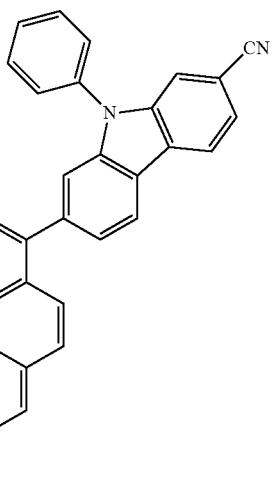
18
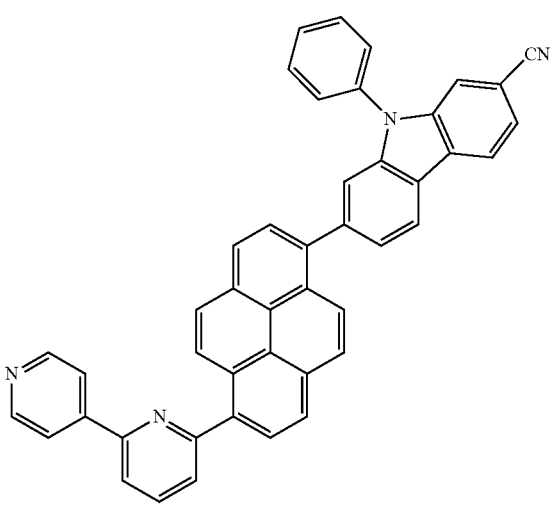

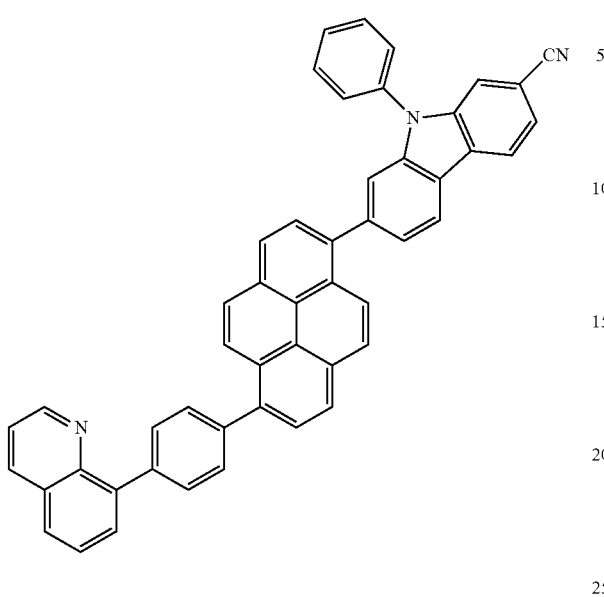
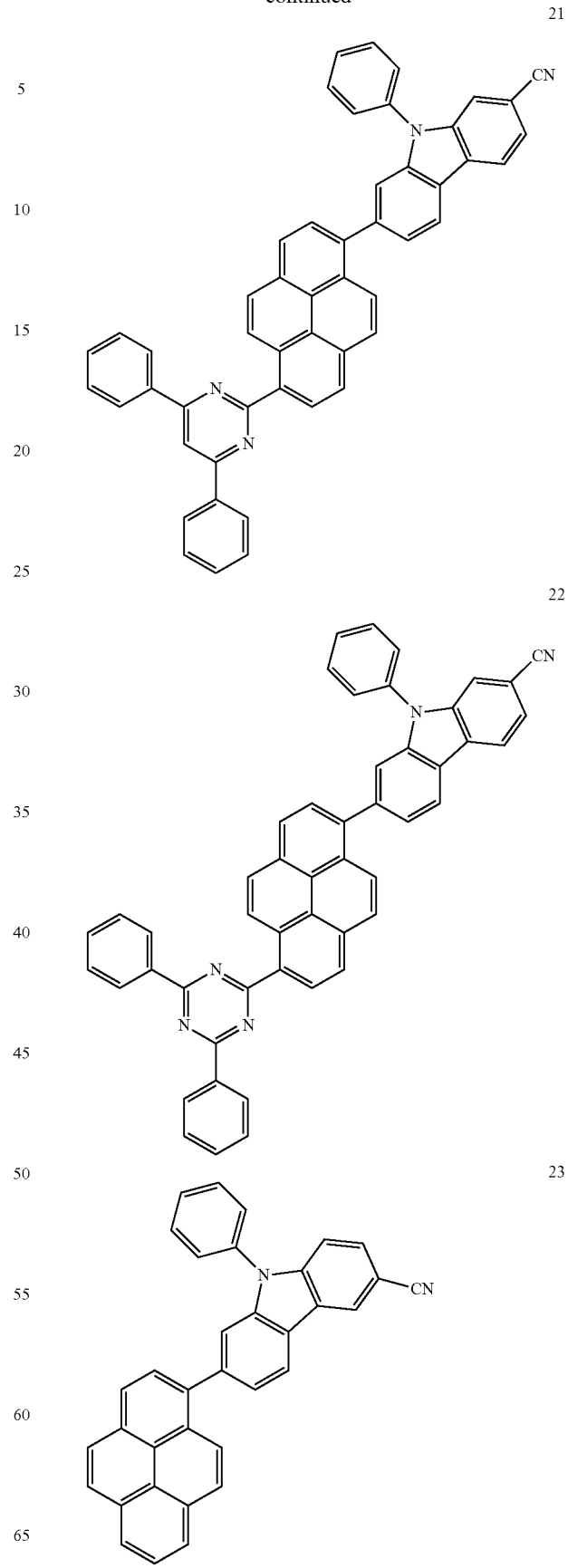

24
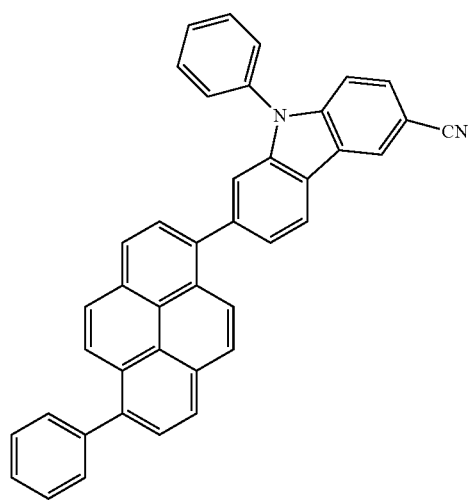
25
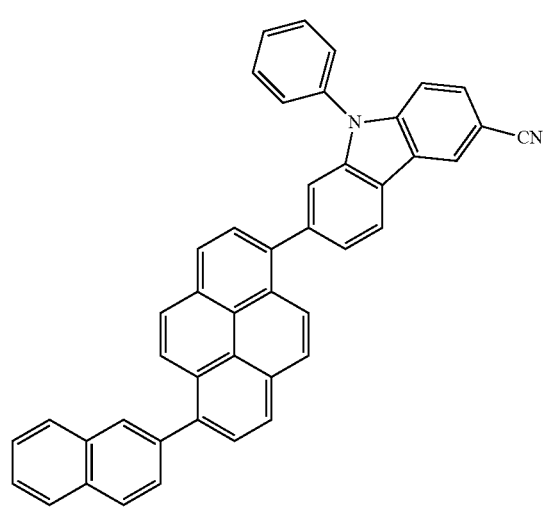
26
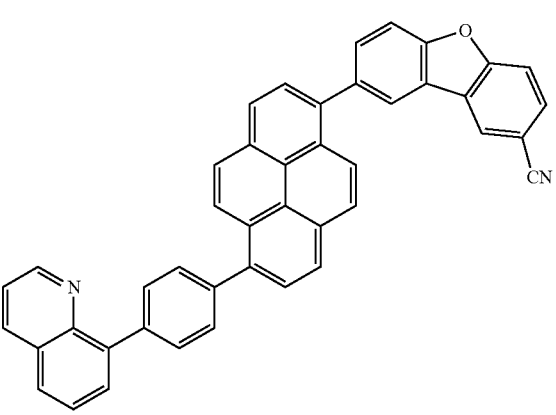
27
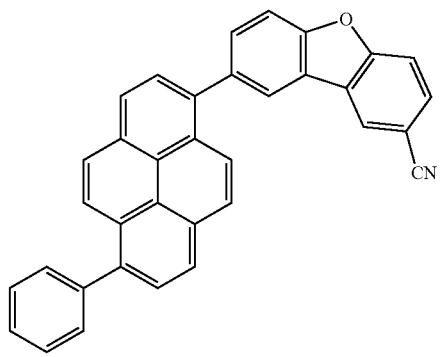
28
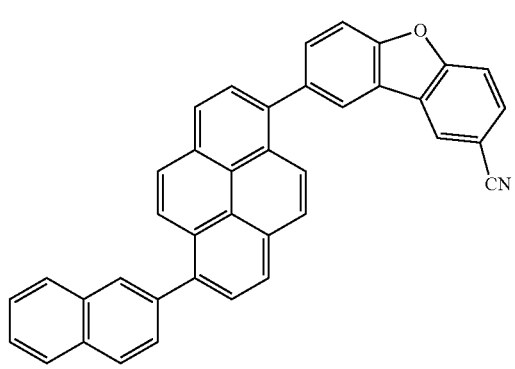
29
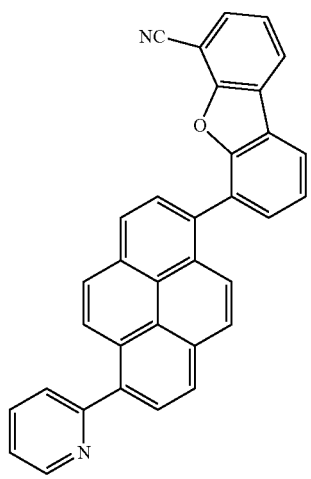

239
-continued
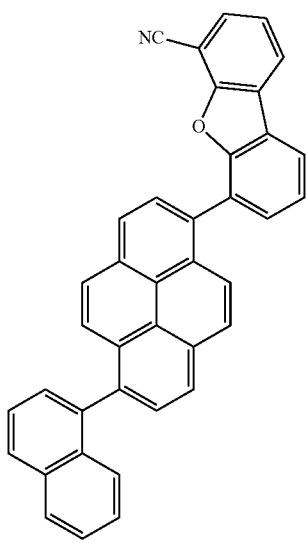
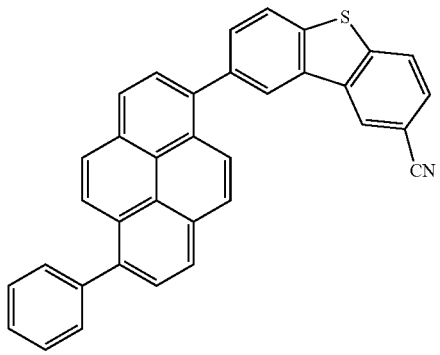
31
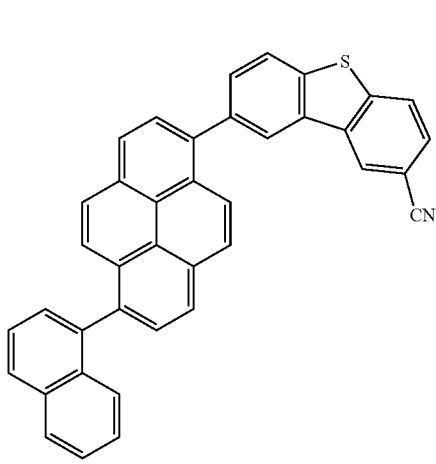
32
240
-continued
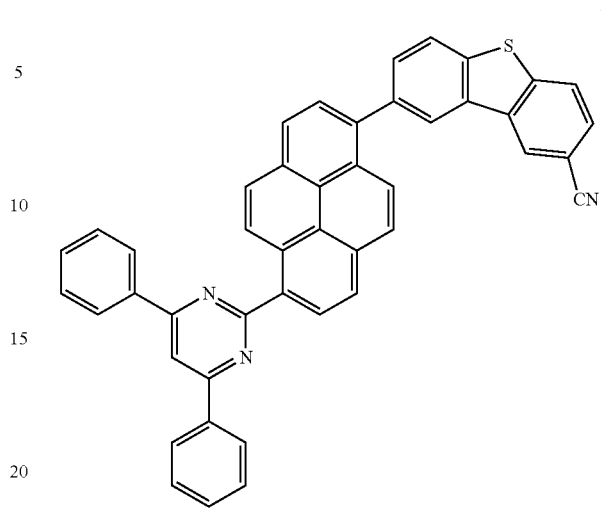
33
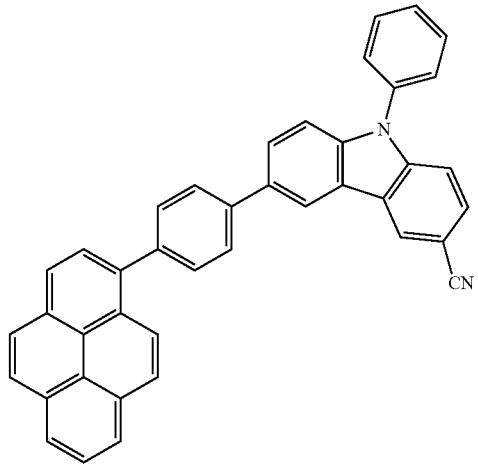
34
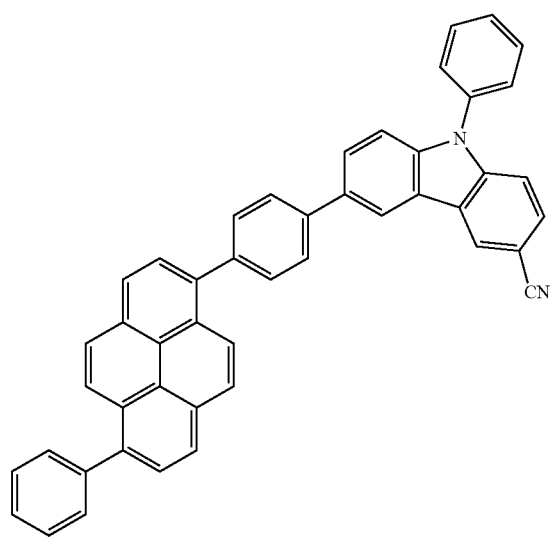
35

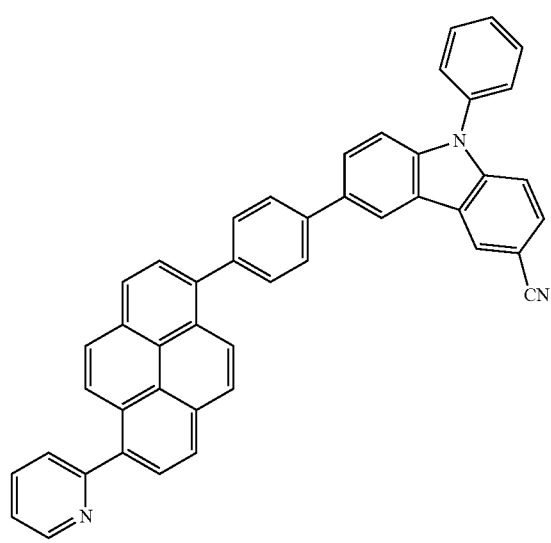
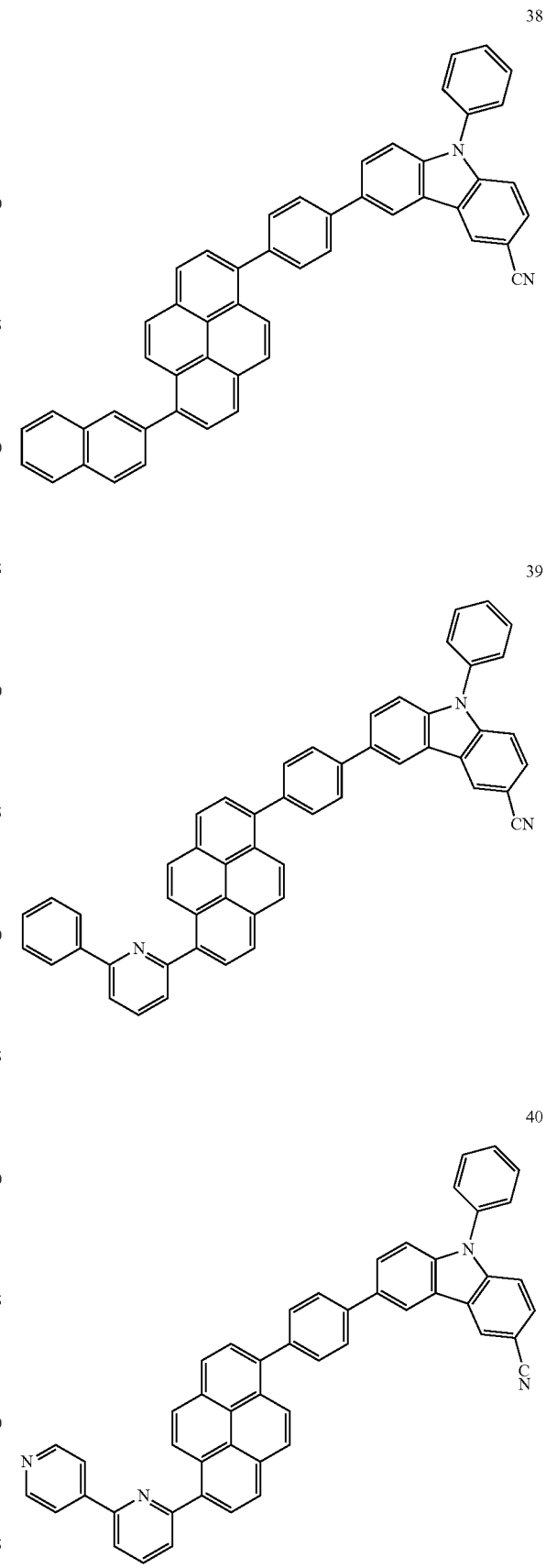

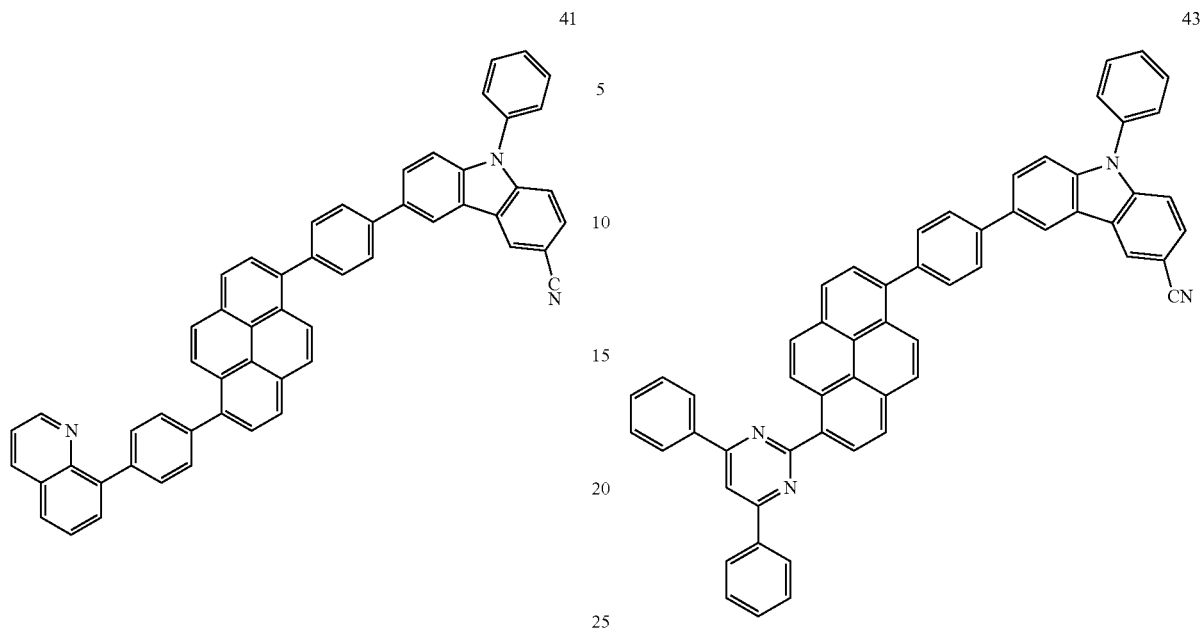

245
-continued
45 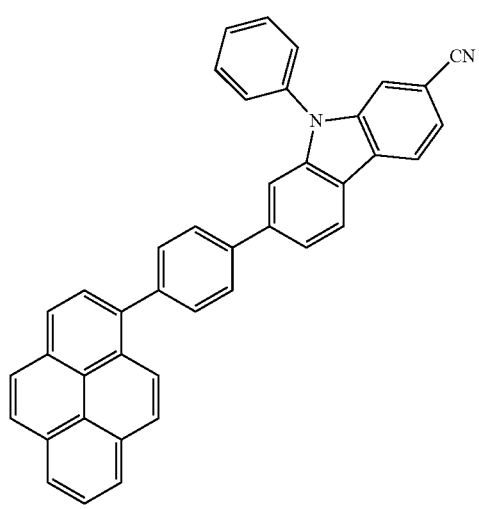
246
-continued
47 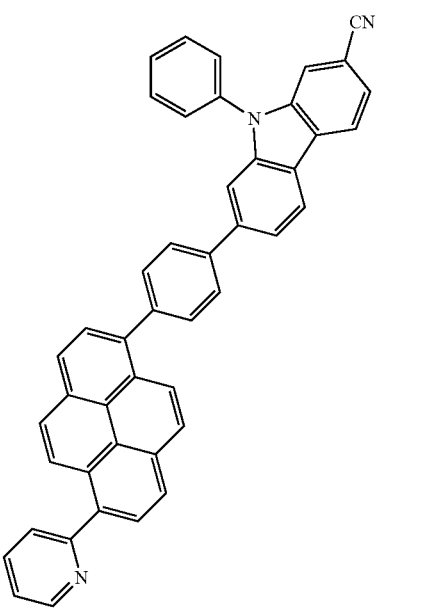
46 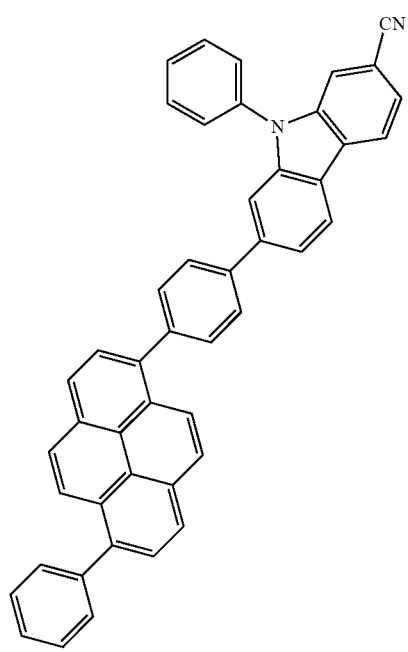
48 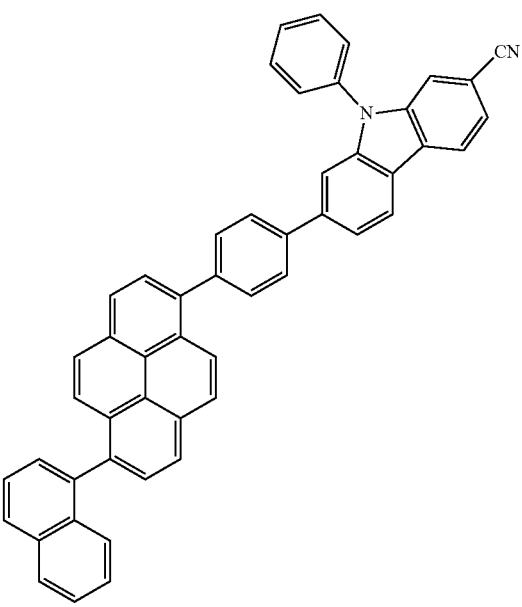

49
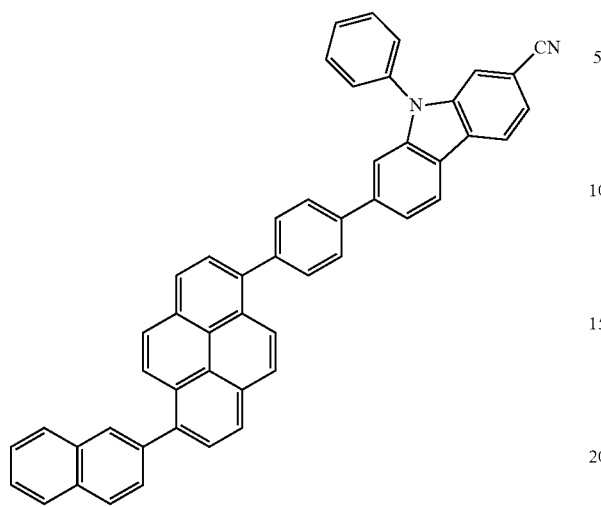
50
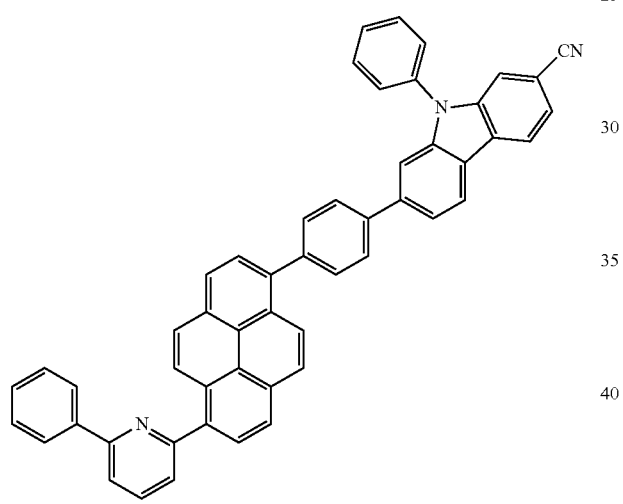
51
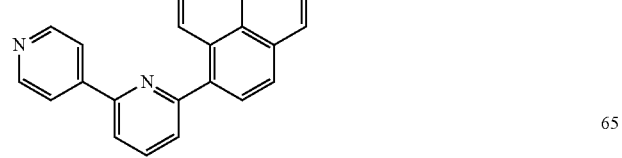
52
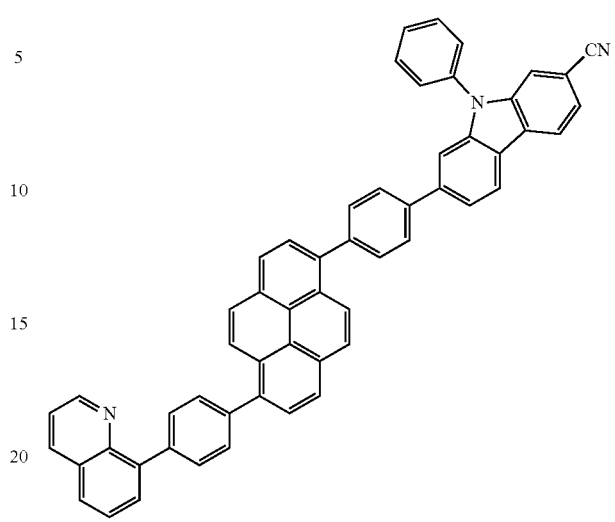
53
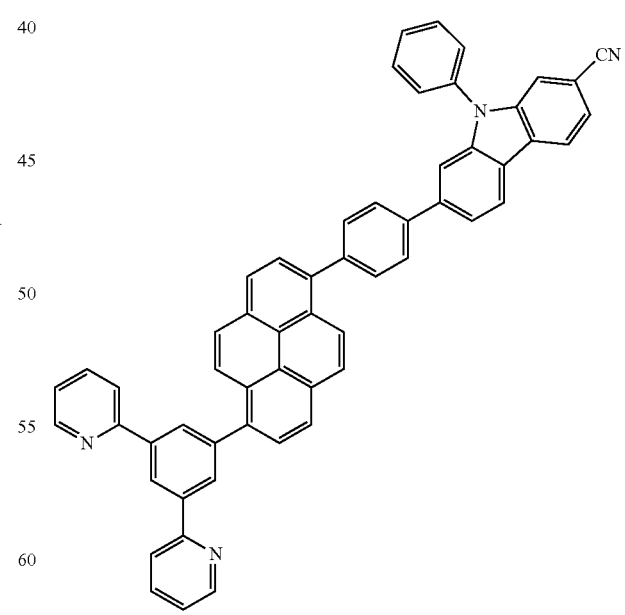

-continued
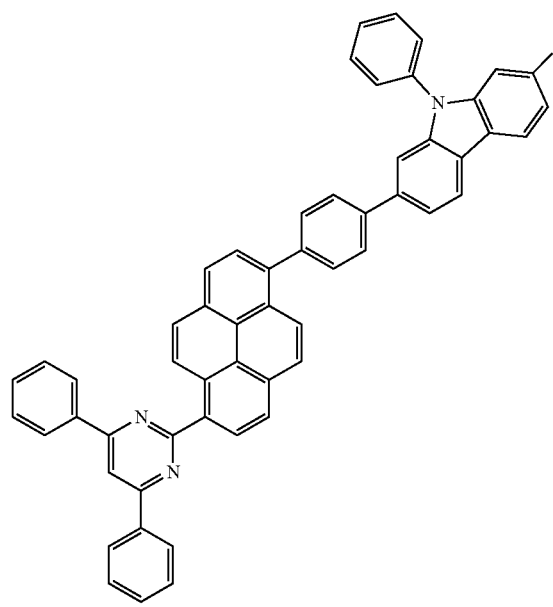
54
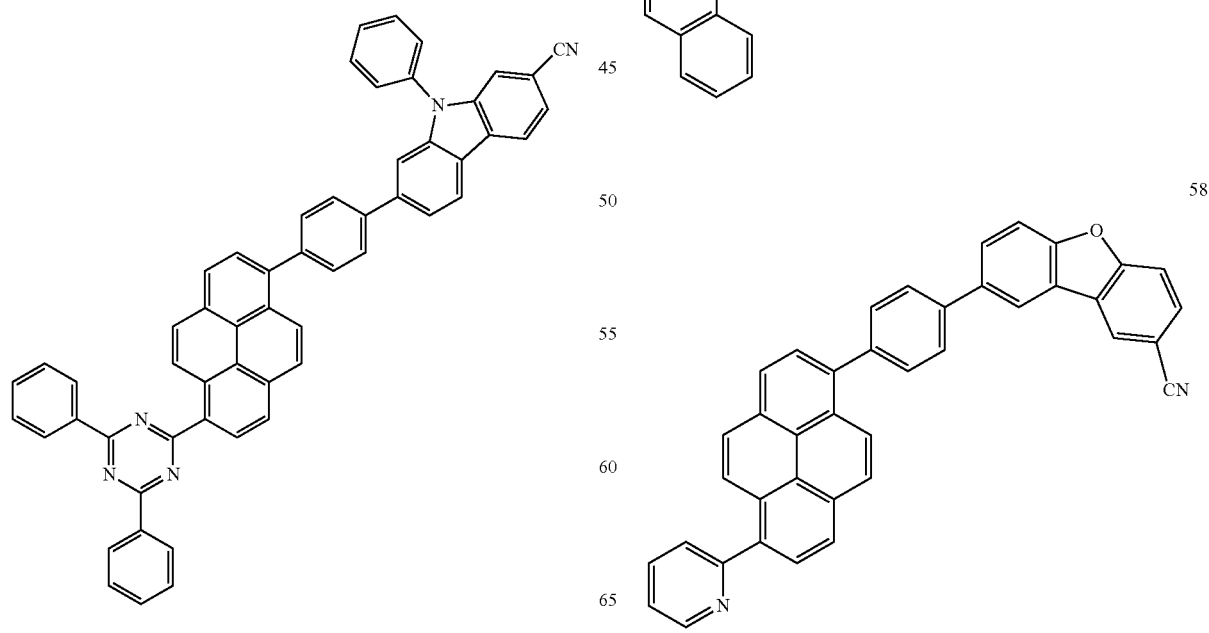
55
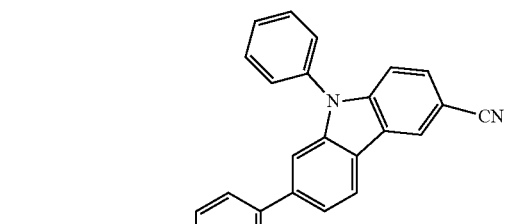
56
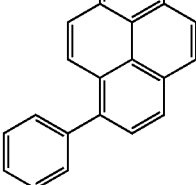
57
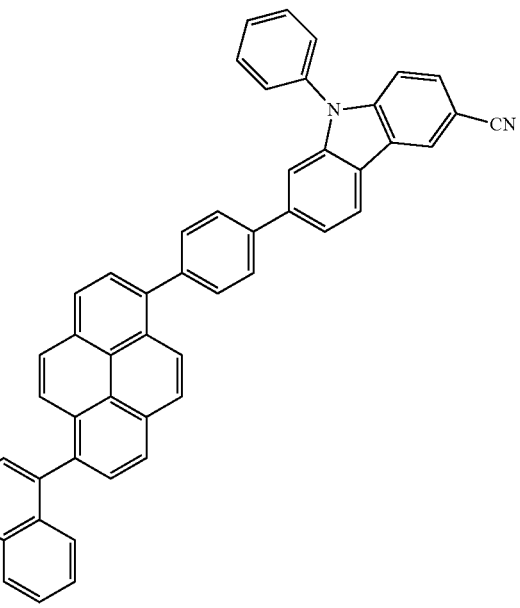
58

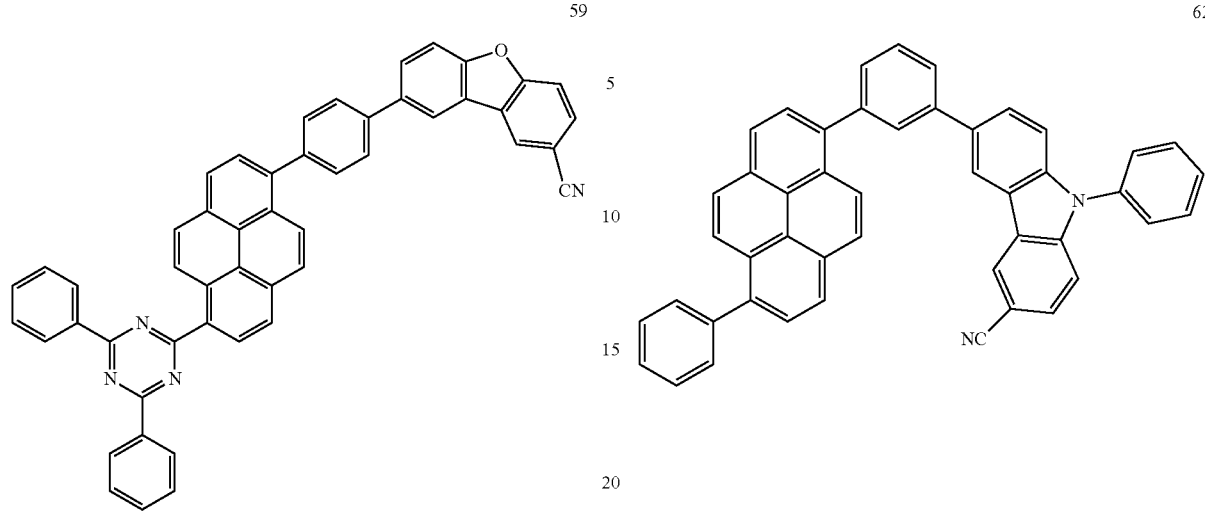
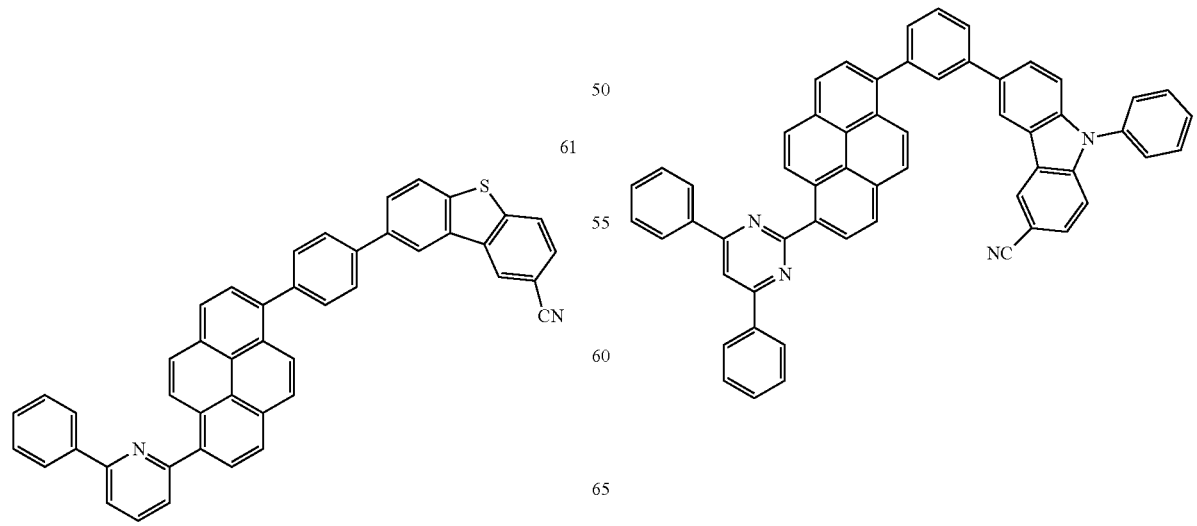

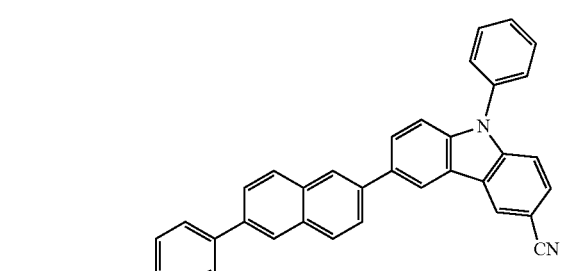
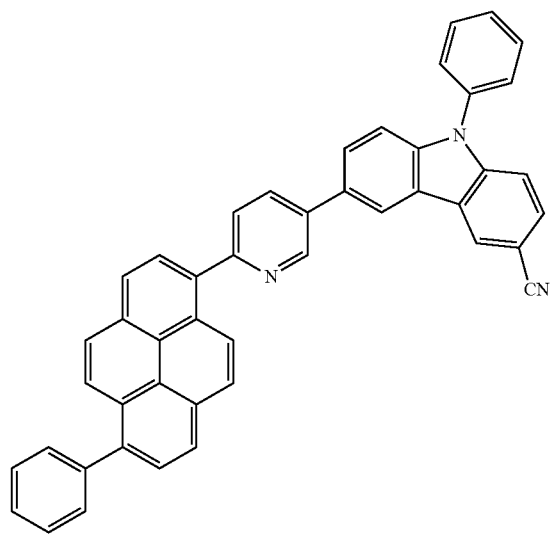
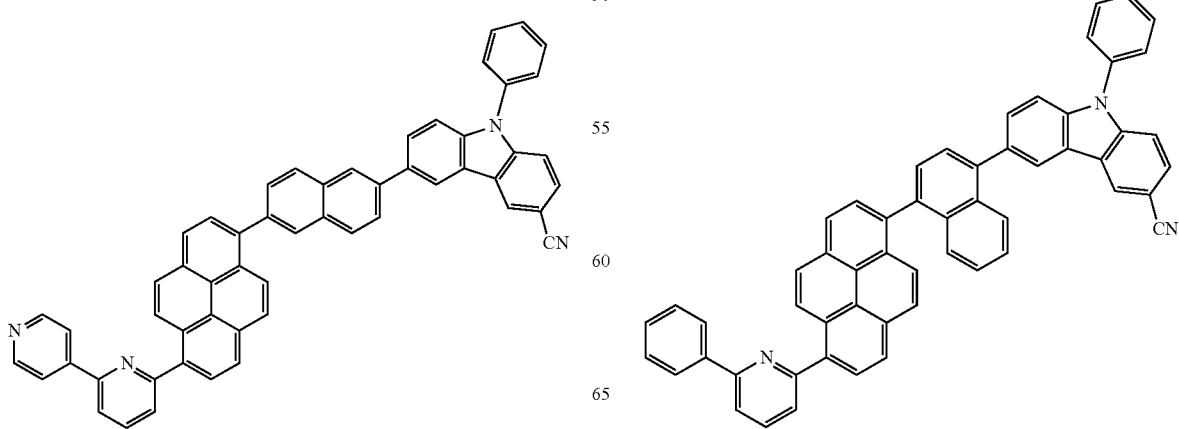

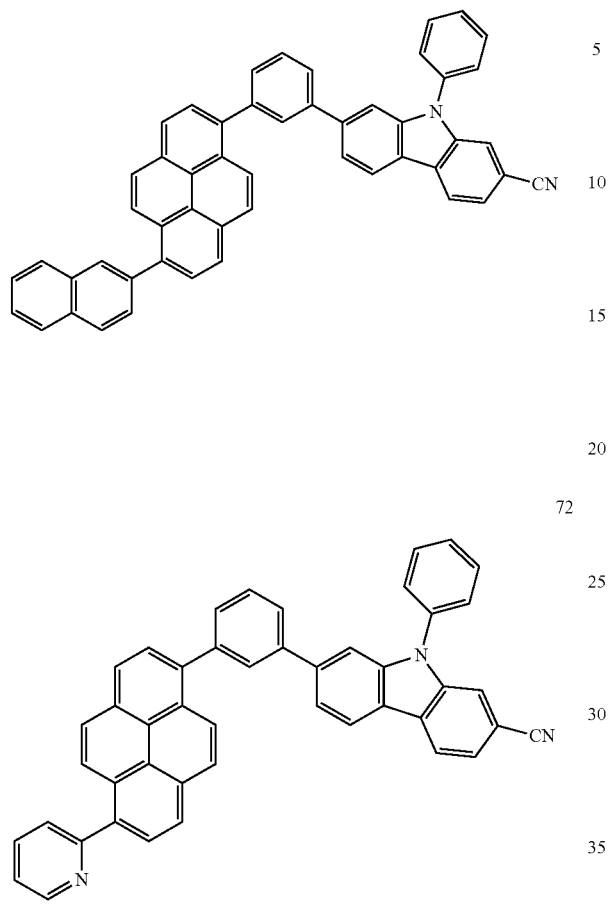
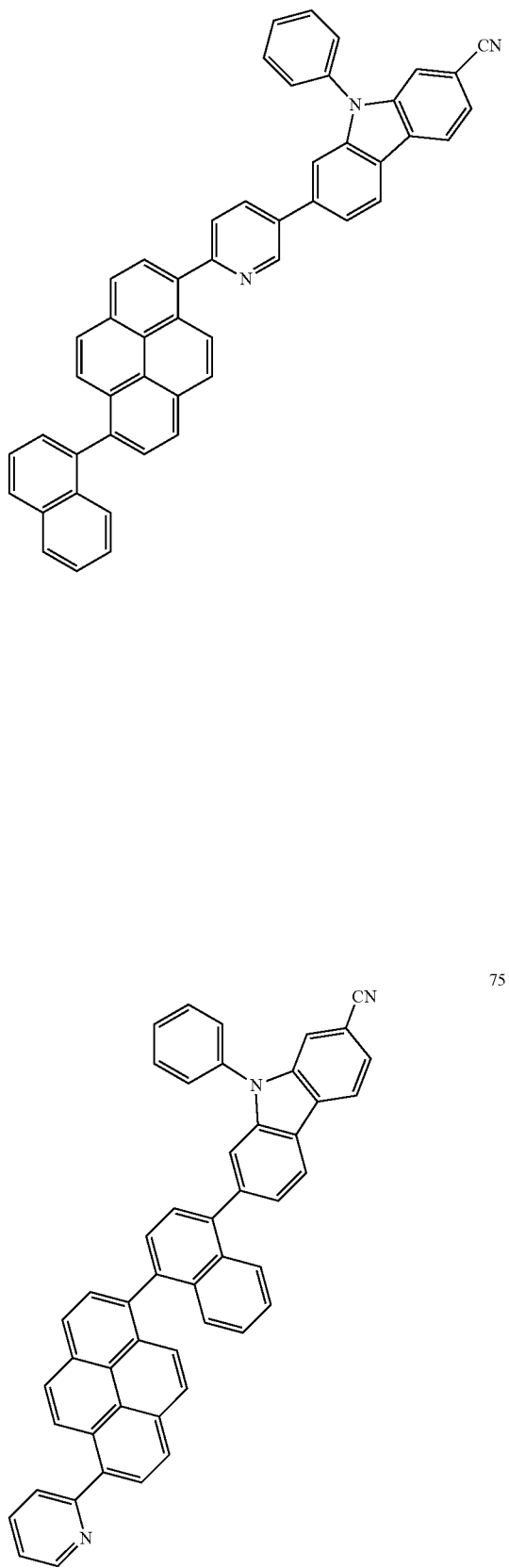

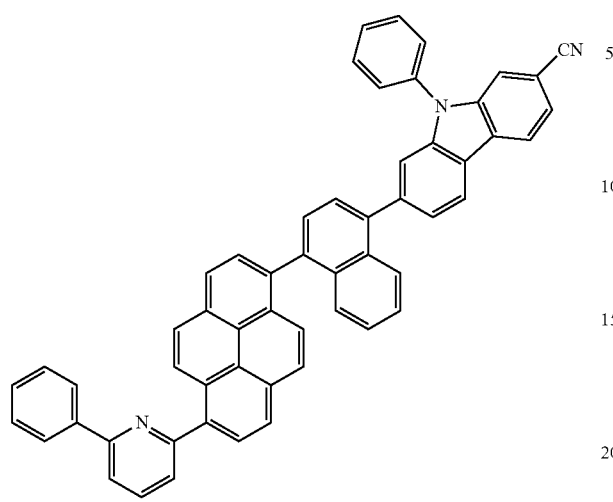
76
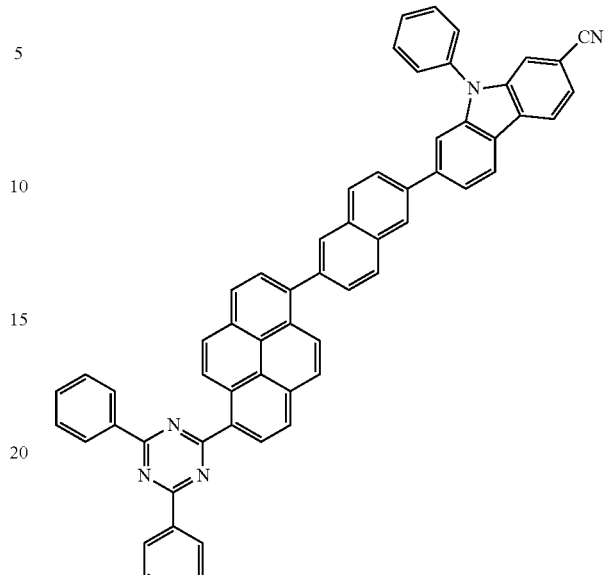
79
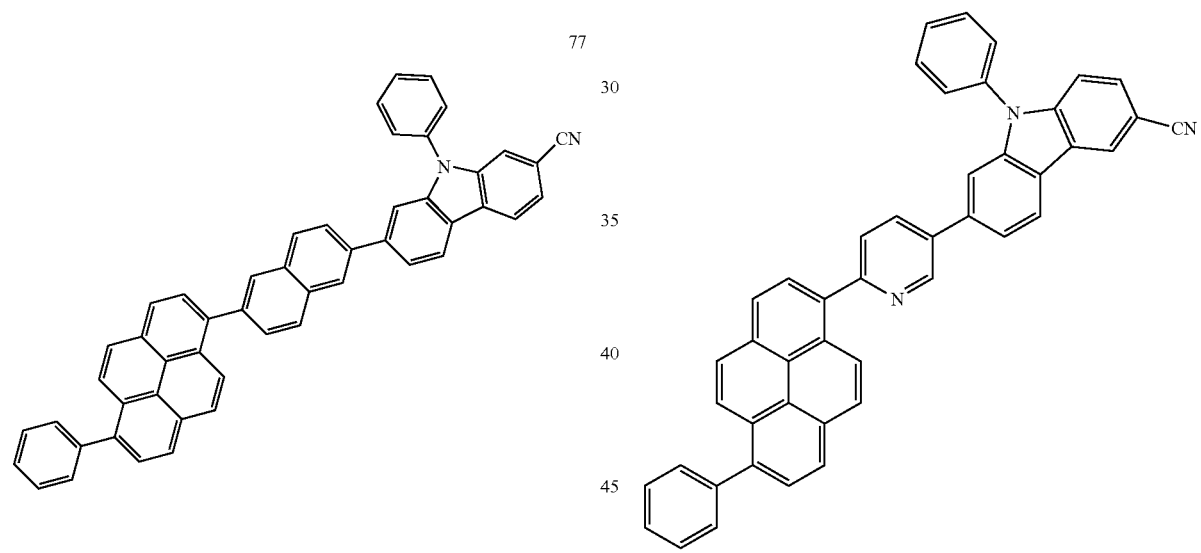
77
80
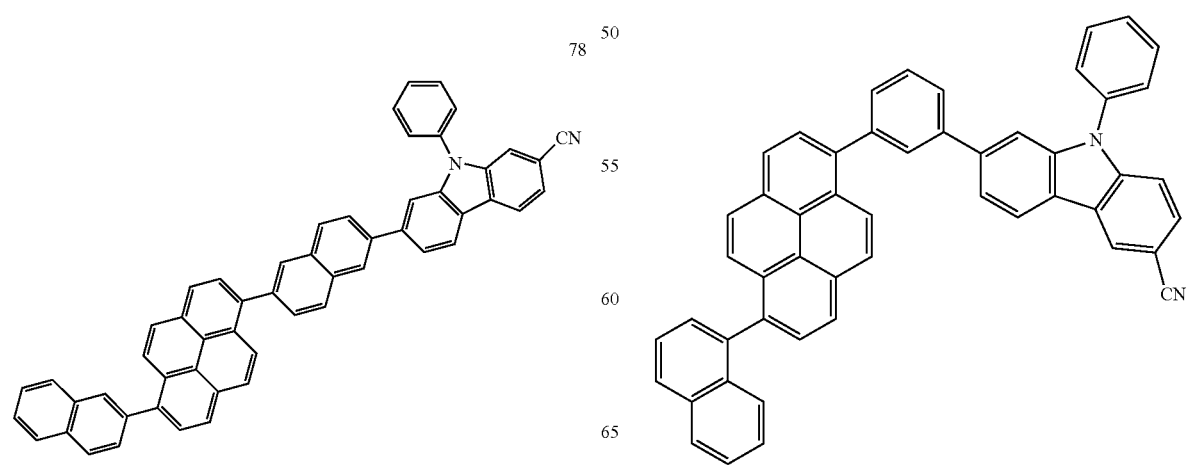
78
81

82
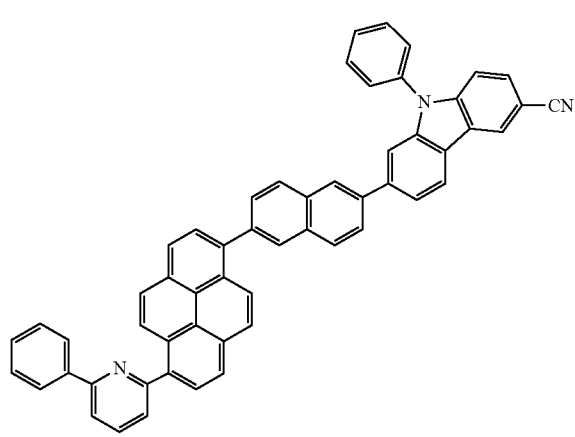
83
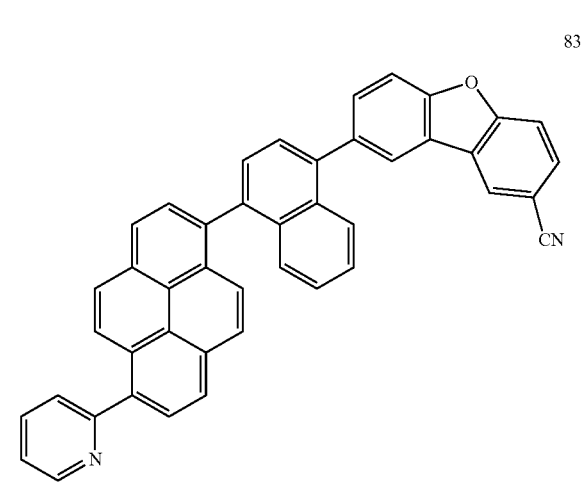
84
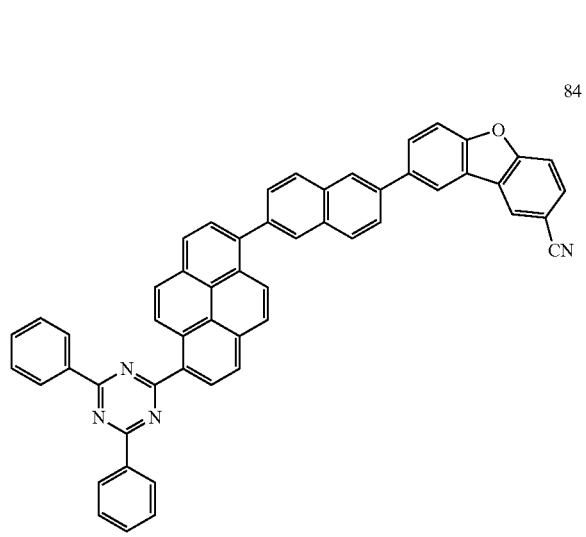
85
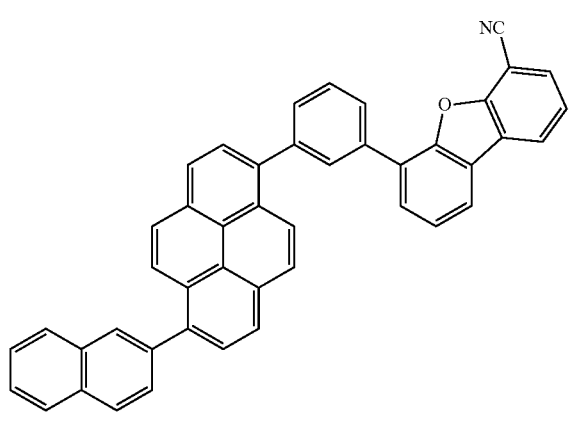
86
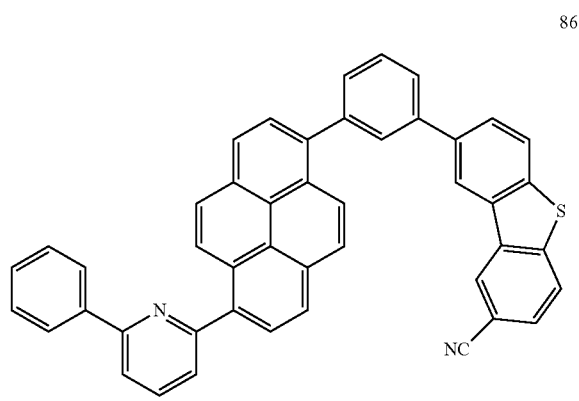
87
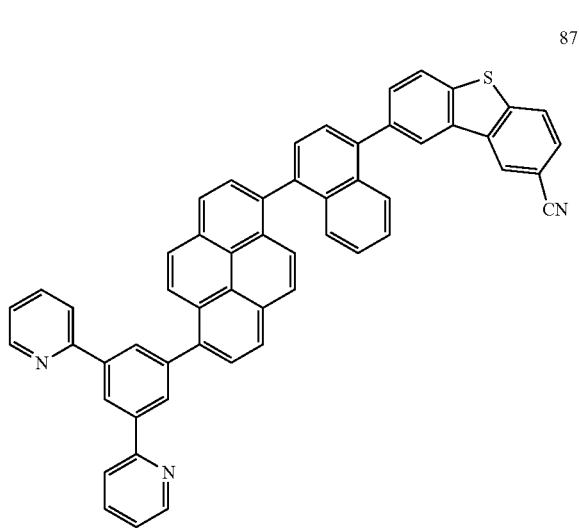

261
-continued
262
-continued
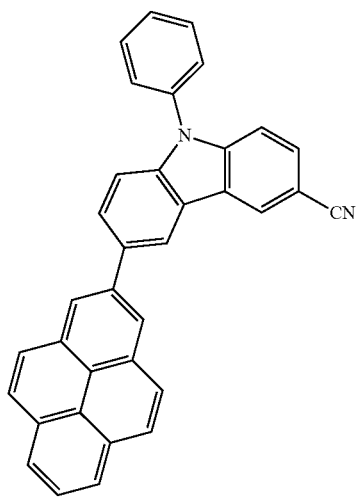
88
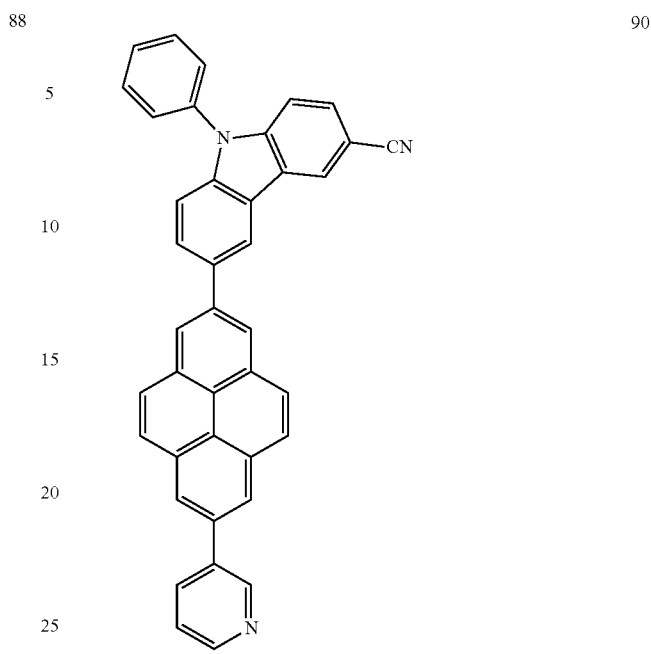
90
89
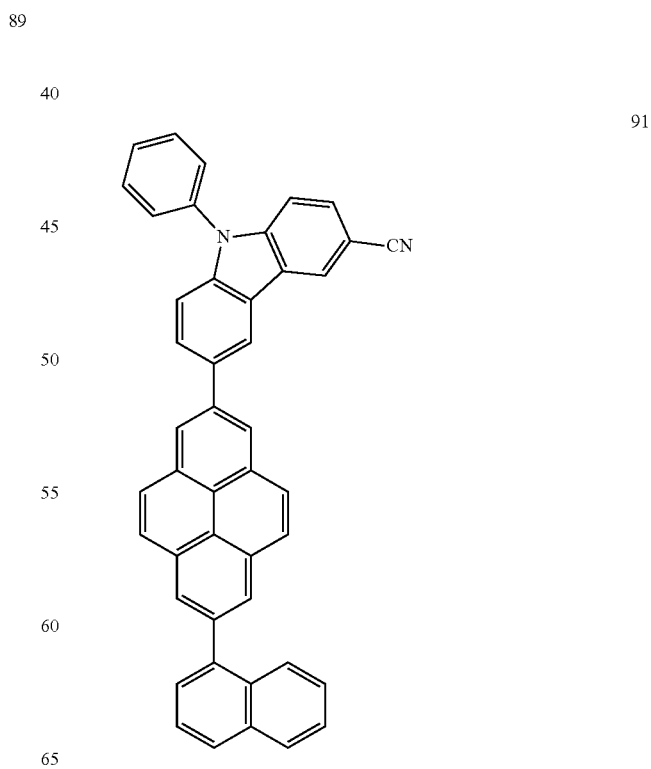
91

92
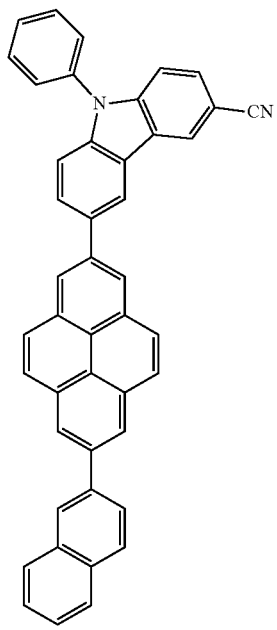
93
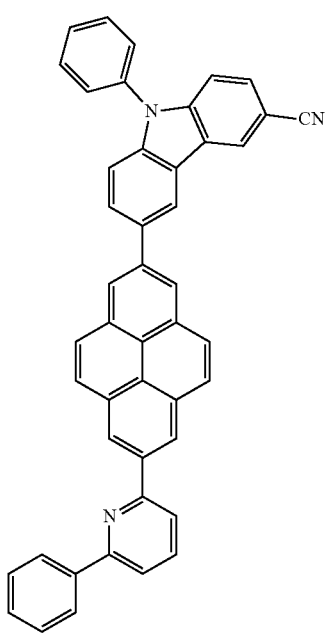
94
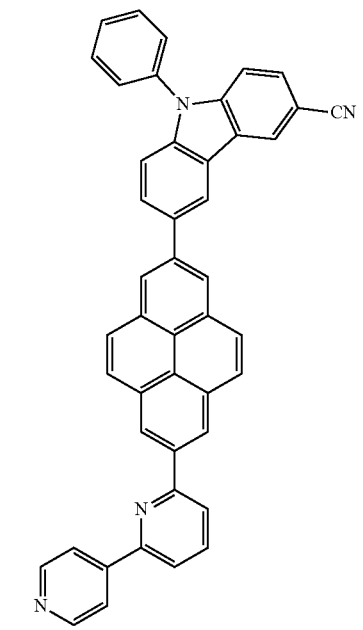
95
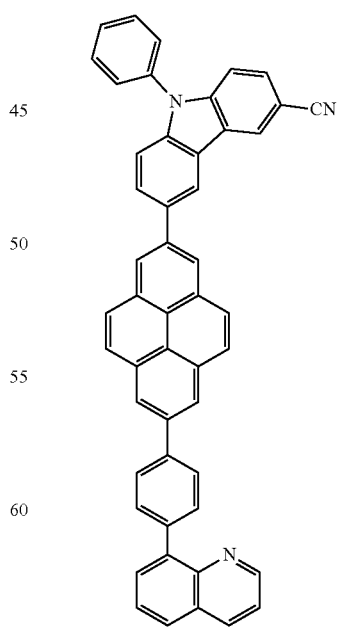

96
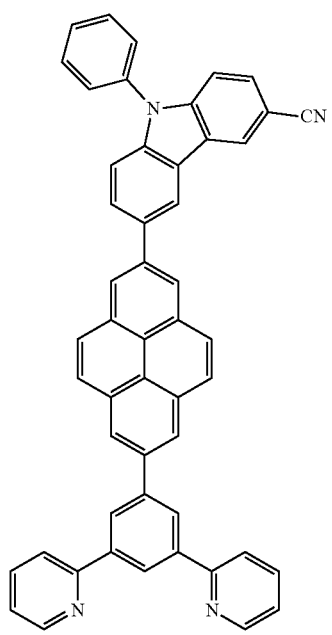
97
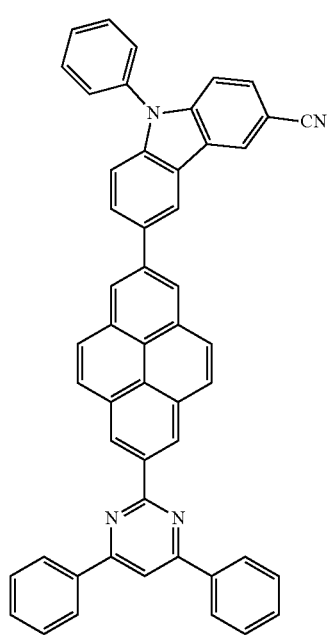
98
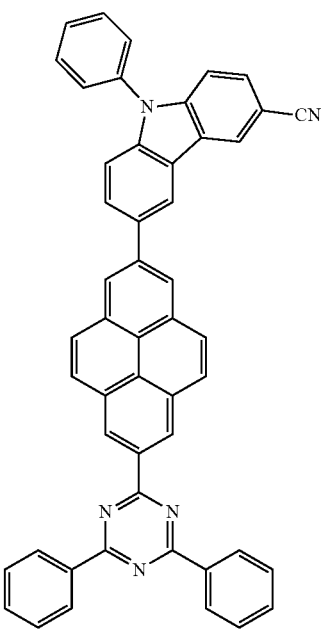
99
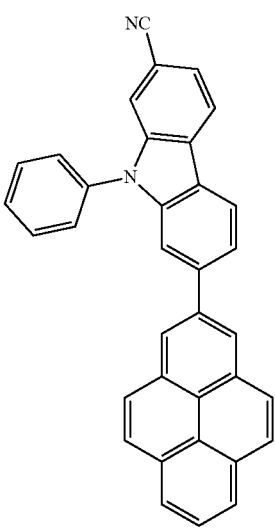

267
-continued
100
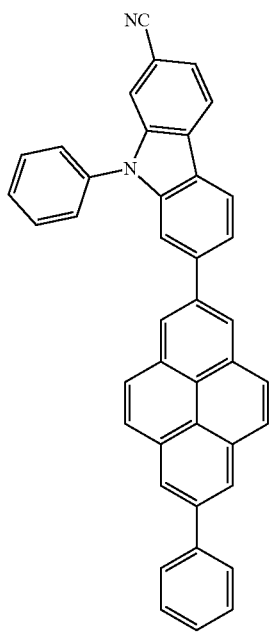
268
-continued
102
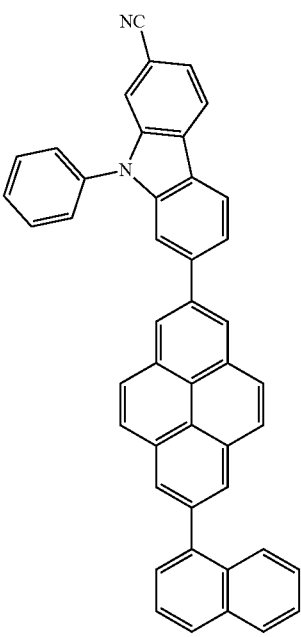
101
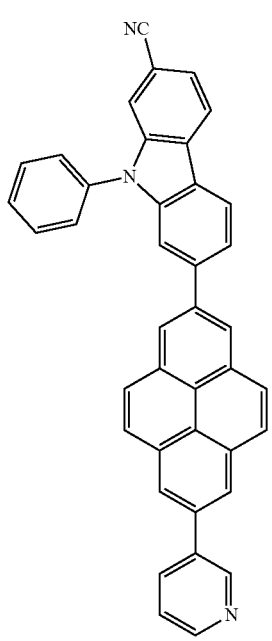
103

269
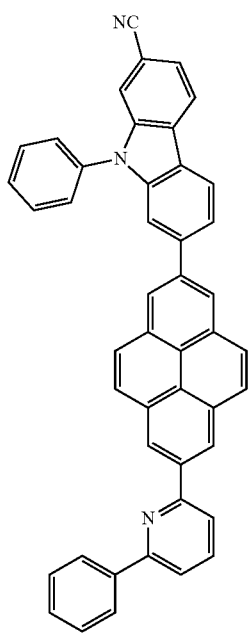
104
270
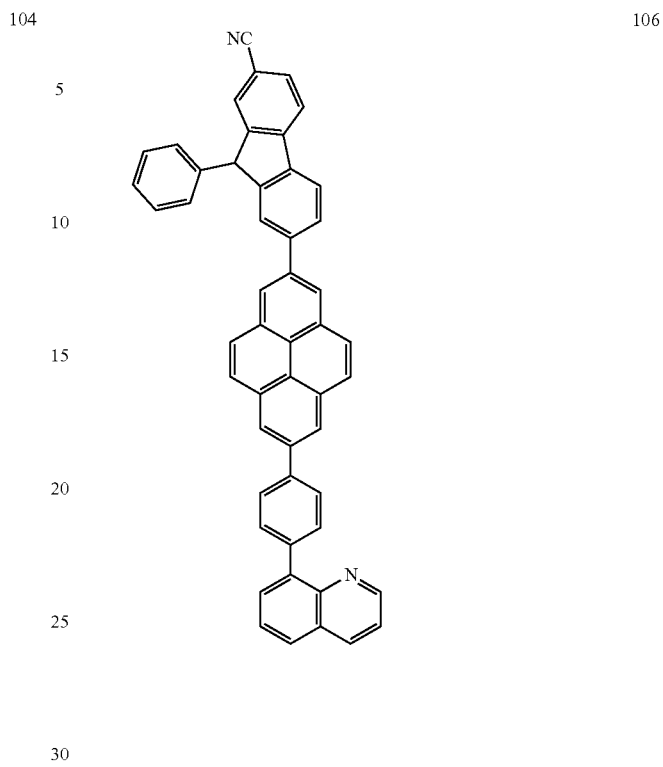
106
105
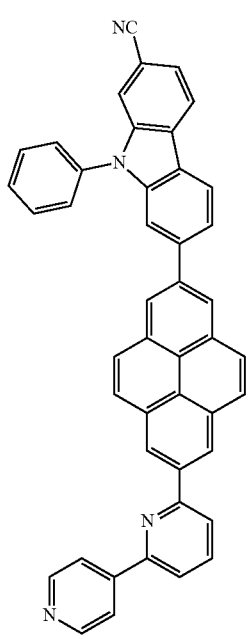
107
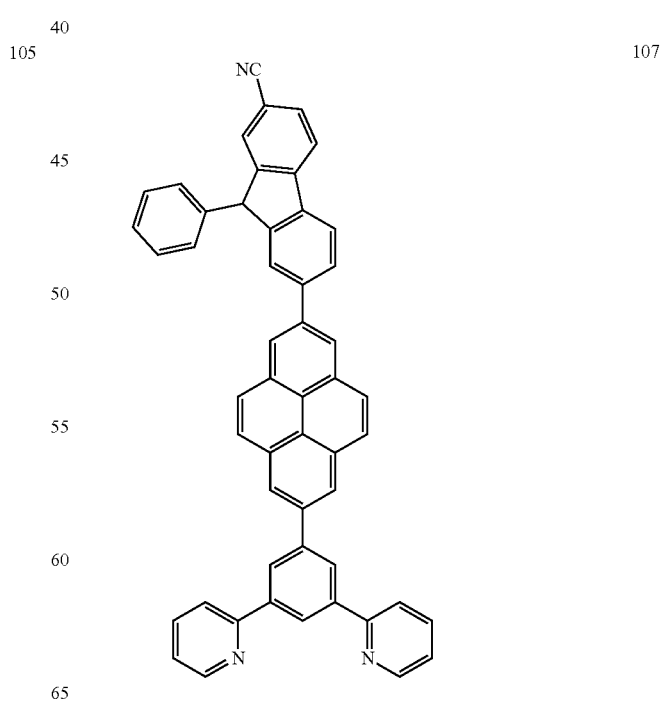

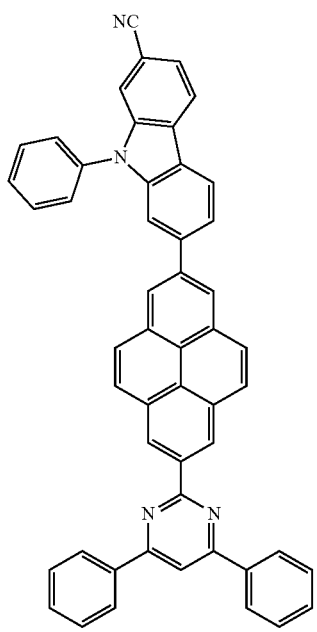
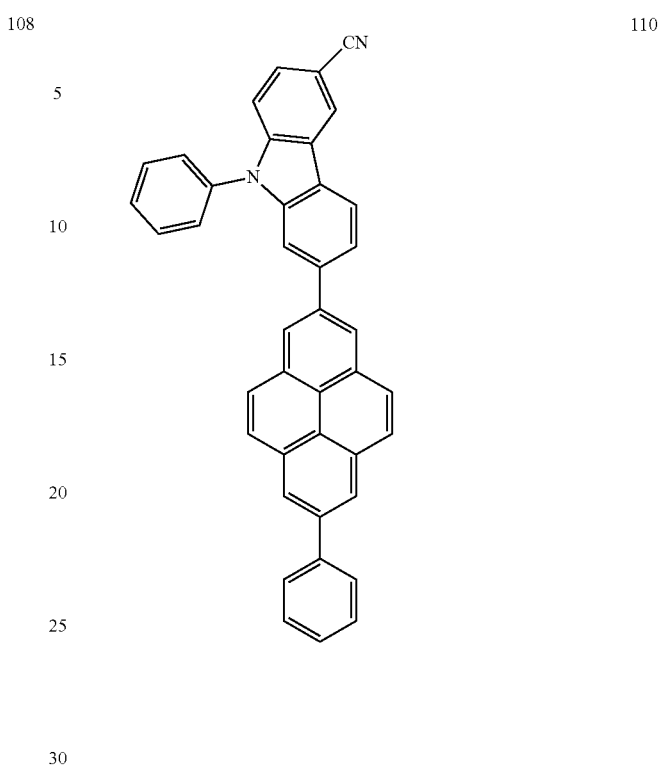
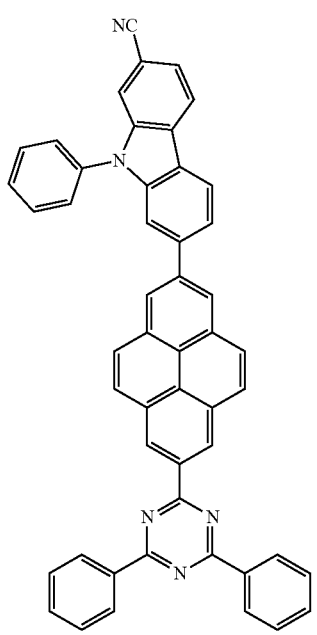
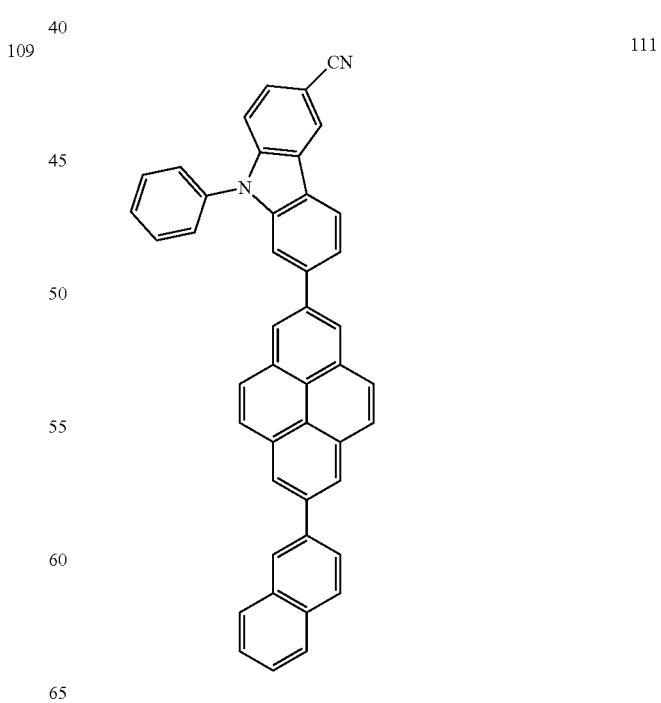

273
-continued
274
-continued
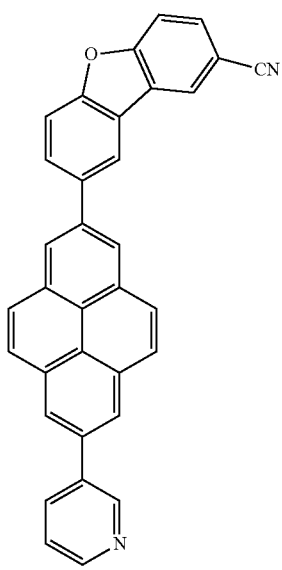
112
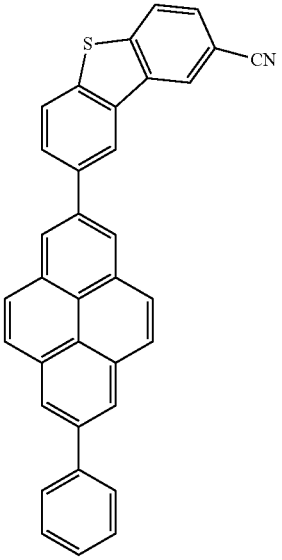
115
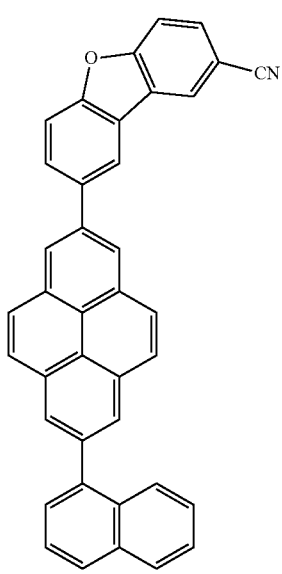
113
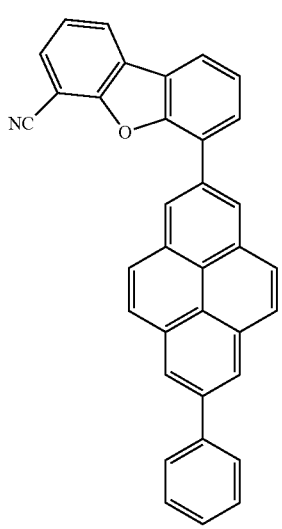
114
116

275
-continued
117
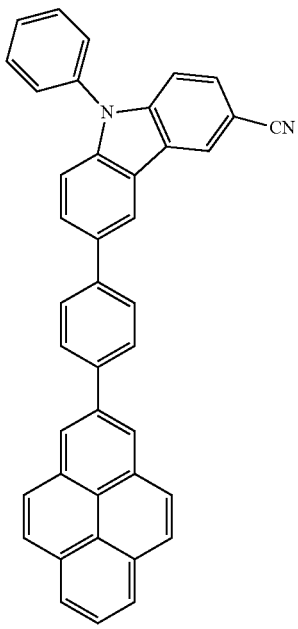
118
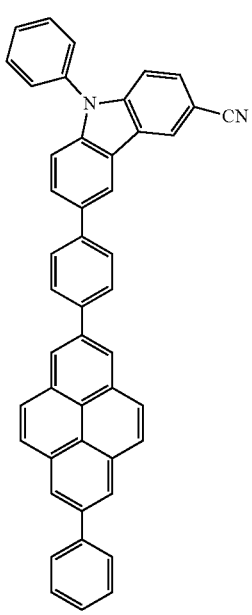
276
-continued
119
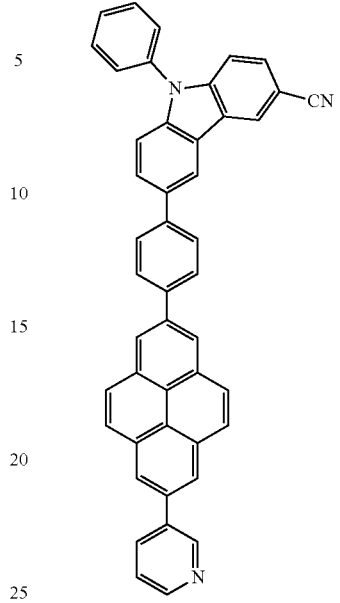
120
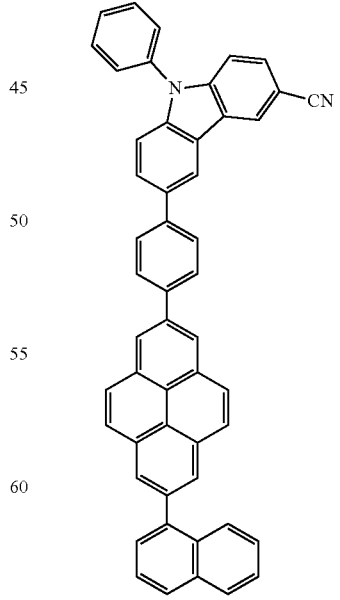

277
-continued
121
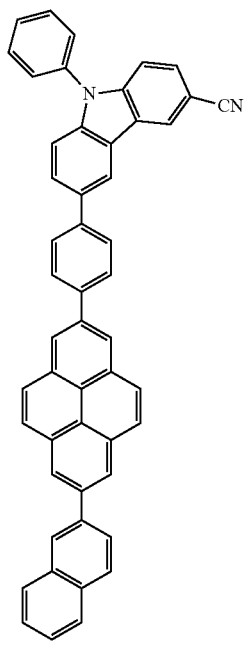
122
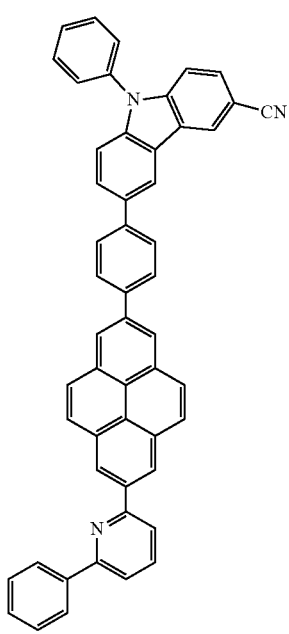
278
-continued
123
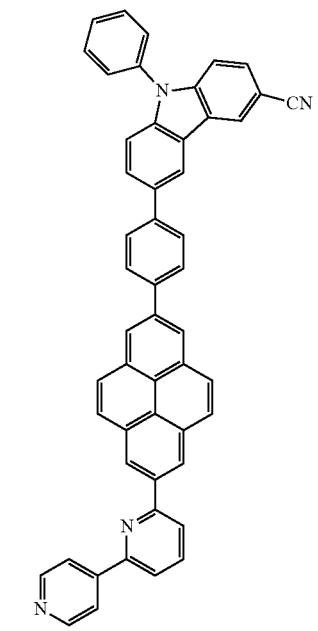
124
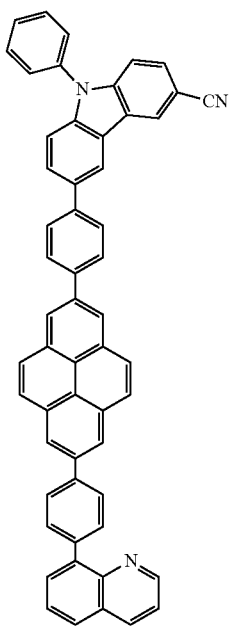

279
-continued
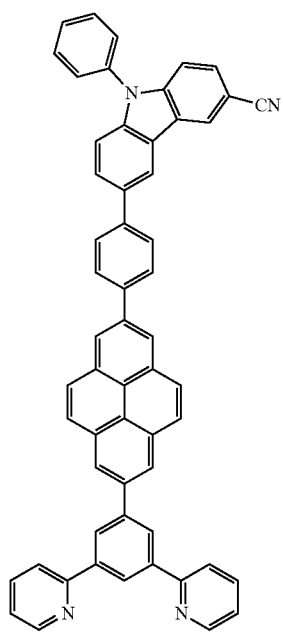
125
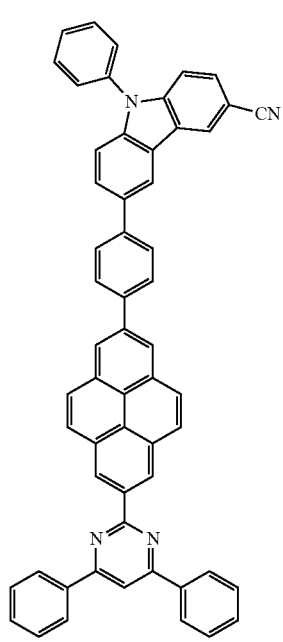
126
280
-continued
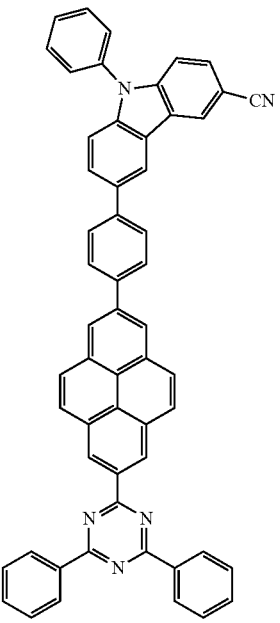
127
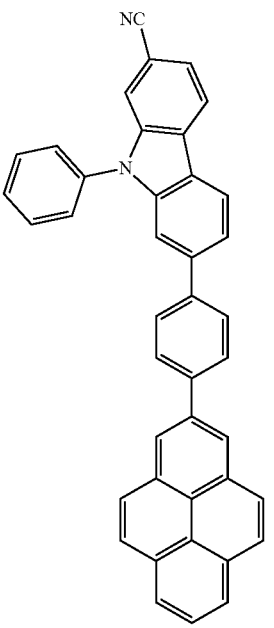
128

-continued
129
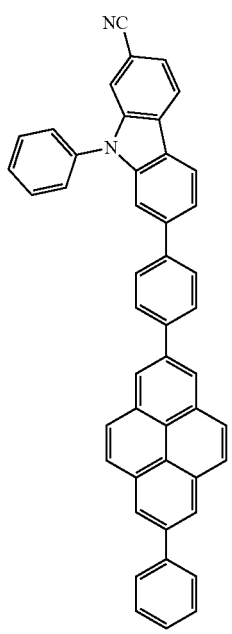
131
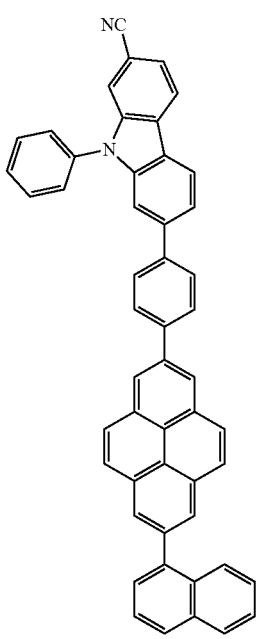
130
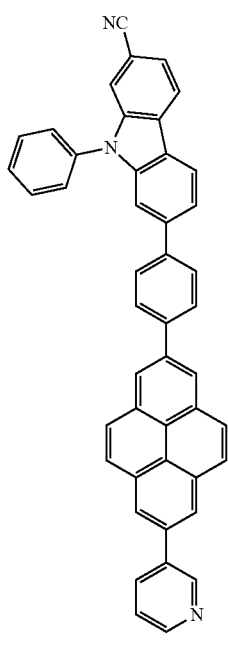
132
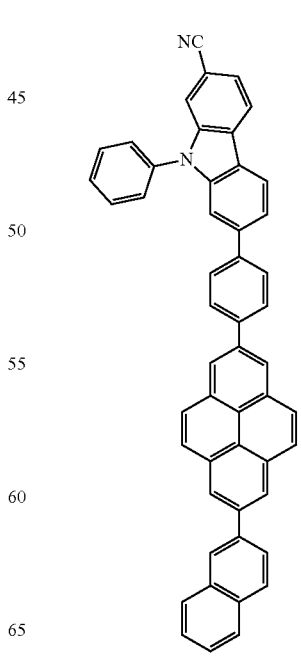

133
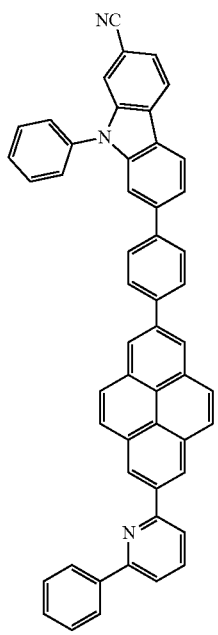
134
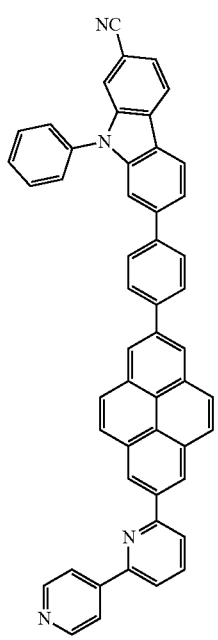
135
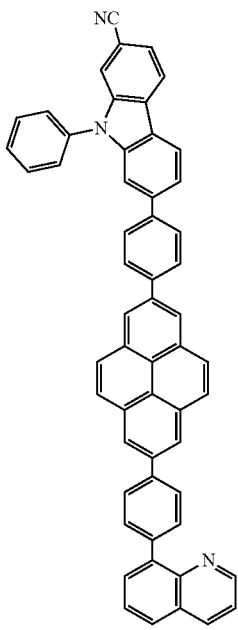
136
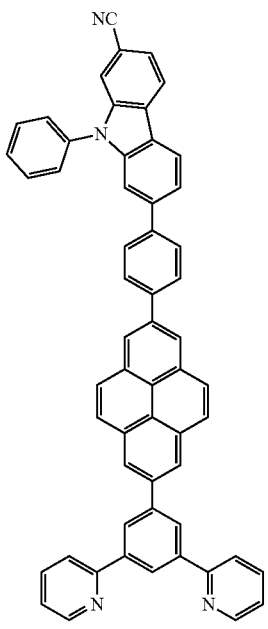

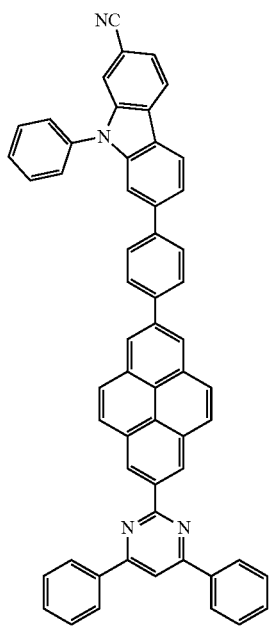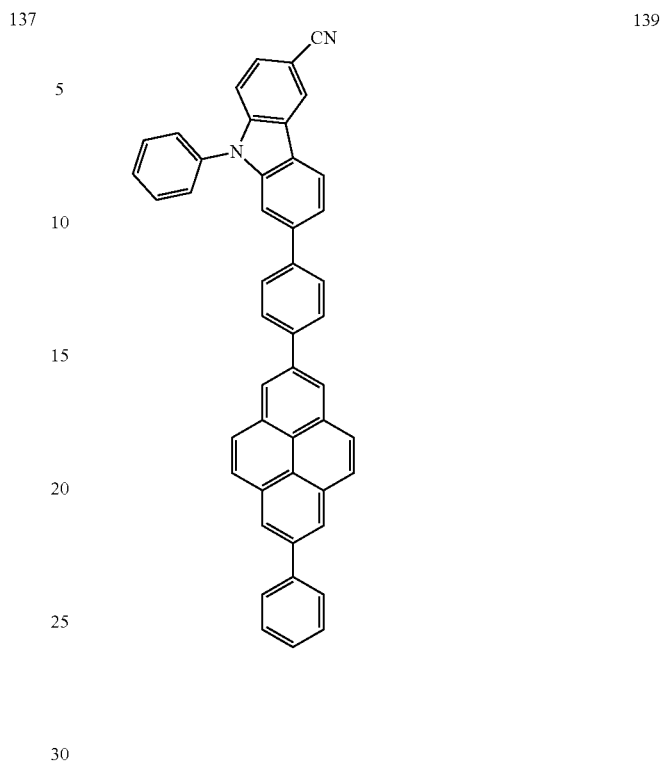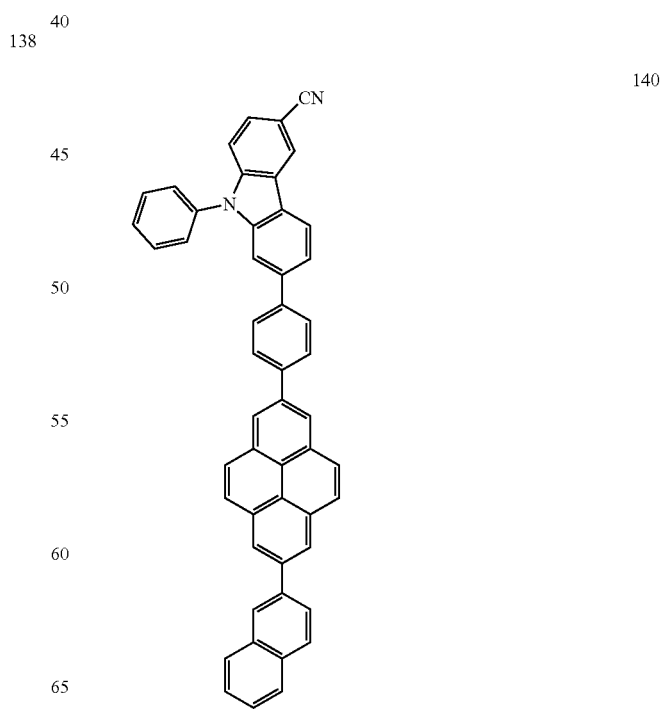

287
-continued
141
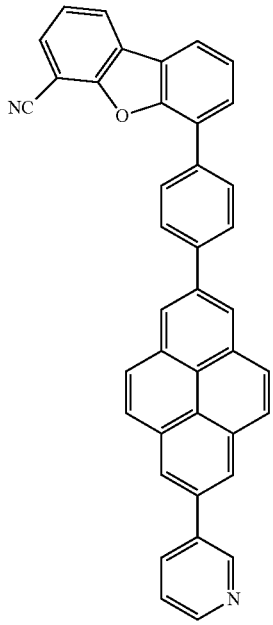
143
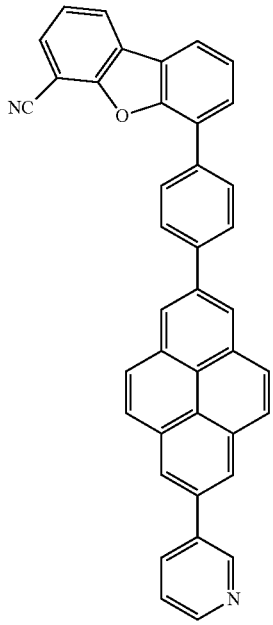
142
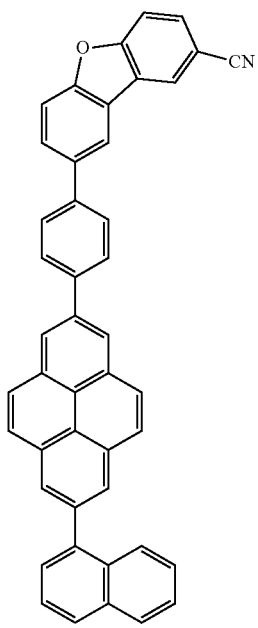
288
-continued
144
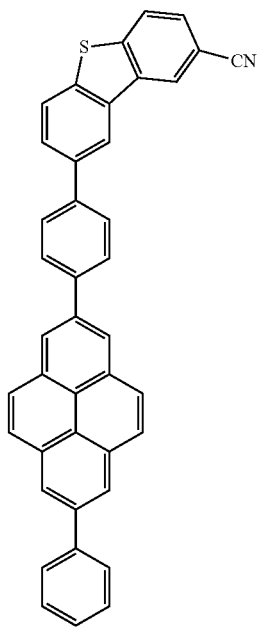

289
-continued
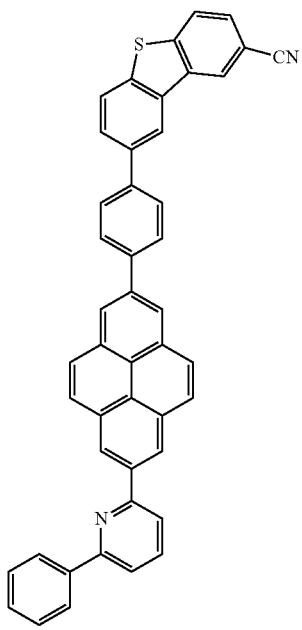
290
-continued
145
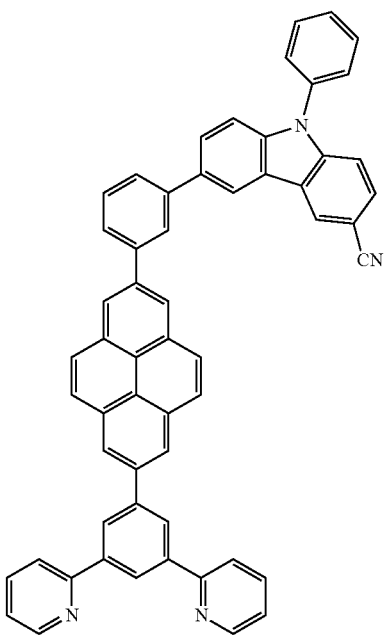
147
146
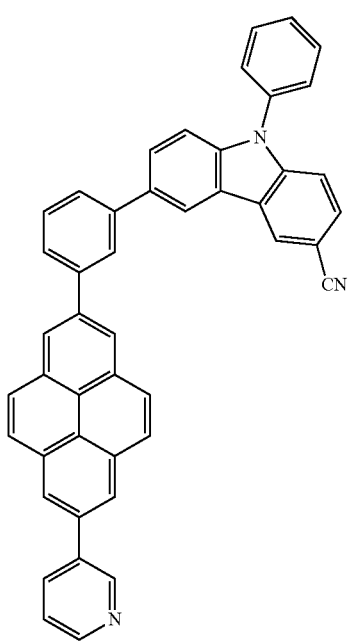
148
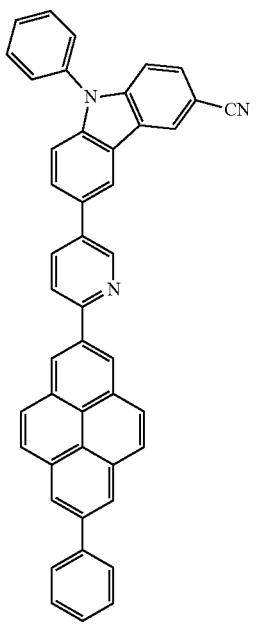

291
-continued
149
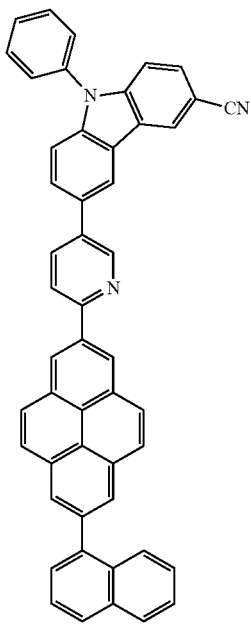
292
-continued
151
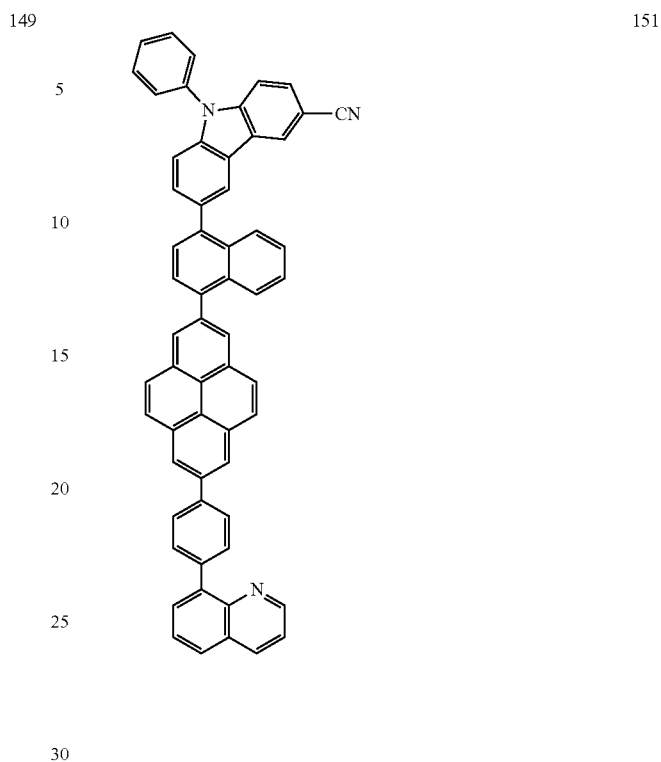
150
152
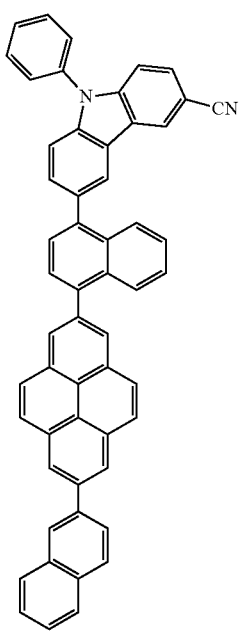
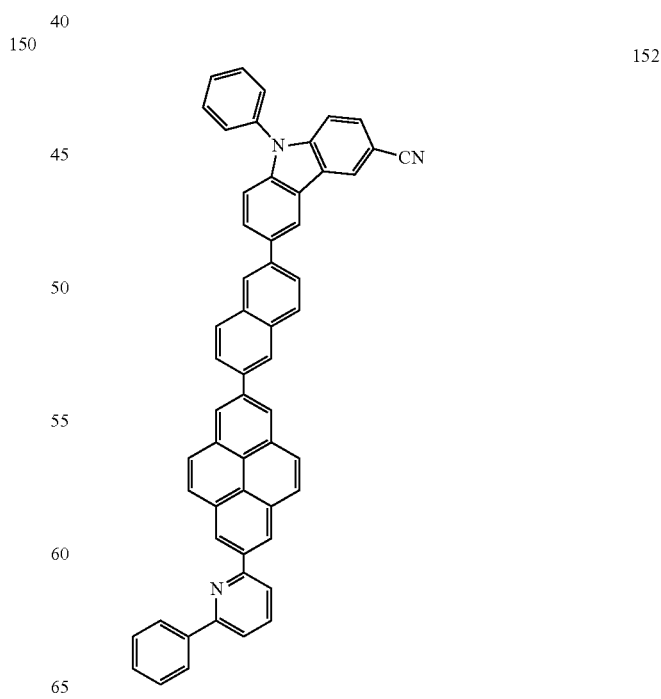

153
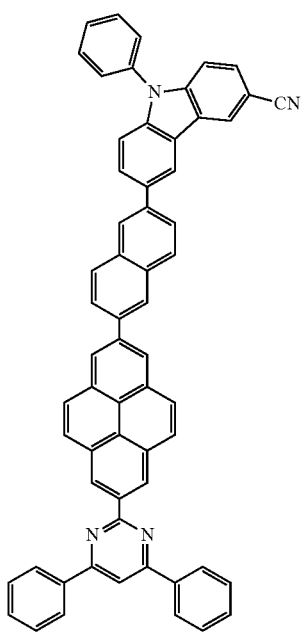
154
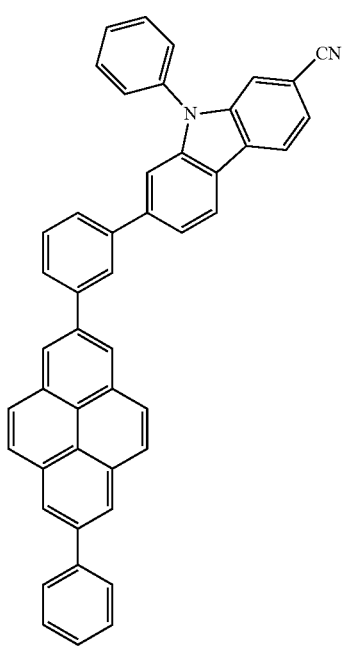
155
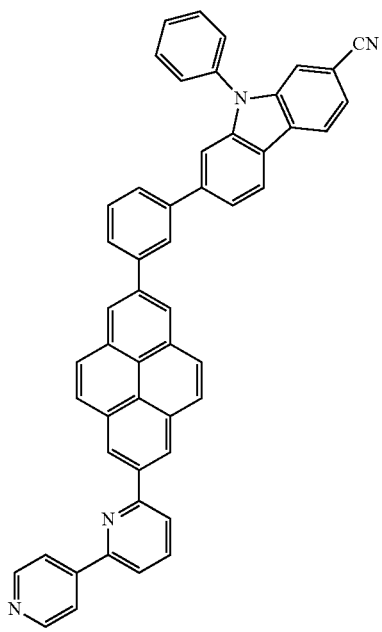
156
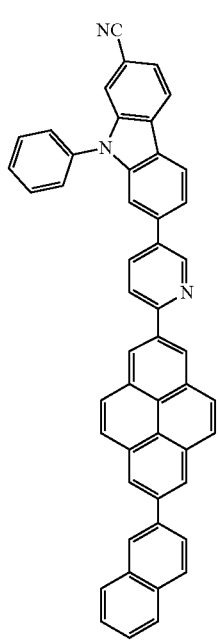

-continued

297
-continued
161
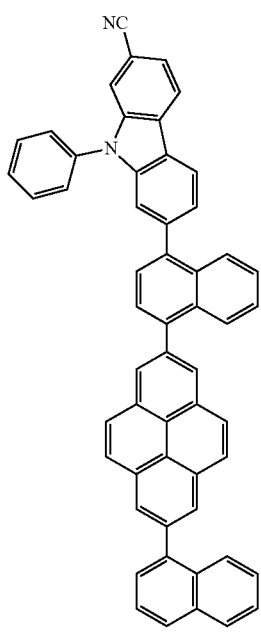
162
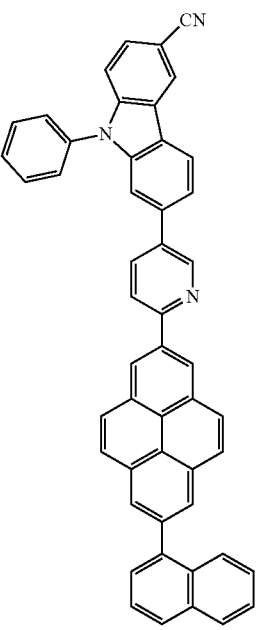
298
-continued
163
164
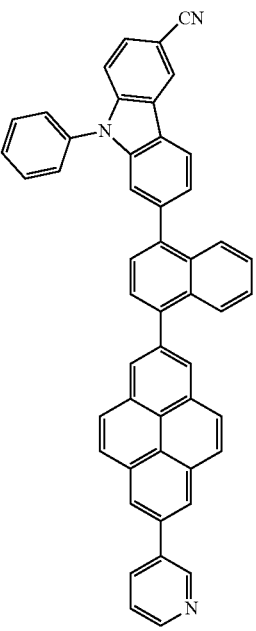

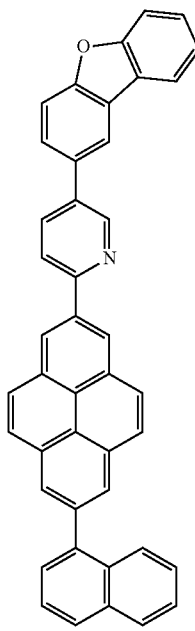
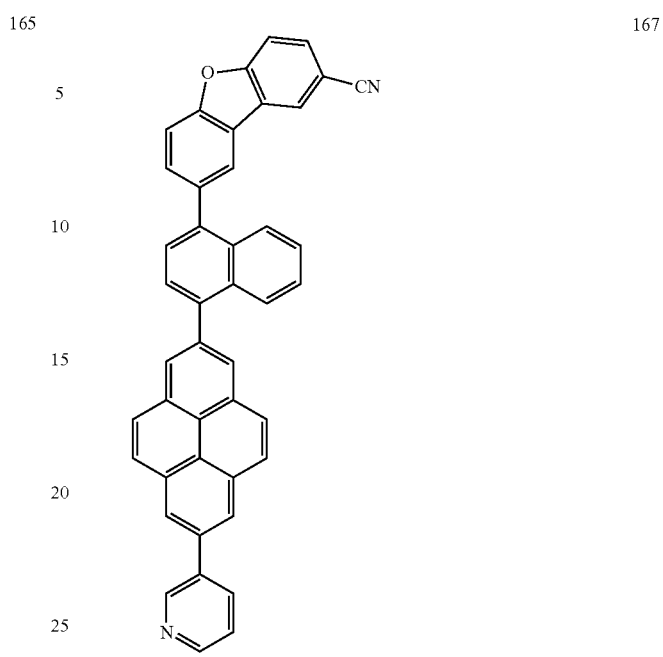

169

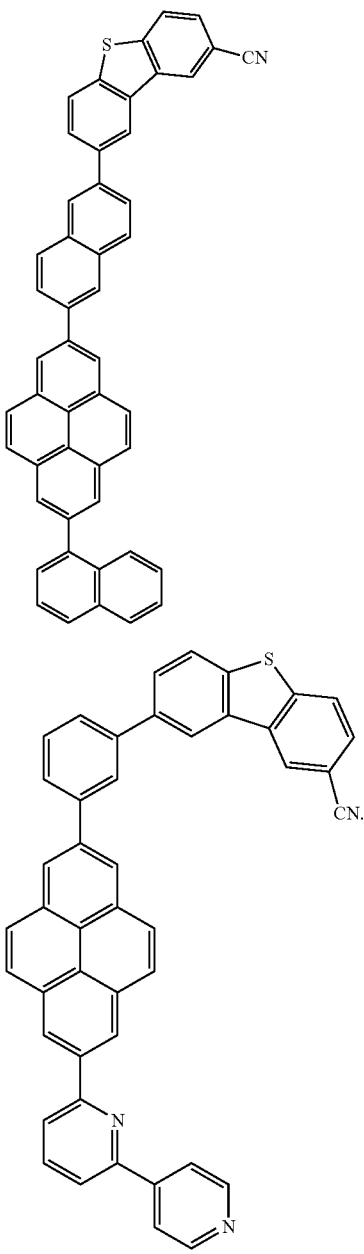

170

16. An organic light-emitting device comprising:
a first electrode;
a second electrode facing the first electrode; and
an organic layer disposed between the first and second electrodes comprising an emission layer, wherein
the organic layer includes at least one condensed-cyclic compound of claim 1.

17. The organic light-emitting device of claim 16, wherein the organic layer comprises
a hole transport region disposed between the first electrode and the emission layer comprising at least one of a hole injection layer, a hole transport layer, a buffer layer, or an electron blocking layer; and
an electron transport region disposed between the emission layer and the second electrode comprising at least one of a hole blocking layer, an electron transport layer, or an electron injection layer.

18. The organic light-emitting device of claim 17, wherein the electron transport region comprises the condensed-cyclic compound.

19. The organic light-emitting device of claim 18, wherein the electron transport region comprises an electron transport layer, and the electron transport layer comprises the condensed-cyclic compound.

20. The organic light-emitting device of claim 17, wherein the hole transport region comprises at least one of a compound represented by Formula 201A below or a compound represented by Formula 202A below:

Formula 201A

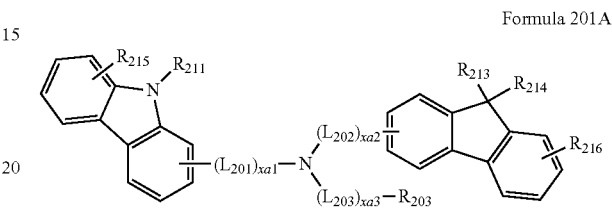

Formula 202A

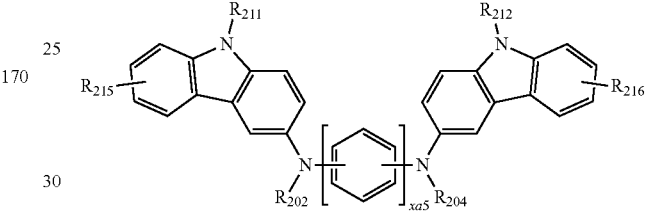

in Formulae 201A and 202A above,
$L_{201}$ to $L_{203}$ are each independently selected from
a phenylene group, a naphthylene group, a fluorenylene group, a spiro-fluorenylene group, a benzofluorenylene group, a dibenzofluorenylene group, a phenalenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, or a triazinylene group; or
a phenylene group, a naphthylene group, a fluorenylene group, a spiro-fluorenylene group, a benzofluorenylene group, a dibenzofluorenylene group, a phenalenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group;

xa1 to xa3 are each independently selected from 0 or 1;

$R_{202}$ to $R_{204}$, $R_{211}$, and $R_{212}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group;

$R_{213}$ and $R_{214}$ are each independently selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group;

$R_{215}$ and $R_{216}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, and a phosphoric acid and a salt thereof, a $C_1$-$C_{20}$ alkyl group or a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; or a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, or a triazinyl group; and xa5 is 1 or 2.

* * * * *